United States Patent
Drummond Samuelson et al.

(10) Patent No.: US 12,010,979 B2
(45) Date of Patent: *Jun. 18, 2024

(54) NON-HUMAN ANIMALS COMPRISING A HUMANIZED TTR LOCUS AND METHODS OF USE

(71) Applicant: Regeneron Pharmaceuticals, Inc., Tarrytown, NY (US)

(72) Inventors: Meghan Drummond Samuelson, Katonah, NY (US); Jeffery Haines, New York, NY (US); Suzanne Hartford, Putnam Valley, NY (US); David Frendewey, New York, NY (US); Brian Zambrowicz, Sleepy Hollow, NY (US); Andrew J. Murphy, Croton-on-Hudson, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/057,960

(22) Filed: Nov. 22, 2022

(65) Prior Publication Data

US 2023/0078551 A1 Mar. 16, 2023

Related U.S. Application Data

(63) Continuation of application No. 16/145,859, filed on Sep. 28, 2018, now abandoned.

(60) Provisional application No. 62/720,292, filed on Aug. 21, 2018, provisional application No. 62/679,142, filed on Jun. 1, 2018, provisional application No. 62/565,980, filed on Sep. 29, 2017.

(51) Int. Cl.
| | | |
|---|---|---|
| *A01K 67/0278* | (2024.01) | |
| *A01K 67/0275* | (2024.01) | |
| *A61K 48/00* | (2006.01) | |
| *C07K 14/47* | (2006.01) | |
| *C12N 15/113* | (2010.01) | |
| *C12N 15/86* | (2006.01) | |

(52) U.S. Cl.
CPC ...... *A01K 67/0275* (2013.01); *A01K 67/0278* (2013.01); *A61K 48/0041* (2013.01); *C07K 14/47* (2013.01); *C12N 15/113* (2013.01); *C12N 15/86* (2013.01); *A01K 2207/15* (2013.01); *A01K 2217/058* (2013.01); *A01K 2217/072* (2013.01); *A01K 2227/105* (2013.01); *A01K 2267/0306* (2013.01); *C07K 2319/02* (2013.01); *C12N 2310/20* (2017.05); *C12N 2710/10041* (2013.01)

(58) Field of Classification Search
CPC ................................................. A01K 67/0278
See application file for complete search history.

(56) References Cited

U.S. PATENT DOCUMENTS

| | | |
|---|---|---|
| 5,942,435 A | 8/1999 | Wheeler |
| 6,340,783 B1 | 1/2002 | Snow |
| 6,586,251 B2 | 7/2003 | Economides et al. |
| 7,294,754 B2 | 11/2007 | Poueymirou et al. |
| 7,309,812 B2 | 12/2007 | Snow |
| 7,576,259 B2 | 8/2009 | Poueymirou et al. |
| 7,659,442 B2 | 2/2010 | Poueymirou et al. |
| 10,329,582 B2 | 6/2019 | Lee et al. |
| 10,385,359 B2 | 8/2019 | Lee et al. |
| 10,577,630 B2 | 3/2020 | Zhang et al. |
| 2002/0160394 A1 | 10/2002 | Wu |
| 2005/0244869 A1 | 11/2005 | Brown-Driver et al. |
| 2008/0038227 A1 | 2/2008 | Torres Aleman et al. |
| 2008/0078000 A1 | 3/2008 | Poueymirou et al. |
| 2010/0215641 A1 | 8/2010 | Roca et al. |
| 2011/0200982 A1 | 8/2011 | Stevens et al. |
| 2013/0042330 A1 | 2/2013 | Murphy et al. |
| 2013/0111617 A1 | 5/2013 | Macdonald et al. |
| 2013/0117873 A1 | 5/2013 | Wang et al. |

(Continued)

FOREIGN PATENT DOCUMENTS

| | | |
|---|---|---|
| EP | 3620524 A1 | 3/2020 |
| WO | WO 2006/105602 A1 | 10/2006 |

(Continued)

OTHER PUBLICATIONS

Zeng et al. (2013) "Viral transduction of male germline stem cells results in transgene transmission after germ cell transplantation in pigs" Biology of reproduction, 88(1), 27-1. (Year: 2013).*
Aigner et al. "Transgenic pigs as models for translational biomedical research" J Mol Med (2010) 88:653-664. (Year: 2010).*
Loi et al. "A New, Dynamic Era for Somatic Cell Nuclear Transfer?" Trends in Biotechnology, vol. 34, No. 10 (published online: Apr. 22, 2016). (Year: 2016).*
Wilmut et al. "Somatic cell nuclear transfer: origins, the present position and future opportunities" Phil. Trans. R. Soc. B 370:20140366, 9 pages (published: Oct. 19, 2015). (Year: 2015).*

(Continued)

*Primary Examiner* — James D Schultz
*Assistant Examiner* — James Joseph Graber
(74) *Attorney, Agent, or Firm* — Yongjin Choi; Alston & Bird LLP

(57) ABSTRACT

Non-human animal genomes, non-human animal cells, and non-human animals comprising a humanized TTR locus and methods of using such non-human animal genomes, non-human animal cells, and non-human animals are provided. Non-human animal cells or non-human animals comprising a humanized TTR locus express a human transthyretin protein or a chimeric transthyretin protein, fragments of which are from human transthyretin. Methods are provided for using such non-human animals comprising a humanized TTR locus to assess in vivo efficacy of human-TTR-targeting reagents such as nuclease agents designed to target human TTR. Methods are also provided for making such non-human animals comprising a humanized TTR locus.

13 Claims, 21 Drawing Sheets

Specification includes a Sequence Listing.

(56) References Cited

U.S. PATENT DOCUMENTS

| | | |
|---|---|---|
| 2013/0340104 A1 | 12/2013 | Murphy |
| 2014/0134662 A1 | 5/2014 | Flavell et al. |
| 2014/0178879 A1 | 6/2014 | Economides et al. |
| 2014/0235933 A1 | 8/2014 | Lee et al. |
| 2014/0245467 A1 | 8/2014 | Macdonald et al. |
| 2014/0310828 A1 | 10/2014 | Lee et al. |
| 2015/0106961 A1 | 4/2015 | Rojas et al. |
| 2015/0176007 A1 | 6/2015 | Prakash et al. |
| 2015/0313194 A1 | 11/2015 | Hu et al. |
| 2015/0320021 A1 | 11/2015 | Wang et al. |
| 2015/0327524 A1 | 11/2015 | Murphy et al. |
| 2015/0342163 A1 | 12/2015 | Voronina et al. |
| 2015/0376628 A1 | 12/2015 | Schoenherr et al. |
| 2015/0376651 A1 | 12/2015 | Frendewey et al. |
| 2016/0090593 A1 | 3/2016 | Sah |
| 2016/0145646 A1 | 5/2016 | Frendewey et al. |
| 2016/0175462 A1 | 6/2016 | Zhang et al. |
| 2016/0257736 A1 | 9/2016 | Nijjar et al. |
| 2017/0080107 A1 | 3/2017 | Chivukula et al. |
| 2017/0142943 A1 | 5/2017 | Mujica et al. |
| 2017/0245481 A1 | 8/2017 | Gusarova et al. |
| 2018/0064827 A1 | 3/2018 | Conway et al. |
| 2018/0110877 A1 | 4/2018 | Wilson et al. |
| 2018/0139940 A1 | 5/2018 | Macdonald et al. |
| 2018/0243450 A1 | 8/2018 | Devalaraja-Narashimha et al. |
| 2019/0002869 A1 | 1/2019 | Yin et al. |
| 2019/0098879 A1 | 4/2019 | Drummond-Samuelson et al. |
| 2019/0100772 A1 | 4/2019 | Prasad et al. |
| 2019/0290783 A1 | 9/2019 | Voronina et al. |
| 2019/0365924 A1 | 12/2019 | Conway et al. |
| 2019/0390195 A1 | 12/2019 | Tondera et al. |
| 2020/0015462 A1 | 1/2020 | Murphy et al. |
| 2020/0248180 A1 | 8/2020 | Kanjolia et al. |
| 2020/0315149 A1 | 10/2020 | Tang et al. |
| 2020/0383304 A1 | 12/2020 | Fang et al. |
| 2020/0385760 A1 | 12/2020 | Haines et al. |
| 2020/0392541 A1 | 12/2020 | Zhang et al. |
| 2023/0102342 A1 | 3/2023 | Drummond Samuelson et al. |

FOREIGN PATENT DOCUMENTS

| | | |
|---|---|---|
| WO | WO 2010/017509 A1 | 2/2010 |
| WO | WO 2010/030203 A1 | 3/2010 |
| WO | WO 2010/048228 A2 | 4/2010 |
| WO | WO 2014/130706 A1 | 8/2014 |
| WO | WO 2014/172489 A2 | 10/2014 |
| WO | WO 2015/006498 A2 | 1/2015 |
| WO | WO 2015/010118 A2 | 1/2015 |
| WO | WO 2015/042557 A1 | 3/2015 |
| WO | WO 2015/051159 A1 | 4/2015 |
| WO | WO 2015/088643 A1 | 6/2015 |
| WO | WO 2015/092077 A1 | 6/2015 |
| WO | WO 2015/115331 A1 | 8/2015 |
| WO | WO 2015/148582 A1 | 10/2015 |
| WO | WO 2015/200334 A1 | 12/2015 |
| WO | WO 2015/200805 A2 | 12/2015 |
| WO | WO 2016/044745 A1 | 3/2016 |
| WO | WO 2016/081923 A2 | 5/2016 |
| WO | WO 2016/176191 A1 | 11/2016 |
| WO | WO 2017/053431 A1 | 3/2017 |
| WO | WO 2017/087780 A1 | 5/2017 |
| WO | WO 2017/173054 A1 | 10/2017 |
| WO | WO 2018/007871 A1 | 1/2018 |
| WO | WO 2018/049009 A2 | 3/2018 |
| WO | WO 2019/067872 A1 | 4/2019 |
| WO | WO 2019/067875 A1 | 4/2019 |
| WO | WO 2019/183123 A1 | 9/2019 |
| WO | WO 2019/237069 A1 | 12/2019 |
| WO | WO 2019/246203 A1 | 12/2019 |
| WO | WO 2020/240876 A1 | 12/2020 |
| WO | WO 2021/108363 A1 | 6/2021 |
| WO | WO 2021/195079 A1 | 9/2021 |

OTHER PUBLICATIONS

Zhao et al. "Inconsistency between hepatic expression and serum concentration of transthyretin in mice humanized at the transthyretin locus" Genes to Cells (2008) 13, 1257-1268. (Year: 2008).*

Ristevski, Sika "Making Better Transgenic Models: Conditional, Temporal, and Spatial Approaches" Molecular Biotechnology, vol. 29, pp. 153-163, 2005. (Year: 2005).*

Teng et al. "Amyloid and Nonfibrillar Deposits in Mice Transgenic for Wild-Type Human Transthyretin: A Possible Model for Senile Systemic Amyloidosis" Laboratory Investigation, vol. 81, No. 3, p. 385-396, 2001. (Year: 2001).*

Buxbaum et al. "Animal models of human amyloidoses: Are transgenic mice worth the time and trouble?" FEBS Letters 583 (2009) 2663-2673. (Year: 2009).*

Birling et al. "Modeling human disease in rodents by CRISPR/Cas9 genome editing" Mamm Genome Jul. 2017, 28:291-301. (Year: 2017).*

Ackermann, et al., "Clinical development of an antisense therapy for the treatment of transthyretin-associated polyneuropathy," Amyloid, 19(51):43-44 (2012).

Aigner, et al., "Transgenic pigs as models for translational biomedical research," J. Mol. Med. (Berl). 88(7):653-664, (2010).

Almeida, et al., "Clearance of extracellular misfolded proteins in systemic amyloidosis: Experience with transthyretin," FEBS Letters, 586:2891-2896, (2012).

Andersson, "Prefibrilar oligomeric Transthyretin mutants—amyloid conformation, toxicity and association with Serum amyloid P component," UMEA University Medical Dissertations, New Series No. 958, ISSN 0346-6612, ISBN 91-7305-862-9, (2005).

Andersson, et al., "Inhibition of TTR Aggregation-Induced Cell Death—A New Role for Serum Amyloid P Component," PLOS One, 8(2):e55766, (Feb. 2013).

Ando, et al., "Guideline of transthyretin-related hereditary amyloidosis for clinicians," Orphanet Journal of Rare Diseases, 8:31, (2013).

Azevedo, et al., "Transthyretin-Related Amyloidoses: A Structural and Thermodynamic Approach," Published by Intech, open sciences, open minds, Retrieved <http://dx.doi.org/10.5772/53148> (2013).

Barthold, "Genetically altered mice: phenotypes, no phenotypes, and Faux phenotypes," Genetica, 122(1):75-88, (2004).

Benson, et al., "Targeted Suppression of an Amyloidogenic Transthyretin with Antisense Oligonucleotides," Muscle Nerve, 33:609-618, (2006).

Birling, et al., "Modeling human disease in rodents by CRISPR/Cas9 genome editing," Mamm. Genome, 28(7-8):291-301, (Jul. 4, 2017).

Brett, et al., "Transthyretin Leu12Pro is associated with systemic, neuropathic and leptomeningeal amyloidosis," Brain, 122:182-190, (1999).

Brevini, et al., "No shortcuts to pig embryonic stem cells," Theriogenology, 74(4):544-550, (2010).

Brevini, et al., "Porcine embryonic stem cells: Facts, challenges and hopes," Theriogenology, 68 Suppl. 1:S206-S213, (2007).

Burova, et al., "Characterization of the Anti-PD-1 Antibody REGN2810 and Its Antitumor Activity in Human PD-1 Knock-In Mice," Mol. Cancer Ther., 16(5):861-870, (Mar. 6, 2017).

Buxbaum, "Animal models of human amyloidoses: Are transgenic mice worth the time and trouble," FEBS Letters, 583:2663-2673, (2009).

Buxbaum, et al., "Transthyretin protects Alzheimer's mice from behavioral and biochemical effects of Aβ toxicity," PNAS, 105(7):2681-2686, (Feb. 19, 2008).

Cao, et al., "Isolation and Culture of Primary Bovine Embryonic Stem Cell Colonies by a Novel Method," J. Exp. Zool. A. Ecol. Genet. Physiol., 311(5):368-376, (2009).

Cardoso, et al., "Doxycycline disrupts transthyretin amyloid: evidence from studies in a FAP transgenic mice model," The FASEB Journal, 20(2):234-239, (Feb. 1, 2006).

Choi, et al., "Accelerated Aβ Deposition in APPswe/PSIΔE9 Mice with Hemizygous Deletions of TTR (Transthyretin)," The Journal of Neurosciences, 27(26):7006-7010, (Jun. 27, 2007).

Chow et al., "AAV-mediated direct in vivo CRISPR screen identifies functional suppressors in glioblastoma," Nat. Neurosci. 20(10):1329-1341 plus supplementary materials, (Aug. 14, 2017).

(56) References Cited

OTHER PUBLICATIONS

Clark, et al., "A future for transgenic livestock," Nat. Rev. Genet., 4(10):825-833, (2003).
Coelho et al., "Compound heterozygotes of transthyretin Met30 and transthyretin Met119 are protected from the devastating effects of familial amyloid polyneuropathy," Neuromuscular Disorders 6(1):S20, (1996).
Coelho, et al., "Safety and Efficacy of RNAi Therapy fro Transthyretin Amyloidosis," N. Engl. J. Med, 369:819-829, (2013).
Conceicao, et al., ""Red-flag" symptom clusters in transthyretin familial amyloid polyneuropathy," Journal of the Peripheral Nervous System, 21:5-9, (Dec. 13, 2015).
Connelly, et al., "Structure-based design of kinetic stabilizers that ameliorate the transthyretin amyloidoses," Curr Opin Struct Biol., 20(1):54-62, (Feb. 2010), Abstract only.
Cornwell, et al., "Evidence that the amyloid fibril protein in senile systemic amyloidosis is derived from normal prealbumin," Biochem Biophys Res Commun., 154(2):648-652 (Jul. 29, 1988), Abstract only.
Dechiara, T.M., et al., "VelociMouse: Fully ES Cell-Derived F0-Generation Mice Obtained from the Injection of ES Cells into Eight-Cell-Stage Embryos," Jan. 1, 2009, Methods in Molecular Biology, 530(16): 311-324.
Dennis, "Welfare Issues of Genetically Modified Animals," ILAR J., 43(2):100-109, (2002).
Ellie, et al., "Recurrent subarachnoid hemorrhage associated with a new transthyretin variant (Gly53Glu)," Neurology, 57:135-137, (2001).
Eneqvist, et al., "The β-Slip: A Novel Concept in Transthyretin Amyloidosis," Molecular Cell, 6:1207-1218, (Nov. 2000).
Ferreira, et al., "Molecular Tweezers Targeting Transthyretin Amyloidosis," Neurothapeutics, 11:451-461, (2014).
Finn, et al., "A Single Administration of CRISPR/Cas9 Lipid Nanoparticles Achieves Robust and Persistent In Vivo Genome Editing," Cell Reports, 22:1-9 plus Supplemental Information, (Feb. 27, 2018).
Fleming, et al., "Transthyretin enhances nerve regeneration," Journal of Neurochemistry, 103:831-839, (2007).
Frendewey, et al., "The Loss-of-Allele Assay for ES Cell Screening and Mouse Genotyping," Methods Enzymol., 476:295-307, (2010).
Genoway, "Humanized Mouse Model," retrieved from https://www.genoway.com/services/customized-mouse/knockin-models/humanisation.htm on May 12, 2018.
Gertz, et al., "Diagnosis, Prognosis, and Therapy of Transthyretin Amyloidosis," J. Am. Coll. Cardiol., 66(21):2451-2466, (2015).
Glik B., Pasternak Dzh. Moleculyarnaya biotehnologiya. Printsipy i primeneniye. Moscow: Mir, 2002, English Translation.
Goldsteins, et al., "Exposure of cryptic epitopes on transthyretin only in amyloid and in amyloidogenic mutants," Proc. Natl. Acad. Sci. USA, 96:3108-3113, (Mar. 1999).
Gomez, et al., "Derivation of cat embryonic stem-like cells from in vitro-produced blastocysts on homologous and heterologous feeder cells," Theriogenology, 74(4): 498-515, (2010).
Graham, et al., "Resources for the design of CRISPR gene editing experiments," Genome Biol., 16:260, (2015).
Groenning, et al., "Considerably Unfolded Transthyretin Monomers Preceed and Exchange with Dynamically Structured Amyloid Protofibrils," Sci. Rep., 5, 11443; doi: 10.1038/srep11443, (2015).
Hammarström, et al., "Prevention of Transthyretin Amyloid Disease by Changing Protein Misfoldings Energentics," Science, 299:713-716, (Jan. 31, 2003).
Hammarström, et al., "Trans-Suppression of Misfolding in an Amyloid Disease," Science, 293:2459-2462, (Sep. 28, 2001).
Harari et al., "Bridging the species divide: transgenic mice humanized for type-I interferon response," PLoS One 9(1):e84259, (2014).
Herndler-Brandstetter, et al., "Humanized mouse model supports development, function, and tissue residency of human natural killer cells," Proc. Natl. Acad. Sci. U.S.A., 114(45):E9626-E9634, (Oct. 25, 2017).

Hofker Marten H., et al., Transgenic mouse methods and protocols, Methods in molecular biology, 209, p. 51-58, 2002-2003.
Houdebine, "Methods to Generate Transgenic Animals," pp. 31-48 in "Genetic Engineering in Livestock: New Applications and Interdisciplinary Perspectives," Ed. Engelhard et al., (2009).
Ibrahim, et al., "Contributions of Animal Models to the Mechanisms and Terapies of Transthyretin Amyloidosis," Front. Physiol., vol. 10, Article 338, (2019).
Inoue, et al., "Specific pathogen free conditions prevent transthyretin amyloidosis in mouse models," Transgenic Res., 17:817-826, (2008).
Intellia Therapeutics, "Company Overview," presented at Jefferies Healthcare Conference (Jun. 6, 2017).
Jacobson, et al., "Transthyretin Pro55, a variant associated with early-onset, aggressive, diffuse amyloidosis with cardiac and neurologic involvement," Hum Genet, 89:353-356, (1992).
Jacobson, et al., "Variant-Sequence Transthyretin (Isoleucine 122) in Late-Onset Cardiac Amyloidosis in Black Americans," The New England Journal of Medicine, 336(7):466-473, (Feb. 13, 1997).
Jean, et al., "Pluripotent genes in avian stem cells," Dev. Growth Differ., 55(1): 41-51, (2013).
Johnson, et al., "The Transthyretin Amyloidoses: From Delineating the Molecular Mechanism of Aggregation Linked to Pathology to a Regulatory Agency Approved Drug," J Mol Biol., 421(2-3): 185-203, doi:10.1016/j.jmb.2011.12.060 (Aug. 10, 2012).
Kan, et al., "Sensory nerve degeneration in a mouse model mimicking early manifestations of familial amyloid polyneuropathy due to transthyretin Ala97Ser," Neuropathol. Appl. Neurobiol. 44(7):673-686, (Mar. 25, 2018).
Karlsson, et al., "Heating of proteins as a means of improving crystallization: a successful case study on a highly amloidogenic triple mutant of human transthyretin," Acta Cryst., F63:695-700, (2007).
Kawamata, et al., "Generation of genetically modified rats from embryonic stem cells," Proc. Natl. Acad. Sci. U.S.A., 7(32):14223-14228, (2010).
Keetch, et al., "L55P Transthyretin Accelerates Subunit Exchange and Leads to Rapid Formation of Hybrid Tetramers," The Journal of Biological Chemistry, 280(50):41667-41674, (Dec. 16, 2005).
Kohno et al., "Analysis of amyloid deposition in a transgenic mouse model of homozygous familial amyloidotic polyneuropathy," Am. J. Pathol. 150(4):1497-1508, (Apr. 1997).
Kohno, et al., "Analysis of Amyloid Deposition in a Transgenic Mouse Model of Homozygous Familial Amyloidotic Polyneuropathy," American Journal of Pathology, 150(4):1497-1508, (Apr. 1997).
Kruse, "Treating TTR Amyloidosis: Introducing CRISPR," Biotechr, published Apr. 30, 2016 at <http://www.biotechr.com/2016/04/hunt-to-cure-ttr-amylodiosis-crispr.html>.
Kumar, et al., "Transgenic Mouse Technology: Principles and Methods," Methods Mol. Biol., 590:335-362, (2009).
Li, et al., "Amyloid deposition in a mouse model humanized at the transthyretin and retinol-binding protein 4 loci," Lab. Invest., published online Jan. 12, 2018 at <https://doi.org/10.1038/s41374-017-0079-y>.
Lobato, et al., "Transthyretin Amyloidosis and the Kidney," Clin J AM Soc Nephrol, 7:1337-1346, doi: 10.2215/CJN.08720811, (2012).
Loi, et al., "A New, Dynamic Era for Somatic Cell Nuclear Transfer?" Trends Biotechnol. 34(10:791-797, (2016).
Lute, et al., "Human CTLA4 knock-in mice unravel the quantitative link between tumor immunity and autoimmunity induced by anti-CTLA-4 antibodies," Blood, 106(9):3127-3133, (2005).
Misumi, et al., "Fibroblasts endocytose and degrade transthyretin aggregates in transthyretin-related amyloidosis," Laboratory Investigation, 93:911-920, (2013).
Mu, et al., "CHF5074 (CSP-1103) stabilizes human transthyretin in mice humanized at the transthyretin and retinol-binding protein loci," FEBS Letters, 589:849-856, (2015).
Mullins, et al., "Transgenesis in the rat and larger mammals," J. Clin. Invest. 97(7):1557-1560, (1996).
Munoz, et al., "Conventional pluripotency markers are unspecific for bovine embryonic-derived cell-lines," Theriogenology, 69(9): 1159-1164, (2008).

(56) References Cited

OTHER PUBLICATIONS

Murakami, et al., "Schwann cells contribute to neurodegeneration in transthyretin amyloidosis," Journal of Neurochemistry, 134:66-74, (2015).
Nagata, et al., "A 6-kb Upstream Region of the Human Transthyretin Gene Can Direct Developmental, Tissue-Specific , and Quantitatively Normal Expression in Transgenic Mouse," J. Biochem., 117: 169-175, (1995).
Niemann, "Transgenic farm animals get off the ground. Transgenic Animals in Agriculture, Conference Tahoe City, California, USA. Aug. 24-27, 1997." Transgenic Res., 7(1): 73-75, (1998).
Noborn, et al., "Heparan sulfate/heparin promotes transthyretin fibrillization through selective binding to a basic motif in the protein," Proc. Natl. Acad. Sci. U.S.A., 108(4):5584-5589, (Apr. 2011).
Olsson, et al., "A possible role for miRNA silencing in disease phenotype variation in Swedish transthyretin V30M carriers," BMC Med. Genet. 11:130, (2010).
Pankowicz, et al., "CRISPR/Cas9: at the cutting edge of hepatology," Gut, 66(7):1329-1340, (May 9, 2017).
Paris, et al., "Equine embryos and embryonic stem cells: defining reliable markers of pluripotency," Theriogenology, 74(4): 516-524, (2010).
Parman, et al., "Sixty years of transthyretin familial amyloid polyneuropathy (TTR-FAB) in Europe: where are we now? A European network approach to defining the epidemiology and management patterns for TTR-FAB," Curr Opin Neurol, 29 (suppl 1): S3-S13, (Fe Published: 2016.
PCT/US2018/053389 International Search Report and Written Opinion of the International Searching Authority dated Jan. 14, 2019.
Poueymirou, et al., "F0 generation mice fully derived from gene-targeted embryonic stem cells allowing immediate phenotypic analyses," Nat. Biotechnol., 25(1):91-99, (2007).
Quadro, et al., "Impaired retinal function and vitamin A availability in mice lacking retinol-binding protein," The EMBO Journal, 18(17):4633-4644, (1999).
Reixach, et al., "Cell based screening of inhibitors of transthyretin aggregation," Biochemical and Biophysical Research Communications, 348:889-897, (2006).
Reixach, et al., "Tissue damage in the amyloidoses: Transthyretin monomers and nonnative oligomers are the major cytotoxic species in tissue culture," Proc. Natl. Acad. Sci. U.S.A., 101(9):2817-2822, (Mar. 2004).
Rezza, et al., "Unexpected genomic rearrangements at targeted loci associated with CRISPR/Cas9-mediated knock-in," Sci. Rep., 9(1):3486, (2019).
Ristevski, "Making better transgenic models: conditional, temporal, and spatial approaches," Mol. Biotechnol., 29(2):153-163, (2005).
Rogers, et al., "Disruption of the CFTR Gene Produces a Model of Cystic Fibrosis in Newborn Pigs," Science, 321(5897):1837-1841, (2008).
Ruberg, et al., "Transthyretin (TTR) Cardiac Amyloidosis," Circulation, 126:1286-1300, doi.10.1161/circulationaha.111.078915, (2012).
Rybchin V.N., Osnovy geneticheskoy inzhenerii, Saint Petersburg, SHbGTU Publishing House, 2002, p. 411-413, English translation.
Saelices, et al., "Amyloid seeding of transthyretin by ex vivo cardiac fibrils and its inhibition," Proc. Natl. Acad. Sci. U.S.A., 115(29):e6741-e6750, (Jun. 2018).
Santos, et al., "The heat shock response modulates transthyretin deposition in the peripheral and autonomic nervous systems," Neurobiology, 21:280-289, (2010).
Saraiva, et al., "Transthyretin amyloidosis: a tale of weak interactions," FEBS Letters, 498:201-203, (2001).
Sasaki, et al., "Generation of Transgenic Mice Producing a Human Transthyretin Variant: A Possible Mouse Model for Familial Amyloidotic Polyneuropathy," Biochemical and Biophysical Research Communications, 139(2):794-799, (Sep. 17, 1986).
Sekijima, et al., "Energetic Characteristics of the New Transthyretin Variant A25T May Explain Its Atypical Central Nervous System Pathology," Laboratory Investigation, 83(3):409-417, (2003).

Sekijima, et al., "R104H may suppress transthyretin amyloidogenesis by thermodynamic stabilization, but not by the kinetic mechanism characterizing T119 interallelic trans-suppression," Amyloid, 12(2): 57-60, (Jun. 2006).
Sigmund, "Viewpoint: Are Studies in Genetically Altered Mice Out of Control?," Arterioscler. Thromb. Vasc. Biol., 20(6):1425-1429, (2000).
Smith, et al., "The Effects of Disease of the Liver, Thyroid, and Kidneys on the Transport of Vitamin A in Human Plasma," The Journal of Clinical Investigation, 50:2426-2436, (1971).
Sosa, et al., "Animal transgenesis: an overview," Brain Struct. Funct. 214(2-3):91-109, (2010).
Sousa, et al., "Deposition and passage of transthyretin through the blood-nerve barrier in recipients of familial amyloid polyneuropathy livers," Laboratory Investigation, 84:865-873, (2004).
Sousa, et al., "Evidence for Early Cytotoxic Aggregates in Transgenic Mice for Human Transthyretin Leu55Pro," American Journal of Pathology, 161(5):1935-1948, (Nov. 2002).
Sousa, et al., "Familial Amyloidotic Polyneuropathy in Sweden: Geographical Distribution, Age of Onset, and Prevalence," Hum Hered, 43:288-294, (1993).
Sousa, et al., "Transthyretin is involved in depression-like behaviour and exploratory activity," J. Neurochem., 88(5):1052-1058, (2004).
Stangou, et al., "Transmission of Systemic Transthyretin Amyloidosis by Means of Domino Liver Transplantation," The New England Journal of Medicine, 352(22):2356, (Jun. 2, 2005).
Steward, et al., "Different disease-causing mutations in transthyretin trigger the same conformational conversion," Protein Engineering, Design Selection, 21(3):187-195, (2008).
Tagoe, et al., "Amyloidogenesis is neither accelerated nor enhanced by injections of preformed fibrils in mice transgenic for wild-type human transthyretin: the question of infectivity," Amyloid: J. Protein Folding Disord., 11:21-26, (2004).
Tagoe, et al., "In vivo stabilization of mutant human transthyretin in transgenic mice," Amyloid, 14(3):227-236, (2007).
Takaoka, et al., "Comparison of amyloid deposition in two lines of transgenic mouse that model familial amyloidotic polyneuropathy, type I," Transgenic Research, 6:261-269, (1997).
Takaoka, et al., "Cysteine 10 Is a Key Residue in Amyloidogenesis of Human Transthyretin Val30Met," American Journal of Pathology, 164(1):337-345, (Jan. 2004).
Teng, et al., "Amyloid and Nonfibrillar Depostis in Mice Transgenic for Wild-Type Human Transtyretin: A Possible Model for Senile Systemic Amyloidosis," Laboratory Investigation, 81(3):385-396, (Mar. 2001).
Terazaki, et al., "Immunization in familial amyloidotic polyneuropathy: counteracting deposition by immunization with a Y78F TTR mutant,", Laboratory Investigation, 86:23-31, (2006).
U.S. Appl. No. 16/145,859, Advisory Action dated Dec. 6, 2021.
U.S. Appl. No. 16/145,859, Final Office Action dated Oct. 1, 2021.
U.S. Appl. No. 16/145,859, Non-Final Office Action dated Apr. 27, 2021.
U.S. Appl. No. 16/145,859, Non-Final Office Action dated Aug. 22, 2022.
U.S. Appl. No. 16/145,859, Requirement for Restriction/Election dated Dec. 15, 2020.
Ueda, et al., "A transgenic rat with the human ATTR V30M: A novel tool for analyses of ATTR metabolisms," Biochemical and Biophysical Research Communications, 352:299-304, (2007).
Ueda, et al., "Recent advances in transthyretin amyloidosis therapy," Translational Neurodegeneration, 3:19, pp. 1-10, (2014).
Valenzuela, et al., "High-throughput engineering of the mouse genome coupled with high-resolution expression analysis," Nature Biotechnology, vol. 21, No. 6, pp. 652-659, (Jun. 2003).
Vasconcelos, et al., "Heterotypic seeding of Tau fibrillization by pre-aggregated Abeta provides potent seeds for prion-like seeding and propagation of Tau-pathology in vivo," Acta Neuropathol, 131(4):549-569, (Apr. 2016).
Vidal, et al., "Meningocerebrovascular Amyloidosis Associated with a Novel Transthyretin Mis-Sense Mutation at Codon 18 (TTRD18G)," American Journal of Pathology, 148(2):361-366, (1996).

(56) References Cited

OTHER PUBLICATIONS

Vranckx, et al., "Immunological quantitation of rat and mouse thyroxime-binding globulins. Ontogenesis and sex-dependence of the circulating levels of the thyroxine-binding globulins," Acta Endocrinologica (Copenh), 123:649-656, (1990).

Wakchaure, et al., "Transgenic Animals: A Review on its Various Dimensions and Applications in Animal Biotechnology," International Journal of Emerging Technology and Advanced Engineering, 5(11):210-213, (2015).

Wang et al., "Mapping a functional cancer genome atlas of tumor suppressors in mouse liver using AAV-CRISPR-mediated direct in vivo screening," Sci. Adv. 4(2):eaao5508, (Feb. 28, 2018).

Wati, et al., "Transthyretin Accelerates Vascular Aβ Deposition in a Mouse Model of Alzheimer's Disease," Brain Pathology, 19(1):48-57, (Jan. 2009) Abstract only.

Wei, et al., "Deposition of transthyretin amyloid is not accelerated by the sam amyloid in vivo," Amyloid, 11(2):113-120, (Jun. 2004).

Westermark, et al., "Prion-like aggregates: infectious agents in human disease," Trends in Molecular Medicine, 16(1):501-507, (Nov. 2010).

White, et al., "Support for the multigenic hypothesis of amyloidosis: The bindng stoichiometry of retinol-binding protein, vitamin A, and thyroid hormone influences transthyretin amyloidogenicity in vitro," PNAS, 98(23):12019-13024, (Nov. 6, 2001).

Wilmut, et al., "Somatic cell nuclear transfer: origins, the present position and future opportunities," Philos. Trans. R. Soc. Lond. B. Biol. Sci. 370(1680):20140366, (2015).

Yamamura, et al., "Expression of tissue-specific genes in transgenic mice," Regulatory Mechanisms in Developmental Processes, eds. G. Eguchi, T.S. Okada, L. Saxén, pp. 47-52, (1998).

Yang, et al., "Initial Conformational Changes of Human Transthyretin under Partially Denaturing Conditions," Biophysical Journal, 89:433-443, (Jul. 2005).

Yi, et al., "Systemic Amyloidosis in Transgenic Mice Carrying the Human Mutant Transthyretin (Met30) Gene," American Journal of Pathology, 138(2):403-412, (1991).

Zeng, et al., "Viral transduction of male germline stem cells results in transgene transmission after germ cell transplantation in pigs," Biol. Reprod. 88(1):27, (2013).

Zhao, et al., "Inconsistency between hepatic expression and serum concentration of transthyretin in mice humanized at the transthyretin locus," Genes to Cells, 13:1257-1268, (2008).

Zhou, et al., "Developing tTA transgenic rats for inducible and reversible gene expression," Int. J. Biol. Sci., 5(2):171-181, (2009).

Zhu et al., "Humanising the mouse genome piece by piece," Nat. Commun. 10(1):1845, (Apr. 23, 2019).

\* cited by examiner

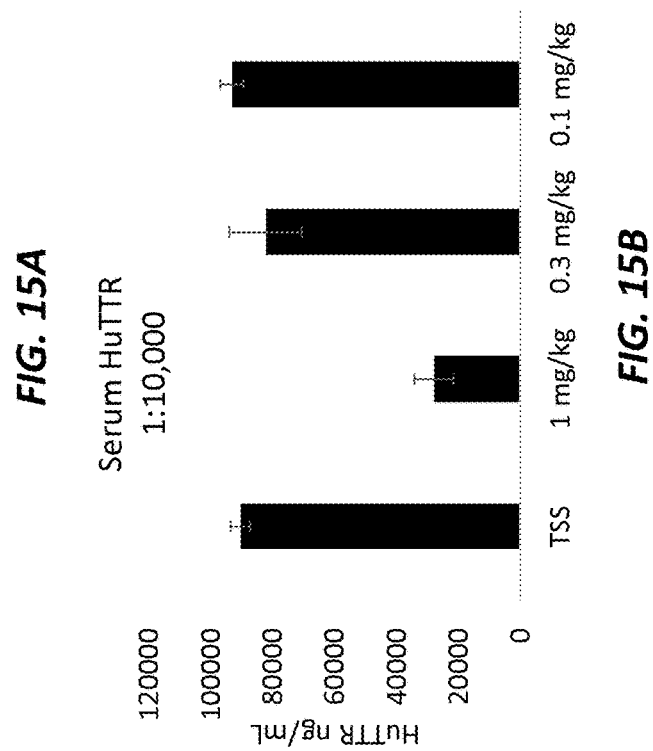
FIG. 15A
FIG. 15B
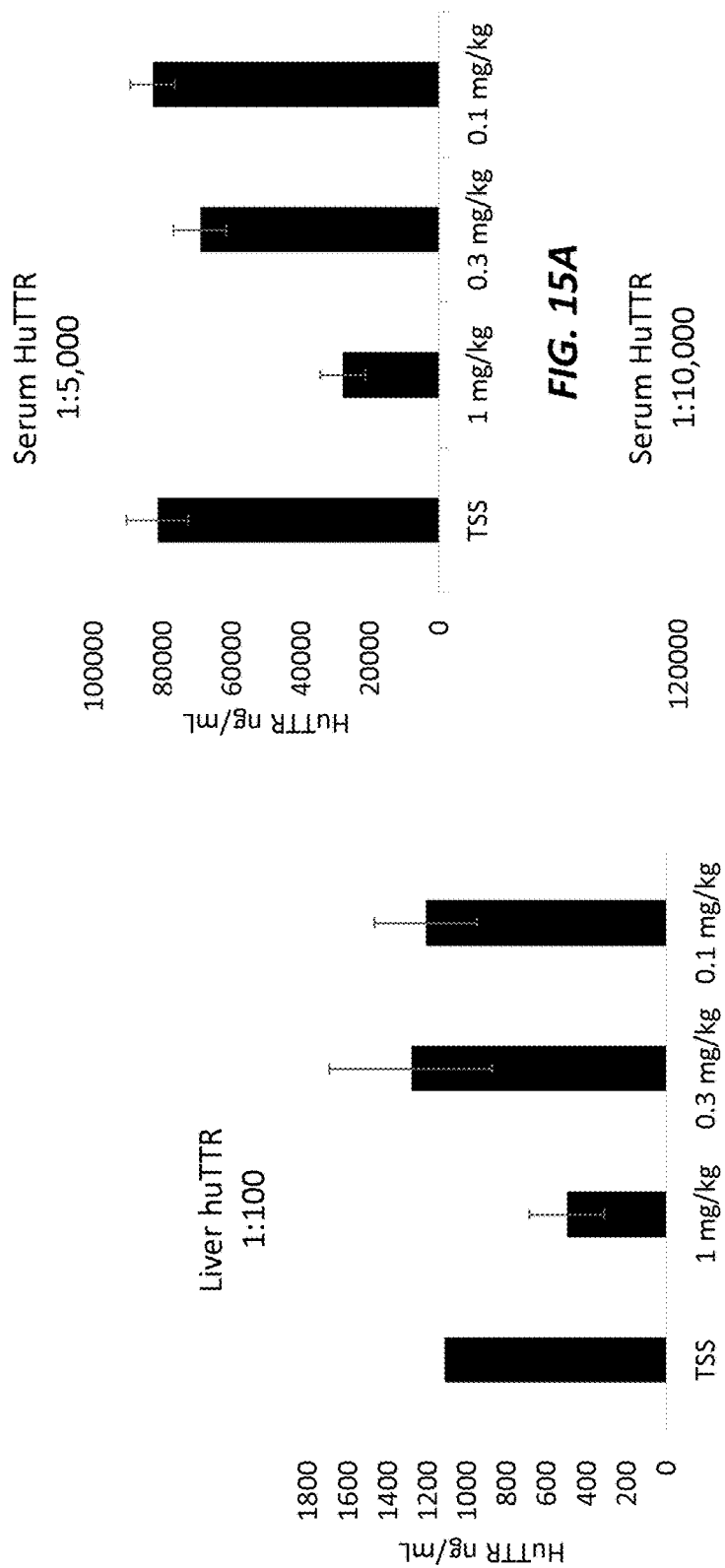
FIG. 14

NON-HUMAN ANIMALS COMPRISING A HUMANIZED TTR LOCUS AND METHODS OF USE

CROSS-REFERENCE TO RELATED APPLICATIONS

This application is a continuation of U.S. application Ser. No. 16/145,859, filed Sep. 28, 2018, which claims the benefit of U.S. Application No. 62/565,980 filed Sep. 29, 2017, U.S. Application No. 62/679,142 filed Jun. 1, 2018, and U.S. Application No. 62/720,292 filed Aug. 21, 2018, each of which is herein incorporated by reference in its entirety for all purposes.

REFERENCE TO A SEQUENCE LISTING SUBMITTED AS A TEXT FILE VIA EFS WEB

The Sequence Listing written in file 587138SEQLIST.xml is 200 kilobytes, was created on Nov. 21, 2022, and is hereby incorporated by reference.

BACKGROUND

Transthyretin (TTR) is a protein found in the serum and cerebrospinal fluid that carries thyroid hormone and retinol-binding protein to retinol. The liver secretes TTR into the blood, while the choroid plexus secretes it into the cerebrospinal fluid. TTR is also produced in the retinal pigmented epithelium and secreted into the vitreous. Misfolded and aggregated TTR accumulates in multiple tissues and organs in the amyloid diseases senile systemic amyloidosis (SSA), familial amyloid polyneuropathy (FAP), and familial amyloid cardiomyopathy (FAC).

One promising therapeutic approach for the TTR amyloidosis diseases is to reduce the TTR load in the patient. However, there remains a need for suitable non-human animals providing the true human target or a close approximation of the true human target of human-TTR-targeting reagents at the endogenous Ttr locus, thereby enabling testing of the efficacy and mode of action of such agents in live animals as well as pharmacokinetic and pharmacodynamics studies in a setting where the humanized protein and humanized gene are the only version of TTR present.

SUMMARY

Non-human animals comprising a humanized TTR locus are provided, as well as methods of using such non-human animals. Non-human animal genomes or cells comprising a humanized TTR locus are also provided.

In one aspect, provided are non-human animal genomes, non-human animal cells, or non-human animals comprising a humanized TTR locus. Such a non-human animal genome, non-human animal cell, or non-human animal can comprise in its genome a genetically modified endogenous Ttr locus comprising a human TTR sequence comprising both TTR coding sequence and non-coding sequence. Some such non-human animal genomes, non-human animal cells, or non-human animals can comprise a genetically modified endogenous Ttr locus, wherein a region of the endogenous Ttr locus comprising both Ttr coding sequence and non-coding sequence has been deleted and replaced with a corresponding human TTR sequence comprising both TTR coding sequence and non-coding sequence. Optionally, the genetically modified endogenous Ttr locus comprises the endogenous Ttr promoter. Optionally, the human TTR sequence is operably linked to the endogenous Ttr promoter. Optionally, at least one intron and at least one exon of the endogenous Ttr locus have been deleted and replaced with the corresponding human TTR sequence.

In some such non-human animal genomes, non-human animal cells, or non-human animals, the entire Ttr coding sequence of the endogenous Ttr locus has been deleted and replaced with the corresponding human TTR sequence. Optionally, the region of the endogenous Ttr locus from the Ttr start codon to the Ttr stop codon has been deleted and replaced with the corresponding human TTR sequence.

In some such non-human animal genomes, non-human animal cells, or non-human animals, the genetically modified endogenous Ttr locus comprises a human TTR 3' untranslated region. In some such non-human animals, the endogenous Ttr 5' untranslated region has not been deleted and replaced with the corresponding human TTR sequence.

In some such non-human animal genomes, non-human animal cells, or non-human animals, the region of the endogenous Ttr locus from the Ttr start codon to the Ttr stop codon has been deleted and replaced with a human TTR sequence comprising the corresponding human TTR sequence and a human TTR 3' untranslated region, and the endogenous Ttr 5' untranslated region has not been deleted and replaced with the corresponding human TTR sequence, and the endogenous Ttr promoter has not been deleted and replaced with the corresponding human TTR sequence. Optionally, the human TTR sequence at the genetically modified endogenous Ttr locus comprises, consists essentially of, or consists of a sequence at least 90%, 95%, 96%, 97%, 98%, 99%, or 100% identical to the sequence set forth in SEQ ID NO: 18. Optionally, the genetically modified endogenous Ttr locus encodes a protein comprising, consisting essentially of, or consisting of a sequence at least 90%, 95%, 96%, 97%, 98%, 99%, or 100% identical to the sequence set forth in SEQ ID NO: 1. Optionally, the genetically modified endogenous Ttr locus comprises a coding sequence comprising, consisting essentially of, or consisting of a sequence at least 90%, 95%, 96%, 97%, 98%, 99%, or 100% identical to the sequence set forth in SEQ ID NO: 90. Optionally, the genetically modified endogenous Ttr locus comprises, consists essentially of, or consists of a sequence at least 90%, 95%, 96%, 97%, 98%, 99%, or 100% identical to the sequence set forth in SEQ ID NO: 14 or 15.

In some such non-human animal genomes, non-human animal cells, or non-human animals, the genetically modified endogenous Ttr locus encodes a transthyretin precursor protein comprising a signal peptide, and the region of the endogenous Ttr locus encoding the signal peptide has not been deleted and replaced with the corresponding human TTR sequence. Optionally, the first exon of the endogenous Ttr locus has not been deleted and replaced with the corresponding human TTR sequence. Optionally, the first exon and first intron of the endogenous Ttr locus have not been deleted and replaced with the corresponding human TTR sequence. Optionally, the region of the endogenous Ttr locus from the start of the second Ttr exon to the Ttr stop codon has been deleted and replaced with the corresponding human TTR sequence. Optionally, the genetically modified endogenous Ttr locus comprises a human TTR 3' untranslated region.

In some such non-human animal genomes, non-human animal cells, or non-human animals, the region of the endogenous Ttr locus from the second Ttr exon to the Ttr stop codon has been deleted and replaced with a human TTR sequence comprising the corresponding human TTR sequence and a human TTR 3' untranslated region, and the endogenous Ttr 5' untranslated region has not been deleted and replaced with the corresponding human TTR sequence, and the endogenous Ttr promoter has not been deleted and replaced with the corresponding human TTR sequence. Optionally, the human TTR sequence at the genetically modified endogenous Ttr locus comprises, consists essentially of, or consists of a sequence at least 90%, 95%, 96%, 97%, 98%, 99%, or 100% identical to the sequence set forth in SEQ ID NO: 19. Optionally, the genetically modified endogenous Ttr locus encodes a protein comprising, consisting essentially of, or consisting of a sequence at least 90%, 95%, 96%, 97%, 98%, 99%, or 100% identical to the sequence set forth in SEQ ID NO: 2. Optionally, the genetically modified endogenous Ttr locus comprises a coding sequence comprising, consisting essentially of, or consisting of a sequence at least 90%, 95%, 96%, 97%, 98%, 99%, or 100% identical to the sequence set forth in SEQ ID NO: 91. Optionally, the genetically modified endogenous Ttr locus comprises, consists essentially of, or consists of a sequence at least 90%, 95%, 96%, 97%, 98%, 99%, or 100% identical to the sequence set forth in SEQ ID NO: 16 or 17.

In some such non-human animal genomes, non-human animal cells, or non-human animals, the genetically modified endogenous Ttr locus does not comprise a selection cassette or a reporter gene. In some such non-human animal genomes, non-human animal cells, or non-human animals, the genetically modified endogenous Ttr locus does comprise a selection cassette or a reporter gene. In some such non-human animal genomes, non-human animal cells, or non-human animals, the non-human animal genome, non-human animal cell, or non-human animal is homozygous for the genetically modified endogenous Ttr locus. In some such non-human animal genomes, non-human animal cells, or non-human animals, the non-human animal genome, non-human animal cell, or non-human animal is heterozygous for the genetically modified endogenous Ttr locus.

In some such non-human animal genomes, non-human animal cells, or non-human animals, the non-human animal is a mammal. Optionally, the mammal is a rodent. Optionally, the rodent is a rat or mouse. Optionally, the non-human animal is a mouse.

In another aspect, provided are methods of using the non-human animals comprising a humanized TTR locus to assess the activity of human-TTR-targeting reagents in vivo. Such methods can comprise: (a) administering the human-TTR-targeting reagent to any of the above non-human animals; and (b) assessing the activity of the human-TTR-targeting reagent in the non-human animal.

In some such methods, the administering comprises adeno-associated virus (AAV)-mediated delivery, lipid nanoparticle (LNP)-mediated delivery, or hydrodynamic delivery (HDD). Optionally, the administering comprises LNP-mediated delivery, and optionally the LNP dose is between about 0.1 mg/kg and about 2 mg/kg. Optionally, the administering comprises AAV8-mediated delivery.

In some such methods, step (b) comprises isolating a liver from the non-human animal and assessing activity of the human-TTR-targeting reagent in the liver. Optionally, step (b) further comprises assessing activity of the human-TTR-targeting reagent in an organ or tissue other than the liver.

In some such methods, the human-TTR-targeting reagent is a genome-editing agent, and the assessing comprises assessing modification of the genetically modified Ttr locus. Optionally, the assessing comprises measuring the frequency of insertions or deletions within the genetically modified Ttr locus. In some such methods, the assessing comprises measuring expression of a Ttr messenger RNA encoded by the genetically modified Ttr locus. In some such methods, the assessing comprises measuring expression of a TTR protein encoded by the genetically modified Ttr locus. Optionally, measuring expression of the TTR protein comprises measuring serum levels of the TTR protein in the non-human animal. Optionally, the activity is assessed in the liver of the non-human animal.

In some such methods, the human-TTR-targeting reagent comprises a nuclease agent designed to target a region of a human TTR gene. Optionally, the nuclease agent comprises a Cas protein and a guide RNA designed to target a guide RNA target sequence in the human TTR gene. Optionally, the Cas protein is a Cas9 protein. Optionally, the human-TTR-targeting reagent further comprises an exogenous donor nucleic acid, wherein the exogenous donor nucleic acid is designed to recombine with the human TTR gene. Optionally, the exogenous donor nucleic acid is a single-stranded oligodeoxynucleotide (ssODN).

In another aspect, provided are methods of optimizing the activity of a human-TTR-targeting reagent in vivo. Such methods can comprise: (I) performing any of the above methods of assessing the activity of human-TTR-targeting reagents in vivo a first time in a first non-human animal comprising in its genome a genetically modified endogenous Ttr locus comprising a human TTR sequence comprising both TTR coding sequence and non-coding sequence; (II) changing a variable and performing the method of step (I) a second time with the changed variable in a second non-human animal comprising in its genome the genetically modified endogenous Ttr locus comprising the human TTR sequence comprising both TTR coding sequence and non-coding sequence; and (III) comparing the activity of the human-TTR-targeting reagent in step (I) with the activity of the human-TTR-targeting reagent in step (II), and selecting the method resulting in the higher activity. Optionally, step (III) can comprise selecting the method resulting in the higher efficacy, higher precision, higher consistency, or higher specificity.

Optionally, the changed variable in step (II) is the delivery method of introducing the human-TTR-targeting reagent into the non-human animal. Optionally, the administering comprises LNP-mediated delivery, and the changed variable in step (II) is the LNP formulation. Optionally, the changed variable in step (II) is the route of administration of introducing the human-TTR-targeting reagent into the non-human animal. Optionally, the changed variable in step (II) is the concentration or amount of the human-TTR-targeting reagent introduced into the non-human animal. Optionally, the changed variable in step (II) is the form of the human-TTR-targeting reagent introduced into the non-human animal. Optionally, the changed variable in step (II) is the human-TTR-targeting reagent introduced into the non-human animal.

In some such methods, the human-TTR-targeting reagent comprises a Cas protein (e.g., a Cas9 protein) and a guide RNA designed to target a guide RNA target sequence in the human TTR gene. Optionally, the changed variable in step (II) is the guide RNA sequence or the guide RNA target sequence. Optionally, the Cas protein and the guide RNA are each administered in the form of RNA, and the changed variable in step (II) is the ratio of Cas mRNA to guide RNA. Optionally, the changed variable in step (II) is guide RNA modifications.

In another aspect, provided are methods of making the non-human animals comprising a humanized TTR locus. Some such methods comprise: (a) introducing into a non-human animal embryonic stem (ES) cell: (i) a nuclease agent that targets a target sequence in the endogenous Ttr locus; and (ii) a targeting vector comprising a nucleic acid insert comprising the human TTR sequence flanked by a 5' homology arm corresponding to a 5' target sequence in the endogenous Ttr locus and a 3' homology arm corresponding to a 3' target sequence in the endogenous Ttr locus, wherein the targeting vector recombines with the endogenous Ttr locus to produce a genetically modified non-human ES cell comprising in its genome the genetically modified endogenous Ttr locus comprising the human TTR sequence; (b) introducing the genetically modified non-human ES cell into a non-human animal host embryo; and (c) gestating the non-human animal host embryo in a surrogate mother, wherein the surrogate mother produces an F0 progeny genetically modified non-human animal comprising in its genome the genetically modified endogenous Ttr locus comprising the human TTR sequence.

In some such methods, the nuclease agent comprises a Cas protein (e.g., a Cas9 protein) and a guide RNA. In some such methods, the targeting vector is a large targeting vector at least 10 kb in length or in which the sum total of the 5' and 3' homology arms is at least 10 kb in length. In some such methods, the non-human animal is a mouse or a rat. In some such methods, the non-human animal is a mouse.

BRIEF DESCRIPTION OF THE FIGURES

FIG. 14 shows results of an ELISA assaying human TTR levels in liver lysates 8 days post-injection of buffer control or lipid nanoparticles containing Cas9 mRNA and human TTR guide RNA 1 designed to target human TTR into F2 generation mice homozygous for the first version of the humanized mouse Ttr locus (MAID 7576; F1 allele from FIG. 3; derived from clone 7576B-F10).

FIGS. 15A and 15B show results of an ELISA assaying human TTR levels in serum samples (1:5000 dilution in FIG. 15A, and 1:10000 dilution in FIG. 15B) 8 days post-injection of buffer control or lipid nanoparticles containing Cas9 mRNA and human TTR guide RNA 1 designed to target human TTR into F2 generation mice homozygous for the first version of the humanized mouse Ttr locus (MAID 7576; F1 allele from FIG. 3; derived from clone 7576B-F10).

DEFINITIONS

Figure 1A:
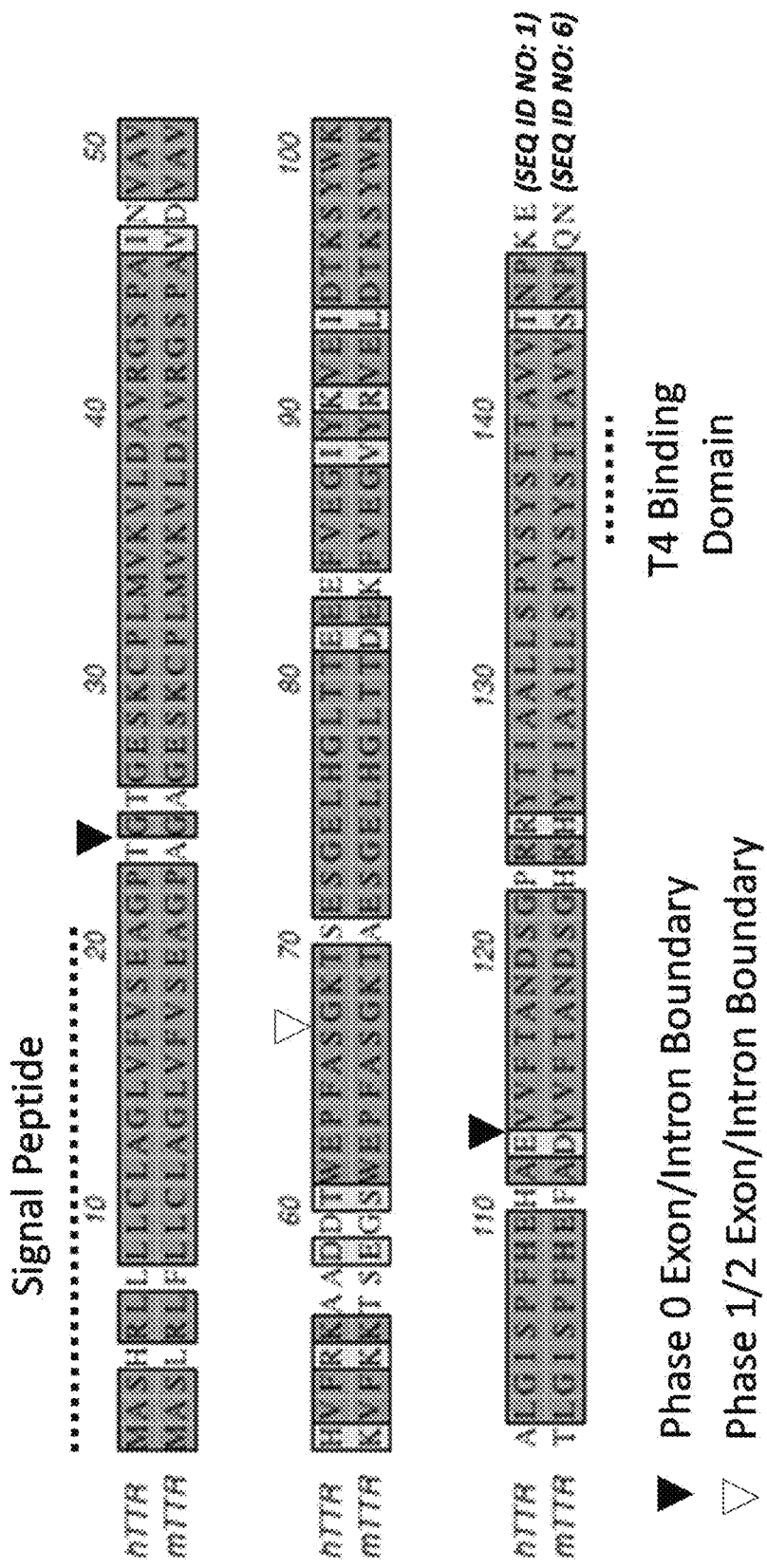
FIG. 1A shows an alignment of human and mouse transthyretin (TTR) precursor proteins (SEQ ID NOS: 1 and 6, respectively). The signal peptide, T4 binding domain, phase 0 exon/intron boundaries, and phase 1/2 exon/intron boundaries are denoted.

The terms "protein," "polypeptide," and "peptide," used interchangeably herein, include polymeric forms of amino acids of any length, including coded and non-coded amino acids and chemically or biochemically modified or derivatized amino acids. The terms also include polymers that have been modified, such as polypeptides having modified peptide backbones. The term "domain" refers to any part of a protein or polypeptide having a particular function or structure.

Proteins are said to have an "N-terminus" and a "C-terminus." The term "N-terminus" relates to the start of a protein or polypeptide, terminated by an amino acid with a free amine group (—NH2). The term "C-terminus" relates to the end of an amino acid chain (protein or polypeptide), terminated by a free carboxyl group (—COOH).

The terms "nucleic acid" and "polynucleotide," used interchangeably herein, include polymeric forms of nucleotides of any length, including ribonucleotides, deoxyribonucleotides, or analogs or modified versions thereof. They include single-, double-, and multi-stranded DNA or RNA, genomic DNA, cDNA, DNA-RNA hybrids, and polymers comprising purine bases, pyrimidine bases, or other natural, chemically modified, biochemically modified, non-natural, or derivatized nucleotide bases.

Nucleic acids are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. An end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. A nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements.

The term "genomically integrated" refers to a nucleic acid that has been introduced into a cell such that the nucleotide sequence integrates into the genome of the cell. Any protocol may be used for the stable incorporation of a nucleic acid into the genome of a cell.

The term "expression vector" or "expression construct" or "expression cassette" refers to a recombinant nucleic acid containing a desired coding sequence operably linked to appropriate nucleic acid sequences necessary for the expression of the operably linked coding sequence in a particular host cell or organism. Nucleic acid sequences necessary for expression in prokaryotes usually include a promoter, an operator (optional), and a ribosome binding site, as well as other sequences. Eukaryotic cells are generally known to utilize promoters, enhancers, and termination and polyadenylation signals, although some elements may be deleted and other elements added without sacrificing the necessary expression.

The term "targeting vector" refers to a recombinant nucleic acid that can be introduced by homologous recombination, non-homologous-end-joining-mediated ligation, or any other means of recombination to a target position in the genome of a cell.

The term "viral vector" refers to a recombinant nucleic acid that includes at least one element of viral origin and includes elements sufficient for or permissive of packaging into a viral vector particle. The vector and/or particle can be utilized for the purpose of transferring DNA, RNA, or other nucleic acids into cells either ex vivo or in vivo. Numerous forms of viral vectors are known.

The term "isolated" with respect to proteins, nucleic acids, and cells includes proteins, nucleic acids, and cells that are relatively purified with respect to other cellular or organism components that may normally be present in situ, up to and including a substantially pure preparation of the protein, nucleic acid, or cell. The term "isolated" also includes proteins and nucleic acids that have no naturally occurring counterpart or proteins or nucleic acids that have been chemically synthesized and are thus substantially uncontaminated by other proteins or nucleic acids. The term "isolated" also includes proteins, nucleic acids, or cells that have been separated or purified from most other cellular components or organism components with which they are naturally accompanied (e.g., other cellular proteins, nucleic acids, or cellular or extracellular components).

The term "wild type" includes entities having a structure and/or activity as found in a normal (as contrasted with mutant, diseased, altered, or so forth) state or context. Wild type genes and polypeptides often exist in multiple different forms (e.g., alleles).

The term "endogenous sequence" refers to a nucleic acid sequence that occurs naturally within a cell or non-human animal. For example, an endogenous Ttr sequence of a non-human animal refers to a native Ttr sequence that naturally occurs at the Ttr locus in the non-human animal.

"Exogenous" molecules or sequences include molecules or sequences that are not normally present in a cell in that form. Normal presence includes presence with respect to the particular developmental stage and environmental conditions of the cell. An exogenous molecule or sequence, for example, can include a mutated version of a corresponding endogenous sequence within the cell, such as a humanized version of the endogenous sequence, or can include a sequence corresponding to an endogenous sequence within the cell but in a different form (i.e., not within a chromosome). In contrast, endogenous molecules or sequences include molecules or sequences that are normally present in that form in a particular cell at a particular developmental stage under particular environmental conditions.

The term "heterologous" when used in the context of a nucleic acid or a protein indicates that the nucleic acid or protein comprises at least two segments that do not naturally occur together in the same molecule. For example, the term "heterologous," when used with reference to segments of a nucleic acid or segments of a protein, indicates that the nucleic acid or protein comprises two or more sub-sequences that are not found in the same relationship to each other (e.g., joined together) in nature. As one example, a "heterologous" region of a nucleic acid vector is a segment of nucleic acid within or attached to another nucleic acid molecule that is not found in association with the other molecule in nature. For example, a heterologous region of a nucleic acid vector could include a coding sequence flanked by sequences not found in association with the coding sequence in nature. Likewise, a "heterologous" region of a protein is a segment of amino acids within or attached to another peptide molecule that is not found in association with the other peptide molecule in nature (e.g., a fusion protein, or a protein with a tag). Similarly, a nucleic acid or protein can comprise a heterologous label or a heterologous secretion or localization sequence.

"Codon optimization" takes advantage of the degeneracy of codons, as exhibited by the multiplicity of three-base pair codon combinations that specify an amino acid, and generally includes a process of modifying a nucleic acid sequence for enhanced expression in particular host cells by replacing at least one codon of the native sequence with a codon that is more frequently or most frequently used in the genes of the host cell while maintaining the native amino acid sequence. For example, a nucleic acid encoding a Cas9 protein can be modified to substitute codons having a higher frequency of usage in a given prokaryotic or eukaryotic cell, including a bacterial cell, a yeast cell, a human cell, a non-human cell, a mammalian cell, a rodent cell, a mouse cell, a rat cell, a hamster cell, or any other host cell, as compared to the naturally occurring nucleic acid sequence. Codon usage tables are readily available, for example, at the "Codon Usage Database." These tables can be adapted in a number of ways. See Nakamura et al. (2000) *Nucleic Acids Research* 28:292, herein incorporated by reference in its entirety for all purposes. Computer algorithms for codon optimization of a particular sequence for expression in a particular host are also available (see, e.g., Gene Forge).

The term "locus" refers to a specific location of a gene (or significant sequence), DNA sequence, polypeptide-encoding sequence, or position on a chromosome of the genome of an organism. For example, a "Ttr locus" may refer to the specific location of a Ttr gene, Ttr DNA sequence, transthyretin-encoding sequence, or Ttr position on a chromosome of the genome of an organism that has been identified as to where such a sequence resides. A "Ttr locus" may comprise a regulatory element of a Ttr gene, including, for example, an enhancer, a promoter, 5' and/or 3' untranslated region (UTR), or a combination thereof.

The term "gene" refers to a DNA sequence in a chromosome that codes for a product (e.g., an RNA product and/or a polypeptide product) and includes the coding region interrupted with non-coding introns and sequence located adjacent to the coding region on both the 5' and 3' ends such that the gene corresponds to the full-length mRNA (including the 5' and 3' untranslated sequences). The term "gene" also includes other non-coding sequences including regulatory sequences (e.g., promoters, enhancers, and transcription factor binding sites), polyadenylation signals, internal ribosome entry sites, silencers, insulating sequence, and matrix attachment regions. These sequences may be close to the coding region of the gene (e.g., within 10 kb) or at distant sites, and they influence the level or rate of transcription and translation of the gene.

The term "allele" refers to a variant form of a gene. Some genes have a variety of different forms, which are located at the same position, or genetic locus, on a chromosome. A diploid organism has two alleles at each genetic locus. Each pair of alleles represents the genotype of a specific genetic locus. Genotypes are described as homozygous if there are two identical alleles at a particular locus and as heterozygous if the two alleles differ.

The "coding region" or "coding sequence" of a gene consists of the portion of a gene's DNA or RNA, composed of exons, that codes for a protein. The region begins at the start codon on the 5' end and ends at the stop codon on the 3' end.

A "promoter" is a regulatory region of DNA usually comprising a TATA box capable of directing RNA polymerase II to initiate RNA synthesis at the appropriate transcription initiation site for a particular polynucleotide sequence. A promoter may additionally comprise other regions which influence the transcription initiation rate. The promoter sequences disclosed herein modulate transcription of an operably linked polynucleotide. A promoter can be active in one or more of the cell types disclosed herein (e.g., a eukaryotic cell, a non-human mammalian cell, a human cell, a rodent cell, a pluripotent cell, a one-cell stage embryo, a differentiated cell, or a combination thereof). A promoter can be, for example, a constitutively active promoter, a conditional promoter, an inducible promoter, a temporally restricted promoter (e.g., a developmentally regulated promoter), or a spatially restricted promoter (e.g., a cell-specific or tissue-specific promoter). Examples of promoters can be found, for example, in WO 2013/176772, herein incorporated by reference in its entirety for all purposes.

"Operable linkage" or being "operably linked" includes juxtaposition of two or more components (e.g., a promoter and another sequence element) such that both components function normally and allow the possibility that at least one of the components can mediate a function that is exerted upon at least one of the other components. For example, a promoter can be operably linked to a coding sequence if the promoter controls the level of transcription of the coding sequence in response to the presence or absence of one or more transcriptional regulatory factors. Operable linkage can include such sequences being contiguous with each other or acting in trans (e.g., a regulatory sequence can act at a distance to control transcription of the coding sequence).

"Complementarity" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

"Hybridization condition" includes the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment. See, e.g., Sambrook et al., Molecular Cloning, A Laboratory Manual, 2.sup.nd ed., pp. 1.90-1.91, 9.47-9.51, 1 1.47-11.57 (Cold Spring Harbor Laboratory Press, Cold Spring Harbor, N.Y., 1989), herein incorporated by reference in its entirety for all purposes.

Hybridization requires that the two nucleic acids contain complementary sequences, although mismatches between bases are possible. The conditions appropriate for hybridization between two nucleic acids depend on the length of the nucleic acids and the degree of complementation, variables which are well known. The greater the degree of complementation between two nucleotide sequences, the greater the value of the melting temperature (Tm) for hybrids of nucleic acids having those sequences. For hybridizations between nucleic acids with short stretches of complementarity (e.g. complementarity over 35 or fewer, 30 or fewer, 25 or fewer, 22 or fewer, 20 or fewer, or 18 or fewer nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid include at least about 15 nucleotides, at least about 20 nucleotides, at least about 22 nucleotides, at least about 25 nucleotides, and at least about 30 nucleotides. Furthermore, the temperature and wash solution salt concentration may be adjusted as necessary according to factors such as length of the region of complementation and the degree of complementation.

The sequence of polynucleotide need not be 100% complementary to that of its target nucleic acid to be specifically hybridizable. Moreover, a polynucleotide may hybridize over one or more segments such that intervening or adjacent segments are not involved in the hybridization event (e.g., a loop structure or hairpin structure). A polynucleotide (e.g., gRNA) can comprise at least 70%, at least 80%, at least 90%, at least 95%, at least 99%, or 100% sequence complementarity to a target region within the target nucleic acid sequence to which they are targeted. For example, a gRNA in which 18 of 20 nucleotides are complementary to a target region, and would therefore specifically hybridize, would represent 90% complementarity. In this example, the remaining noncomplementary nucleotides may be clustered or interspersed with complementary nucleotides and need not be contiguous to each other or to complementary nucleotides.

Percent complementarity between particular stretches of nucleic acid sequences within nucleic acids can be determined routinely using BLAST programs (basic local alignment search tools) and PowerBLAST programs (Altschul et al. (1990) *J. Mol. Biol.* 215:403-410; Zhang and Madden (1997) *Genome Res.* 7:649-656, each of which is herein incorporated by reference in its entirety for all purposes) or by using the Gap program (Wisconsin Sequence Analysis Package, Version 8 for Unix, Genetics Computer Group, University Research Park, Madison Wis.), using default settings, which uses the algorithm of Smith and Waterman (1981) *Adv. Appl. Math.* 2:482-489, herein incorporated by reference in its entirety for all purposes.

The methods and compositions provided herein employ a variety of different components. Some components throughout the description can have active variants and fragments. Such components include, for example, Cas proteins, CRISPR RNAs, tracrRNAs, and guide RNAs. Biological activity for each of these components is described elsewhere herein. The term "functional" refers to the innate ability of a protein or nucleic acid (or a fragment or variant thereof) to exhibit a biological activity or function. Such biological activities or functions can include, for example, the ability of a Cas protein to bind to a guide RNA and to a target DNA sequence. The biological functions of functional fragments or variants may be the same or may in fact be changed (e.g., with respect to their specificity or selectivity or efficacy) in comparison to the original, but with retention of the basic biological function.

The term "variant" refers to a nucleotide sequence differing from the sequence most prevalent in a population (e.g., by one nucleotide) or a protein sequence different from the sequence most prevalent in a population (e.g., by one amino acid).

The term "fragment" when referring to a protein means a protein that is shorter or has fewer amino acids than the full-length protein. The term "fragment" when referring to a nucleic acid means a nucleic acid that is shorter or has fewer nucleotides than the full-length nucleic acid. A fragment can be, for example, an N-terminal fragment (i.e., removal of a portion of the C-terminal end of the protein), a C-terminal fragment (i.e., removal of a portion of the N-terminal end of the protein), or an internal fragment.

"Sequence identity" or "identity" in the context of two polynucleotides or polypeptide sequences makes reference to the residues in the two sequences that are the same when aligned for maximum correspondence over a specified comparison window. When percentage of sequence identity is used in reference to proteins, residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

"Percentage of sequence identity" includes the value determined by comparing two optimally aligned sequences (greatest number of perfectly matched residues) over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity. Unless otherwise specified (e.g., the shorter sequence includes a linked heterologous sequence), the comparison window is the full length of the shorter of the two sequences being compared.

Unless otherwise stated, sequence identity/similarity values include the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof "Equivalent program" includes any sequence comparison program that, for any two sequences in question, generates an alignment having identical nucleotide or amino acid residue matches and an identical percent sequence identity when compared to the corresponding alignment generated by GAP Version 10.

The term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine, or leucine for another non-polar residue. Likewise, examples of conservative substitutions include the substitution of one polar (hydrophilic) residue for another such as between arginine and lysine, between glutamine and asparagine, or between glycine and serine. Additionally, the substitution of a basic residue such as lysine, arginine, or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, or methionine for a polar (hydrophilic) residue such as cysteine, glutamine, glutamic acid or lysine and/or a polar residue for a non-polar residue. Typical amino acid categorizations are summarized in Table 1 below.

TABLE 1

Amino Acid Categorizations.

| | | | | | |
|---|---|---|---|---|---|
| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |

TABLE 1-continued

Amino Acid Categorizations.

| Tyrosine | Tyr | Y | Polar    | Neutral | −1.3 |
| Valine   | Val | V | Nonpolar | Neutral |  4.2 |

A "homologous" sequence (e.g., nucleic acid sequence) includes a sequence that is either identical or substantially similar to a known reference sequence, such that it is, for example, at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to the known reference sequence. Homologous sequences can include, for example, orthologous sequence and paralogous sequences. Homologous genes, for example, typically descend from a common ancestral DNA sequence, either through a speciation event (orthologous genes) or a genetic duplication event (paralogous genes). "Orthologous" genes include genes in different species that evolved from a common ancestral gene by speciation. Orthologs typically retain the same function in the course of evolution. "Paralogous" genes include genes related by duplication within a genome. Paralogs can evolve new functions in the course of evolution.

The term "in vitro" includes artificial environments and to processes or reactions that occur within an artificial environment (e.g., a test tube). The term "in vivo" includes natural environments (e.g., a cell or organism or body) and to processes or reactions that occur within a natural environment. The term "ex vivo" includes cells that have been removed from the body of an individual and to processes or reactions that occur within such cells.

The term "reporter gene" refers to a nucleic acid having a sequence encoding a gene product (typically an enzyme) that is easily and quantifiably assayed when a construct comprising the reporter gene sequence operably linked to an endogenous or heterologous promoter and/or enhancer element is introduced into cells containing (or which can be made to contain) the factors necessary for the activation of the promoter and/or enhancer elements. Examples of reporter genes include, but are not limited to, genes encoding beta-galactosidase (lacZ), the bacterial chloramphenicol acetyltransferase (cat) genes, firefly luciferase genes, genes encoding beta-glucuronidase (GUS), and genes encoding fluorescent proteins. A "reporter protein" refers to a protein encoded by a reporter gene.

The term "fluorescent reporter protein" as used herein means a reporter protein that is detectable based on fluorescence wherein the fluorescence may be either from the reporter protein directly, activity of the reporter protein on a fluorogenic substrate, or a protein with affinity for binding to a fluorescent tagged compound. Examples of fluorescent proteins include green fluorescent proteins (e.g., GFP, GFP-2, tagGFP, turboGFP, eGFP, Emerald, Azami Green, Monomeric Azami Green, CopGFP, AceGFP, and ZsGreen1), yellow fluorescent proteins (e.g., YFP, eYFP, Citrine, Venus, YPet, PhiYFP, and ZsYellow1), blue fluorescent proteins (e.g., BFP, eBFP, eBFP2, Azurite, mKalama1, GFPuv, Sapphire, and T-sapphire), cyan fluorescent proteins (e.g., CFP, eCFP, Cerulean, CyPet, AmCyan1, and Midoriishi-Cyan), red fluorescent proteins (e.g., RFP, mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, and Jred), orange fluorescent proteins (e.g., mOrange, mKO, Kusabira-Orange, Monomeric Kusabira-Orange, mTangerine, and tdTomato), and any other suitable fluorescent protein whose presence in cells can be detected by flow cytometry methods.

Repair in response to double-strand breaks (DSBs) occurs principally through two conserved DNA repair pathways: homologous recombination (HR) and non-homologous end joining (NHEJ). See Kasparek & Humphrey (2011) Seminars in Cell & Dev. Biol. 22:886-897, herein incorporated by reference in its entirety for all purposes. Likewise, repair of a target nucleic acid mediated by an exogenous donor nucleic acid can include any process of exchange of genetic information between the two polynucleotides.

The term "recombination" includes any process of exchange of genetic information between two polynucleotides and can occur by any mechanism. Recombination can occur via homology directed repair (HDR) or homologous recombination (HR). HDR or HR includes a form of nucleic acid repair that can require nucleotide sequence homology, uses a "donor" molecule as a template for repair of a "target" molecule (i.e., the one that experienced the double-strand break), and leads to transfer of genetic information from the donor to target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. In some cases, the donor polynucleotide, a portion of the donor polynucleotide, a copy of the donor polynucleotide, or a portion of a copy of the donor polynucleotide integrates into the target DNA. See Wang et al. (2013) Cell 153:910-918; Mandalos et al. (2012) PLOS ONE 7: e45768:1-9; and Wang et al. (2013) Nat Biotechnol. 31:530-532, each of which is herein incorporated by reference in its entirety for all purposes.

NHEJ includes the repair of double-strand breaks in a nucleic acid by direct ligation of the break ends to one another or to an exogenous sequence without the need for a homologous template. Ligation of non-contiguous sequences by NHEJ can often result in deletions, insertions, or translocations near the site of the double-strand break. For example, NHEJ can also result in the targeted integration of an exogenous donor nucleic acid through direct ligation of the break ends with the ends of the exogenous donor nucleic acid (i.e., NHEJ-based capture). Such NHEJ-mediated targeted integration can be preferred for insertion of an exogenous donor nucleic acid when homology directed repair (HDR) pathways are not readily usable (e.g., in non-dividing cells, primary cells, and cells which perform homology-based DNA repair poorly). In addition, in contrast to homology-directed repair, knowledge concerning large regions of sequence identity flanking the cleavage site is not needed, which can be beneficial when attempting targeted insertion into organisms that have genomes for which there is limited knowledge of the genomic sequence. The integration can proceed via ligation of blunt ends between the exogenous donor nucleic acid and the cleaved genomic sequence, or via ligation of sticky ends (i.e., having 5' or 3' overhangs) using an exogenous donor nucleic acid that is flanked by overhangs that are compatible with those generated by a nuclease agent in the cleaved genomic sequence. See, e.g., US 2011/020722, WO 2014/033644, WO 2014/089290, and Maresca et al. (2013) Genome Res. 23(3):539-546, each of which is herein incorporated by reference in its entirety for all purposes. If blunt ends are ligated, target and/or donor resection may be needed to generation regions of microhomology needed for fragment joining, which may create unwanted alterations in the target sequence.

The term "antigen-binding protein" includes any protein that binds to an antigen. Examples of antigen-binding proteins include an antibody, an antigen-binding fragment of an antibody, a multispecific antibody (e.g., a bi-specific antibody), an scFV, a bis-scFV, a diabody, a triabody, a tetrabody, a V-NAR, a VHH, a VL, a F(ab), a F(ab)$_2$, a DVD (dual variable domain antigen-binding protein), an SVD (single variable domain antigen-binding protein), a bispecific T-cell engager (BiTE), or a Davisbody (U.S. Pat. No. 8,586,713, herein incorporated by reference herein in its entirety for all purposes).

The term "antigen" refers to a substance, whether an entire molecule or a domain within a molecule, which is capable of eliciting production of antibodies with binding specificity to that substance. The term antigen also includes substances, which in wild type host organisms would not elicit antibody production by virtue of self-recognition, but can elicit such a response in a host animal with appropriate genetic engineering to break immunological tolerance.

The term "epitope" refers to a site on an antigen to which an antigen-binding protein (e.g., antibody) binds. An epitope can be formed from contiguous amino acids or noncontiguous amino acids juxtaposed by tertiary folding of one or more proteins. Epitopes formed from contiguous amino acids (also known as linear epitopes) are typically retained on exposure to denaturing solvents whereas epitopes formed by tertiary folding (also known as conformational epitopes) are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996), herein incorporated by reference in its entirety for all purposes.

An antibody paratope as described herein generally comprises at a minimum a complementarity determining region (CDR) that specifically recognizes the heterologous epitope (e.g., a CDR3 region of a heavy and/or light chain variable domain).

The term "antibody" includes immunoglobulin molecules comprising four polypeptide chains, two heavy (H) chains and two light (L) chains inter-connected by disulfide bonds. Each heavy chain comprises a heavy chain variable domain and a heavy chain constant region ($C_H$). The heavy chain constant region comprises three domains: $C_H1$, $C_H2$ and $C_H3$. Each light chain comprises a light chain variable domain and a light chain constant region (CO. The heavy chain and light chain variable domains can be further subdivided into regions of hypervariability, termed complementarity determining regions (CDR), interspersed with regions that are more conserved, termed framework regions (FR). Each heavy and light chain variable domain comprises three CDRs and four FRs, arranged from amino-terminus to carboxy-terminus in the following order: FR1, CDR1, FR2, CDR2, FR3, CDR3, FR4 (heavy chain CDRs may be abbreviated as HCDR1, HCDR2 and HCDR3; light chain CDRs may be abbreviated as LCDR1, LCDR2 and LCDR3). The term "high affinity" antibody refers to an antibody that has a $K_D$ with respect to its target epitope about of $10^{-9}$ M or lower (e.g., about $1\times10^{-9}$M, $1\times10^{-10}$ M, $1\times10^{-11}$ M, or about $1\times10^{-12}$M). In one embodiment, $K_D$ is measured by surface plasmon resonance, e.g., BIACORE™; in another embodiment, $K_D$ is measured by ELISA.

Specific binding of an antigen-binding protein to its target antigen includes binding with an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas non-specific binding is usually the result of van der Waals forces. Specific binding does not however necessarily imply that an antigen-binding protein binds one and only one target.

The term "antisense RNA" refers to a single-stranded RNA that is complementary to a messenger RNA strand transcribed in a cell.

The term "small interfering RNA (siRNA)" refers to a typically double-stranded RNA molecule that induces the RNA interference (RNAi) pathway. These molecules can vary in length (generally between 18-30 base pairs) and contain varying degrees of complementarity to their target mRNA in the antisense strand. Some, but not all, siRNAs have unpaired overhanging bases on the 5' or 3' end of the sense strand and/or the antisense strand. The term "siRNA" includes duplexes of two separate strands, as well as single strands that can form hairpin structures comprising a duplex region. The double-stranded structure can be, for example, less than 20, 25, 30, 35, 40, 45, or 50 nucleotides in length. For example, the double-stranded structure can be from about 21-23 nucleotides in length, from about 19-25 nucleotides in length, or from about 19-23 nucleotides in length.

The term "short hairpin RNA (shRNA)" refers to a single strand of RNA bases that self-hybridizes in a hairpin structure and can induce the RNA interference (RNAi) pathway upon processing. These molecules can vary in length (generally about 50-90 nucleotides in length, or in some cases up to greater than 250 nucleotides in length, e.g., for microRNA-adapted shRNA). shRNA molecules are processed within the cell to form siRNAs, which in turn can knock down gene expression. shRNAs can be incorporated into vectors. The term "shRNA" also refers to a DNA molecule from which a short, hairpin RNA molecule may be transcribed.

Compositions or methods "comprising" or "including" one or more recited elements may include other elements not specifically recited. For example, a composition that "comprises" or "includes" a protein may contain the protein alone or in combination with other ingredients. The transitional phrase "consisting essentially of" means that the scope of a claim is to be interpreted to encompass the specified elements recited in the claim and those that do not materially affect the basic and novel characteristic(s) of the claimed invention. Thus, the term "consisting essentially of" when used in a claim of this invention is not intended to be interpreted to be equivalent to "comprising."

"Optional" or "optionally" means that the subsequently described event or circumstance may or may not occur and that the description includes instances in which the event or circumstance occurs and instances in which it does not.

Designation of a range of values includes all integers within or defining the range, and all subranges defined by integers within the range.

Unless otherwise apparent from the context, the term "about" encompasses values within a standard margin of error of measurement (e.g., SEM) of a stated value.

The term "and/or" refers to and encompasses any and all possible combinations of one or more of the associated listed items, as well as the lack of combinations when interpreted in the alternative ("or").

The term "or" refers to any one member of a particular list and also includes any combination of members of that list.

The singular forms of the articles "a," "an," and "the" include plural references unless the context clearly dictates otherwise. For example, the term "a protein" or "at least one protein" can include a plurality of proteins, including mixtures thereof.

Statistically significant means p<0.05.

DETAILED DESCRIPTION

I. Overview

Disclosed herein are non-human animal genomes, non-human animal cells, and non-human animals comprising in their genome a humanized TTR locus and methods of using such non-human animal cells and non-human animals. Non-human animal cells or non-human animals comprising a humanized TTR locus express a human transthyretin protein or a chimeric transthyretin protein comprising one or more fragments of a human transthyretin protein. Such non-human animal cells and non-human animals can be used to assess delivery or efficacy of human-TTR-targeting agents (e.g., CRISPR/Cas9 genome editing agents) ex vivo or in vivo and can be used in methods of optimizing the delivery of efficacy of such agents ex vivo or in vivo.

In some of the non-human animal cells and non-human animals disclosed herein, most or all of the human TTR genomic DNA is inserted into the corresponding orthologous non-human animal Ttr locus. In some of the non-human animal cells and non-human animals disclosed herein, most or all of the non-human animal Ttr genomic DNA is replaced one-for-one with corresponding orthologous human TTR genomic DNA. Compared to non-human animals with cDNA insertions, expression levels should be higher when the intron-exon structure and splicing machinery are maintained because conserved regulator elements are more likely to be left intact, and spliced transcripts that undergo RNA processing are more stable than cDNAs. In contrast, insertion of human TTR cDNA (e.g., along with insertion of an artificial beta-globin intron in the 5' UTR) into a non-human animal Ttr locus would abolish conserved regulatory elements such as those contained within the first exon and intron of the non-human animal Ttr. Replacing the non-human animal genomic sequence with the corresponding orthologous human genomic sequence or inserting human TTR genomic sequence in the corresponding orthologous non-human Ttr locus is more likely to result in faithful expression of the transgene from the endogenous Ttr locus. Similarly, transgenic non-human animals with transgenic insertion of human-TTR-coding sequences at a random genomic locus rather than the endogenous non-human-animal Ttr locus will not as accurately reflect the endogenous regulation of Ttr expression. A humanized TTR allele resulting from replacing most or all of the non-human animal genomic DNA one-for-one with corresponding orthologous human genomic DNA or inserting human TTR genomic sequence in the corresponding orthologous non-human Ttr locus will provide the true human target or a close approximation of the true human target of human-TTR-targeting reagents (e.g., CRISPR/Cas9 reagents designed to target human TTR), thereby enabling testing of the efficacy and mode of action of such agents in live animals as well as pharmacokinetic and pharmacodynamics studies in a setting where the humanized protein and humanized gene are the only version of TTR present.

II. Non-Human Animals Comprising a Humanized TTR Locus

The cells and non-human animals disclosed herein comprise in their genome a humanized TTR locus. Cells or non-human animals comprising a humanized TTR locus express a human transthyretin protein or a partially humanized, chimeric transthyretin protein in which one or more fragments of the native transthyretin protein have been replaced with corresponding fragments from human transthyretin.

A. Transthyretin (TTR)

The cells and non-human animals described herein comprise a humanized transthyretin (Ttr) locus. Transthyretin (TTR) is a 127-amino acid, 55 kDa serum and cerebrospinal fluid transport protein primarily synthesized by the liver but also produced by the choroid plexus. It has also been referred to as prealbumin, thyroxine binding prealbumin, ATTR, TBPA, CTS, CTS1, HEL111, HsT2651, and PALB. In its native state, TTR exists as a tetramer. In homozygotes, homo-tetramers comprise identical 127-amino-acid beta-sheet-rich subunits. In heterozygotes, TTR tetramers can be made up of variant and/or wild-type subunits, typically combined in a statistical fashion. TTR is responsible for carrying thyroxine (T4) and retinol-bound RBP (retinol-binding protein) in both the serum and the cerebrospinal fluid.

Unless otherwise apparent from context, reference to human transthyretin (TTR) or its fragments or domains includes the natural, wild type human amino acid sequences including isoforms and allelic variants thereof. Transthyretin precursor protein includes a signal sequence (typically 20 amino acids), whereas the mature transthyretin protein does not. Exemplary TTR polypeptide sequences are designated by Accession Numbers NP_000362.1 (NCBI) and P02766.1 (UniProt) (identical, each set forth SEQ ID NO: 1). Residues may be numbered according to UniProt Accession Number P02766.1, with the first amino acid of the mature protein (i.e., not including the 20 amino acid signal sequence) designated residue 1. In any other TTR protein, residues are numbered according to the corresponding residues in UniProt Accession Number P02766.1 on maximum alignment.

The human TTR gene is located on chromosome 18 and includes four exons and three introns. An exemplary human TTR gene is from residues 5001-12258 in the sequence designated by GenBank Accession Number NG_009490.1 (SEQ ID NO: 3). The four exons in SEQ ID NO: 3 include residues 1-205, 1130-1260, 3354-3489, and 6802-7258, respectively. The TTR coding sequence in SEQ ID NO: 3 includes residues 137-205, 1130-1260, 3354-3489, and 6802-6909. An exemplary human TTR mRNA is designated by NCBI Accession Number NM_000371.3 (SEQ ID NO: 4).

The mouse Ttr gene is located and chromosome 18 and also includes four exons and three introns. An exemplary mouse Ttr gene is from residues 20665250 to 20674326 the sequence designated by GenBank Accession Number NC_000084.6 (SEQ ID NO: 5). The four exons in SEQ ID NO: 5 include residues 1-258, 1207-1337, 4730-4865, and 8382-9077, respectively. The Ttr coding sequence in SEQ ID NO: 5 includes residues 190-258, 1207-1337, 4730-4865, and 8382-8489. An exemplary mouse TTR protein is designated by UniProt Accession Number P07309.1 or NCBI Accession Number NP_038725.1 (identical, each set forth SEQ ID NO: 6). An exemplary mouse Ttr mRNA is designated by NCBI Accession Number NM_013697.5 (SEQ ID NO: 7).

An exemplary rat TTR protein is designated by UniProt Accession Number P02767. An exemplary pig TTR protein is designated by UniProt Accession Number P50390. An exemplary chicken TTR protein is designated by UniProt Accession Number P27731. An exemplary cow TTR protein is designated by UniProt Accession Number 046375. An exemplary sheep TTR protein is designated by UniProt Accession Number P12303. An exemplary chimpanzee TTR protein designated by UniProt Accession Number Q5U715. An exemplary orangutan TTR protein is designated by UniProt Accession Number Q5NVS2. An exemplary rabbit TTR protein is designated by UniProt Accession Number P07489. An exemplary cynomolgus monkey (macaque) TTR protein is designated by UniProt Accession Number Q8HXW1.

Transthyretin (TTR) amyloidosis is a systemic disorder characterized by pathogenic, misfolded TTR and the extracellular deposition of amyloid fibrils composed of TTR. TTR amyloidosis is generally caused by destabilization of the native TTR tetramer form (due to environmental or genetic conditions), leading to dissociation, misfolding, and aggregation of TTR into amyloid fibrils that accumulate in various organs and tissues, causing progressive dysfunction. The dissociated monomers have a propensity to form misfolded protein aggregates and amyloid fibrils.

In humans, both wild-type TTR tetramers and mixed tetramers made up of mutant and wild-type subunits can dissociate, misfold, and aggregate, with the process of amyloidogenesis leading to the degeneration of post-mitotic tissue. Thus, TTR amyloidoses encompass diseases caused by pathogenic misfolded TTR resulting from mutations in TTR or resulting from non-mutated, misfolded TTR.

Senile systemic amyloidosis (SSA) and senile cardiac amyloidosis (SCA) are age-related types of amyloidosis that result from the deposition of wild-type TTR amyloid outside and within the cardiomyocytes of the heart. TTR amyloidosis is also the most common form of hereditary (familial) amyloidosis, which is caused by mutations that destabilize the TTR protein. TTR amyloidoses associated with point mutations in the TTR gene include familial amyloid polyneuropathy (FAP), familial amyloid cardiomyopathy (FAC), and central nervous system selective amyloidosis (CNSA).

B. Humanized TTR Loci

A humanized TTR locus disclosed herein can be a Ttr locus in which the entire Ttr gene is replaced with the corresponding orthologous human TTR sequence, or it can be a Ttr locus in which only a portion of the Ttr gene is replaced with the corresponding orthologous human TTR sequence (i.e., humanized). A humanized TTR locus can also comprise human TTR sequence inserted into an endogenous Ttr locus without replacing the corresponding orthologous endogenous sequence. A human TTR sequence corresponding to a particular segment of endogenous Ttr sequence refers to the region of human TTR that aligns with the particular segment of endogenous Ttr sequence when human TTR and the endogenous Ttr are optimally aligned. Optionally, the human TTR sequence is modified to be codon-optimized based on codon usage in the non-human animal. Replaced or inserted (i.e., humanized) regions can include coding regions such as an exon, non-coding regions such as an intron, untranslated regions, or regulatory regions (e.g., a promoter, an enhancer, or a transcriptional repressor-binding element), or any combination thereof.

A humanized TTR locus is one in which a region of the endogenous Ttr locus has been deleted and replaced with a corresponding orthologous human TTR sequence (e.g., orthologous wild type human TTR sequence). Alternatively, a humanized TTR locus is one in which a region of the human TTR locus has been inserted into a corresponding endogenous non-human-animal Ttr locus. As one example, the replaced or inserted region of the endogenous Ttr locus can comprise both a coding sequence (i.e., all or part of an exon) and a non-coding sequence (i.e., all or part of intron), such as at least one exon and at least one intron. For example, the replaced or inserted region can comprise at least one exon and at least one intron. The replaced or inserted region comprising both coding sequence and non-coding sequence can be a contiguous region of the endogenous Ttr locus, meaning there is no intervening sequence between the replaced or inserted coding sequence and the replaced or inserted non-coding sequence. For example, the replaced or inserted region can comprise at least one exon and at least one adjacent intron. The replaced or inserted region can comprise one exon, two exons, three exons, four exons, or all exons of the endogenous Ttr locus. The inserted human TTR sequence can comprise one exon, two exons, three exons, four exons, or all exons of a human TTR gene. Likewise, the replaced region can comprise one intron, two introns, three introns, or all introns of the endogenous Ttr locus. The inserted human TTR sequence can comprise one intron, two introns, three introns, or all introns of a human TTR gene. Optionally, one or more introns and/or one or more exons of the endogenous Ttr locus remain unmodified (i.e., not deleted and replaced). For example, the first exon of the endogenous Ttr locus can remain unmodified. Similarly, the first exon and the first intron of the endogenous Ttr locus can remain unmodified.

In one specific example, the entire coding sequence for the transthyretin precursor protein can be deleted and replaced with the corresponding orthologous human TTR sequence. For example, the region of the endogenous Ttr locus beginning at the start codon and ending at the stop codon can be deleted and replaced with the corresponding orthologous human TTR sequence. In another specific example, the entire coding sequence for the human transthyretin precursor protein can be inserted. For example, the region of the human TTR locus beginning at the start codon and ending at the stop codon can be inserted.

Flanking untranslated regions including regulatory sequences can also be humanized. The first exon of a Ttr locus typically include a 5' untranslated region upstream of the start codon. Likewise, the last exon of a Ttr locus typically includes a 3' untranslated region downstream of the stop codon. Regions upstream of the Ttr start codon and downstream of the Ttr stop codon can either be unmodified or can be deleted and replaced with the corresponding orthologous human TTR sequence. For example, the 5' untranslated region (UTR), the 3'UTR, or both the 5' UTR and the 3' UTR can be humanized, or the 5' UTR, the 3'UTR, or both the 5' UTR and the 3' UTR can remain endogenous. In one specific example, the 5' UTR remains endogenous. In another specific example, the 3' UTR is humanized, but the 5' UTR remains endogenous. In another specific example, the 5' UTR remains endogenous, and a human TTR 3' UTR is inserted into the endogenous Ttr locus. For example, the human TTR 3' UTR can replace the endogenous 3' UTR or can be inserted without replacing the endogenous 3' UTR (e.g., it can be inserted upstream of the endogenous 3' UTR).

One or more regions of the endogenous Ttr locus encoding one or more domains of the transthyretin precursor protein can be humanized. Likewise, one or more regions of the endogenous Ttr locus encoding one or more domains of the transthyretin precursor protein can remain unmodified (i.e., not deleted and replaced). For example, transthyretin precursor proteins typically have a signal peptide at the N-terminus. The signal peptide can be, for example, about 20 amino acids in length. The region of the endogenous Ttr locus encoding the signal peptide can remain unmodified (i.e., not deleted and replaced), or can be deleted and replaced with the corresponding orthologous human TTR sequence. Similarly, a region of the endogenous Ttr locus encoding an epitope recognized by an anti-human-TTR antigen-binding protein can be humanized.

Depending on the extent of replacement by corresponding orthologous sequences or the extent of insertion of human TTR sequences, regulatory sequences, such as a promoter, can be endogenous or supplied by the replacing or inserted human orthologous sequence. For example, the humanized TTR locus can include the endogenous non-human animal Ttr promoter. The coding sequence for the transthyretin precursor protein at the genetically modified endogenous Ttr locus can be operably linked to the endogenous Ttr promoter. For example, the human TTR sequence can be operably linked to the endogenous Ttr promoter.

As a specific example, the humanized TTR locus can be one in which the region of the endogenous Ttr locus being deleted and replaced with the corresponding orthologous human TTR sequence or the region of the human TTR locus being inserted comprises, consists essentially of, or consists of the region from the Ttr start codon to the stop codon. The human TTR sequence being inserted can further comprise a human TTR 3' UTR. For example, the human TTR sequence at the humanized TTR locus can comprise, consist essentially of, or consist of the region from the TTR start codon to the end of the 3' UTR. Optionally, the Ttr coding sequence in the modified endogenous Ttr locus is operably linked to the endogenous Ttr promoter. The human TTR sequence at the humanized TTR locus can comprise, consist essentially of, or consist of a sequence that is at least 85%, 90%, 95%, 96%, 97%, 98%, 99%, or 100% identical to SEQ ID NO: 18. The humanized TTR locus can comprise, consist essentially of, or consist of a sequence that is at least 85%, 90%, 95%, 96%, 97%, 98%, 99%, or 100% identical to SEQ ID NO: 14 or 15. The coding sequence (CDS) at the humanized TTR locus can comprise, consist essentially of, or consist of a sequence that is at least 85%, 90%, 95%, 96%, 97%, 98%, 99%, or 100% identical to SEQ ID NO: 90 (or degenerates thereof that encode the same protein). The resulting human transthyretin precursor protein encoded by the humanized TTR locus can comprise, consist essentially of, or consist of a sequence that is at least 85%, 90%, 95%, 96%, 97%, 98%, 99%, or 100% identical to SEQ ID NO: 1.

As another specific example, the humanized TTR locus can be one in which the region of the endogenous Ttr locus being deleted and replaced with the corresponding orthologous human TTR sequence or the region of the human TTR locus being inserted comprises, consists essentially of, or consists of the region from the start of the second Ttr exon to the stop codon. The human TTR sequence being inserted can further comprise a human TTR 3' UTR. For example, the human TTR sequence at the humanized TTR locus can comprise, consist essentially of, or consist of the region from the start of the second human TTR exon to the end of the 3' UTR. Optionally, the Ttr coding sequence in the modified endogenous Ttr locus is operably linked to the endogenous Ttr promoter. The human TTR sequence at the humanized TTR locus can comprise, consist essentially of, or consist of a sequence that is at least 85%, 90%, 95%, 96%, 97%, 98%, 99%, or 100% identical to SEQ ID NO: 19. The humanized TTR locus can comprise, consist essentially of, or consist of a sequence that is at least 85%, 90%, 95%, 96%, 97%, 98%, 99%, or 100% identical to SEQ ID NO: 16 or 17. The coding sequence (CDS) at the humanized TTR locus can comprise, consist essentially of, or consist of a sequence that is at least 85%, 90%, 95%, 96%, 97%, 98%, 99%, or 100% identical to SEQ ID NO: 91 (or degenerates thereof that encode the same protein). The resulting chimeric transthyretin precursor protein encoded by the humanized TTR locus can comprise, consist essentially of, or consist of a sequence that is at least 85%, 90%, 95%, 96%, 97%, 98%, 99%, or 100% identical to SEQ ID NO: 2.

TTR protein expressed from a humanized TTR locus can be an entirely human TTR protein or a chimeric endogenous/human TTR protein (e.g., if the non-human animal is a mouse, a chimeric mouse/human TTR protein). For example, the signal peptide of the transthyretin precursor protein can be endogenous, and the remainder of the protein can be human. Alternatively, the N-terminus of the transthyretin precursor protein can be endogenous, and the remainder of the protein can be human. For example, the N-terminal 5, 6, 7, 8, 9, 10, 11, 12, 13, 14, 15, 16, 17, 18, 19, 20, 21, 22, 23, 24, or 25 amino acids can be endogenous, and the remainder can be human. In a specific example, the 23 amino acids at the N-terminus are endogenous, and the remainder of the protein is human.

Optionally, a humanized TTR locus can comprise other elements. Examples of such elements can include selection cassettes, reporter genes, recombinase recognition sites, or other elements. As one example, a humanized TTR locus can comprise a removable selection cassette (e.g., a self-deleting selection cassette) flanked by recombinase recognition sequences (e.g., loxP sites). Alternatively, the humanized TTR locus can lack other elements (e.g., can lack a selection cassette and/or can lack a reporter gene). Examples of suitable reporter genes and reporter proteins are disclosed elsewhere herein. Examples of suitable selection markers include neomycin phosphotransferase (neon), hygromycin B phosphotransferase ($hyg_r$), puromycin-N-acetyltransferase ($puro_r$), blasticidin S deaminase ($bsr_r$), xanthine/guanine phosphoribosyl transferase (gpt), and herpes simplex virus thymidine kinase (HSV-k). Examples of recombinases include Cre, Flp, and Dre recombinases. One example of a Cre recombinase gene is Crei, in which two exons encoding the Cre recombinase are separated by an intron to prevent its expression in a prokaryotic cell. Such recombinases can further comprise a nuclear localization signal to facilitate localization to the nucleus (e.g., NLS-Crei). Recombinase recognition sites include nucleotide sequences that are recognized by a site-specific recombinase and can serve as a substrate for a recombination event. Examples of recombinase recognition sites include FRT, FRT11, FRT71, attp, att, rox, and lox sites such as loxP, lox511, lox2272, lox66, lox71, loxM2, and lox5171.

Other elements such as reporter genes or selection cassettes can be self-deleting cassettes flanked by recombinase recognition sites. See, e.g., U.S. Pat. No. 8,697,851 and US 2013/0312129, each of which is herein incorporated by reference in its entirety for all purposes. As an example, the self-deleting cassette can comprise a Crei gene (comprises two exons encoding a Cre recombinase, which are separated by an intron) operably linked to a mouse Prm1 promoter and a neomycin resistance gene operably linked to a human ubiquitin promoter. By employing the Prm1 promoter, the self-deleting cassette can be deleted specifically in male germ cells of F0 animals. The polynucleotide encoding the selection marker can be operably linked to a promoter active in a cell being targeted. Examples of promoters are described elsewhere herein. As another specific example, a self-deleting selection cassette can comprise a hygromycin resistance gene coding sequence operably linked to one or more promoters (e.g., both human ubiquitin and EM7 promoters) followed by a polyadenylation signal, followed by a Crei coding sequence operably linked to one or more promoters (e.g., an mPrm1 promoter), followed by another polyadenylation signal, wherein the entire cassette is flanked by loxP sites.

The humanized TTR locus can also be a conditional allele. For example, the conditional allele can be a multifunctional allele, as described in US 2011/0104799, herein incorporated by reference in its entirety for all purposes. For example, the conditional allele can comprise: (a) an actuating sequence in sense orientation with respect to transcription of a target gene; (b) a drug selection cassette (DSC) in sense or antisense orientation; (c) a nucleotide sequence of interest (NSI) in antisense orientation; and (d) a conditional by inversion module (COIN, which utilizes an exon-splitting intron and an invertible gene-trap-like module) in reverse orientation. See, e.g., US 2011/0104799. The conditional allele can further comprise recombinable units that recombine upon exposure to a first recombinase to form a conditional allele that (i) lacks the actuating sequence and the DSC; and (ii) contains the NSI in sense orientation and the COIN in antisense orientation. See, e.g., US 2011/0104799.

C. Non-Human Animal Genomes, Non-Human Animal Cells, and Non-Human Animals Comprising a Humanized TTR Locus Non-human animal genomes, non-human animal cells, and non-human animals comprising a humanized TTR locus as described elsewhere herein are provided. The genomes, cells, or non-human animals can be heterozygous or homozygous for the humanized TTR locus. A diploid organism has two alleles at each genetic locus. Each pair of alleles represents the genotype of a specific genetic locus. Genotypes are described as homozygous if there are two identical alleles at a particular locus and as heterozygous if the two alleles differ.

The non-human animal genomes or cells provided herein can be, for example, any non-human cell comprising a Ttr locus or a genomic locus homologous or orthologous to the human TTR locus. The genomes can be from or the cells can be eukaryotic cells, which include, for example, animal cells, mammalian cells, non-human mammalian cells, and human cells. The term "animal" includes mammals, fishes, and birds. A mammalian cell can be, for example, a non-human mammalian cell, a rodent cell, a rat cell, a mouse cell, or a hamster cell. Other non-human mammals include, for example, non-human primates, monkeys, apes, orangutans, cats, dogs, rabbits, horses, livestock (e.g., bovine species such as cows, steer, and so forth; ovine species such as sheep, goats, and so forth; and porcine species such as pigs and boars). Domesticated animals and agricultural animals are also included. The term "non-human" excludes humans.

The cells can also be any type of undifferentiated or differentiated state. For example, a cell can be a totipotent cell, a pluripotent cell (e.g., a human pluripotent cell or a non-human pluripotent cell such as a mouse embryonic stem (ES) cell or a rat ES cell), or a non-pluripotent cell. Totipotent cells include undifferentiated cells that can give rise to any cell type, and pluripotent cells include undifferentiated cells that possess the ability to develop into more than one differentiated cell types. Such pluripotent and/or totipotent cells can be, for example, ES cells or ES-like cells, such as an induced pluripotent stem (iPS) cells. ES cells include embryo-derived totipotent or pluripotent cells that are capable of contributing to any tissue of the developing embryo upon introduction into an embryo. ES cells can be derived from the inner cell mass of a blastocyst and are capable of differentiating into cells of any of the three vertebrate germ layers (endoderm, ectoderm, and mesoderm).

The cells provided herein can also be germ cells (e.g., sperm or oocytes). The cells can be mitotically competent cells or mitotically-inactive cells, meiotically competent cells or meiotically-inactive cells. Similarly, the cells can also be primary somatic cells or cells that are not a primary somatic cell. Somatic cells include any cell that is not a gamete, germ cell, gametocyte, or undifferentiated stem cell. For example, the cells can be liver cells, such as hepatoblasts or hepatocytes.

Suitable cells provided herein also include primary cells. Primary cells include cells or cultures of cells that have been isolated directly from an organism, organ, or tissue. Primary cells include cells that are neither transformed nor immortal. They include any cell obtained from an organism, organ, or tissue which was not previously passed in tissue culture or has been previously passed in tissue culture but is incapable of being indefinitely passed in tissue culture. Such cells can be isolated by conventional techniques and include, for example, hepatocytes.

Other suitable cells provided herein include immortalized cells. Immortalized cells include cells from a multicellular organism that would normally not proliferate indefinitely but, due to mutation or alteration, have evaded normal cellular senescence and instead can keep undergoing division. Such mutations or alterations can occur naturally or be intentionally induced. A specific example of an immortalized cell line is the HepG2 human liver cancer cell line. Numerous types of immortalized cells are well known. Immortalized or primary cells include cells that are typically used for culturing or for expressing recombinant genes or proteins.

The cells provided herein also include one-cell stage embryos (i.e., fertilized oocytes or zygotes). Such one-cell stage embryos can be from any genetic background (e.g., BALB/c, C57BL/6, 129, or a combination thereof for mice), can be fresh or frozen, and can be derived from natural breeding or in vitro fertilization.

The cells provided herein can be normal, healthy cells, or can be diseased or mutant-bearing cells.

In a specific example, the non-human animal cells are embryonic stem (ES) cells or liver cells, such as mouse or rat ES cells or liver cells.

Non-human animals comprising a humanized TTR locus as described herein can be made by the methods described elsewhere herein. The term "animal" includes mammals, fishes, and birds. Non-human mammals include, for example, non-human primates, monkeys, apes, orangutans, cats, dogs, horses, rabbits, rodents (e.g., mice, rats, hamsters, and guinea pigs), and livestock (e.g., bovine species such as cows and steer; ovine species such as sheep and goats; and porcine species such as pigs and boars). Domesticated animals and agricultural animals are also included. The term "non-human animal" excludes humans. Preferred non-human animals include, for example, rodents, such as mice and rats.

The non-human animals can be from any genetic background. For example, suitable mice can be from a 129 strain, a C57BL/6 strain, a mix of 129 and C57BL/6, a BALB/c strain, or a Swiss Webster strain. Examples of 129 strains include 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, and 129T2.

See, e.g., Festing et al. (1999) *Mammalian Genome* 10:836, herein incorporated by reference in its entirety for all purposes. Examples of C57BL strains include C57BL/A, C57BL/An, C57BL/GrFa, C57BL/Kal_wN, C57BL/6, C57BL/6J, C57BL/6ByJ, C57BL/6NJ, C57BL/10, C57BL/10ScSn, C57BL/10Cr, and C57BL/Ola. Suitable mice can also be from a mix of an aforementioned 129 strain and an aforementioned C57BL/6 strain (e.g., 50% 129 and 50% C57BL/6). Likewise, suitable mice can be from a mix of aforementioned 129 strains or a mix of aforementioned BL/6 strains (e.g., the 129S6 (129/SvEvTac) strain).

Similarly, rats can be from any rat strain, including, for example, an ACI rat strain, a Dark Agouti (DA) rat strain, a Wistar rat strain, a LEA rat strain, a Sprague Dawley (SD) rat strain, or a Fischer rat strain such as Fisher F344 or Fisher F6. Rats can also be obtained from a strain derived from a mix of two or more strains recited above. For example, a suitable rat can be from a DA strain or an ACI strain. The ACI rat strain is characterized as having black agouti, with white belly and feet and an $RT1^{av1}$ haplotype. Such strains are available from a variety of sources including Harlan Laboratories. The Dark Agouti (DA) rat strain is characterized as having an agouti coat and an $RT1^{av1}$ haplotype. Such rats are available from a variety of sources including Charles River and Harlan Laboratories. Some suitable rats can be from an inbred rat strain. See, e.g., US 2014/0235933, herein incorporated by reference in its entirety for all purposes.

III. Methods of Using Non-Human Animals Comprising a Humanized TTR Locus for Assessing Efficacy of Human-TTR-Targeting Reagents In Vivo or Ex Vivo Various methods are provided for using the non-human animals comprising a humanized TTR locus as described elsewhere herein for assessing or optimizing delivery or efficacy of human-TTR-targeting reagents (e.g., therapeutic molecules or complexes) in vivo or ex vivo. Because the non-human animals comprise a humanized TTR locus, the non-human animals will more accurately reflect the efficacy of a human TTR-targeting reagent. Such non-human animals are particularly useful for testing genome-editing reagents designed to target the human TTR gene because the non-human animals disclosed herein comprise humanized endogenous Ttr loci rather than transgenic insertions of human TTR sequence at random genomic loci, and the humanized endogenous Ttr loci comprise orthologous human genomic TTR sequence from both coding and non-coding regions rather than an artificial cDNA sequence.

A. Methods of Testing Efficacy of Human-TTR-Targeting Reagents In Vivo or Ex Vivo Various methods are provided for assessing delivery or efficacy of human-TTR-targeting reagents in vivo using non-human animals comprising a humanized TTR locus as described elsewhere herein. Such methods can comprise: (a) introducing into the non-human animal a human-TTR-targeting reagent (i.e., administering the human-TTR-targeting reagent to the non-human animal); and (b) assessing the activity of the human-TTR-targeting reagent.

The human-TTR-targeting reagent can be any biological or chemical agent that targets the human TTR locus (the human TTR gene), the human TTR mRNA, or the human transthyretin protein. Examples of human-TTR-targeting reagents are disclosed elsewhere herein and include, for example, genome-editing agents. For example, the human-TTR-targeting reagent can be a TTR-targeting nucleic acid (e.g., CRISPR/Cas guide RNAs, short hairpin RNAs (shRNAs), or small interfering RNAs (siRNAs)) or nucleic acid encoding a TTR-targeting protein (e.g., a Cas proteins such as Cas9, a ZFN, or a TALEN). Alternatively, the human-TTR-targeting reagent can be a TTR-targeting antibody or antigen-binding protein, or any other large molecule or small molecule that targets human TTR.

Such human-TTR-targeting reagents can be administered by any delivery method (e.g., AAV, LNP, or HDD) as disclosed in more detail elsewhere herein and by any route of administration. Means of delivering therapeutic complexes and molecules and routes of administration are disclosed in more detail elsewhere herein. In particular methods, the reagents delivered via AAV-mediated delivery. For example, AAV8 can be used to target the liver. In other particular methods, the reagents are delivered by LNP-mediated delivery. In other particular methods, the reagents are delivered by hydrodynamic delivery (HDD). The dose can be any suitable dose. For example, in some methods in which the reagents (e.g., Cas9 mRNA and gRNA) are delivered by LNP-mediated delivery, the dose can be between about 0.01 and about 10 mg/kg, about 0.01 and about 5 mg/kg, between about 0.01 and about 4 mg/kg, between about 0.01 and about 3 mg/kg, between about 0.01 and about 2 mg/kg, between about 0.01 and about 1 mg/kg, between about 0.1 and about 10 mg/kg, between about 0.1 and about 6 mg/kg; between about 0.1 and about 5 mg/kg, between about 0.1 and about 4 mg/kg, between about 0.1 and about 3 mg/kg, between about 0.1 and about 2 mg/kg, between about 0.1 and about 1 mg/kg, between about 0.3 and about 10 mg/kg, between about 0.3 and about 6 mg/kg; between about 0.3 and about 5 mg/kg, between about 0.3 and about 4 mg/kg, between about 0.3 and about 3 mg/kg, between about 0.3 and about 2 mg/kg, between about 0.3 and about 1 mg/kg, about 0.1 mg/kg, about 0.3 mg/kg, about 1 mg/kg, about 2 mg/kg, or about 3 mg/kg. In a specific example, the dose is between about 0.1 and about 6 mg/kg; between about 0.1 and about 3 mg/kg, or between about 0.1 and about 2 mg/kg. In a specific example, the human-TTR-targeting reagent is a genome editing reagent, the LNP dose is about 1 mg/kg, and the percent genome editing at the humanized TTR locus is between about 70% and about 80%. In another specific example, the human-TTR-targeting reagent is a genome editing reagent, the LNP dose is about 0.3 mg/kg, and the percent editing is between about 50% and about 80%. In another specific example, the human-TTR-targeting reagent is a genome editing reagent, the LNP dose is about 0.1 mg/kg, and the percent editing is between about 20% and about 80%. In another specific example, the LNP dose is about 1 mg/kg, and the serum TTR levels are reduced to between about 0% and about 10% or between about 0% and about 35% of control levels. In another specific example, the LNP dose is about 0.3 mg/kg, and the serum TTR levels are reduced to between about 0% and about 20% or about 0% and about 95% of control levels. In another specific example, the LNP dose is about 0.1 mg/kg, and the serum TTR levels are reduced to between about 0% and about 60% or about 0% and about 99% of control levels.

Methods for assessing activity of the human-TTR-targeting reagent are well-known and are provided elsewhere herein. Assessment of activity can be in any cell type, any tissue type, or any organ type as disclosed elsewhere herein. In some methods, assessment of activity is in liver cells. If the TTR-targeting reagent is a genome editing reagent (e.g., a nuclease agent), such methods can comprise assessing modification of the humanized TTR locus. As one example, the assessing can comprise measuring non-homologous end joining (NHEJ) activity at the humanized TTR locus. This can comprise, for example, measuring the frequency of insertions or deletions within the humanized TTR locus. For example, the assessing can comprise sequencing the humanized TTR locus in one or more cells isolated from the non-human animal (e.g., next-generation sequencing). Assessment can comprise isolating a target organ (e.g., liver) or tissue from the non-human animal and assessing modification of humanized TTR locus in the target organ or tissue. Assessment can also comprise assessing modification of humanized TTR locus in two or more different cell types within the target organ or tissue. Similarly, assessment can comprise isolating a non-target organ or tissue (e.g., two or more non-target organs or tissues) from the non-human animal and assessing modification of humanized TTR locus in the non-target organ or tissue.

Such methods can also comprise measuring expression levels of the mRNA produced by the humanized TTR locus, or by measuring expression levels of the protein encoded by the humanized TTR locus. For example, protein levels can be measured in a particular cell, tissue, or organ type (e.g., liver), or secreted levels can be measured in the serum. Methods for assessing expression of Ttr mRNA or protein expressed from the humanized TTR locus are provided elsewhere herein and are well-known.

The various methods provided above for assessing activity in vivo can also be used to assess the activity of human-TTR-targeting reagents ex vivo as described elsewhere herein.

As one example, if the human-TTR-targeting reagent is a genome editing reagent (e.g., a nuclease agent), percent editing at the humanized TTR locus can be assessed (e.g., in liver cells). For example, the percent editing (e.g., total number of insertions or deletions observed over the total number of sequences read in the PCR reaction from a pool of lysed cells) can be at least about 10%, at least about 20%, at least about 30%, at least about 40%, at least about 50%, at least about 60%, at least about 70%, at least about 80%, at least about 90%, at least about 95%, at least about 99%, or, for example, between about 1% and about 99%, between about 10% and about 99%, between about 20% and about 99%, between about 30% and about 99%, between about 40% and about 99%, between about 50% and about 99%, between about 60% and about 99%, between about 1% and about 90%, between about 10% and about 90%, between about 20% and about 90%, between about 30% and about 90%, between about 40% and about 90%, between about 50% and about 90%, between about 60% and about 90%, between about 1% and about 80%, between about 10% and about 80%, between about 20% and about 80%, between about 30% and about 80%, between about 40% and about 80%, between about 50% and about 80%, or between about 60% and about 80%.

As another example, serum TTR levels can be assessed. For example, serum TTR levels can be reduced by at least about 10%, at least about 20%, at least about 30%, at least about 40%, at least about 50%, at least about 60%, at least about 65%, at least about 70%, at least about 80%, at least about 90%, at least about 95%, at least about 99%, or, for example, between about 1% and about 99%, between about 10% and about 99%, between about 20% and about 99%, between about 30% and about 99%, between about 40% and about 99%, between about 50% and about 99%, between about 60% and about 99%, between about 70% and about 99%, between about 80% and about 99%, between about 1% and about 90%, between about 10% and about 90%, between about 20% and about 90%, between about 30% and about 90%, between about 40% and about 90%, between about 50% and about 90%, between about 60% and about 90%, between about 70% and about 90%, or between about 80% and about 90%.

In some methods, the human-TTR-targeting reagent is a nuclease agent, such as a CRISPR/Cas nuclease agent, that targets the human TTR gene. Such methods can comprise, for example: (a) introducing into the non-human animal a nuclease agent designed to cleave the human TTR gene (e.g., Cas protein such as Cas9 and a guide RNA designed to target a guide RNA target sequence in the human TTR gene); and (b) assessing modification of the humanized TTR locus.

In the case of a CRISPR/Cas nuclease, for example, modification of the humanized TTR locus will be induced when the guide RNA forms a complex with the Cas protein and directs the Cas protein to the humanized TTR locus, and the Cas/guide RNA complex cleaves the guide RNA target sequence, triggering repair by the cell (e.g., via non-homologous end joining (NHEJ) if no donor sequence is present).

Optionally, two or more guide RNAs can be introduced, each designed to target a different guide RNA target sequence within the human TTR gene. For example, two guide RNAs can be designed to excise a genomic sequence between the two guide RNA target sequences. Modification of the humanized TTR locus will be induced when the first guide RNA forms a complex with the Cas protein and directs the Cas protein to the humanized TTR locus, the second guide RNA forms a complex with the Cas protein and directs the Cas protein to the humanized TTR locus, the first Cas/guide RNA complex cleaves the first guide RNA target sequence, and the second Cas/guide RNA complex cleaves the second guide RNA target sequence, resulting in excision of the intervening sequence.

Optionally, an exogenous donor nucleic acid capable of recombining with and modifying a human TTR gene is also introduced into the non-human animal. Optionally, the nuclease agent or Cas protein can be tethered to the exogenous donor nucleic acid as described elsewhere herein. Modification of the humanized TTR locus will be induced, for example, when the guide RNA forms a complex with the Cas protein and directs the Cas protein to the humanized TTR locus, the Cas/guide RNA complex cleaves the guide RNA target sequence, and the humanized TTR locus recombines with the exogenous donor nucleic acid to modify the humanized TTR locus. The exogenous donor nucleic acid can recombine with the humanized TTR locus, for example, via homology-directed repair (HDR) or via NHEJ-mediated insertion. Any type of exogenous donor nucleic acid can be used, examples of which are provided elsewhere herein.

B. Methods of Optimizing Delivery or Efficacy of Human-TTR-Targeting Reagent In Vivo or Ex Vivo Various methods are provided for optimizing delivery of human-TTR-targeting reagents to a cell or non-human animal or optimizing the activity or efficacy of human-TTR-targeting reagents in vivo. Such methods can comprise, for example: (a) performing the method of testing the efficacy of a human-TTR-targeting reagent as described above a first time in a first non-human animal or first cell comprising a humanized TTR locus; (b) changing a variable and performing the method a second time in a second non-human animal (i.e., of the same species) or a second cell comprising a humanized TTR locus with the changed variable; and (c) comparing the activity of the human-TTR-targeting reagent in step (a) with the activity of the human-TTR-targeting reagent in step (b), and selecting the method resulting in the higher activity.

Methods of measuring delivery, efficacy, or activity of human-TTR-targeting reagents are disclosed elsewhere herein. For example, such methods can comprise measuring modification of the humanized TTR locus. More effective modification of the humanized TTR locus can mean different things depending on the desired effect within the non-human animal or cell. For example, more effective modification of the humanized TTR locus can mean one or more or all of higher levels of modification, higher precision, higher consistency, or higher specificity. Higher levels of modification (i.e., higher efficacy) of the humanized TTR locus refers to a higher percentage of cells is targeted within a particular target cell type, within a particular target tissue, or within a particular target organ (e.g., liver). Higher precision refers to more precise modification of the humanized TTR locus (e.g., a higher percentage of targeted cells having the same modification or having the desired modification without extra unintended insertions and deletions (e.g., NHEJ indels)). Higher consistency refers to more consistent modification of the humanized TTR locus among different types of targeted cells, tissues, or organs if more than one type of cell, tissue, or organ is being targeted (e.g., modification of a greater number of cell types within the liver). If a particular organ is being targeted, higher consistency can also refer to more consistent modification throughout all locations within the organ (e.g., the liver). Higher specificity can refer to higher specificity with respect to the genomic locus or loci targeted, higher specificity with respect to the cell type targeted, higher specificity with respect to the tissue type targeted, or higher specificity with respect to the organ targeted. For example, increased genomic locus specificity refers to less modification of off-target genomic loci (e.g., a lower percentage of targeted cells having modifications at unintended, off-target genomic loci instead of or in addition to modification of the target genomic locus). Likewise, increased cell type, tissue, or organ type specificity refers to less modification of off-target cell types, tissue types, or organ types if a particular cell type, tissue type, or organ type is being targeted (e.g., when a particular organ is targeted (e.g., the liver), there is less modification of cells in organs or tissues that are not intended targets).

The variable that is changed can be any parameter. As one example, the changed variable can be the packaging or the delivery method by which the human-TTR-targeting reagent or reagents are introduced into the cell or non-human animal. Examples of delivery methods, such as LNP, HDD, and AAV, are disclosed elsewhere herein. For example, the changed variable can be the AAV serotype. Similarly, the administering can comprise LNP-mediated delivery, and the changed variable can be the LNP formulation. As another example, the changed variable can be the route of administration for introduction of the human-TTR-targeting reagent or reagents into the cell or non-human animal. Examples of routes of administration, such as intravenous, intravitreal, intraparenchymal, and nasal instillation, are disclosed elsewhere herein.

As another example, the changed variable can be the concentration or amount of the human-TTR-targeting reagent or reagents introduced. As another example, the changed variable can be the concentration or the amount of one human-TTR-targeting reagent introduced (e.g., guide RNA, Cas protein, or exogenous donor nucleic acid) relative to the concentration or the amount another human-TTR-targeting reagent introduced (e.g., guide RNA, Cas protein, or exogenous donor nucleic acid).

As another example, the changed variable can be the timing of introducing the human-TTR-targeting reagent or reagents relative to the timing of assessing the activity or efficacy of the reagents. As another example, the changed variable can be the number of times or frequency with which the human-TTR-targeting reagent or reagents are introduced. As another example, the changed variable can be the timing of introduction of one human-TTR-targeting reagent introduced (e.g., guide RNA, Cas protein, or exogenous donor nucleic acid) relative to the timing of introduction of another human-TTR-targeting reagent introduced (e.g., guide RNA, Cas protein, or exogenous donor nucleic acid).

As another example, the changed variable can be the form in which the human-TTR-targeting reagent or reagents are introduced. For example, a guide RNA can be introduced in the form of DNA or in the form of RNA. A Cas protein (e.g., Cas9) can be introduced in the form of DNA, in the form of RNA, or in the form of a protein (e.g., complexed with a guide RNA). An exogenous donor nucleic acid can be DNA, RNA, single-stranded, double-stranded, linear, circular, and so forth. Similarly, each of the components can comprise various combinations of modifications for stability, to reduce off-target effects, to facilitate delivery, and so forth. As another example, the changed variable can be the human-TTR-targeting reagent or reagents that are introduced (e.g., introducing a different guide RNA with a different sequence, introducing a different Cas protein (e.g., introducing a different Cas protein with a different sequence, or a nucleic acid with a different sequence but encoding the same Cas protein amino acid sequence), or introducing a different exogenous donor nucleic acid with a different sequence).

In a specific example, the human-TTR-targeting reagent comprises a Cas protein and a guide RNA designed to target a guide RNA target sequence in a human TTR gene. In such methods, the changed variable can be the guide RNA sequence and/or the guide RNA target sequence. In some such methods, the Cas protein and the guide RNA can each be administered in the form of RNA, and the changed variable can be the ratio of Cas mRNA to guide RNA (e.g., in an LNP formulation). In some such methods, the changed variable can be guide RNA modifications (e.g., a guide RNA with a modification is compared to a guide RNA without the modification).

C. Human-TTR-Targeting Reagents

A human-TTR-targeting reagent can be any reagent that targets a human TTR gene, a human TTR mRNA, or a human TTR protein. For example, it can be a genome editing reagent such as a nuclease agent that cleaves a target sequence within the human TTR gene, it can be an antisense oligonucleotide targeting a human TTR mRNA, it can be an antigen-binding protein targeting an epitope of a human TTR protein, or it can be a small molecule targeting human TTR. Human-TTR-targeting reagents in the methods disclosed herein can be known human-TTR-targeting reagents, can be putative-TTR-targeting reagents (e.g., candidate reagents designed to target human TTR), or can be reagents being screened for human-TTR-targeting activity.

(1) Nuclease Agents Targeting Human TTR Gene

A human-TTR-targeting reagent can be a genome editing reagent such as a nuclease agent that cleaves a target sequence within the human TTR gene. A nuclease target sequence includes a DNA sequence at which a nick or double-strand break is induced by a nuclease agent. The target sequence for a nuclease agent can be endogenous (or native) to the cell or the target sequence can be exogenous to the cell. A target sequence that is exogenous to the cell is not naturally occurring in the genome of the cell. The target sequence can also exogenous to the polynucleotides of interest that one desires to be positioned at the target locus. In some cases, the target sequence is present only once in the genome of the host cell.

The length of the target sequence can vary, and includes, for example, target sequences that are about 30-36 bp for a zinc finger nuclease (ZFN) pair (i.e., about 15-18 bp for each ZFN), about 36 bp for a Transcription Activator-Like Effector Nuclease (TALEN), or about 20 bp for a CRISPR/Cas9 guide RNA.

Any nuclease agent that induces a nick or double-strand break at a desired target sequence can be used in the methods and compositions disclosed herein. A naturally occurring or native nuclease agent can be employed so long as the nuclease agent induces a nick or double-strand break in a desired target sequence. Alternatively, a modified or engineered nuclease agent can be employed. An "engineered nuclease agent" includes a nuclease that is engineered (modified or derived) from its native form to specifically recognize and induce a nick or double-strand break in the desired target sequence. Thus, an engineered nuclease agent can be derived from a native, naturally occurring nuclease agent or it can be artificially created or synthesized. The engineered nuclease can induce a nick or double-strand break in a target sequence, for example, wherein the target sequence is not a sequence that would have been recognized by a native (non-engineered or non-modified) nuclease agent. The modification of the nuclease agent can be as little as one amino acid in a protein cleavage agent or one nucleotide in a nucleic acid cleavage agent. Producing a nick or double-strand break in a target sequence or other DNA can be referred to herein as "cutting" or "cleaving" the target sequence or other DNA.

Active variants and fragments of the exemplified target sequences are also provided. Such active variants can comprise at least 65%, 70%, 75%, 80%, 85%, 90%, 91%, 92%, 93%, 94%, 95%, 96%, 97%, 98%, 99% or more sequence identity to the given target sequence, wherein the active variants retain biological activity and hence are capable of being recognized and cleaved by a nuclease agent in a sequence-specific manner. Assays to measure the double-strand break of a target sequence by a nuclease agent are well-known. See, e.g., Frendewey et al. (2010) *Methods in Enzymology* 476:295-307, which is incorporated by reference herein in its entirety for all purposes.

The target sequence of the nuclease agent can be positioned anywhere in or near the Ttr locus. The target sequence can be located within a coding region of the Ttr gene, or within regulatory regions that influence the expression of the gene. A target sequence of the nuclease agent can be located in an intron, an exon, a promoter, an enhancer, a regulatory region, or any non-protein coding region.

One type of nuclease agent is a Transcription Activator-Like Effector Nuclease (TALEN). TAL effector nucleases are a class of sequence-specific nucleases that can be used to make double-strand breaks at specific target sequences in the genome of a prokaryotic or eukaryotic organism. TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences. See WO 2010/079430; Morbitzer et al. (2010) *PNAS* 10.1073/pnas.1013133107; Scholze & Boch (2010) *Virulence* 1:428-432; Christian et al. *Genetics* (2010) 186:757-761; Li et al. (2010) *Nuc. Acids Res.* (2010) doi:10.1093/nar/gkq704; and Miller et al. (2011) *Nature Biotechnology* 29:143-148, each of which is herein incorporated by reference in its entirety.

Examples of suitable TAL nucleases, and methods for preparing suitable TAL nucleases, are disclosed, e.g., in US 2011/0239315 A1, US 2011/0269234 A1, US 2011/0145940 A1, US 2003/0232410 A1, US 2005/0208489 A1, US 2005/0026157 A1, US 2005/0064474 A1, US 2006/0188987 A1, and US 2006/0063231 A1, each of which is herein incorporated by reference in its entirety. In various embodiments, TAL effector nucleases are engineered that cut in or near a target nucleic acid sequence in, e.g., a locus of interest or a genomic locus of interest, wherein the target nucleic acid sequence is at or near a sequence to be modified by a targeting vector. The TAL nucleases suitable for use with the various methods and compositions provided herein include those that are specifically designed to bind at or near target nucleic acid sequences to be modified by targeting vectors as described herein.

In some TALENs, each monomer of the TALEN comprises 33-35 TAL repeats that recognize a single base pair via two hypervariable residues. In some TALENs, the nuclease agent is a chimeric protein comprising a TAL-repeat-based DNA binding domain operably linked to an independent nuclease such as a FokI endonuclease. For example, the nuclease agent can comprise a first TAL-repeat-based DNA binding domain and a second TAL-repeat-based DNA binding domain, wherein each of the first and the second TAL-repeat-based DNA binding domains is operably linked to a FokI nuclease, wherein the first and the second TAL-repeat-based DNA binding domain recognize two contiguous target DNA sequences in each strand of the target DNA sequence separated by a spacer sequence of varying length (12-20 bp), and wherein the FokI nuclease subunits dimerize to create an active nuclease that makes a double strand break at a target sequence.

The nuclease agent employed in the various methods and compositions disclosed herein can further comprise a zinc-finger nuclease (ZFN). In some ZFNs, each monomer of the ZFN comprises 3 or more zinc finger-based DNA binding domains, wherein each zinc finger-based DNA binding domain binds to a 3 bp subsite. In other ZFNs, the ZFN is a chimeric protein comprising a zinc finger-based DNA binding domain operably linked to an independent nuclease such as a FokI endonuclease. For example, the nuclease agent can comprise a first ZFN and a second ZFN, wherein each of the first ZFN and the second ZFN is operably linked to a FokI nuclease subunit, wherein the first and the second ZFN recognize two contiguous target DNA sequences in each strand of the target DNA sequence separated by about 5-7 bp spacer, and wherein the FokI nuclease subunits dimerize to create an active nuclease that makes a double strand break. See, e.g., US20060246567; US20080182332; US20020081614; US20030021776; WO/2002/057308A2; US20130123484; US20100291048; WO/2011/017293A2; and Gaj et al. (2013) *Trends in Biotechnology*, 31(7):397-405, each of which is herein incorporated by reference.

Another type of nuclease agent is a meganuclease. Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. Meganucleases are notable for their long target sequences, and for tolerating some sequence polymorphisms in their DNA substrates. Meganuclease domains, structure and function are known, see for example, Guhan and Muniyappa (2003) *Crit Rev Biochem Mol Biol* 38:199-248; Lucas et al., (2001) *Nucleic*

*Acids Res* 29:960-9; Jurica and Stoddard, (1999) *Cell Mol Life Sci* 55:1304-26; Stoddard, (2006) *Q Rev Biophys* 38:49-95; and Moure et al., (2002) *Nat Struct Biol* 9:764. In some examples, a naturally occurring variant and/or engineered derivative meganuclease is used. Methods for modifying the kinetics, cofactor interactions, expression, optimal conditions, and/or target sequence specificity, and screening for activity are known. See, e.g., Epinat et al., (2003) *Nucleic Acids Res* 31:2952-62; Chevalier et al., (2002) *Mol Cell* 10:895-905; Gimble et al., (2003) *Mol Biol* 334:993-1008; Seligman et al., (2002) *Nucleic Acids Res* 30:3870-9; Sussman et al., (2004) *J Mol Biol* 342:31-41; Rosen et al., (2006) *Nucleic Acids Res* 34:4791-800; Chames et al., (2005) *Nucleic Acids Res* 33: e178; Smith et al., (2006) *Nucleic Acids Res* 34: e149; Gruen et al., (2002) *Nucleic Acids Res* 30: e29; Chen and Zhao, (2005) *Nucleic Acids Res* 33: e154; WO2005105989; WO2003078619; WO2006097854; WO2006097853; WO2006097784; and WO2004031346, each of which is herein incorporated by reference in its entirety.

Any meganuclease can be used, including, for example, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, PI-PspI, F-SceI, F-SceII, F-SuvI, F-TeeI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NcIIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp6803I, I-SthPhiJP, I-SthPhiST3P, I-SthPhiSTe3bP, I-TdeIP, I-TeeI, I-TevII, I-TevIII, I-UarAP, I-UarHGPAIP, I-UarHGPA13P, I-VinIP, I-ZbiIP, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, PI-TliII, or any active variants or fragments thereof.

Meganucleases can recognize, for example, double-stranded DNA sequences of 12 to 40 base pairs. In some cases, the meganuclease recognizes one perfectly matched target sequence in the genome.

Some meganucleases are homing nucleases. One type of homing nuclease is a LAGLIDADG family of homing nucleases including, for example, I-SceI, I-CreI, and I-DmoI.

Nuclease agents can further comprise CRISPR/Cas systems as described in more detail below.

Active variants and fragments of nuclease agents (i.e., an engineered nuclease agent) are also provided. Such active variants can comprise at least 65%, 70%, 75%, 80%, 85%, 90%, 91%, 92%, 93%, 94%, 95%, 96%, 97%, 98%, 99% or more sequence identity to the native nuclease agent, wherein the active variants retain the ability to cut at a desired target sequence and hence retain nick or double-strand-break-inducing activity. For example, any of the nuclease agents described herein can be modified from a native endonuclease sequence and designed to recognize and induce a nick or double-strand break at a target sequence that was not recognized by the native nuclease agent. Thus, some engineered nucleases have a specificity to induce a nick or double-strand break at a target sequence that is different from the corresponding native nuclease agent target sequence. Assays for nick or double-strand-break-inducing activity are known and generally measure the overall activity and specificity of the endonuclease on DNA substrates containing the target sequence.

The nuclease agent may be introduced into a cell or non-human animal by any known means. A polypeptide encoding the nuclease agent may be directly introduced into the cell or non-human animal. Alternatively, a polynucleotide encoding the nuclease agent can be introduced into the cell or non-human animal. When a polynucleotide encoding the nuclease agent is introduced, the nuclease agent can be transiently, conditionally, or constitutively expressed within the cell. The polynucleotide encoding the nuclease agent can be contained in an expression cassette and be operably linked to a conditional promoter, an inducible promoter, a constitutive promoter, or a tissue-specific promoter. Examples of promoters are discussed in further detail elsewhere herein. Alternatively, the nuclease agent can be introduced into the cell as an mRNA encoding the nuclease agent.

A polynucleotide encoding a nuclease agent can be stably integrated in the genome of a cell and operably linked to a promoter active in the cell. Alternatively, a polynucleotide encoding a nuclease agent can be in a targeting vector.

When the nuclease agent is provided to the cell through the introduction of a polynucleotide encoding the nuclease agent, such a polynucleotide encoding a nuclease agent can be modified to substitute codons having a higher frequency of usage in the cell of interest, as compared to the naturally occurring polynucleotide sequence encoding the nuclease agent. For example, the polynucleotide encoding the nuclease agent can be modified to substitute codons having a higher frequency of usage in a given eukaryotic cell of interest, including a human cell, a non-human cell, a mammalian cell, a rodent cell, a mouse cell, a rat cell or any other host cell of interest, as compared to the naturally occurring polynucleotide sequence.

(2) CRISPR/Cas Systems Targeting Human TTR Gene

A particular type of human-TTR-targeting reagent can be a CRISPR/Cas system that targets the human TTR gene. CRISPR/Cas systems include transcripts and other elements involved in the expression of, or directing the activity of, Cas genes. A CRISPR/Cas system can be, for example, a type I, a type II, or a type III system. Alternatively, a CRISPR/Cas system can be a type V system (e.g., subtype V-A or subtype V-B). CRISPR/Cas systems used in the compositions and methods disclosed herein can be non-naturally occurring. A "non-naturally occurring" system includes anything indicating the involvement of the hand of man, such as one or more components of the system being altered or mutated from their naturally occurring state, being at least substantially free from at least one other component with which they are naturally associated in nature, or being associated with at least one other component with which they are not naturally associated. For example, non-naturally occurring CRISPR/Cas systems can employ CRISPR complexes comprising a gRNA and a Cas protein that do not naturally occur together, a Cas protein that does not occur naturally, or a gRNA that does not occur naturally.

Cas Proteins and Polynucleotides Encoding Cas Proteins. Cas proteins generally comprise at least one RNA recognition or binding domain that can interact with guide RNAs (gRNAs, described in more detail below). Cas proteins can also comprise nuclease domains (e.g., DNase or RNase domains), DNA-binding domains, helicase domains, protein-protein interaction domains, dimerization domains, and other domains. Some such domains (e.g., DNase domains) can be from a native Cas protein. Other such domains can be added to make a modified Cas protein. A nuclease domain possesses catalytic activity for nucleic acid cleavage, which includes the breakage of the covalent bonds of a nucleic acid molecule. Cleavage can produce blunt ends or staggered ends, and it can be single-stranded or double-stranded. For example, a wild type Cas9 protein will typically create a blunt cleavage product. Alternatively, a wild type Cpf1 protein (e.g., FnCpf1) can result in a cleavage product with a 5-nucleotide 5' overhang, with the cleavage occurring after the 18th base pair from the PAM sequence on the non-targeted strand and after the 23rd base on the targeted strand. A Cas protein can have full cleavage activity to create a double-strand break at a target genomic locus (e.g., a double-strand break with blunt ends), or it can be a nickase that creates a single-strand break at a target genomic locus.

Examples of Cas proteins include Cas1, Cas1B, Cas2, Cas3, Cas4, Cas5, Cas5e (CasD), Cash, Cas6e, Cas6f, Cas7, Cas8a1, Cas8a2, Cas8b, Cas8c, Cas9 (Csn1 or Csx12), Cas10, Cas10d, CasF, CasG, CasH, Csy1, Csy2, Csy3, Cse1 (CasA), Cse2 (CasB), Cse3 (CasE), Cse4 (CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, and Cu1966, and homologs or modified versions thereof.

An exemplary Cas protein is a Cas9 protein or a protein derived from Cas9 protein. Cas9 proteins are from a type II CRISPR/Cas system and typically share four key motifs with a conserved architecture. Motifs 1, 2, and 4 are RuvC-like motifs, and motif 3 is an HNH motif. Exemplary Cas9 proteins are from *Streptococcus pyogenes, Streptococcus thermophilus, Streptococcus* sp., *Staphylococcus aureus, Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp *Arthrospira maxima, Arthrospira platensis, Arthrospira* sp., *Lyngbya* sp., *Microcoleus chthonoplastes, Oscillatoria* sp., *Petrotoga mobilis, Thermosipho africanus, Acaryochloris marina, Neisseria meningitidis,* or *Campylobacter jejuni*. Additional examples of the Cas9 family members are described in WO 2014/131833, herein incorporated by reference in its entirety for all purposes. Cas9 from *S. pyogenes* (SpCas9) (assigned SwissProt accession number Q99ZW2) is an exemplary Cas9 protein. Cas9 from *S. aureus* (SaCas9) (assigned UniProt accession number J7RUA5) is another exemplary Cas9 protein. Cas9 from *Campylobacter jejuni* (CjCas9) (assigned UniProt accession number Q0P897) is another exemplary Cas9 protein. See, e.g., Kim et al. (2017) *Nat. Comm.* 8:14500, herein incorporated by reference in its entirety for all purposes. SaCas9 is smaller than SpCas9, and CjCas9 is smaller than both SaCas9 and SpCas9. An exemplary Cas9 protein sequence can comprise, consist essentially of, or consist of SEQ ID NO: 94. An exemplary DNA encoding the Cas9 protein can comprise, consist essentially of, or consist of SEQ ID NO: 93.

Another example of a Cas protein is a Cpf1 (CRISPR from *Prevotella* and *Francisella* 1) protein. Cpf1 is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in Cas9 proteins, and the RuvC-like domain is contiguous in the Cpf1 sequence, in contrast to Cas9 where it contains long inserts including the HNH domain. See, e.g., Zetsche et al. (2015) *Cell* 163(3): 759-771, herein incorporated by reference in its entirety for all purposes. Exemplary Cpf1 proteins are from *Francisella tularensis* 1, *Francisella tularensis* subsp. *novicida, Prevotella albensis, Lachnospiraceae bacterium* MC2017 1, *Butyrivibrio proteoclasticus, Peregrinibacteria bacterium* GW2011_GWA2_33_10, Parcubacteria bacterium GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens,* and *Porphyromonas macacae*. Cpf1 from *Francisella novicida* U112 (FnCpf1; assigned UniProt accession number A0Q7Q2) is an exemplary Cpf1 protein.

Cas proteins can be wild type proteins (i.e., those that occur in nature), modified Cas proteins (i.e., Cas protein variants), or fragments of wild type or modified Cas proteins. Cas proteins can also be active variants or fragments with respect to catalytic activity of wild type or modified Cas proteins. Active variants or fragments with respect to catalytic activity can comprise at least 80%, 85%, 90%, 91%, 92%, 93%, 94%, 95%, 96%, 97%, 98%, 99% or more sequence identity to the wild type or modified Cas protein or a portion thereof, wherein the active variants retain the ability to cut at a desired cleavage site and hence retain nick-inducing or double-strand-break-inducing activity. Assays for nick-inducing or double-strand-break-inducing activity are known and generally measure the overall activity and specificity of the Cas protein on DNA substrates containing the cleavage site.

Cas proteins can be modified to increase or decrease one or more of nucleic acid binding affinity, nucleic acid binding specificity, and enzymatic activity. Cas proteins can also be modified to change any other activity or property of the protein, such as stability. For example, one or more nuclease domains of the Cas protein can be modified, deleted, or inactivated, or a Cas protein can be truncated to remove domains that are not essential for the function of the protein or to optimize (e.g., enhance or reduce) the activity or a property of the Cas protein.

One example of a modified Cas protein is the modified SpCas9-HF1 protein, which is a high-fidelity variant of *Streptococcus pyogenes* Cas9 harboring alterations (N497A/R661A/Q695A/Q926A) designed to reduce non-specific DNA contacts. See, e.g., Kleinstiver et al. (2016) *Nature* 529(7587):490-495, herein incorporated by reference in its entirety for all purposes. Another example of a modified Cas protein is the modified eSpCas9 variant (K848A/K1003A/R1060A) designed to reduce off-target effects. See, e.g., Slaymaker et al. (2016) *Science* 351(6268):84-88, herein incorporated by reference in its entirety for all purposes. Other SpCas9 variants include K855A and K810A/K1003A/R1060A.

Cas proteins can comprise at least one nuclease domain, such as a DNase domain. For example, a wild type Cpf1 protein generally comprises a RuvC-like domain that cleaves both strands of target DNA, perhaps in a dimeric configuration. Cas proteins can also comprise at least two nuclease domains, such as DNase domains. For example, a wild type Cas9 protein generally comprises a RuvC-like nuclease domain and an HNH-like nuclease domain. The RuvC and HNH domains can each cut a different strand of double-stranded DNA to make a double-stranded break in the DNA. See, e.g., Jinek et al. (2012) *Science* 337:816-821, herein incorporated by reference in its entirety for all purposes.

One or more or all of the nuclease domains can be deleted or mutated so that they are no longer functional or have reduced nuclease activity. For example, if one of the nuclease domains is deleted or mutated in a Cas9 protein, the resulting Cas9 protein can be referred to as a nickase and can generate a single-strand break at a guide RNA target sequence within a double-stranded DNA but not a double-strand break (i.e., it can cleave the complementary strand or the non-complementary strand, but not both). If both of the nuclease domains are deleted or mutated, the resulting Cas protein (e.g., Cas9) will have a reduced ability to cleave both strands of a double-stranded DNA (e.g., a nuclease-null or nuclease-inactive Cas protein, or a catalytically dead Cas protein (dCas)). An example of a mutation that converts Cas9 into a nickase is a D10A (aspartate to alanine at position 10 of Cas9) mutation in the RuvC domain of Cas9 from *S. pyogenes*. Likewise, H939A (histidine to alanine at amino acid position 839), H840A (histidine to alanine at amino acid position 840), or N863A (asparagine to alanine at amino acid position N863) in the HNH domain of Cas9 from *S. pyogenes* can convert the Cas9 into a nickase. Other examples of mutations that convert Cas9 into a nickase include the corresponding mutations to Cas9 from *S. thermophilus*. See, e.g., Sapranauskas et al. (2011) *Nucleic Acids Research* 39:9275-9282 and WO 2013/141680, each of which is herein incorporated by reference in its entirety for all purposes. Such mutations can be generated using methods such as site-directed mutagenesis, PCR-mediated mutagenesis, or total gene synthesis. Examples of other mutations creating nickases can be found, for example, in WO 2013/176772 and WO 2013/142578, each of which is herein incorporated by reference in its entirety for all purposes. If all of the nuclease domains are deleted or mutated in a Cas protein (e.g., both of the nuclease domains are deleted or mutated in a Cas9 protein), the resulting Cas protein (e.g., Cas9) will have a reduced ability to cleave both strands of a double-stranded DNA (e.g., a nuclease-null or nuclease-inactive Cas protein). One specific example is a D10A/H840A *S. pyogenes* Cas9 double mutant or a corresponding double mutant in a Cas9 from another species when optimally aligned with *S. pyogenes* Cas9. Another specific example is a D10A/N863A *S. pyogenes* Cas9 double mutant or a corresponding double mutant in a Cas9 from another species when optimally aligned with *S. pyogenes* Cas9.

Examples of inactivating mutations in the catalytic domains of *Staphylococcus aureus* Cas9 proteins are also known. For example, the *Staphyloccocus aureus* Cas9 enzyme (SaCas9) may comprise a substitution at position N580 (e.g., N580A substitution) and a substitution at position D10 (e.g., D10A substitution) to generate a nuclease-inactive Cas protein. See, e.g., WO 2016/106236, herein incorporated by reference in its entirety for all purposes.

Examples of inactivating mutations in the catalytic domains of Cpf1 proteins are also known. With reference to Cpf1 proteins from *Francisella novicida* U112 (FnCpf1), *Acidaminococcus* sp. BV3L6 (AsCpf1), *Lachnospiraceae bacterium* ND2006 (LbCpf1), and *Moraxella bovoculi* 237 (MbCpf1 Cpf1), such mutations can include mutations at positions 908, 993, or 1263 of AsCpf1 or corresponding positions in Cpf1 orthologs, or positions 832, 925, 947, or 1180 of LbCpf1 or corresponding positions in Cpf1 orthologs. Such mutations can include, for example one or more of mutations D908A, E993A, and D1263A of AsCpf1 or corresponding mutations in Cpf1 orthologs, or D832A, E925A, D947A, and D1180A of LbCpf1 or corresponding mutations in Cpf1 orthologs. See, e.g., US 2016/0208243, herein incorporated by reference in its entirety for all purposes.

Cas proteins (e.g., nuclease-active Cas proteins or nuclease-inactive Cas proteins) can also be operably linked to heterologous polypeptides as fusion proteins. For example, a Cas protein can be fused to a cleavage domain or an epigenetic modification domain. See WO 2014/089290, herein incorporated by reference in its entirety for all purposes. Cas proteins can also be fused to a heterologous polypeptide providing increased or decreased stability. The fused domain or heterologous polypeptide can be located at the N-terminus, the C-terminus, or internally within the Cas protein.

As one example, a Cas protein can be fused to one or more heterologous polypeptides that provide for subcellular localization. Such heterologous polypeptides can include, for example, one or more nuclear localization signals (NLS) such as the monopartite SV40 NLS and/or a bipartite alpha-importin NLS for targeting to the nucleus, a mitochondrial localization signal for targeting to the mitochondria, an ER retention signal, and the like. See, e.g., Lange et al. (2007) *J. Biol. Chem.* 282:5101-5105, herein incorporated by reference in its entirety for all purposes. Such subcellular localization signals can be located at the N-terminus, the C-terminus, or anywhere within the Cas protein. An NLS can comprise a stretch of basic amino acids, and can be a monopartite sequence or a bipartite sequence. Optionally, a Cas protein can comprise two or more NLSs, including an NLS (e.g., an alpha-importin NLS or a monopartite NLS) at the N-terminus and an NLS (e.g., an SV40 NLS or a bipartite NLS) at the C-terminus. A Cas protein can also comprise two or more NLSs at the N-terminus and/or two or more NLSs at the C-terminus.

Cas proteins can also be operably linked to a cell-penetrating domain or protein transduction domain. For example, the cell-penetrating domain can be derived from the HIV-1 TAT protein, the TLM cell-penetrating motif from human hepatitis B virus, MPG, Pep-1, VP22, a cell penetrating peptide from Herpes simplex virus, or a polyarginine peptide sequence. See, e.g., WO 2014/089290 and WO 2013/176772, each of which is herein incorporated by reference in its entirety for all purposes. The cell-penetrating domain can be located at the N-terminus, the C-terminus, or anywhere within the Cas protein.

Cas proteins can also be operably linked to a heterologous polypeptide for ease of tracking or purification, such as a fluorescent protein, a purification tag, or an epitope tag. Examples of fluorescent proteins include green fluorescent proteins (e.g., GFP, GFP-2, tagGFP, turboGFP, eGFP, Emerald, Azami Green, Monomeric Azami Green, CopGFP, AceGFP, ZsGreen1), yellow fluorescent proteins (e.g., YFP, eYFP, Citrine, Venus, YPet, PhiYFP, ZsYellow1), blue fluorescent proteins (e.g., eBFP, eBFP2, Azurite, mKalama1, GFPuv, Sapphire, T-sapphire), cyan fluorescent proteins (e.g., eCFP, Cerulean, CyPet, AmCyan1, Midoriishi-Cyan), red fluorescent proteins (e.g., mKate, mKate2, mPlum, DsRed monomer, mCherry, mRFP1, DsRed-Express, DsRed2, DsRed-Monomer, HcRed-Tandem, HcRed1, AsRed2, eqFP611, mRaspberry, mStrawberry, Jred), orange fluorescent proteins (e.g., mOrange, mKO, Kusabira-Orange, Monomeric Kusabira-Orange, mTangerine, tdTomato), and any other suitable fluorescent protein. Examples of tags include glutathione-S-transferase (GST), chitin binding protein (CBP), maltose binding protein, thioredoxin (TRX), poly(NANP), tandem affinity purification (TAP) tag, myc, AcV5, AU1, AUS, E, ECS, E2, FLAG, hemagglutinin (HA), nus, Softag 1, Softag 3, Strep, SBP, Glu-Glu, HSV, KT3, S, S1, T7, V5, VSV-G, histidine (His), biotin carboxyl carrier protein (BCCP), and calmodulin.

Cas proteins can also be tethered to exogenous donor nucleic acids or labeled nucleic acids. Such tethering (i.e., physical linking) can be achieved through covalent interactions or noncovalent interactions, and the tethering can be direct (e.g., through direct fusion or chemical conjugation, which can be achieved by modification of cysteine or lysine residues on the protein or intein modification), or can be achieved through one or more intervening linkers or adapter molecules such as streptavidin or aptamers. See, e.g., Pierce et al. (2005) *Mini Rev. Med. Chem.* 5(1):41-55; Duckworth et al. (2007) *Angew. Chem. Int. Ed. Engl.* 46(46):8819-8822; Schaeffer and Dixon (2009) *Australian J. Chem.* 62(10): 1328-1332; Goodman et al. (2009) *Chembiochem.* 10(9): 1551-1557; and Khatwani et al. (2012) *Bioorg. Med. Chem.* 20(14):4532-4539, each of which is herein incorporated by reference in its entirety for all purposes. Noncovalent strategies for synthesizing protein-nucleic acid conjugates include biotin-streptavidin and nickel-histidine methods. Covalent protein-nucleic acid conjugates can be synthesized by connecting appropriately functionalized nucleic acids and proteins using a wide variety of chemistries. Some of these chemistries involve direct attachment of the oligonucleotide to an amino acid residue on the protein surface (e.g., a lysine amine or a cysteine thiol), while other more complex schemes require post-translational modification of the protein or the involvement of a catalytic or reactive protein domain. Methods for covalent attachment of proteins to nucleic acids can include, for example, chemical cross-linking of oligonucleotides to protein lysine or cysteine residues, expressed protein-ligation, chemoenzymatic methods, and the use of photoaptamers. The exogenous donor nucleic acid or labeled nucleic acid can be tethered to the C-terminus, the N-terminus, or to an internal region within the Cas protein. In one example, the exogenous donor nucleic acid or labeled nucleic acid is tethered to the C-terminus or the N-terminus of the Cas protein. Likewise, the Cas protein can be tethered to the 5' end, the 3' end, or to an internal region within the exogenous donor nucleic acid or labeled nucleic acid. That is, the exogenous donor nucleic acid or labeled nucleic acid can be tethered in any orientation and polarity. For example, the Cas protein can be tethered to the 5' end or the 3' end of the exogenous donor nucleic acid or labeled nucleic acid.

Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a bacterial cell, a yeast cell, a human cell, a non-human cell, a mammalian cell, a rodent cell, a mouse cell, a rat cell, or any other host cell of interest, as compared to the naturally occurring polynucleotide sequence. When a nucleic acid encoding the Cas protein is introduced into the cell, the Cas protein can be transiently, conditionally, or constitutively expressed in the cell.

Cas proteins provided as mRNAs can be modified for improved stability and/or immunogenicity properties. The modifications may be made to one or more nucleosides within the mRNA. Examples of chemical modifications to mRNA nucleobases include pseudouridine, 1-methyl-pseudouridine, and 5-methyl-cytidine. For example, capped and polyadenylated Cas mRNA containing N1-methyl pseudouridine can be used. Likewise, Cas mRNAs can be modified by depletion of uridine using synonymous codons.

Nucleic acids encoding Cas proteins can be stably integrated in the genome of the cell and operably linked to a promoter active in the cell. Alternatively, nucleic acids encoding Cas proteins can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a targeting vector comprising a nucleic acid insert and/or a vector comprising a DNA encoding a gRNA. Alternatively, it can be in a vector or plasmid that is separate from the targeting vector comprising the nucleic acid insert and/or separate from the vector comprising the DNA encoding the gRNA. Promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, or a zygote. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allow for the generation of compact expression cassettes to facilitate delivery.

Guide RNAs. A "guide RNA" or "gRNA" is an RNA molecule that binds to a Cas protein (e.g., Cas9 protein) and targets the Cas protein to a specific location within a target DNA. Guide RNAs can comprise two segments: a "DNA-targeting segment" and a "protein-binding segment." "Segment" includes a section or region of a molecule, such as a contiguous stretch of nucleotides in an RNA. Some gRNAs, such as those for Cas9, can comprise two separate RNA molecules: an "activator-RNA" (e.g., tracrRNA) and a "targeter-RNA" (e.g., CRISPR RNA or crRNA). Other gRNAs are a single RNA molecule (single RNA polynucleotide), which can also be called a "single-molecule gRNA," a "single-guide RNA," or an "sgRNA." See, e.g., WO 2013/176772, WO 2014/065596, WO 2014/089290, WO 2014/093622, WO 2014/099750, WO 2013/142578, and WO 2014/131833, each of which is herein incorporated by reference in its entirety for all purposes. For Cas9, for example, a single-guide RNA can comprise a crRNA fused to a tracrRNA (e.g., via a linker). For Cpf1, for example, only a crRNA is needed to achieve binding to and/or cleavage of a target sequence. The terms "guide RNA" and "gRNA" include both double-molecule (i.e., modular) gRNAs and single-molecule gRNAs.

An exemplary two-molecule gRNA comprises a crRNA-like ("CRISPR RNA" or "targeter-RNA" or "crRNA" or "crRNA repeat") molecule and a corresponding tracrRNA-like ("trans-acting CRISPR RNA" or "activator-RNA" or "tracrRNA") molecule. A crRNA comprises both the DNA-targeting segment (single-stranded) of the gRNA and a stretch of nucleotides (i.e., the crRNA tail) that forms one half of the dsRNA duplex of the protein-binding segment of the gRNA. An example of a crRNA tail, located downstream (3') of the DNA-targeting segment, comprises, consists essentially of, or consists of GUUUUAGAGCUAUGCU (SEQ ID NO: 87). Any of the DNA-targeting segments disclosed herein can be joined to the 5' end of SEQ ID NO: 87 to form a crRNA.

A corresponding tracrRNA (activator-RNA) comprises a stretch of nucleotides that forms the other half of the dsRNA duplex of the protein-binding segment of the gRNA. A stretch of nucleotides of a crRNA are complementary to and hybridize with a stretch of nucleotides of a tracrRNA to form the dsRNA duplex of the protein-binding domain of the gRNA. As such, each crRNA can be said to have a corresponding tracrRNA. An example of a tracrRNA sequence comprises, consists essentially of, or consists of (SEQ ID NO: 88)
AGCAUAGCAAGUUAAAAUAAGGCUAGUCCGUUAUCAACUUGAAAAAGUGG

CACCGAGUCGGUGCUUU.

In systems in which both a crRNA and a tracrRNA are needed, the crRNA and the corresponding tracrRNA hybridize to form a gRNA. In systems in which only a crRNA is needed, the crRNA can be the gRNA. The crRNA additionally provides the single-stranded DNA-targeting segment that targets a guide RNA target sequence by hybridizing to the opposite strand (i.e., the complementary strand). If used for modification within a cell, the exact sequence of a given crRNA or tracrRNA molecule can be designed to be specific to the species in which the RNA molecules will be used. See, e.g., Mali et al. (2013) Science 339:823-826; Jinek et al. (2012) Science 337:816-821; Hwang et al. (2013) Nat. Biotechnol. 31:227-229; Jiang et al. (2013) Nat. Biotechnol. 31:233-239; and Cong et al. (2013) Science 339:819-823, each of which is herein incorporated by reference in its entirety for all purposes.

The DNA-targeting segment (crRNA) of a given gRNA comprises a nucleotide sequence that is complementary to a sequence (i.e., the complementary strand of the guide RNA recognition sequence on the strand opposite of the guide RNA target sequence) in a target DNA. The DNA-targeting segment of a gRNA interacts with a target DNA in a sequence-specific manner via hybridization (i.e., base pairing). As such, the nucleotide sequence of the DNA-targeting segment may vary and determines the location within the target DNA with which the gRNA and the target DNA will interact. The DNA-targeting segment of a subject gRNA can be modified to hybridize to any desired sequence within a target DNA. Naturally occurring crRNAs differ depending on the CRISPR/Cas system and organism but often contain a targeting segment of between 21 to 72 nucleotides length, flanked by two direct repeats (DR) of a length of between 21 to 46 nucleotides (see, e.g., WO 2014/131833, herein incorporated by reference in its entirety for all purposes). In the case of S. pyogenes, the DRs are 36 nucleotides long and the targeting segment is 30 nucleotides long. The 3' located DR is complementary to and hybridizes with the corresponding tracrRNA, which in turn binds to the Cas protein.

The DNA-targeting segment can have a length of at least about 12 nucleotides, at least about 15 nucleotides, at least about 17 nucleotides, at least about 18 nucleotides, at least about 19 nucleotides, at least about 20 nucleotides, at least about 25 nucleotides, at least about 30 nucleotides, at least about 35 nucleotides, or at least about 40 nucleotides. Such DNA-targeting segments can have a length from about 12 nucleotides to about 100 nucleotides, from about 12 nucleotides to about 80 nucleotides, from about 12 nucleotides to about 50 nucleotides, from about 12 nucleotides to about 40 nucleotides, from about 12 nucleotides to about 30 nucleotides, from about 12 nucleotides to about 25 nucleotides, or from about 12 nucleotides to about 20 nucleotides. For example, the DNA targeting segment can be from about 15 nucleotides to about 25 nucleotides (e.g., from about 17 nucleotides to about 20 nucleotides, or about 17 nucleotides, about 18 nucleotides, about 19 nucleotides, or about 20 nucleotides). See, e.g., US 2016/0024523, herein incorporated by reference in its entirety for all purposes. For Cas9 from S. pyogenes, a typical DNA-targeting segment is between 16 and 20 nucleotides in length or between 17 and 20 nucleotides in length. For Cas9 from S. aureus, a typical DNA-targeting segment is between 21 and 23 nucleotides in length. For Cpf1, a typical DNA-targeting segment is at least 16 nucleotides in length or at least 18 nucleotides in length.

TracrRNAs can be in any form (e.g., full-length tracrRNAs or active partial tracrRNAs) and of varying lengths. They can include primary transcripts or processed forms. For example, tracrRNAs (as part of a single-guide RNA or as a separate molecule as part of a two-molecule gRNA) may comprise, consist essentially of, or consist of all or a portion of a wild type tracrRNA sequence (e.g., about or more than about 20, 26, 32, 45, 48, 54, 63, 67, 85, or more nucleotides of a wild type tracrRNA sequence). Examples of wild type tracrRNA sequences from S. pyogenes include 171-nucleotide, 89-nucleotide, 75-nucleotide, and 65-nucleotide versions. See, e.g., Deltcheva et al. (2011) Nature 471:602-607; WO 2014/093661, each of which is herein incorporated by reference in its entirety for all purposes. Examples of tracrRNAs within single-guide RNAs (sgRNAs) include the tracrRNA segments found within +48, +54, +67, and +85 versions of sgRNAs, where "+n" indicates that up to the +n nucleotide of wild type tracrRNA is included in the sgRNA. See U.S. Pat. No. 8,697,359, herein incorporated by reference in its entirety for all purposes.

The percent complementarity between the DNA-targeting segment and the complementary strand of the guide RNA recognition sequence within the target DNA can be at least 60% (e.g., at least 65%, at least 70%, at least 75%, at least 80%, at least 85%, at least 90%, at least 95%, at least 97%, at least 98%, at least 99%, or 100%). The percent complementarity between the DNA-targeting segment and the complementary strand of the guide RNA recognition sequence within the target DNA can be at least 60% over about 20 contiguous nucleotides. As an example, the percent complementarity between the DNA-targeting segment and the complementary strand of the guide RNA recognition sequence within the target DNA is 100% over the 14 contiguous nucleotides at the 5' end of the complementary strand of the guide RNA recognition sequence within the complementary strand of the target DNA and as low as 0% over the remainder. In such a case, the DNA-targeting segment can be considered to be 14 nucleotides in length. As another example, the percent complementarity between the DNA-targeting segment and the complementary strand of the guide RNA recognition sequence within the target DNA is 100% over the seven contiguous nucleotides at the 5' end of the complementary strand of the guide RNA recognition sequence within the complementary strand of the target DNA and as low as 0% over the remainder. In such a case, the DNA-targeting segment can be considered to be 7 nucleotides in length. In some guide RNAs, at least 17 nucleotides within the DNA-targeting segment are complementary to the target DNA. For example, the DNA-targeting segment can be 20 nucleotides in length and can comprise 1, 2, or 3 mismatches with the complementary strand of the guide RNA recognition sequence. Preferably, the mismatches are not adjacent to a protospacer adjacent motif (PAM) sequence (e.g., the mismatches are in the 5' end of the DNA-targeting segment, or the mismatches are at least 2, 3, 4, 5, 6, 7, 8, 9, 10, 11, 12, 13, 14, 15, 16, 17, 18, or 19 base pairs away from the PAM sequence).

The protein-binding segment of a gRNA can comprise two stretches of nucleotides that are complementary to one another. The complementary nucleotides of the protein-binding segment hybridize to form a double-stranded RNA duplex (dsRNA). The protein-binding segment of a subject gRNA interacts with a Cas protein, and the gRNA directs the bound Cas protein to a specific nucleotide sequence within target DNA via the DNA-targeting segment.

Single-guide RNAs have the DNA-targeting segment and a scaffold sequence (i.e., the protein-binding or Cas-binding sequence of the guide RNA). For example, such guide RNAs have a 5' DNA-targeting segment and a 3' scaffold sequence. Exemplary scaffold sequences comprise, consist essentially of, or consist of:

GUUUUAGAGCUAGAAAUAGCAAGUUAAAAUAAGGCUAGUCCGUUAUCAAC

UUGAAAAAGUGGCACCGAGUCGGUGCU (version 1; SEQ ID NO: 89);

GUUGGAACCAUUCAAAACAGCAUAGCAAGUUAAAAUAAGGCUAGUCCGUU

AUCAACUUGAAAAAGUGGCACCGAGUCGGUGC (version 2; SEQ

ID NO: 8);

GUUUUAGAGCUAGAAAUAGCAAGUUAAAAUAAGGCUAGUCCGUUAUCAAC

UUGAAAAAGUGGCACCGAGUCGGUGC (version 3; SEQ ID NO: 9);

and

GUUUAAGAGCUAUGCUGGAAACAGCAUAGCAAGUUUAAAUAAGGCUAGUC

CGUUAUCAACUUGAAAAAGUGGCACCGAGUCGGUGC (version 4;

SEQ ID NO: 10).

Guide RNAs targeting any guide RNA target sequence can include, for example, a DNA-targeting segment on the 5' end of the guide RNA fused to any of the exemplary guide RNA scaffold sequences on the 3' end of the guide RNA. That is, any of the DNA-targeting segments disclosed herein can be joined to the 5' end of any one of SEQ ID NOS: 89, 8, 9, or 10 to form a single guide RNA (chimeric guide RNA). Guide RNA versions 1, 2, 3, and 4 as disclosed elsewhere herein refer to DNA-targeting segments (i.e., guide sequences or guides) joined with scaffold versions 1, 2, 3, and 4, respectively.

Guide RNAs can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (e.g., a 7-methylguanylate cap (m7G)); a 3' polyadenylated tail (i.e., a 3' poly(A) tail); a riboswitch sequence (e.g., to allow for regulated stability and/or regulated accessibility by proteins and/or protein complexes); a stability control sequence; a sequence that forms a dsRNA duplex (i.e., a hairpin); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth); a modification or sequence that provides a binding site for proteins (e.g., proteins that act on DNA, including DNA methyltransferases, DNA demethylases, histone acetyltransferases, histone deacetylases, and the like); and combinations thereof. Other examples of modifications include engineered stem loop duplex structures, engineered bulge regions, engineered hairpins 3' of the stem loop duplex structure, or any combination thereof. See, e.g., US 2015/0376586, herein incorporated by reference in its entirety for all purposes. A bulge can be an unpaired region of nucleotides within the duplex made up of the crRNA-like region and the minimum tracrRNA-like region. A bulge can comprise, on one side of the duplex, an unpaired 5'-XXXY-3' where X is any purine and Y can be a nucleotide that can form a wobble pair with a nucleotide on the opposite strand, and an unpaired nucleotide region on the other side of the duplex.

Unmodified nucleic acids can be prone to degradation. Exogenous nucleic acids can also induce an innate immune response. Modifications can help introduce stability and reduce immunogenicity. Guide RNAs can comprise modified nucleosides and modified nucleotides including, for example, one or more of the following: (1) alteration or replacement of one or both of the non-linking phosphate oxygens and/or of one or more of the linking phosphate oxygens in the phosphodiester backbone linkage; (2) alteration or replacement of a constituent of the ribose sugar such as alteration or replacement of the 2' hydroxyl on the ribose sugar; (3) replacement of the phosphate moiety with dephospho linkers; (4) modification or replacement of a naturally occurring nucleobase; (5) replacement or modification of the ribose-phosphate backbone; (6) modification of the 3' end or 5' end of the oligonucleotide (e.g., removal, modification or replacement of a terminal phosphate group or conjugation of a moiety); and (7) modification of the sugar. Other possible guide RNA modifications include modifications of or replacement of uracils or poly-uracil tracts. See, e.g., WO 2015/048577 and US 2016/0237455, each of which is herein incorporated by reference in its entirety for all purposes. Similar modifications can be made to Cas-encoding nucleic acids, such as Cas mRNAs.

As one example, nucleotides at the 5' or 3' end of a guide RNA can include phosphorothioate linkages (e.g., the bases can have a modified phosphate group that is a phosphorothioate group). For example, a guide RNA can include phosphorothioate linkages between the 2, 3, or 4 terminal nucleotides at the 5' or 3' end of the guide RNA. As another example, nucleotides at the 5' and/or 3' end of a guide RNA can have 2'-O-methyl modifications. For example, a guide RNA can include 2'-O-methyl modifications at the 2, 3, or 4 terminal nucleotides at the 5' and/or 3' end of the guide RNA (e.g., the 5' end). See, e.g., WO 2017/173054 A1 and Finn et al. (2018) *Cell Reports* 22:1-9, each of which is herein incorporated by reference in its entirety for all purposes. In one specific example, the guide RNA comprises 2'-O-methyl analogs and 3' phosphorothioate internucleotide linkages at the first three 5' and 3' terminal RNA residues. In another specific example, the guide RNA is modified such that all 2' OH groups that do not interact with the Cas9 protein are replaced with 2'-O-methyl analogs, and the tail region of the guide RNA, which has minimal interaction with Cas9, is modified with 5' and 3' phosphorothioate internucleotide linkages. See, e.g., Yin et al. (2017) *Nat. Biotech.* 35(12): 1179-1187, herein incorporated by reference in its entirety for all purposes. Other examples of modified guide RNAs are provided, e.g., in WO 2018/107028 A1, herein incorporated by reference in its entirety for all purposes.

Guide RNAs can be provided in any form. For example, the gRNA can be provided in the form of RNA, either as two molecules (separate crRNA and tracrRNA) or as one molecule (sgRNA), and optionally in the form of a complex with a Cas protein. The gRNA can also be provided in the form of DNA encoding the gRNA. The DNA encoding the gRNA can encode a single RNA molecule (sgRNA) or separate RNA molecules (e.g., separate crRNA and tracrRNA). In the latter case, the DNA encoding the gRNA can be provided as one DNA molecule or as separate DNA molecules encoding the crRNA and tracrRNA, respectively.

When a gRNA is provided in the form of DNA, the gRNA can be transiently, conditionally, or constitutively expressed in the cell. DNAs encoding gRNAs can be stably integrated into the genome of the cell and operably linked to a promoter active in the cell. Alternatively, DNAs encoding gRNAs can be operably linked to a promoter in an expression construct. For example, the DNA encoding the gRNA can be in a vector comprising a heterologous nucleic acid, such as a nucleic acid encoding a Cas protein. Alternatively, it can be in a vector or a plasmid that is separate from the vector comprising the nucleic acid encoding the Cas protein. Promoters that can be used in such expression constructs include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Such promoters can also be, for example, bidirectional promoters. Specific examples of suitable promoters include an RNA polymerase III promoter, such as a human U6 promoter, a rat U6 polymerase III promoter, or a mouse U6 polymerase III promoter.

Alternatively, gRNAs can be prepared by various other methods. For example, gRNAs can be prepared by in vitro transcription using, for example, T7 RNA polymerase (see, e.g., WO 2014/089290 and WO 2014/065596, each of which is herein incorporated by reference in its entirety for all purposes). Guide RNAs can also be a synthetically produced molecule prepared by chemical synthesis.

Guide RNA Recognition Sequences and Guide RNA Target Sequences. The term "guide RNA recognition sequence" includes nucleic acid sequences present in a target DNA to which a DNA-targeting segment of a gRNA will bind, provided sufficient conditions for binding exist. The term guide RNA recognition sequence as used herein encompasses both strands of the target double-stranded DNA (i.e., the sequence on the complementary strand to which the guide RNA hybridizes and the corresponding sequence on the non-complementary strand adjacent to the protospacer adjacent motif (PAM)). The term "guide RNA target sequence" as used herein refers specifically to the sequence on the non-complementary strand adjacent to the PAM (i.e., upstream or 5' of the PAM). That is, the guide RNA target sequence refers to the sequence on the non-complementary strand corresponding to the sequence to which the guide RNA hybridizes on the complementary strand. A guide RNA target sequence is equivalent to the DNA-targeting segment of a guide RNA, but with thymines instead of uracils. As one example, a guide RNA target sequence for a Cas9 enzyme would refer to the sequence on the non-complementary strand adjacent to the 5'-NGG-3' PAM. Guide RNA recognition sequences include sequences to which a guide RNA is designed to have complementarity, where hybridization between the complementary strand of a guide RNA recognition sequence and a DNA-targeting segment of a guide RNA promotes the formation of a CRISPR complex. Full complementarity is not necessarily required, provided that there is sufficient complementarity to cause hybridization and promote formation of a CRISPR complex. Guide RNA recognition sequences or guide RNA target sequences also include cleavage sites for Cas proteins, described in more detail below. A guide RNA recognition sequence or a guide RNA target sequence can comprise any polynucleotide, which can be located, for example, in the nucleus or cytoplasm of a cell or within an organelle of a cell, such as a mitochondrion or chloroplast.

The guide RNA recognition sequence within a target DNA can be targeted by (i.e., be bound by, or hybridize with, or be complementary to) a Cas protein or a gRNA. Suitable DNA/RNA binding conditions include physiological conditions normally present in a cell. Other suitable DNA/RNA binding conditions (e.g., conditions in a cell-free system) are known (see, e.g., Molecular Cloning: A Laboratory Manual, 3rd Ed. (Sambrook et al., Harbor Laboratory Press 2001), herein incorporated by reference in its entirety for all purposes). The strand of the target DNA that is complementary to and hybridizes with the Cas protein or gRNA can be called the "complementary strand," and the strand of the target DNA that is complementary to the "complementary strand" (and is therefore not complementary to the Cas protein or gRNA) can be called "non-complementary strand" or "template strand."

The Cas protein can cleave the nucleic acid at a site within or outside of the nucleic acid sequence present in the target DNA to which the DNA-targeting segment of a gRNA will bind. The "cleavage site" includes the position of a nucleic acid at which a Cas protein produces a single-strand break or a double-strand break. For example, formation of a CRISPR complex (comprising a gRNA hybridized to the complementary strand of a guide RNA recognition sequence and complexed with a Cas protein) can result in cleavage of one or both strands in or near (e.g., within 1, 2, 3, 4, 5, 6, 7, 8, 9, 10, 20, 50, or more base pairs from) the nucleic acid sequence present in a target DNA to which a DNA-targeting segment of a gRNA will bind. If the cleavage site is outside of the nucleic acid sequence to which the DNA-targeting segment of the gRNA will bind, the cleavage site is still considered to be within the "guide RNA recognition sequence" or guide RNA target sequence. The cleavage site can be on only one strand or on both strands of a nucleic acid. Cleavage sites can be at the same position on both strands of the nucleic acid (producing blunt ends) or can be at different sites on each strand (producing staggered ends (i.e., overhangs)). Staggered ends can be produced, for example, by using two Cas proteins, each of which produces a single-strand break at a different cleavage site on a different strand, thereby producing a double-strand break. For example, a first nickase can create a single-strand break on the first strand of double-stranded DNA (dsDNA), and a second nickase can create a single-strand break on the second strand of dsDNA such that overhanging sequences are created. In some cases, the guide RNA recognition sequence or guide RNA target sequence of the nickase on the first strand is separated from the guide RNA recognition sequence or guide RNA target sequence of the nickase on the second strand by at least 2, 3, 4, 5, 6, 7, 8, 9, 10, 15, 20, 25, 30, 40, 50, 75, 100, 250, 500, or 1,000 base pairs.

Site-specific binding and/or cleavage of target DNA by Cas proteins can occur at locations determined by both (i) base-pairing complementarity between the gRNA and the target DNA and (ii) a short motif, called the protospacer adjacent motif (PAM), in the target DNA. The PAM can flank the guide RNA target sequence on the non-complementary strand opposite of the strand to which the guide RNA hybridizes. Optionally, the guide RNA target sequence can be flanked on the 3' end by the PAM. Alternatively, the guide RNA target sequence can be flanked on the 5' end by the PAM. For example, the cleavage site of Cas proteins can be about 1 to about 10 or about 2 to about 5 base pairs (e.g., 3 base pairs) upstream or downstream of the PAM sequence. In some cases (e.g., when Cas9 from *S. pyogenes* or a closely related Cas9 is used), the PAM sequence of the non-complementary strand can be 5'-$N_1$GG-3', where $N_1$ is any DNA nucleotide and is immediately 3' of the guide RNA recognition sequence of the non-complementary strand of the target DNA (i.e., immediately 3' of the guide RNA target sequence). As such, the PAM sequence of the complementary strand would be 5'-CC$N_2$-3', where $N_2$ is any DNA nucleotide and is immediately 5' of the guide RNA recognition sequence of the complementary strand of the target DNA. In some such cases, $N_1$ and $N_2$ can be complementary and the $N_1$-$N_2$ base pair can be any base pair (e.g., $N_1$=C and $N_2$=G; $N_1$=G and $N_2$=C; $N_1$=A and $N_2$=T; or $N_1$=T, and $N_2$=A). In the case of Cas9 from *S. aureus*, the PAM can be NNGRRT or NNGRR, where N can be A, G, C, or T, and R can be G or A. In the case of Cas9 from *C. jejuni*, the PAM can be, for example, NNNNACAC or NNNNRYAC, where N can be A, G, C, or T, and R can be G or A. In some cases (e.g., for FnCpf1), the PAM sequence can be upstream of the 5' end and have the sequence 5'-TTN-3'.

Examples of guide RNA target sequences or guide RNA target sequences in addition to a PAM sequence are provided below. For example, the guide RNA target sequence can be a 20-nucleotide DNA sequence immediately preceding an NGG motif recognized by a Cas9 protein. Examples of such guide RNA target sequences plus a PAM sequence are GN19NGG (SEQ ID NO: 11) or $N_{20}$NGG (SEQ ID NO: 12). See, e.g., WO 2014/165825, herein incorporated by reference in its entirety for all purposes. The guanine at the 5' end can facilitate transcription by RNA polymerase in cells. Other examples of guide RNA target sequences plus a PAM sequence can include two guanine nucleotides at the 5' end (e.g., GG$N_{20}$NGG; SEQ ID NO: 13) to facilitate efficient transcription by T7 polymerase in vitro. See, e.g., WO 2014/065596, herein incorporated by reference in its entirety for all purposes. Other guide RNA target sequences plus a PAM sequence can have between 4-22 nucleotides in length of SEQ ID NOS: 11-13, including the 5' G or GG and the 3' GG or NGG. Yet other guide RNA target sequences can have between 14 and 20 nucleotides in length of SEQ ID NOS: 11-13.

The guide RNA recognition sequence or guide RNA target sequence can be any nucleic acid sequence endogenous or exogenous to a cell. The guide RNA recognition sequence or guide RNA target sequence can be a sequence coding a gene product (e.g., a protein) or a non-coding sequence (e.g., a regulatory sequence) or can include both.

(3) Exogenous Donor Nucleic Acids Targeting Human TTR Gene

The methods and compositions disclosed herein can utilize exogenous donor nucleic acids to modify the humanized TTR locus following cleavage of the humanized TTR locus with a nuclease agent. In such methods, the nuclease agent protein cleaves the humanized TTR locus to create a single-strand break (nick) or double-strand break, and the exogenous donor nucleic acid recombines the humanized TTR locus via non-homologous end joining (NHEJ)-mediated ligation or through a homology-directed repair event. Optionally, repair with the exogenous donor nucleic acid removes or disrupts the nuclease target sequence so that alleles that have been targeted cannot be re-targeted by the nuclease agent.

Exogenous donor nucleic acids can comprise deoxyribonucleic acid (DNA) or ribonucleic acid (RNA), they can be single-stranded or double-stranded, and they can be in linear or circular form. For example, an exogenous donor nucleic acid can be a single-stranded oligodeoxynucleotide (ssODN). See, e.g., Yoshimi et al. (2016) *Nat. Commun.* 7:10431, herein incorporated by reference in its entirety for all purposes. An exemplary exogenous donor nucleic acid is between about 50 nucleotides to about 5 kb in length, is between about 50 nucleotides to about 3 kb in length, or is between about 50 to about 1,000 nucleotides in length. Other exemplary exogenous donor nucleic acids are between about 40 to about 200 nucleotides in length. For example, an exogenous donor nucleic acid can be between about 50-60, 60-70, 70-80, 80-90, 90-100, 100-110, 110-120, 120-130, 130-140, 140-150, 150-160, 160-170, 170-180, 180-190, or 190-200 nucleotides in length. Alternatively, an exogenous donor nucleic acid can be between about 50-100, 100-200, 200-300, 300-400, 400-500, 500-600, 600-700, 700-800, 800-900, or 900-1000 nucleotides in length. Alternatively, an exogenous donor nucleic acid can be between about 1-1.5, 1.5-2, 2-2.5, 2.5-3, 3-3.5, 3.5-4, 4-4.5, or 4.5-5 kb in length. Alternatively, an exogenous donor nucleic acid can be, for example, no more than 5 kb, 4.5 kb, 4 kb, 3.5 kb, 3 kb, 2.5 kb, 2 kb, 1.5 kb, 1 kb, 900 nucleotides, 800 nucleotides, 700 nucleotides, 600 nucleotides, 500 nucleotides, 400 nucleotides, 300 nucleotides, 200 nucleotides, 100 nucleotides, or 50 nucleotides in length. Exogenous donor nucleic acids (e.g., targeting vectors) can also be longer.

In one example, an exogenous donor nucleic acid is an ssODN that is between about 80 nucleotides and about 200 nucleotides in length. In another example, an exogenous donor nucleic acids is an ssODN that is between about 80 nucleotides and about 3 kb in length. Such an ssODN can have homology arms, for example, that are each between about 40 nucleotides and about 60 nucleotides in length.

Such an ssODN can also have homology arms, for example, that are each between about 30 nucleotides and 100 nucleotides in length. The homology arms can be symmetrical (e.g., each 40 nucleotides or each 60 nucleotides in length), or they can be asymmetrical (e.g., one homology arm that is 36 nucleotides in length, and one homology arm that is 91 nucleotides in length).

Exogenous donor nucleic acids can include modifications or sequences that provide for additional desirable features (e.g., modified or regulated stability; tracking or detecting with a fluorescent label; a binding site for a protein or protein complex; and so forth). Exogenous donor nucleic acids can comprise one or more fluorescent labels, purification tags, epitope tags, or a combination thereof. For example, an exogenous donor nucleic acid can comprise one or more fluorescent labels (e.g., fluorescent proteins or other fluorophores or dyes), such as at least 1, at least 2, at least 3, at least 4, or at least 5 fluorescent labels. Exemplary fluorescent labels include fluorophores such as fluorescein (e.g., 6-carboxyfluorescein (6-FAM)), Texas Red, HEX, Cy3, Cy5, Cy5.5, Pacific Blue, 5-(and -6)-carboxytetramethylrhodamine (TAMRA), and Cy7. A wide range of fluorescent dyes are available commercially for labeling oligonucleotides (e.g., from Integrated DNA Technologies). Such fluorescent labels (e.g., internal fluorescent labels) can be used, for example, to detect an exogenous donor nucleic acid that has been directly integrated into a cleaved target nucleic acid having protruding ends compatible with the ends of the exogenous donor nucleic acid. The label or tag can be at the 5' end, the 3' end, or internally within the exogenous donor nucleic acid. For example, an exogenous donor nucleic acid can be conjugated at 5' end with the IR700 fluorophore from Integrated DNA Technologies (5'IRDYE® 700).

Exogenous donor nucleic acids can also comprise nucleic acid inserts including segments of DNA to be integrated at the humanized TTR locus. Integration of a nucleic acid insert at a humanized TTR locus can result in addition of a nucleic acid sequence of interest to the humanized TTR locus, deletion of a nucleic acid sequence of interest at the humanized TTR locus, or replacement of a nucleic acid sequence of interest at the humanized TTR locus (i.e., deletion and insertion). Some exogenous donor nucleic acids are designed for insertion of a nucleic acid insert at the humanized TTR locus without any corresponding deletion at the humanized TTR locus. Other exogenous donor nucleic acids are designed to delete a nucleic acid sequence of interest at the humanized TTR locus without any corresponding insertion of a nucleic acid insert. Yet other exogenous donor nucleic acids are designed to delete a nucleic acid sequence of interest at the humanized TTR locus and replace it with a nucleic acid insert.

The nucleic acid insert or the corresponding nucleic acid at the humanized TTR locus being deleted and/or replaced can be various lengths. An exemplary nucleic acid insert or corresponding nucleic acid at the humanized TTR locus being deleted and/or replaced is between about 1 nucleotide to about 5 kb in length or is between about 1 nucleotide to about 1,000 nucleotides in length. For example, a nucleic acid insert or a corresponding nucleic acid at the humanized TTR locus being deleted and/or replaced can be between about 1-10, 10-20, 20-30, 30-40, 40-50, 50-60, 60-70, 70-80, 80-90, 90-100, 100-110, 110-120, 120-130, 130-140, 140-150, 150-160, 160-170, 170-180, 180-190, or 190-120 nucleotides in length. Likewise, a nucleic acid insert or a corresponding nucleic acid at the humanized TTR locus being deleted and/or replaced can be between 1-100, 100-200, 200-300, 300-400, 400-500, 500-600, 600-700, 700-800, 800-900, or 900-1000 nucleotides in length. Likewise, a nucleic acid insert or a corresponding nucleic acid at the humanized TTR locus being deleted and/or replaced can be between about 1-1.5, 1.5-2, 2-2.5, 2.5-3, 3-3.5, 3.5-4, 4-4.5, or 4.5-5 kb in length or longer.

The nucleic acid insert can comprise a sequence that is homologous or orthologous to all or part of sequence targeted for replacement. For example, the nucleic acid insert can comprise a sequence that comprises one or more point mutations (e.g., 1, 2, 3, 4, 5, or more) compared with a sequence targeted for replacement at the humanized TTR locus. Optionally, such point mutations can result in a conservative amino acid substitution (e.g., substitution of aspartic acid [Asp, D] with glutamic acid [Glu, E]) in the encoded polypeptide.

Donor Nucleic Acids for Non-Homologous-End-Joining-Mediated Insertion. Some exogenous donor nucleic acids have short single-stranded regions at the 5' end and/or the 3' end that are complementary to one or more overhangs created by nuclease-mediated cleavage at the humanized TTR locus. These overhangs can also be referred to as 5' and 3' homology arms. For example, some exogenous donor nucleic acids have short single-stranded regions at the 5' end and/or the 3' end that are complementary to one or more overhangs created by nuclease-mediated cleavage at 5' and/or 3' target sequences at the humanized TTR locus. Some such exogenous donor nucleic acids have a complementary region only at the 5' end or only at the 3' end. For example, some such exogenous donor nucleic acids have a complementary region only at the 5' end complementary to an overhang created at a 5' target sequence at the humanized TTR locus or only at the 3' end complementary to an overhang created at a 3' target sequence at the humanized TTR locus. Other such exogenous donor nucleic acids have complementary regions at both the 5' and 3' ends. For example, other such exogenous donor nucleic acids have complementary regions at both the 5' and 3' ends e.g., complementary to first and second overhangs, respectively, generated by nuclease-mediated cleavage at the humanized TTR locus. For example, if the exogenous donor nucleic acid is double-stranded, the single-stranded complementary regions can extend from the 5' end of the top strand of the donor nucleic acid and the 5' end of the bottom strand of the donor nucleic acid, creating 5' overhangs on each end. Alternatively, the single-stranded complementary region can extend from the 3' end of the top strand of the donor nucleic acid and from the 3' end of the bottom strand of the template, creating 3' overhangs.

The complementary regions can be of any length sufficient to promote ligation between the exogenous donor nucleic acid and the target nucleic acid. Exemplary complementary regions are between about 1 to about 5 nucleotides in length, between about 1 to about 25 nucleotides in length, or between about 5 to about 150 nucleotides in length. For example, a complementary region can be at least about 1, 2, 3, 4, 5, 6, 7, 8, 9, 10, 11, 12, 13, 14, 15, 16, 17, 18, 19, 20, 21, 22, 23, 24, or 25 nucleotides in length. Alternatively, the complementary region can be about 5-10, 10-20, 20-30, 30-40, 40-50, 50-60, 60-70, 70-80, 80-90, 90-100, 100-110, 110-120, 120-130, 130-140, or 140-150 nucleotides in length, or longer.

Such complementary regions can be complementary to overhangs created by two pairs of nickases. Two double-strand breaks with staggered ends can be created by using first and second nickases that cleave opposite strands of DNA to create a first double-strand break, and third and fourth nickases that cleave opposite strands of DNA to create a second double-strand break. For example, a Cas protein can be used to nick first, second, third, and fourth guide RNA target sequences corresponding with first, second, third, and fourth guide RNAs. The first and second guide RNA target sequences can be positioned to create a first cleavage site such that the nicks created by the first and second nickases on the first and second strands of DNA create a double-strand break (i.e., the first cleavage site comprises the nicks within the first and second guide RNA target sequences). Likewise, the third and fourth guide RNA target sequences can be positioned to create a second cleavage site such that the nicks created by the third and fourth nickases on the first and second strands of DNA create a double-strand break (i.e., the second cleavage site comprises the nicks within the third and fourth guide RNA target sequences). Preferably, the nicks within the first and second guide RNA target sequences and/or the third and fourth guide RNA target sequences can be off-set nicks that create overhangs. The offset window can be, for example, at least about 5 bp, 10 bp, 20 bp, 30 bp, 40 bp, 50 bp, 60 bp, 70 bp, 80 bp, 90 bp, 100 bp or more. See Ran et al. (2013) *Cell* 154:1380-1389; Mali et al. (2013) *Nat. Biotech.* 31:833-838; and Shen et al. (2014) *Nat. Methods* 11:399-404, each of which is herein incorporated by reference in its entirety for all purposes. In such cases, a double-stranded exogenous donor nucleic acid can be designed with single-stranded complementary regions that are complementary to the overhangs created by the nicks within the first and second guide RNA target sequences and by the nicks within the third and fourth guide RNA target sequences. Such an exogenous donor nucleic acid can then be inserted by non-homologous-end-joining-mediated ligation.

Donor Nucleic Acids for Insertion by Homology-Directed Repair. Some exogenous donor nucleic acids comprise homology arms. If the exogenous donor nucleic acid also comprises a nucleic acid insert, the homology arms can flank the nucleic acid insert. For ease of reference, the homology arms are referred to herein as 5' and 3' (i.e., upstream and downstream) homology arms. This terminology relates to the relative position of the homology arms to the nucleic acid insert within the exogenous donor nucleic acid. The 5' and 3' homology arms correspond to regions within the humanized TTR locus, which are referred to herein as "5' target sequence" and "3' target sequence," respectively.

A homology arm and a target sequence "correspond" or are "corresponding" to one another when the two regions share a sufficient level of sequence identity to one another to act as substrates for a homologous recombination reaction. The term "homology" includes DNA sequences that are either identical or share sequence identity to a corresponding sequence. The sequence identity between a given target sequence and the corresponding homology arm found in the exogenous donor nucleic acid can be any degree of sequence identity that allows for homologous recombination to occur. For example, the amount of sequence identity shared by the homology arm of the exogenous donor nucleic acid (or a fragment thereof) and the target sequence (or a fragment thereof) can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination. Moreover, a corresponding region of homology between the homology arm and the corresponding target sequence can be of any length that is sufficient to promote homologous recombination. Exemplary homology arms are between about 25 nucleotides to about 2.5 kb in length, are between about 25 nucleotides to about 1.5 kb in length, or are between about 25 to about 500 nucleotides in length. For example, a given homology arm (or each of the homology arms) and/or corresponding target sequence can comprise corresponding regions of homology that are between about 25-30, 30-40, 40-50, 50-60, 60-70, 70-80, 80-90, 90-100, 100-150, 150-200, 200-250, 250-300, 300-350, 350-400, 400-450, or 450-500 nucleotides in length, such that the homology arms have sufficient homology to undergo homologous recombination with the corresponding target sequences within the target nucleic acid. Alternatively, a given homology arm (or each homology arm) and/or corresponding target sequence can comprise corresponding regions of homology that are between about 0.5 kb to about 1 kb, about 1 kb to about 1.5 kb, about 1.5 kb to about 2 kb, or about 2 kb to about 2.5 kb in length. For example, the homology arms can each be about 750 nucleotides in length. The homology arms can be symmetrical (each about the same size in length), or they can be asymmetrical (one longer than the other).

When a nuclease agent is used in combination with an exogenous donor nucleic acid, the 5' and 3' target sequences are preferably located in sufficient proximity to the nuclease cleavage site (e.g., within sufficient proximity to a the nuclease target sequence) so as to promote the occurrence of a homologous recombination event between the target sequences and the homology arms upon a single-strand break (nick) or double-strand break at the nuclease cleavage site. The term "nuclease cleavage site" includes a DNA sequence at which a nick or double-strand break is created by a nuclease agent (e.g., a Cas9 protein complexed with a guide RNA). The target sequences within the targeted locus that correspond to the 5' and 3' homology arms of the exogenous donor nucleic acid are "located in sufficient proximity" to a nuclease cleavage site if the distance is such as to promote the occurrence of a homologous recombination event between the 5' and 3' target sequences and the homology arms upon a single-strand break or double-strand break at the nuclease cleavage site. Thus, the target sequences corresponding to the 5' and/or 3' homology arms of the exogenous donor nucleic acid can be, for example, within at least 1 nucleotide of a given nuclease cleavage site or within at least 10 nucleotides to about 1,000 nucleotides of a given nuclease cleavage site. As an example, the nuclease cleavage site can be immediately adjacent to at least one or both of the target sequences.

The spatial relationship of the target sequences that correspond to the homology arms of the exogenous donor nucleic acid and the nuclease cleavage site can vary. For example, target sequences can be located 5' to the nuclease cleavage site, target sequences can be located 3' to the nuclease cleavage site, or the target sequences can flank the nuclease cleavage site.

(4) Other Human-TTR-Targeting Reagents

The activity of any other known or putative human-TTR-targeting reagent can also be assessed using the non-human animals disclosed herein. Similarly, any other molecule can be screened for human-TTR-targeting activity using the non-human animals disclosed herein.

Examples of other human-TTR-targeting reagents include antisense oligonucleotides (e.g., siRNAs or shRNAs) that act through RNA interference (RNAi). Antisense oligonucleotides (ASOs) or antisense RNAs are short synthetic strings of nucleotides designed to prevent the expression of a targeted protein by selectively binding to the RNA that encodes the targeted protein and thereby preventing translation. These compounds bind to RNA with high affinity and selectivity through well characterized Watson-Crick base pairing (hybridization). RNA interference (RNAi) is an endogenous cellular mechanism for controlling gene expression in which small interfering RNAs (siRNAs) that are bound to the RNA-induced silencing complex (RISC) mediate the cleavage of target messenger RNA (mRNA). Examples of human-TTR-targeting antisense oligonucleotides are known. See, e.g., Ackermann et al. (2012) *Amyloid Suppl* 1:43-44 and Coelho et al. (2013) *N. Engl. J. Med.* 369(9):819-829, each of which is herein incorporated by reference in its entirety for all purposes.

Other human-TTR-targeting reagents include antibodies or antigen-binding proteins designed to specifically bind a human TTR epitope.

Other human-TTR-targeting reagents include small-molecule reagents. One example of such a small-molecule reagent is tafamidis, which functions by kinetic stabilization of the correctly folded tetrameric form of the transthyretin (TTR) protein. See, e.g., Hammarstrom et al. (2003) *Science* 299:713-716, herein incorporated by reference in its entirety for all purposes.

D. Administering Human-TTR-Targeting Reagents to Non-Human Animals or Cells

The methods disclosed herein can comprise introducing into a non-human animal or cell various molecules (e.g., human-TTR-targeting reagents such as therapeutic molecules or complexes), including nucleic acids, proteins, nucleic-acid-protein complexes, or protein complexes. "Introducing" includes presenting to the cell or non-human animal the molecule (e.g., nucleic acid or protein) in such a manner that it gains access to the interior of the cell or to the interior of cells within the non-human animal. The introducing can be accomplished by any means, and two or more of the components (e.g., two of the components, or all of the components) can be introduced into the cell or non-human animal simultaneously or sequentially in any combination. For example, a Cas protein can be introduced into a cell or non-human animal before introduction of a guide RNA, or it can be introduced following introduction of the guide RNA. As another example, an exogenous donor nucleic acid can be introduced prior to the introduction of a Cas protein and a guide RNA, or it can be introduced following introduction of the Cas protein and the guide RNA (e.g., the exogenous donor nucleic acid can be administered about 1, 2, 3, 4, 8, 12, 24, 36, 48, or 72 hours before or after introduction of the Cas protein and the guide RNA). See, e.g., US 2015/0240263 and US 2015/0110762, each of which is herein incorporated by reference in its entirety for all purposes. In addition, two or more of the components can be introduced into the cell or non-human animal by the same delivery method or different delivery methods. Similarly, two or more of the components can be introduced into a non-human animal by the same route of administration or different routes of administration.

In some methods, components of a CRISPR/Cas system are introduced into a non-human animal or cell. A guide RNA can be introduced into a non-human animal or cell in the form of an RNA (e.g., in vitro transcribed RNA) or in the form of a DNA encoding the guide RNA. When introduced in the form of a DNA, the DNA encoding a guide RNA can be operably linked to a promoter active in a cell in the non-human animal. For example, a guide RNA may be delivered via AAV and expressed in vivo under a U6 promoter. Such DNAs can be in one or more expression constructs. For example, such expression constructs can be components of a single nucleic acid molecule. Alternatively, they can be separated in any combination among two or more nucleic acid molecules (i.e., DNAs encoding one or more CRISPR RNAs and DNAs encoding one or more tracrRNAs can be components of a separate nucleic acid molecules).

Likewise, Cas proteins can be provided in any form. For example, a Cas protein can be provided in the form of a protein, such as a Cas protein complexed with a gRNA. Alternatively, a Cas protein can be provided in the form of a nucleic acid encoding the Cas protein, such as an RNA (e.g., messenger RNA (mRNA)) or DNA. Optionally, the nucleic acid encoding the Cas protein can be codon optimized for efficient translation into protein in a particular cell or organism. For example, the nucleic acid encoding the Cas protein can be modified to substitute codons having a higher frequency of usage in a mammalian cell, a rodent cell, a mouse cell, a rat cell, or any other host cell of interest, as compared to the naturally occurring polynucleotide sequence. When a nucleic acid encoding the Cas protein is introduced into a non-human animal, the Cas protein can be transiently, conditionally, or constitutively expressed in a cell in the non-human animal.

Nucleic acids encoding Cas proteins or guide RNAs can be operably linked to a promoter in an expression construct. Expression constructs include any nucleic acid constructs capable of directing expression of a gene or other nucleic acid sequence of interest (e.g., a Cas gene) and which can transfer such a nucleic acid sequence of interest to a target cell. For example, the nucleic acid encoding the Cas protein can be in a vector comprising a DNA encoding one or more gRNAs. Alternatively, it can be in a vector or plasmid that is separate from the vector comprising the DNA encoding one or more gRNAs. Suitable promoters that can be used in an expression construct include promoters active, for example, in one or more of a eukaryotic cell, a human cell, a non-human cell, a mammalian cell, a non-human mammalian cell, a rodent cell, a mouse cell, a rat cell, a hamster cell, a rabbit cell, a pluripotent cell, an embryonic stem (ES) cell, an adult stem cell, a developmentally restricted progenitor cell, an induced pluripotent stem (iPS) cell, or a one-cell stage embryo. Such promoters can be, for example, conditional promoters, inducible promoters, constitutive promoters, or tissue-specific promoters. Optionally, the promoter can be a bidirectional promoter driving expression of both a Cas protein in one direction and a guide RNA in the other direction. Such bidirectional promoters can consist of (1) a complete, conventional, unidirectional Pol III promoter that contains 3 external control elements: a distal sequence element (DSE), a proximal sequence element (PSE), and a TATA box; and (2) a second basic Pol III promoter that includes a PSE and a TATA box fused to the 5' terminus of the DSE in reverse orientation. For example, in the H1 promoter, the DSE is adjacent to the PSE and the TATA box, and the promoter can be rendered bidirectional by creating a hybrid promoter in which transcription in the reverse direction is controlled by appending a PSE and TATA box derived from the U6 promoter. See, e.g., US 2016/0074535, herein incorporated by references in its entirety for all purposes. Use of a bidirectional promoter to express genes encoding a Cas protein and a guide RNA simultaneously allows for the generation of compact expression cassettes to facilitate delivery.

Molecules (e.g., Cas proteins or guide RNAs) introduced into the non-human animal or cell can be provided in compositions comprising a carrier increasing the stability of the introduced molecules (e.g., prolonging the period under given conditions of storage (e.g., −20° C., 4° C., or ambient temperature) for which degradation products remain below a threshold, such below 0.5% by weight of the starting nucleic acid or protein; or increasing the stability in vivo). Non-limiting examples of such carriers include poly(lactic acid) (PLA) microspheres, poly(D,L-lactic-coglycolic-acid) (PLGA) microspheres, liposomes, micelles, inverse micelles, lipid cochleates, and lipid microtubules.

Various methods and compositions are provided herein to allow for introduction of a nucleic acid or protein into a cell or non-human animal. Methods for introducing nucleic acids into various cell types are known and include, for example, stable transfection methods, transient transfection methods, and virus-mediated methods.

Transfection protocols as well as protocols for introducing nucleic acid sequences into cells may vary. Non-limiting transfection methods include chemical-based transfection methods using liposomes; nanoparticles; calcium phosphate (Graham et al. (1973) *Virology* 52 (2): 456-67, Bacchetti et al. (1977) *Proc. Natl. Acad. Sci. USA* 74 (4): 1590-4, and Kriegler, M (1991). Transfer and Expression: A Laboratory Manual. New York: W. H. Freeman and Company. pp. 96-97); dendrimers; or cationic polymers such as DEAE-dextran or polyethylenimine. Non-chemical methods include electroporation, Sono-poration, and optical transfection. Particle-based transfection includes the use of a gene gun, or magnet-assisted transfection (Bertram (2006) *Current Pharmaceutical Biotechnology* 7, 277-28). Viral methods can also be used for transfection.

Introduction of nucleic acids or proteins into a cell can also be mediated by electroporation, by intracytoplasmic injection, by viral infection, by adenovirus, by adeno-associated virus, by lentivirus, by retrovirus, by transfection, by lipid-mediated transfection, or by nucleofection. Nucleofection is an improved electroporation technology that enables nucleic acid substrates to be delivered not only to the cytoplasm but also through the nuclear membrane and into the nucleus. In addition, use of nucleofection in the methods disclosed herein typically requires much fewer cells than regular electroporation (e.g., only about 2 million compared with 7 million by regular electroporation). In one example, nucleofection is performed using the LONZA® NUCLEO-FECTOR™ system.

Introduction of nucleic acids or proteins into a cell (e.g., a zygote) can also be accomplished by microinjection. In zygotes (i.e., one-cell stage embryos), microinjection can be into the maternal and/or paternal pronucleus or into the cytoplasm. If the microinjection is into only one pronucleus, the paternal pronucleus is preferable due to its larger size. Microinjection of an mRNA is preferably into the cytoplasm (e.g., to deliver mRNA directly to the translation machinery), while microinjection of a Cas protein or a polynucleotide encoding a Cas protein or encoding an RNA is preferable into the nucleus/pronucleus. Alternatively, microinjection can be carried out by injection into both the nucleus/pronucleus and the cytoplasm: a needle can first be introduced into the nucleus/pronucleus and a first amount can be injected, and while removing the needle from the one-cell stage embryo a second amount can be injected into the cytoplasm. If a Cas protein is injected into the cytoplasm, the Cas protein preferably comprises a nuclear localization signal to ensure delivery to the nucleus/pronucleus. Methods for carrying out microinjection are well known. See, e.g., Nagy et al. (Nagy A, Gertsenstein M, Vintersten K, Behringer R., 2003, Manipulating the Mouse Embryo. Cold Spring Harbor, New York: Cold Spring Harbor Laboratory Press); see also Meyer et al. (2010) *Proc. Natl. Acad. Sci. USA* 107:15022-15026 and Meyer et al. (2012) *Proc. Natl. Acad. Sci. USA* 109:9354-9359.

Other methods for introducing nucleic acid or proteins into a cell or non-human animal can include, for example, vector delivery, particle-mediated delivery, exosome-mediated delivery, lipid-nanoparticle-mediated delivery, cell-penetrating-peptide-mediated delivery, or implantable-device-mediated delivery. As specific examples, a nucleic acid or protein can be introduced into a cell or non-human animal in a carrier such as a poly(lactic acid) (PLA) microsphere, a poly(D,L-lactic-coglycolic-acid) (PLGA) microsphere, a liposome, a micelle, an inverse micelle, a lipid cochleate, or a lipid microtubule. Some specific examples of delivery to a non-human animal include hydrodynamic delivery, virus-mediated delivery (e.g., adeno-associated virus (AAV)-mediated delivery), and lipid-nanoparticle-mediated delivery.

Introduction of nucleic acids and proteins into cells or non-human animals can be accomplished by hydrodynamic delivery (HDD). Hydrodynamic delivery has emerged as a method for intracellular DNA delivery in vivo. For gene delivery to parenchymal cells, only essential DNA sequences need to be injected via a selected blood vessel, eliminating safety concerns associated with current viral and synthetic vectors. When injected into the bloodstream, DNA is capable of reaching cells in the different tissues accessible to the blood. Hydrodynamic delivery employs the force generated by the rapid injection of a large volume of solution into the incompressible blood in the circulation to overcome the physical barriers of endothelium and cell membranes that prevent large and membrane-impermeable compounds from entering parenchymal cells. In addition to the delivery of DNA, this method is useful for the efficient intracellular delivery of RNA, proteins, and other small compounds in vivo. See, e.g., Bonamassa et al. (2011) *Pharm. Res.* 28(4): 694-701, herein incorporated by reference in its entirety for all purposes.

Introduction of nucleic acids can also be accomplished by virus-mediated delivery, such as AAV-mediated delivery or lentivirus-mediated delivery. Other exemplary viruses/viral vectors include retroviruses, adenoviruses, vaccinia viruses, poxviruses, and herpes simplex viruses. The viruses can infect dividing cells, non-dividing cells, or both dividing and non-dividing cells. The viruses can integrate into the host genome or alternatively do not integrate into the host genome. Such viruses can also be engineered to have reduced immunity. The viruses can be replication-competent or can be replication-defective (e.g., defective in one or more genes necessary for additional rounds of virion replication and/or packaging). Viruses can cause transient expression, long-lasting expression (e.g., at least 1 week, 2 weeks, 1 month, 2 months, or 3 months), or permanent expression (e.g., of Cas9 and/or gRNA). Exemplary viral titers (e.g., AAV titers) include $10^{12}$, $10^{13}$, $10^{14}$, $10^{15}$, and $10^{16}$ vector genomes/mL.

The ssDNA AAV genome consists of two open reading frames, Rep and Cap, flanked by two inverted terminal repeats that allow for synthesis of the complementary DNA strand. When constructing an AAV transfer plasmid, the transgene is placed between the two ITRs, and Rep and Cap can be supplied in trans. In addition to Rep and Cap, AAV can require a helper plasmid containing genes from adenovirus. These genes (E4, E2a, and VA) mediated AAV replication. For example, the transfer plasmid, Rep/Cap, and the helper plasmid can be transfected into HEK293 cells containing the adenovirus gene E1+ to produce infectious AAV particles. Alternatively, the Rep, Cap, and adenovirus helper genes may be combined into a single plasmid. Similar packaging cells and methods can be used for other viruses, such as retroviruses.

Multiple serotypes of AAV have been identified. These serotypes differ in the types of cells they infect (i.e., their tropism), allowing preferential transduction of specific cell types. Serotypes for CNS tissue include AAV1, AAV2, AAV4, AAV5, AAV8, and AAV9. Serotypes for heart tissue include AAV1, AAV8, and AAV9. Serotypes for kidney tissue include AAV2. Serotypes for lung tissue include AAV4, AAV5, AAV6, and AAV9. Serotypes for pancreas tissue include AAV8. Serotypes for photoreceptor cells include AAV2, AAV5, and AAV8. Serotypes for retinal pigment epithelium tissue include AAV1, AAV2, AAV4, AAV5, and AAV8. Serotypes for skeletal muscle tissue include AAV1, AAV6, AAV7, AAV8, and AAV9. Serotypes for liver tissue include AAV7, AAV8, and AAV9, and particularly AAV8.

Tropism can be further refined through pseudotyping, which is the mixing of a capsid and a genome from different viral serotypes. For example AAV2/5 indicates a virus containing the genome of serotype 2 packaged in the capsid from serotype 5. Use of pseudotyped viruses can improve transduction efficiency, as well as alter tropism. Hybrid capsids derived from different serotypes can also be used to alter viral tropism. For example, AAV-DJ contains a hybrid capsid from eight serotypes and displays high infectivity across a broad range of cell types in vivo. AAV-DJ8 is another example that displays the properties of AAV-DJ but with enhanced brain uptake. AAV serotypes can also be modified through mutations. Examples of mutational modifications of AAV2 include Y444F, Y500F, Y730F, and S662V. Examples of mutational modifications of AAV3 include Y705F, Y731F, and T492V. Examples of mutational modifications of AAV6 include S663V and T492V. Other pseudotyped/modified AAV variants include AAV2/1, AAV2/6, AAV2/7, AAV2/8, AAV2/9, AAV2.5, AAV8.2, and AAV/SASTG.

To accelerate transgene expression, self-complementary AAV (scAAV) variants can be used. Because AAV depends on the cell's DNA replication machinery to synthesize the complementary strand of the AAV's single-stranded DNA genome, transgene expression may be delayed. To address this delay, scAAV containing complementary sequences that are capable of spontaneously annealing upon infection can be used, eliminating the requirement for host cell DNA synthesis. However, single-stranded AAV (ssAAV) vectors can also be used.

To increase packaging capacity, longer transgenes may be split between two AAV transfer plasmids, the first with a 3' splice donor and the second with a 5' splice acceptor. Upon co-infection of a cell, these viruses form concatemers, are spliced together, and the full-length transgene can be expressed. Although this allows for longer transgene expression, expression is less efficient. Similar methods for increasing capacity utilize homologous recombination. For example, a transgene can be divided between two transfer plasmids but with substantial sequence overlap such that co-expression induces homologous recombination and expression of the full-length transgene.

Introduction of nucleic acids and proteins can also be accomplished by lipid nanoparticle (LNP)-mediated delivery. For example, LNP-mediated delivery can be used to deliver a combination of Cas mRNA and guide RNA or a combination of Cas protein and guide RNA. Delivery through such methods results in transient Cas expression, and the biodegradable lipids improve clearance, improve tolerability, and decrease immunogenicity. Lipid formulations can protect biological molecules from degradation while improving their cellular uptake. Lipid nanoparticles are particles comprising a plurality of lipid molecules physically associated with each other by intermolecular forces. These include microspheres (including unilamellar and multilamellar vesicles, e.g., liposomes), a dispersed phase in an emulsion, micelles, or an internal phase in a suspension. Such lipid nanoparticles can be used to encapsulate one or more nucleic acids or proteins for delivery. Formulations which contain cationic lipids are useful for delivering polyanions such as nucleic acids. Other lipids that can be included are neutral lipids (i.e., uncharged or zwitterionic lipids), anionic lipids, helper lipids that enhance transfection, and stealth lipids that increase the length of time for which nanoparticles can exist in vivo. Examples of suitable cationic lipids, neutral lipids, anionic lipids, helper lipids, and stealth lipids can be found in WO 2016/010840 A1, herein incorporated by reference in its entirety for all purposes. An exemplary lipid nanoparticle can comprise a cationic lipid and one or more other components. In one example, the other component can comprise a helper lipid such as cholesterol. In another example, the other components can comprise a helper lipid such as cholesterol and a neutral lipid such as DSPC. In another example, the other components can comprise a helper lipid such as cholesterol, an optional neutral lipid such as DSPC, and a stealth lipid such as S010, 5024, 5027, 5031, or 5033.

The LNP may contain one or more or all of the following: (i) a lipid for encapsulation and for endosomal escape; (ii) a neutral lipid for stabilization; (iii) a helper lipid for stabilization; and (iv) a stealth lipid. See, e.g., Finn et al. (2018) *Cell Reports* 22:1-9 and WO 2017/173054 A1, each of which is herein incorporated by reference in its entirety for all purposes. In certain LNPs, the cargo can include a guide RNA or a nucleic acid encoding a guide RNA. In certain LNPs, the cargo can include an mRNA encoding a Cas nuclease, such as Cas9, and a guide RNA or a nucleic acid encoding a guide RNA.

The lipid for encapsulation and endosomal escape can be a cationic lipid. The lipid can also be a biodegradable lipid, such as a biodegradable ionizable lipid. One example of a suitable lipid is Lipid A or LP01, which is (9Z,12Z)-3-((4, 4-bis(octyloxy)butanoyl)oxy)-2-((((3-(diethylamino) propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z, 12Z)-octadeca-9,12-dienoate. See, e.g., Finn et al. (2018) *Cell Reports* 22:1-9 and WO 2017/173054 A1, each of which is herein incorporated by reference in its entirety for all purposes. Another example of a suitable lipid is Lipid B, which is ((5-((dimethylamino)methyl)-1,3-phenylene)bis (oxy))bis(octane-8,1-diyl)bis(decanoate), also called ((5-((dimethylamino)methyl)-1,3-phenylene)bis(oxy))bis(octane-8,1-diyl)bis(decanoate). Another example of a suitable lipid is Lipid C, which is 2-((4-(((3-(dimethylamino) propoxy)carbonyl)oxy)hexadecanoyl)oxy)propane-1,3-diyl (9Z,9'Z,12Z,12'Z)-bis(octadeca-9,12-dienoate). Another example of a suitable lipid is Lipid D, which is 3-(((3-(dimethylamino)propoxy)carbonyl)oxy)-13-(octanoyloxy) tridecyl 3-octylundecanoate. Other suitable lipids include heptatriaconta-6,9,28,31-tetraen-19-yl 4-(dimethylamino) butanoate (also known as Dlin-MC3-DMA (MC3))).

Some such lipids suitable for use in the LNPs described herein are biodegradable in vivo. For example, LNPs comprising such a lipid include those where at least 75% of the lipid is cleared from the plasma within 8, 10, 12, 24, or 48 hours, or 3, 4, 5, 6, 7, or 10 days. As another example, at least 50% of the LNP is cleared from the plasma within 8, 10, 12, 24, or 48 hours, or 3, 4, 5, 6, 7, or 10 days.

Such lipids may be ionizable depending upon the pH of the medium they are in. For example, in a slightly acidic medium, the lipids may be protonated and thus bear a positive charge. Conversely, in a slightly basic medium, such as, for example, blood where pH is approximately 7.35, the lipids may not be protonated and thus bear no charge. In some embodiments, the lipids may be protonated at a pH of at least about 9, 9.5, or 10. The ability of such a lipid to bear a charge is related to its intrinsic pKa. For example, the lipid may, independently, have a pKa in the range of from about 5.8 to about 6.2.

Neutral lipids function to stabilize and improve processing of the LNPs. Examples of suitable neutral lipids include a variety of neutral, uncharged or zwitterionic lipids. Examples of neutral phospholipids suitable for use in the present disclosure include, but are not limited to, 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphosphatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine, and combinations thereof. For example, the neutral phospholipid may be selected from the group consisting of distearoylphosphatidylcholine (DSPC) and dimyristoyl phosphatidyl ethanolamine (DMPE).

Helper lipids include lipids that enhance transfection. The mechanism by which the helper lipid enhances transfection can include enhancing particle stability. In certain cases, the helper lipid can enhance membrane fusogenicity. Helper lipids include steroids, sterols, and alkyl resorcinols. Examples of suitable helper lipids suitable include cholesterol, 5-heptadecylresorcinol, and cholesterol hemisuccinate. In one example, the helper lipid may be cholesterol or cholesterol hemisuccinate.

Stealth lipids include lipids that alter the length of time the nanoparticles can exist in vivo. Stealth lipids may assist in the formulation process by, for example, reducing particle aggregation and controlling particle size. Stealth lipids may modulate pharmacokinetic properties of the LNP. Suitable stealth lipids include lipids having a hydrophilic head group linked to a lipid moiety.

The hydrophilic head group of stealth lipid can comprise, for example, a polymer moiety selected from polymers based on PEG (sometimes referred to as poly(ethylene oxide)), poly(oxazoline), poly(vinyl alcohol), poly(glycerol), poly(N-vinylpyrrolidone), polyaminoacids, and poly N-(2-hydroxypropyl)methacrylamide. The term PEG means any polyethylene glycol or other polyalkylene ether polymer. In certain LNP formulations, the PEG, is a PEG-2K, also termed PEG 2000, which has an average molecular weight of about 2,000 daltons. See, e.g., WO 2017/173054 A1, herein incorporated by reference in its entirety for all purposes.

The lipid moiety of the stealth lipid may be derived, for example, from diacylglycerol or diacylglycamide, including those comprising a dialkylglycerol or dialkylglycamide group having alkyl chain length independently comprising from about C4 to about C40 saturated or unsaturated carbon atoms, wherein the chain may comprise one or more functional groups such as, for example, an amide or ester. The dialkylglycerol or dialkylglycamide group can further comprise one or more substituted alkyl groups.

As one example, the stealth lipid may be selected from PEG-dilauroylglycerol, PEG-dimyristoylglycerol (PEG-DMG), PEG-dipalmitoylglycerol, PEG-di stearoylglycerol (PEG-DSPE), PEG-dilaurylglycamide, PEG-dimyristylglycamide, PEG-dipalmitoylglycamide, and PEG-di stearoylglycamide, PEG-cholesterol (1-[8'-(Cholest-5-en-3[beta]-oxy)carboxamido-3',6'-dioxaoctanyl]carbamoyl-[omega]-methyl-poly(ethylene glycol), PEG-DMB (3,4-ditetradecoxylbenzyl-[omega]-methyl-poly(ethylene glycol)ether), 1,2-dimyristoyl-sn-glycero-3-phosphoethanolamine-N-[methoxy(polyethylene glycol)-2000] (PEG2k-DMG), 1,2-distearoyl-sn-glycero-3-phosphoethanolamine-N-[methoxy(polyethylene glycol)-2000] (PEG2k-DSPE), 1,2-distearoyl-sn-glycerol, methoxypoly ethylene glycol (PEG2k-DSG), poly(ethylene glycol)-2000-dimethacrylate (PEG2k-DMA), and 1,2-distearyloxypropyl-3-amine-N-[methoxy(polyethylene glycol)-2000] (PEG2k-DSA). In one particular example, the stealth lipid may be PEG2k-DMG.

The LNPs can comprise different respective molar ratios of the component lipids in the formulation. The mol-% of the CCD lipid may be, for example, from about 30 mol-% to about 60 mol-%, from about 35 mol-% to about 55 mol-%, from about 40 mol-% to about 50 mol-%, from about 42 mol-% to about 47 mol-%, or about 45%. The mol-% of the helper lipid may be, for example, from about 30 mol-% to about 60 mol-%, from about 35 mol-% to about 55 mol-%, from about 40 mol-% to about 50 mol-%, from about 41 mol-% to about 46 mol-%, or about 44 mol-%. The mol-% of the neutral lipid may be, for example, from about 1 mol-% to about 20 mol-%, from about 5 mol-% to about 15 mol-%, from about 7 mol-% to about 12 mol-%, or about 9 mol-%. The mol-% of the stealth lipid may be, for example, from about 1 mol-% to about 10 mol-%, from about 1 mol-% to about 5 mol-%, from about 1 mol-% to about 3 mol-%, about 2 mol-%, or about 1 mol-%.

The LNPs can have different ratios between the positively charged amine groups of the biodegradable lipid (N) and the negatively charged phosphate groups (P) of the nucleic acid to be encapsulated. This may be mathematically represented by the equation N/P. For example, the N/P ratio may be from about 0.5 to about 100, from about 1 to about 50, from about 1 to about 25, from about 1 to about 10, from about 1 to about 7, from about 3 to about 5, from about 4 to about 5, about 4, about 4.5, or about 5. The N/P ratio can also be from about 4 to about 7 or from about 4.5 to about 6. In specific examples, the N/P ratio can be 4.5 or can be 6.

In some LNPs, the cargo can comprise Cas mRNA and gRNA. The Cas mRNA and gRNAs can be in different ratios. For example, the LNP formulation can include a ratio of Cas mRNA to gRNA nucleic acid ranging from about 25:1 to about 1:25, ranging from about 10:1 to about 1:10, ranging from about 5:1 to about 1:5, or about 1:1. Alternatively, the LNP formulation can include a ratio of Cas mRNA to gRNA nucleic acid from about 1:1 to about 1:5, or about 10:1. Alternatively, the LNP formulation can include a ratio of Cas mRNA to gRNA nucleic acid of about 1:10, 25:1, 10:1, 5:1, 3:1, 1:1, 1:3, 1:5, 1:10, or 1:25. Alternatively, the LNP formulation can include a ratio of Cas mRNA to gRNA nucleic acid of from about 1:1 to about 1:2. In specific examples, the ratio of Cas mRNA to gRNA can be about 1:1 or about 1:2.

In some LNPs, the cargo can comprise exogenous donor nucleic acid and gRNA. The exogenous donor nucleic acid and gRNAs can be in different ratios. For example, the LNP formulation can include a ratio of exogenous donor nucleic acid to gRNA nucleic acid ranging from about 25:1 to about 1:25, ranging from about 10:1 to about 1:10, ranging from about 5:1 to about 1:5, or about 1:1. Alternatively, the LNP formulation can include a ratio of exogenous donor nucleic acid to gRNA nucleic acid from about 1:1 to about 1:5, about 5:1 to about 1:1, about 10:1, or about 1:10. Alternatively, the LNP formulation can include a ratio of exogenous donor nucleic acid to gRNA nucleic acid of about 1:10, 25:1, 10:1, 5:1, 3:1, 1:1, 1:3, 1:5, 1:10, or 1:25.

A specific example of a suitable LNP has a nitrogen-to-phosphate (N/P) ratio of 4.5 and contains biodegradable cationic lipid, cholesterol, DSPC, and PEG2k-DMG in a 45:44:9:2 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl) propyl (9Z,12Z)-octadeca-9,12-dienoate. See, e.g., Finn et al. (2018) *Cell Reports* 22:1-9, herein incorporated by reference in its entirety for all purposes. The Cas9 mRNA can be in a 1:1 ratio by weight to the guide RNA. Another specific example of a suitable LNP contains Dlin-MC3-DMA (MC3), cholesterol, DSPC, and PEG-DMG in a 50:38.5:10:1.5 molar ratio.

Another specific example of a suitable LNP has a nitrogen-to-phosphate (N/P) ratio of 6 and contains biodegradable cationic lipid, cholesterol, DSPC, and PEG2k-DMG in a 50:38:9:3 molar ratio. The biodegradable cationic lipid can be (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl) propyl (9Z,12Z)-octadeca-9,12-dienoate. The Cas9 mRNA can be in a 1:2 ratio by weight to the guide RNA.

The mode of delivery can be selected to decrease immunogenicity. For example, a Cas protein and a gRNA may be delivered by different modes (e.g., bi-modal delivery). These different modes may confer different pharmacodynamics or pharmacokinetic properties on the subject delivered molecule (e.g., Cas or nucleic acid encoding, gRNA or nucleic acid encoding, or exogenous donor nucleic acid/repair template). For example, the different modes can result in different tissue distribution, different half-life, or different temporal distribution. Some modes of delivery (e.g., delivery of a nucleic acid vector that persists in a cell by autonomous replication or genomic integration) result in more persistent expression and presence of the molecule, whereas other modes of delivery are transient and less persistent (e.g., delivery of an RNA or a protein). Delivery of Cas proteins in a more transient manner, for example as mRNA or protein, can ensure that the Cas/gRNA complex is only present and active for a short period of time and can reduce immunogenicity caused by peptides from the bacterially-derived Cas enzyme being displayed on the surface of the cell by WIC molecules. Such transient delivery can also reduce the possibility of off-target modifications.

Administration in vivo can be by any suitable route including, for example, parenteral, intravenous, oral, subcutaneous, intra-arterial, intracranial, intrathecal, intraperitoneal, topical, intranasal, or intramuscular. Systemic modes of administration include, for example, oral and parenteral routes. Examples of parenteral routes include intravenous, intraarterial, intraosseous, intramuscular, intradermal, subcutaneous, intranasal, and intraperitoneal routes. A specific example is intravenous infusion. Nasal instillation and intravitreal injection are other specific examples. Local modes of administration include, for example, intrathecal, intracerebroventricular, intraparenchymal (e.g., localized intraparenchymal delivery to the striatum (e.g., into the caudate or into the putamen), cerebral cortex, precentral gyms, hippocampus (e.g., into the dentate gyrus or CA3 region), temporal cortex, amygdala, frontal cortex, thalamus, cerebellum, medulla, hypothalamus, tectum, tegmentum, or substantia nigra), intraocular, intraorbital, subconjuctival, intravitreal, subretinal, and transscleral routes. Significantly smaller amounts of the components (compared with systemic approaches) may exert an effect when administered locally (for example, intraparenchymal or intravitreal) compared to when administered systemically (for example, intravenously). Local modes of administration may also reduce or eliminate the incidence of potentially toxic side effects that may occur when therapeutically effective amounts of a component are administered systemically.

Administration in vivo can be by any suitable route including, for example, parenteral, intravenous, oral, subcutaneous, intra-arterial, intracranial, intrathecal, intraperitoneal, topical, intranasal, or intramuscular. A specific example is intravenous infusion. Compositions comprising the guide RNAs and/or Cas proteins (or nucleic acids encoding the guide RNAs and/or Cas proteins) can be formulated using one or more physiologically and pharmaceutically acceptable carriers, diluents, excipients or auxiliaries. The formulation can depend on the route of administration chosen. The term "pharmaceutically acceptable" means that the carrier, diluent, excipient, or auxiliary is compatible with the other ingredients of the formulation and not substantially deleterious to the recipient thereof.

The frequency of administration and the number of dosages can be depend on the half-life of the exogenous donor nucleic acids, guide RNAs, or Cas proteins (or nucleic acids encoding the guide RNAs or Cas proteins) and the route of administration among other factors. The introduction of nucleic acids or proteins into the cell or non-human animal can be performed one time or multiple times over a period of time. For example, the introduction can be performed at least two times over a period of time, at least three times over a period of time, at least four times over a period of time, at least five times over a period of time, at least six times over a period of time, at least seven times over a period of time, at least eight times over a period of time, at least nine times over a period of times, at least ten times over a period of time, at least eleven times, at least twelve times over a period of time, at least thirteen times over a period of time, at least fourteen times over a period of time, at least fifteen times over a period of time, at least sixteen times over a period of time, at least seventeen times over a period of time, at least eighteen times over a period of time, at least nineteen times over a period of time, or at least twenty times over a period of time.

E. Measuring Delivery, Activity, or Efficacy of Human-TTR-Targeting Reagents In Vivo or Ex Vivo The methods disclosed herein can further comprise detecting or measuring activity of human-TTR-targeting reagents. For example, if the human-TTR-targeting reagent is a genome editing reagent (e.g., CRISPR/Cas designed to target the human TTR locus), the measuring can comprise assessing the humanized TTR locus for modifications.

Various methods can be used to identify cells having a targeted genetic modification. The screening can comprise a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence. Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, herein incorporated by reference in its entirety for all purposes).

Next-generation sequencing (NGS) can also be used for screening. Next-generation sequencing can also be referred to as "NGS" or "massively parallel sequencing" or "high throughput sequencing." NGS can be used as a screening tool in addition to the MOA assays to define the exact nature of the targeted genetic modification and whether it is consistent across cell types or tissue types or organ types.

Assessing modification of the humanized TTR locus in a non-human animal can be in any cell type from any tissue or organ. For example, the assessment can be in multiple cell types from the same tissue or organ or in cells from multiple locations within the tissue or organ. This can provide information about which cell types within a target tissue or organ are being targeted or which sections of a tissue or organ are being reached by the human-TTR-targeting reagent. As another example, the assessment can be in multiple types of tissue or in multiple organs. In methods in which a particular tissue, organ, or cell type is being targeted, this can provide information about how effectively that tissue or organ is being targeted and whether there are off-target effects in other tissues or organs.

If the reagent is designed to inactivate the humanized TTR locus, affect expression of the humanized TTR locus, prevent translation of the humanized TTR mRNA, or clear the humanized TTR protein, the measuring can comprise assessing humanized TTR mRNA or protein expression. This measuring can be within the liver or particular cell types or regions within the liver, or it can involve measuring serum levels of secreted humanized TTR protein.

Production and secretion of the humanized TTR protein can be assessed by any known means. For example, expression can be assessed by measuring levels of the encoded mRNA in the liver of the non-human animal or levels of the encoded protein in the liver of the non-human animal using known assays. Secretion of the humanized TTR protein can be assessed by measuring or plasma levels or serum levels of the encoded humanized TTR protein in the non-human animal using known assays.

IV. Methods of Making Non-Human Animals Comprising a Humanized TTR Locus

Various methods are provided for making a non-human animal comprising a humanized TTR locus as disclosed elsewhere herein. Any convenient method or protocol for producing a genetically modified organism is suitable for producing such a genetically modified non-human animal. See, e.g., Cho et al. (2009) *Current Protocols in Cell Biology* 42:19.11:19.11.1-19.11.22 and Gama Sosa et al. (2010) *Brain Struct. Funct.* 214(2-3):91-109, each of which is herein incorporated by reference in its entirety for all purposes. Such genetically modified non-human animals can be generated, for example, through gene knock-in at a targeted Ttr locus.

For example, the method of producing a non-human animal comprising a humanized TTR locus can comprise: (1) modifying the genome of a pluripotent cell to comprise the humanized TTR locus; (2) identifying or selecting the genetically modified pluripotent cell comprising the humanized TTR locus; (3) introducing the genetically modified pluripotent cell into a non-human animal host embryo; and (4) implanting and gestating the host embryo in a surrogate mother. Optionally, the host embryo comprising modified pluripotent cell (e.g., a non-human ES cell) can be incubated until the blastocyst stage before being implanted into and gestated in the surrogate mother to produce an F0 non-human animal. The surrogate mother can then produce an F0 generation non-human animal comprising the humanized TTR locus.

The methods can further comprise identifying a cell or animal having a modified target genomic locus (i.e., a humanized TTR locus). Various methods can be used to identify cells and animals having a targeted genetic modification.

The screening step can comprise, for example, a quantitative assay for assessing modification of allele (MOA) of a parental chromosome. For example, the quantitative assay can be carried out via a quantitative PCR, such as a real-time PCR (qPCR). The real-time PCR can utilize a first primer set that recognizes the target locus and a second primer set that recognizes a non-targeted reference locus. The primer set can comprise a fluorescent probe that recognizes the amplified sequence.

Other examples of suitable quantitative assays include fluorescence-mediated in situ hybridization (FISH), comparative genomic hybridization, isothermic DNA amplification, quantitative hybridization to an immobilized probe(s), INVADER® Probes, TAQMAN® Molecular Beacon probes, or ECLIPSE™ probe technology (see, e.g., US 2005/0144655, incorporated herein by reference in its entirety for all purposes).

An example of a suitable pluripotent cell is an embryonic stem (ES) cell (e.g., a mouse ES cell or a rat ES cell). The modified pluripotent cell can be generated, for example, through recombination by (a) introducing into the cell one or more targeting vectors comprising an insert nucleic acid flanked by 5' and 3' homology arms corresponding to 5' and 3' target sites, wherein the insert nucleic acid comprises a humanized TTR locus; and (b) identifying at least one cell comprising in its genome the insert nucleic acid integrated at the endogenous Ttr locus. Alternatively, the modified pluripotent cell can be generated by (a) introducing into the cell: (i) a nuclease agent, wherein the nuclease agent induces a nick or double-strand break at a target sequence within the endogenous Ttr locus; and (ii) one or more targeting vectors comprising an insert nucleic acid flanked by 5' and 3' homology arms corresponding to 5' and 3' target sites located in sufficient proximity to the target sequence, wherein the insert nucleic acid comprises the humanized TTR locus; and (c) identifying at least one cell comprising a modification (e.g., integration of the insert nucleic acid) at the endogenous Ttr locus. Any nuclease agent that induces a nick or double-strand break into a desired target sequence can be used. Examples of suitable nucleases include a Transcription Activator-Like Effector Nuclease (TALEN), a zinc-finger nuclease (ZFN), a meganuclease, and Clustered Regularly Interspersed Short Palindromic Repeats (CRISPR)/CRISPR-associated (Cas) systems or components of such systems (e.g., CRISPR/Cas9). See, e.g., US 2013/0309670 and US 2015/0159175, each of which is herein incorporated by reference in its entirety for all purposes.

In a specific example, a method of making a non-human animal comprising a humanized TTR locus can comprise: (a) introducing into a non-human animal embryonic stem (ES) cell: (i) a nuclease agent that targets a target sequence in the endogenous Ttr locus; and (ii) a targeting vector comprising a nucleic acid insert comprising the human TTR sequence flanked by a 5' homology arm corresponding to a 5' target sequence in the endogenous Ttr locus and a 3' homology arm corresponding to a 3' target sequence in the endogenous Ttr locus, wherein the targeting vector recombines with the endogenous Ttr locus to produce a genetically modified non-human ES cell comprising in its genome the genetically modified endogenous Ttr locus comprising the human TTR sequence; (b) introducing the genetically modified non-human ES cell into a non-human animal host embryo; and (c) gestating the non-human animal host embryo in a surrogate mother, wherein the surrogate mother produces an F0 progeny genetically modified non-human animal comprising in its genome the genetically modified endogenous Ttr locus comprising the human TTR sequence.

In some such methods, the nuclease agent can comprise a Cas protein (e.g., a Cas9 protein) and a guide RNA that targets a target sequence in the endogenous Ttr locus, but other suitable nuclease agents can also be used. CRISPR/Cas and CRISPR/Cas9 systems are described in more detail elsewhere herein. Optionally, two or more (e.g., three or four) nuclease agents (e.g., guide RNAs) can be used. The target sequence(s) can be any suitable target sequence within the endogenous Ttr locus. For example, the target sequence(s) can be within about 10, about 20, about 30, about 40, about 50, about 100, about 200, about 300, about 400, about 500, about 1000 nucleotides about 2000, about 3000, about 4000, or about 5000 nucleotides of the start codon and/or the stop codon (e.g., one target sequence in proximity to the start codon and one target sequence in proximity to the stop codon).

In some such methods, the targeting vector is a large targeting vector at least 10 kb in length or in which the sum total of the 5' and 3' homology arms is at least 10 kb in length, but other types of exogenous donor nucleic acids can also be used and are well-known. The 5' and 3' homology arms can correspond with 5' and 3' target sequences, respectively, that flank the region being replaced by the human TTR insert nucleic acid or that flank the region into which the human TTR insert nucleic acid is to be inserted. The exogenous donor nucleic acid or targeting vector can recombine with the target locus via homology directed repair or can be inserted via NHEJ-mediated insertion to generate the humanized TTR locus.

The donor cell can be introduced into a host embryo at any stage, such as the blastocyst stage or the pre-morula stage (i.e., the 4 cell stage or the 8 cell stage). Progeny that are capable of transmitting the genetic modification though the germline are generated. See, e.g., U.S. Pat. No. 7,294,754, herein incorporated by reference in its entirety for all purposes.

Alternatively, the method of producing the non-human animals described elsewhere herein can comprise: (1) modifying the genome of a one-cell stage embryo to comprise the humanized TTR locus using the methods described above for modifying pluripotent cells; (2) selecting the genetically modified embryo; and (3) implanting and gestating the genetically modified embryo into a surrogate mother. Progeny that are capable of transmitting the genetic modification though the germline are generated.

Nuclear transfer techniques can also be used to generate the non-human mammalian animals. Briefly, methods for nuclear transfer can include the steps of: (1) enucleating an oocyte or providing an enucleated oocyte; (2) isolating or providing a donor cell or nucleus to be combined with the enucleated oocyte; (3) inserting the cell or nucleus into the enucleated oocyte to form a reconstituted cell; (4) implanting the reconstituted cell into the womb of an animal to form an embryo; and (5) allowing the embryo to develop. In such methods, oocytes are generally retrieved from deceased animals, although they may be isolated also from either oviducts and/or ovaries of live animals. Oocytes can be matured in a variety of well-known media prior to enucleation. Enucleation of the oocyte can be performed in a number of well-known manners. Insertion of the donor cell or nucleus into the enucleated oocyte to form a reconstituted cell can be by microinjection of a donor cell under the zona pellucida prior to fusion. Fusion may be induced by application of a DC electrical pulse across the contact/fusion plane (electrofusion), by exposure of the cells to fusion-promoting chemicals, such as polyethylene glycol, or by way of an inactivated virus, such as the Sendai virus. A reconstituted cell can be activated by electrical and/or non-electrical means before, during, and/or after fusion of the nuclear donor and recipient oocyte. Activation methods include electric pulses, chemically induced shock, penetration by sperm, increasing levels of divalent cations in the oocyte, and reducing phosphorylation of cellular proteins (as by way of kinase inhibitors) in the oocyte. The activated reconstituted cells, or embryos, can be cultured in well-known media and then transferred to the womb of an animal. See, e.g., US 2008/0092249, WO 1999/005266, US 2004/0177390, WO 2008/017234, and U.S. Pat. No. 7,612,250, each of which is herein incorporated by reference in its entirety for all purposes.

The various methods provided herein allow for the generation of a genetically modified non-human F0 animal wherein the cells of the genetically modified F0 animal comprise the humanized TTR locus. Depending on the method used to generate the F0 animal, the number of cells within the F0 animal that have the humanized TTR locus will vary. The introduction of the donor ES cells into a pre-morula stage embryo from a corresponding organism (e.g., an 8-cell stage mouse embryo) via for example, the VELOCIMOUSE® method allows for a greater percentage of the cell population of the F0 animal to comprise cells having the nucleotide sequence of interest comprising the targeted genetic modification. For example, at least 50%, 60%, 65%, 70%, 75%, 85%, 86%, 87%, 87%, 88%, 89%, 90%, 91%, 92%, 93%, 94%, 95%, 96%, 97%, 98%, 99% or 100% of the cellular contribution of the non-human F0 animal can comprise a cell population having the targeted modification.

The cells of the genetically modified F0 animal can be heterozygous for the humanized TTR locus or can be homozygous for the humanized TTR locus.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

BRIEF DESCRIPTION OF THE SEQUENCES

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleotide sequence is shown, but the complementary strand is understood to be included by any reference to the displayed strand. When a nucleotide sequence encoding an amino acid sequence is provided, it is understood that codon degenerate variants thereof that encode the same amino acid sequence are also provided. The amino acid sequences follow the standard convention of beginning at the amino terminus of the sequence and proceeding forward (i.e., from left to right in each line) to the carboxy terminus.

TABLE 2

Description of Sequences.

| SEQ ID NO | Type | Description |
|---|---|---|
| 1 | Protein | Human TTR Protein NP_000362.1 and P02766.1 |
| 2 | Protein | Expected Chimeric Mouse/Human TTR Protein - Humanization V2 |
| 3 | DNA | Human TTR Gene NG_009490.1 |
| 4 | DNA | Human TTR mRNA NM_000371.3 |
| 5 | DNA | Mouse Ttr gene NC_000084.6 |
| 6 | Protein | Mouse TTR protein P07309.1 and NP_038725.1 |
| 7 | DNA | Mouse Ttr mRNA NM_013697.5 |
| 8 | RNA | Generic Guide RNA Scaffold v.2 |
| 9 | RNA | Generic Guide RNA Scaffold v.3 |
| 10 | RNA | Generic Guide RNA Scaffold v.4 |
| 11 | DNA | Generic Guide RNA Target Sequence plus PAM v.1 |
| 12 | DNA | Generic Guide RNA Target Sequence plus PAM v.2 |
| 13 | DNA | Generic Guide RNA Target Sequence plus PAM v.3 |
| 14 | DNA | Expected Humanization V1 - F0, with SDC Pmci2 UbiNeo cassette |
| 15 | DNA | Expected Humanization V1 - F1, Cassette-Deleted |
| 16 | DNA | Expected Humanization V2 - F0, with SDC Pmci2 UbiNeo cassette |
| 17 | DNA | Expected Humanization V2 - F1, Cassette-Deleted |
| 18 | DNA | Human TTR Sequence Inserted in Humanized TTR V1 |
| 19 | DNA | Human TTR Sequence Inserted in Humanized TTR V2 |
| 20 | DNA | Mouse Ttr Locus - Start Codon to Stop Codon |
| 21 | DNA | 9090retU3 - F Primer |
| 22 | DNA | 9090retU2 - F Primer |
| 23 | DNA | 9090retU - F Primer |
| 24 | DNA | 9090mTGU - F Primer |

TABLE 2-continued

Description of Sequences.

| SEQ ID NO | Type | Description |
|---|---|---|
| 25 | DNA | 7576mTU - F Primer |
| 26 | DNA | 9090mTM - F Primer |
| 27 | DNA | 7576mTD - F Primer |
| 28 | DNA | 9090mTGD - F Primer |
| 29 | DNA | 9090retD - F Primer |
| 30 | DNA | 9090retD2 - F Primer |
| 31 | DNA | 9090retD3 - F Primer |
| 32 | DNA | 7576hTU - F Primer |
| 33 | DNA | 7576hTD - F Primer |
| 34 | DNA | Neo - F Primer |
| 35 | DNA | 7655hTU - F Primer |
| 36 | DNA | 9212mTU - F Primer |
| 37 | DNA | 9212mTGD - F Primer |
| 38 | DNA | 7655mTU - F Primer |
| 39 | DNA | 7655mTD - F Primer |
| 40 | DNA | 9204mretD - F Primer |
| 41 | DNA | 9204mretU - F Primer |
| 42 | DNA | 4552mTU - F Primer |
| 43 | DNA | 9090retU3 - R Primer |
| 44 | DNA | 9090retU2 - R Primer |
| 45 | DNA | 9090retU - R Primer |
| 46 | DNA | 9090mTGU - R Primer |
| 47 | DNA | 7576mTU - R Primer |
| 48 | DNA | 9090mTM - R Primer |
| 49 | DNA | 7576mTD - R Primer |
| 50 | DNA | 9090mTGD - R Primer |
| 51 | DNA | 9090retD - R Primer |
| 52 | DNA | 9090retD2 - R Primer |
| 53 | DNA | 9090retD3 - R Primer |
| 54 | DNA | 7576hTU - R Primer |
| 55 | DNA | 7576hTD - R Primer |
| 56 | DNA | Neo - R Primer |
| 57 | DNA | 7655hTU - R Primer |
| 58 | DNA | 9212mTU - R Primer |
| 59 | DNA | 9212mTGD - R Primer |
| 60 | DNA | 7655mTU - R Primer |
| 61 | DNA | 7655mTD - R Primer |
| 62 | DNA | 9204mretD - R Primer |
| 63 | DNA | 9204mretU - R Primer |
| 64 | DNA | 4552mTU - R Primer |
| 65 | DNA | 9090retU3 - Probe |
| 66 | DNA | 9090retU2 - Probe |
| 67 | DNA | 9090retU - Probe |
| 68 | DNA | 9090mTGU - Probe |
| 69 | DNA | 7576mTU - Probe |
| 70 | DNA | 9090mTM - Probe |
| 71 | DNA | 7576mTD - Probe |
| 72 | DNA | 9090mTGD - Probe |
| 73 | DNA | 9090retD - Probe |
| 74 | DNA | 9090retD2 - Probe |
| 75 | DNA | 9090retD3 - Probe |
| 76 | DNA | 7576hTU - Probe |
| 77 | DNA | 7576hTD - Probe |
| 78 | DNA | Neo - Probe |
| 79 | DNA | 7655hTU - Probe |
| 80 | DNA | 9212mTU - Probe |
| 81 | DNA | 9212mTGD - Probe |
| 82 | DNA | 7655mTU - Probe |
| 83 | DNA | 7655mTD - Probe |
| 84 | DNA | 9204mretD - Probe |
| 85 | DNA | 9204mretU - Probe |
| 86 | DNA | 4552mTU - Probe |
| 87 | RNA | crRNA tail |
| 88 | RNA | tracrRNA |
| 89 | RNA | Generic Guide RNA Scaffold v.1 |
| 90 | DNA | Humanized TTR CDS v1.0 |
| 91 | DNA | Humanized TTR CDS v2.0 |
| 92 | DNA | Mouse TTR CDS |
| 93 | DNA | Cas9 DNA Sequence |
| 94 | Protein | Cas9 Protein Sequence |

EXAMPLES

Example 1. Generation of Mice Comprising a Humanized TTR Locus

One promising therapeutic approach for the TTR amyloidosis diseases is to reduce the TTR load in the patient by inactivation of the gene with genome editing technology, such as CRISPR/Cas9 technology. To assist in the development of CRISPR/Cas9 therapeutics, mice with targeted modifications in the Ttr gene were developed.

Figure 3:
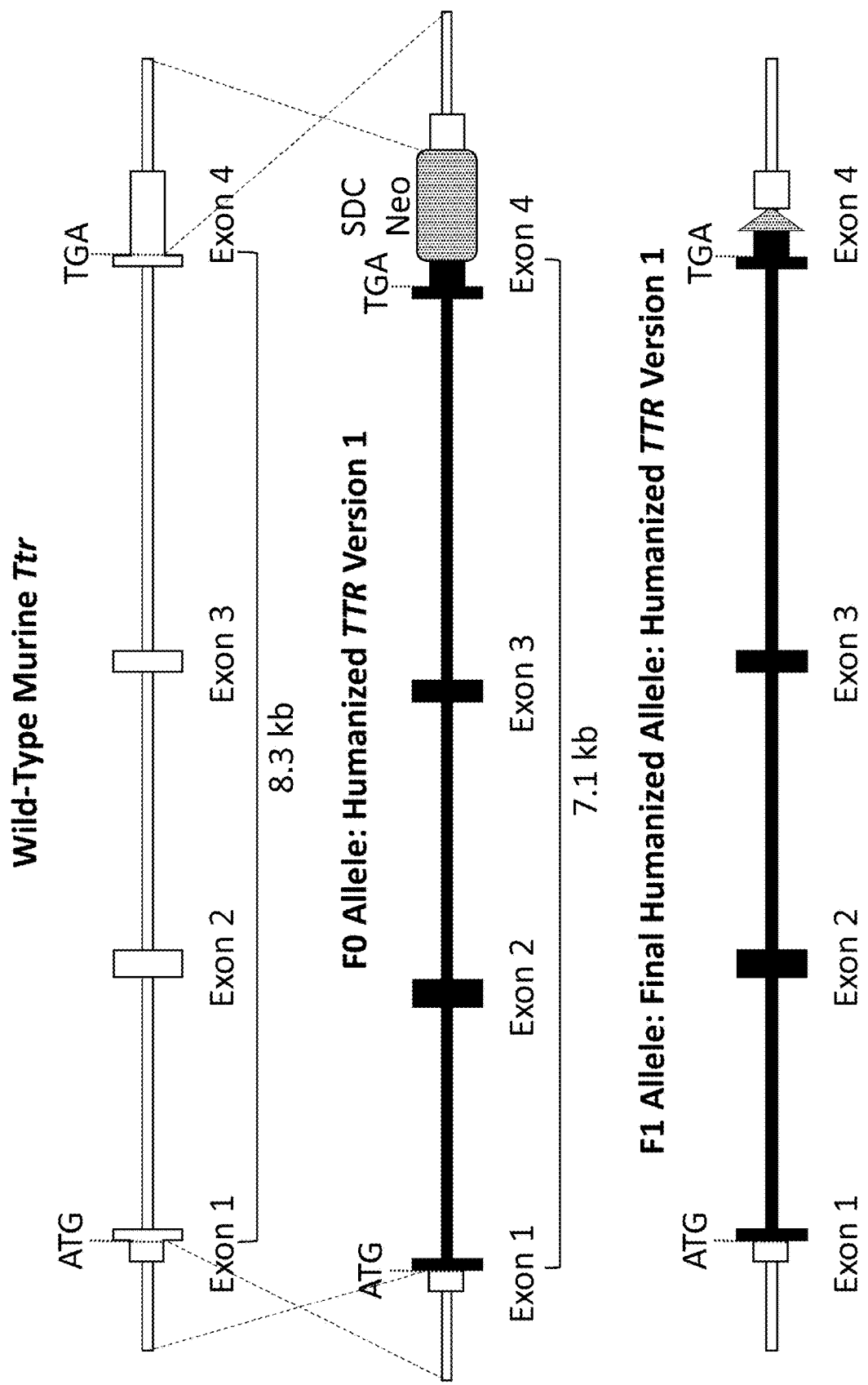
FIG. 3 shows a schematic (not drawn to scale) of the targeting to create the first version of the humanized mouse Ttr locus. The wild type mouse Ttr locus, the F0 allele of the humanized mouse Ttr locus with the self-deleting neomycin (SDC-Neo) selection cassette (MAID 7576), and the F1 allele of the humanized mouse Ttr locus with the loxP scar from removal of the SDC-Neo selection cassette (MAID 7577) are shown. White boxes indicate murine sequence; black boxes indicate human sequence.
Figure 5A:
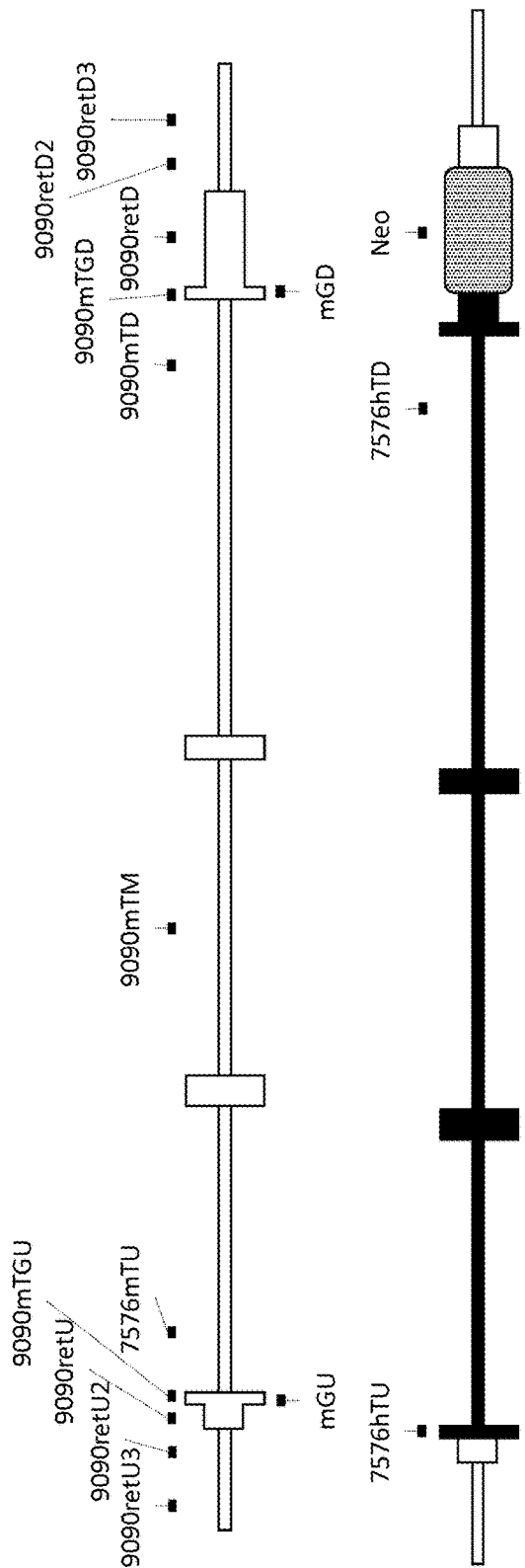
FIG. 5A shows a schematic (not drawn to scale) of the strategy for screening of the first targeted mouse Ttr locus, including loss-of-allele assays (7576mTU, 9090mTM, and 9090mTD), gain of allele assays (7576hTU, 7576hTD, Neo), retention assays (9090retU, 9090retU2, 9090retU3, 9090retD, 9090retD2, 9090retD3), and CRISPR assays designed to cover the region that is disrupted by the CRISPR guides (9090mTGU, mGU, 9090mTGD, and mGD). White boxes indicate murine sequence; black boxes indicate human sequence.

The first Ttr allele made was a complete deletion of the mouse transthyretin coding sequence and its replacement with the orthologous part of the human TTR gene. A large targeting vector comprising a 5' homology arm including 33.7 kb of sequence upstream from the mouse Ttr start codon and 34.5 kb of the sequence downstream of the mouse Ttr stop codon was generated to replace the approximately 8.3 kb region from the mouse Ttr start codon to the mouse Ttr stop codon with the approximately 7.1 kb orthologous human TTR sequence from the human TTR start codon to the end of the last human TTR exon (exon 4, including the human 3' UTR) and a self-deleting neomycin selection cassette (SDC Neo) flanked by loxP sites. See FIG. 3. The SDC Neo cassette includes the following components from 5' to 3': loxP site, mouse protamine (Prm1) promoter, Crei (Cre coding sequence optimized to include intron), polyA, human ubiquitin promoter, neomycin phosphotransferase (neon) coding sequence, polyA, loxP. To generate the humanized allele, CRISPR/Cas9 components targeting the mouse Ttr locus were introduced into F1H4 mouse embryonic stem cells together with the large targeting vector. Loss-of-allele assays, gain-of-allele assays, retention assays, and CRISPR assays using primers and probes set forth in FIG. 5A and in Table 3 were performed to confirm the humanization of the mouse Ttr allele. Loss-of-allele, gain-of-allele assays, and retention assays are described, for example, in US 2014/0178879; US 2016/0145646; WO 2016/081923; and Frendewey et al. (2010) *Methods Enzymol.* 476:295-307, each of which is herein incorporated by reference in its entirety for all purposes. CRISPR assays are TAQMAN® assays designed to cover the region that is disrupted by the CRISPR gRNAs. When a CRISPR gRNA cuts and creates an indel (insertion or deletion), the TAQMAN® assay will fail to amplify and thus reports CRISPR cleavage. Versions with the SDC Neo cassette and after excision of the SDC Neo cassette are shown in FIG. 3. F0 mice were then generated using the VELOCIMOUSE® method. See, e.g., U.S. Pat. Nos. 7,576,259; 7,659,442; 7,294,754; US 2008/007800; and Poueymirou et al. (2007) *Nature Biotech.* 25(1):91-99, each of which is herein incorporated by reference in its entirety for all purposes.

F0 generation mice (50% C57BL/6NTac and 50% 129S6/SvEvTac) were generated from multiple humanized ES cell clones, including clones 7576A-A5, 7576C-G7, and 7576B-F10. The sequence for the expected humanized mouse Ttr locus in the F0 generation mice is set forth in SEQ ID NO: 14 and includes the SDC Neo cassette. F1 and F2 generation mice (75% C57BL/6NTac and 25% 129S6/SvEvTac) were then generated by breeding. The sequence for the expected humanized mouse Ttr locus in the F1 and F2 generation mice is set forth in SEQ ID NO: 15 and does not include the SDC Neo cassette.

Figure 1B:
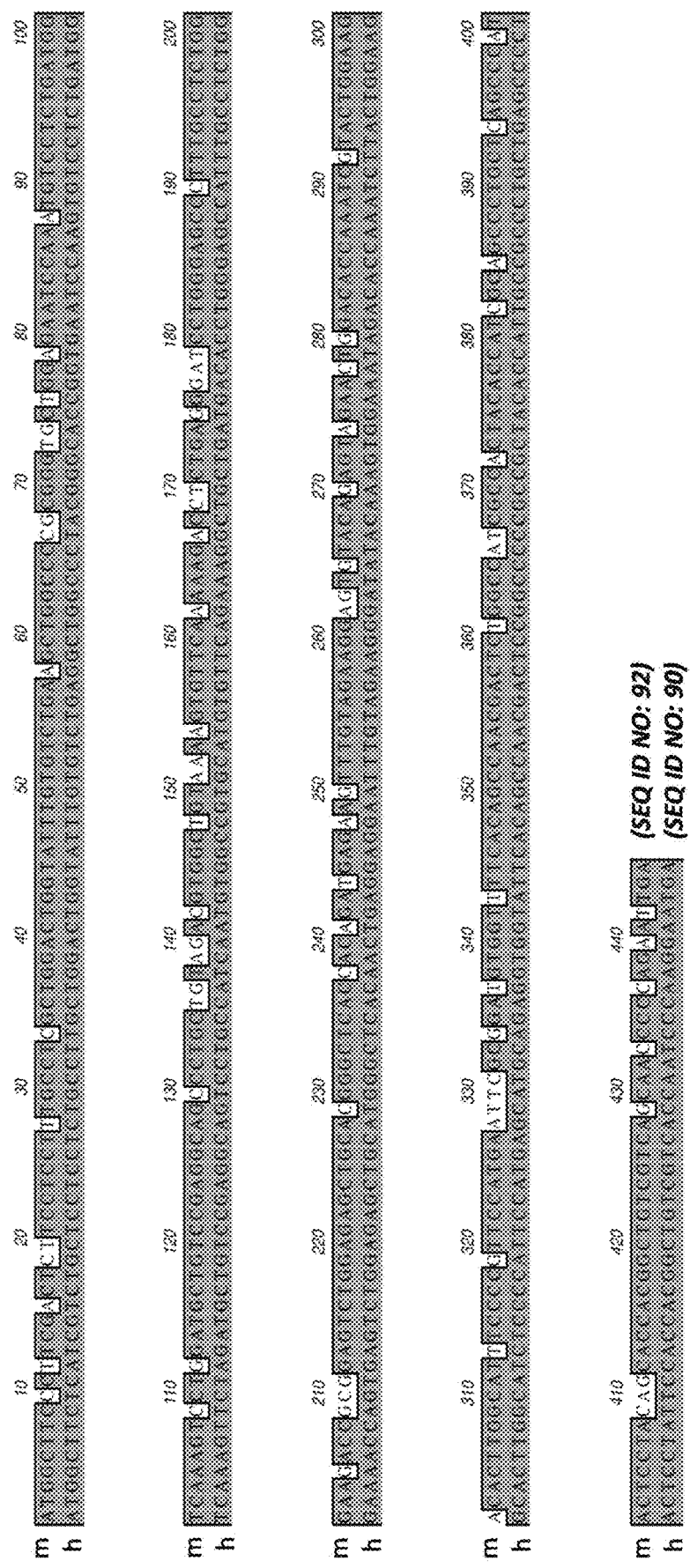
FIG. 1B shows an alignment of human and mouse transthyretin (TTR) coding sequences (SEQ ID NOS: 90 and 92, respectively).
Figure 2:
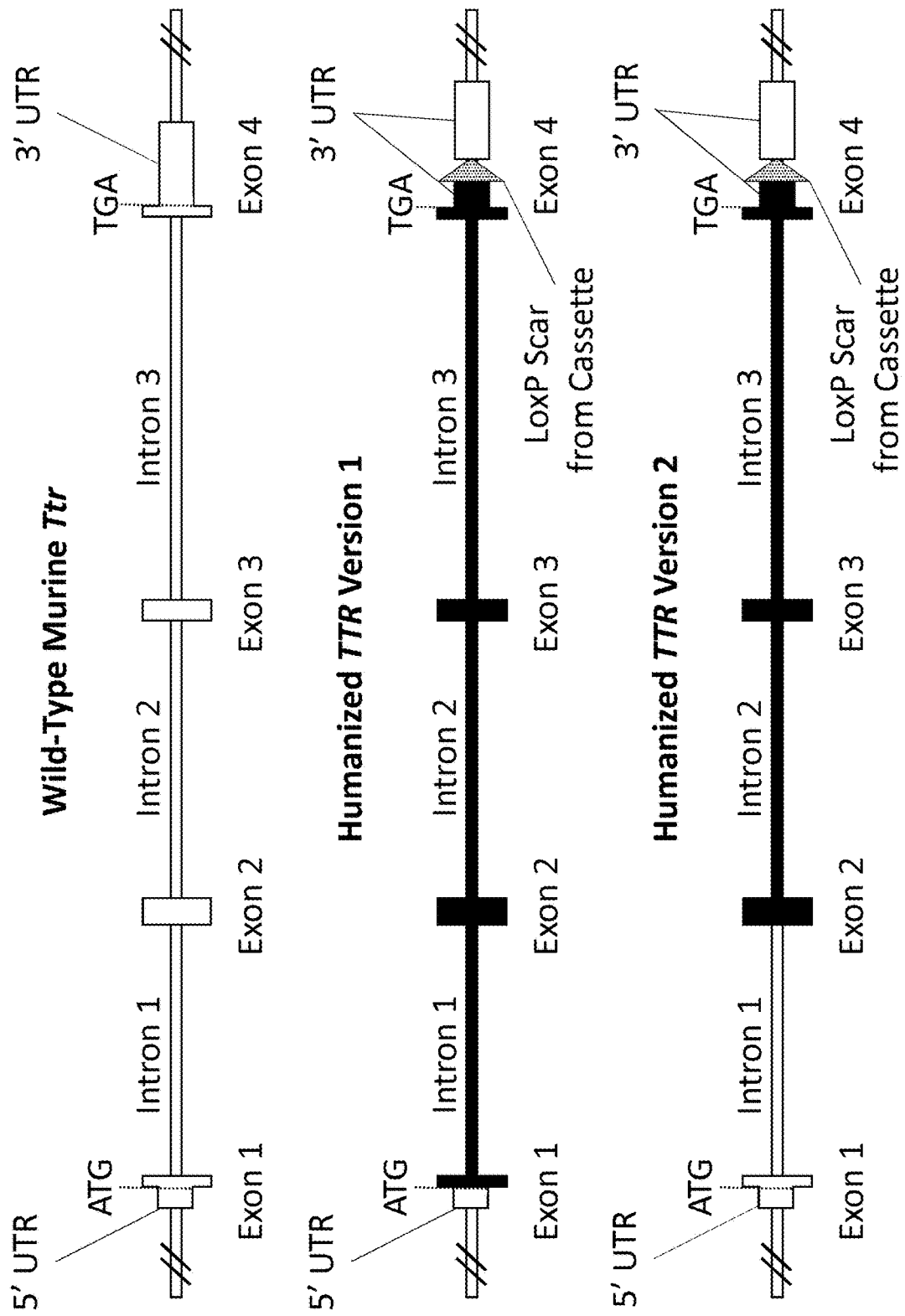
FIG. 2 shows schematics (not drawn to scale) of the wild-type murine Ttr locus, a first version of a humanized mouse Ttr locus, and a second version of a humanized mouse Ttr locus. Exons, introns, 5' untranslated regions (UTRs), 3' UTRs, start codons (ATG), stop codons (TGA), and loxP scars from selection cassettes are denoted. White boxes indicate murine sequence; black boxes indicate human sequence.

A comparison of the human and mouse transthyretin precursor protein sequences is shown in FIG. 1A, a comparison of the human and mouse transthyretin coding sequences is shown in FIG. 1B, and a schematic showing the wild type mouse Ttr locus and the final humanized mouse Ttr locus (humanized TTR version 1 with the SDC Neo cassette deleted) is shown in FIG. 2. The endogenous mouse Ttr locus sequence from the start codon to the stop codon is provided in SEQ ID NO: 20. Sequences for the expected humanized mouse Ttr locus with the SDC Neo cassette and without the SDC Neo cassette are set forth in SEQ ID NOS: 14 and 15, respectively. The expected transthyretin precursor protein encoded by the humanized mouse Ttr locus is set forth in SEQ ID NO: 1. This allele provides the true human target of human TTR CRISPR/Cas9 therapeutics, thereby enabling testing of the efficacy and mode of action of CRISPR/Cas9 therapeutics in live animals as well as pharmacokinetic and pharmacodynamics studies in a setting where the human protein is the only version of TTR present.

TABLE 3

Primers and Probes for Loss-of-Allele Assays, Gain-of-Allele Assays, Retention Assays, and CRISPR Assays.

| Assay | Forward Primer | Reverse Primer | Probe |
|---|---|---|---|
| 9090retU3 | CACAGACAATCAGACGTACCAGTA (SEQ ID NO: 21) | GGGACATCTCGGTTTCCTGACT (SEQ ID NO: 43) | TCATGTAATCTGGCTTCAGAGTGGGA (SEQ ID NO: 65) |
| 9090retU2 | CCAGCTTTGCCAGTTTACGA (SEQ ID NO: 22) | TCCACACTACTGAACTCCACAA (SEQ ID NO: 44) | TGGGAGGCAATTCTTAGTTTCAATGGA (SEQ ID NO: 66) |
| 9090retU | TTGGACGGTTGCCCTCTT (SEQ ID NO: 23) | CGGAACACTCGCTCTACGAAA (SEQ ID NO: 45) | TCCCAAAGGTGTCTGTCTGCACA (SEQ ID NO: 67) |
| 9090mTGU | GATGGCTTCCCTTCGACTCTTC (SEQ ID NO: 24) | GGGCCAGCTTCAGACACA (SEQ ID NO: 46) | CTCCTTTGCCTCGCTGGACTGG (SEQ ID NO: 68) |
| 7576mTU | CACTGACATTTCTCTTGTCTCCTCT (SEQ ID NO: 25) | CCCAGGGTGCTGGAGAATCCAA (SEQ ID NO: 47) | CGGACAGCATCCAGGACTT (SEQ ID NO: 69) |
| 9090mTM | GGGCTCACCACAGATGAGAAG (SEQ ID NO: 26) | GCCAAGTGTCTTCCAGTACGAT (SEQ ID NO: 48) | AGAAGGAGTGTACAGAGTAGAACTGGACA (SEQ ID NO: 70) |
| 7576mTD | CACTGTTCGCCACAGGTCTT (SEQ ID NO: 27) | GTTCCCTTTCTTGGGTTCAGA (SEQ ID NO: 49) | TGTTTGTGGGTGTCAGTGTTTCTACTC (SEQ ID NO: 71) |

TABLE 3-continued

Primers and Probes for Loss-of-Allele Assays, Gain-of-Allele Assays, Retention Assays, and CRISPR Assays.

| Assay | Forward Primer | Reverse Primer | Probe |
|---|---|---|---|
| 9090mTGD | GCTCAGCCCATACTCCTACA (SEQ ID NO: 28) | GATGCTACTGCTTTGGCAAGAT C (SEQ ID NO: 50) | CACCACGGCTGTCGTCAGCAA (SEQ ID NO: 72) |
| 9090retD | GCCCAGGAGGACCAGGAT (SEQ ID NO: 29) | CCTGAGCTGCTAACACGGTT (SEQ ID NO: 51) | CTTGCCAAAGCAGTAGCATCCCA (SEQ ID NO: 73) |
| 9090retD2 | GGCAACTTGCTTGAGGAAGA (SEQ ID NO: 30) | AGCTACAGACCATGCTTAGTGT A (SEQ ID NO: 52) | AGGTCAGAAAGCAGAGTGGACCA (SEQ ID NO: 74) |
| 9090retD3 | GCAGCAACCCAGCTTCACTT (SEQ ID NO: 31) | TGCCAGTTTAGGAGGAATATGT TC (SEQ ID NO: 53) | CCCAGGCAATTCCTACCTTCCCA (SEQ ID NO: 75) |
| 7576hTU | ACTGAGCTGGGACTTGAAC (SEQ ID NO: 32) | CTGAGGAAACAGAGGTACCAGA TAT (SEQ ID NO: 54) | TCTGAGCATTCTACCTCATTGCT TTGGT (SEQ ID NO: 76) |
| 7576hTD | TGCCTCACTCTGAGAACCA (SEQ ID NO: 33) | AGTCACACAGTTCTGTCAAATC AG (SEQ ID NO: 55) | AGGCTGTCCCAGCACCTGAGTCG (SEQ ID NO: 77) |
| Neo | GGTGGAGAGGCTATTCGGC (SEQ ID NO: 34) | GAACACGGCGGCATCAG (SEQ ID NO: 56) | TGGGCACAACAGACAATCGGCTG (SEQ ID NO: 78) |
| 7655hTU | GGCCGTGCATGTGTTCAG (SEQ ID NO: 35) | TCCTGTGGGAGGGTTCTTTG (SEQ ID NO: 57) | AAGGCTGCTGATGACACCTGGGA (SEQ ID NO: 79) |
| 9212mTU | GGTTCCCATTTGCTCTTATT CGT (SEQ ID NO: 36) | CCCTCTCTCTGAGCCCTCTA (SEQ ID NO: 58) | AGATTCAGACACACACAACTTAC CAGC (SEQ ID NO: 80) |
| 9212mTGD | CCCACACTGCAGAAGGAAAC TTG (SEQ ID NO: 37) | GCTGCCTAAGTCTTTGGAGCT (SEQ ID NO: 59) | AGACCTGCAATTCTCTAAGAGCT CCACA (SEQ ID NO: 81) |
| 7655mTU | GGTTCCCATTTGCTCTTATT CGT (SEQ ID NO: 38) | CCCTCTCTCTGAGCCCTCTA (SEQ ID NO: 60) | AGATTCAGACACACACAACTTAC CAGC (SEQ ID NO: 82) |
| 7655mTD | CCAGCTTAGCATCCTGTGAA CA (SEQ ID NO: 39) | GAGAGGAGAGACAGCTAGTTCT AAC (SEQ ID NO: 61) | TTGTCTGCAGCTCCTACCTCTGG G (SEQ ID NO: 83) |
| 9204mretD | GGCAACTTGCTTGAGGAAGA (SEQ ID NO: 40) | AGCTACAGACCATGCTTAGTGT A (SEQ ID NO: 62) | AGGTCAGAAAGCAGAGTGGACCA (SEQ ID NO: 84) |
| 9204mretU | TGTGGAGTTCAGTAGTGTGG AG (SEQ ID NO: 41) | GCCCTCTTCATACAGGAATCAC (SEQ ID NO: 63) | TTGACATGTGTGGGTGAGAGATT TTACTG (SEQ ID NO: 85) |
| 4552mTU | CACTGACATTTCTCTTGTCT CCTCT (SEQ ID NO: 42) | CGGACAGCATCCAGGACTT (SEQ ID NO: 64) | CCCAGGGTGCTGGAGAATCCAA (SEQ ID NO: 86) |

Example 2. Characterization of Mice Comprising a Humanized TTR Locus

Figure 6:
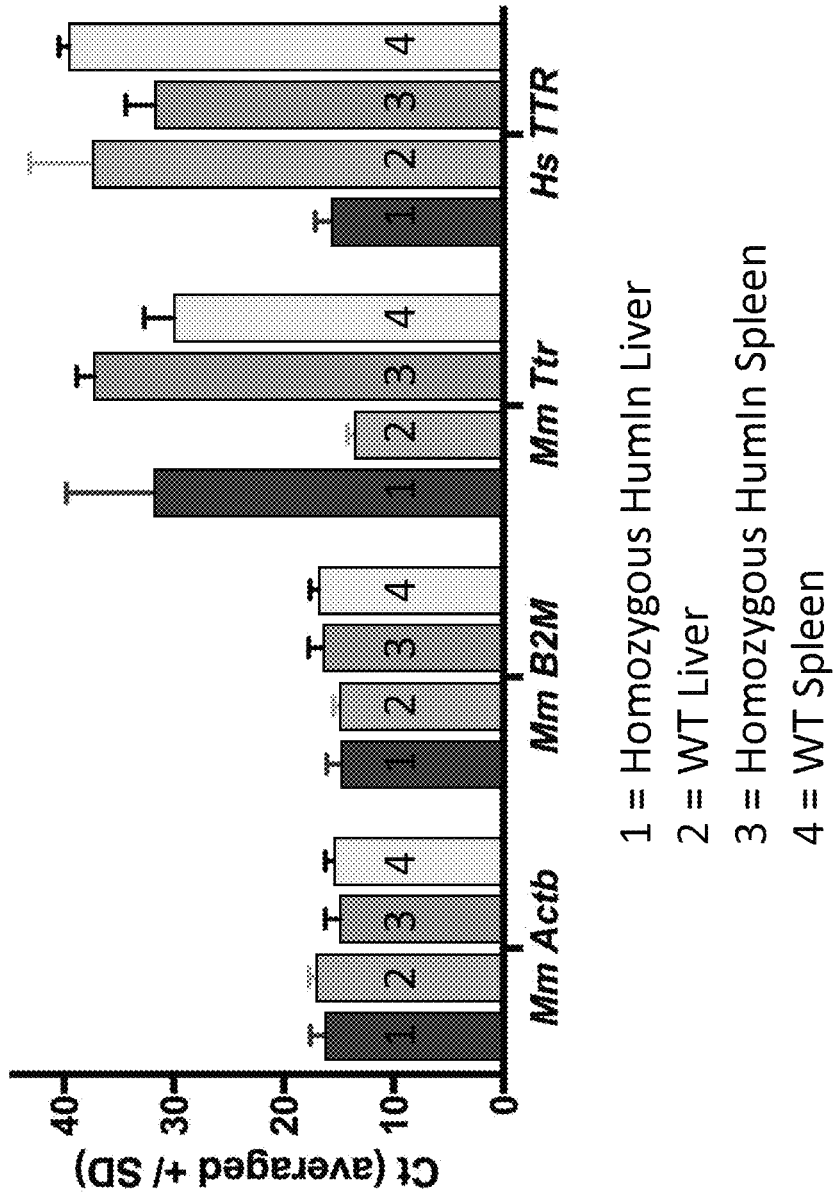
FIG. 6 shows beta-actin (Actb), beta-2-microglobulin (B2M), *Mus musculus* transthyretin (Mm Ttr), and *Homo sapiens* transthyretin (Hs TTR) mRNA expression in liver samples from (1) F0 generation mice homozygous for the first version of the humanized mouse Ttr locus (MAID 7576; F0 allele from FIG. 3), (2) liver samples from wild type mice, (3) spleen samples from F0 generation mice homozygous for the first version of the humanized mouse Ttr locus, and (4) spleen samples from wild type mice. Lower Ct values indicate higher expression.

Humanized TTR mice F0 cohorts from clones 7576A-A5 and 7576C-G7 were then characterized. As shown in FIG. 6, humanized TTR mRNA was robustly expressed in the liver of 8-week old, homozygous F0 generation humanized TTR mice. Equal mass amounts of RNA from each tissue were assayed by RT-qPCR. Five mice were assayed per genotype, with four technical replicates per sample. Each tissue had the RNA extracted. The genomic DNA was degraded so that it would not count towards the qPCR reaction. The RNA was reverse transcribed, and assays specific to human TTR and mouse Ttr were used to detect human TTR transcripts and mouse Ttr transcripts, respectively. As expected, the homozygous humanized TTR mouse showed significant expression of human TTR in liver (ct values below 30), while WT mice showed ct values of 30 and higher indicating that there was no expression of human TTR. In contrast, the wild type mouse showed significant expression of mouse Ttr in the liver, while homozygous humanized TTR mice showed ct values of 30 and higher indicating that there is no endogenous expression of mouse Ttr.

Figures 7A, 7B:
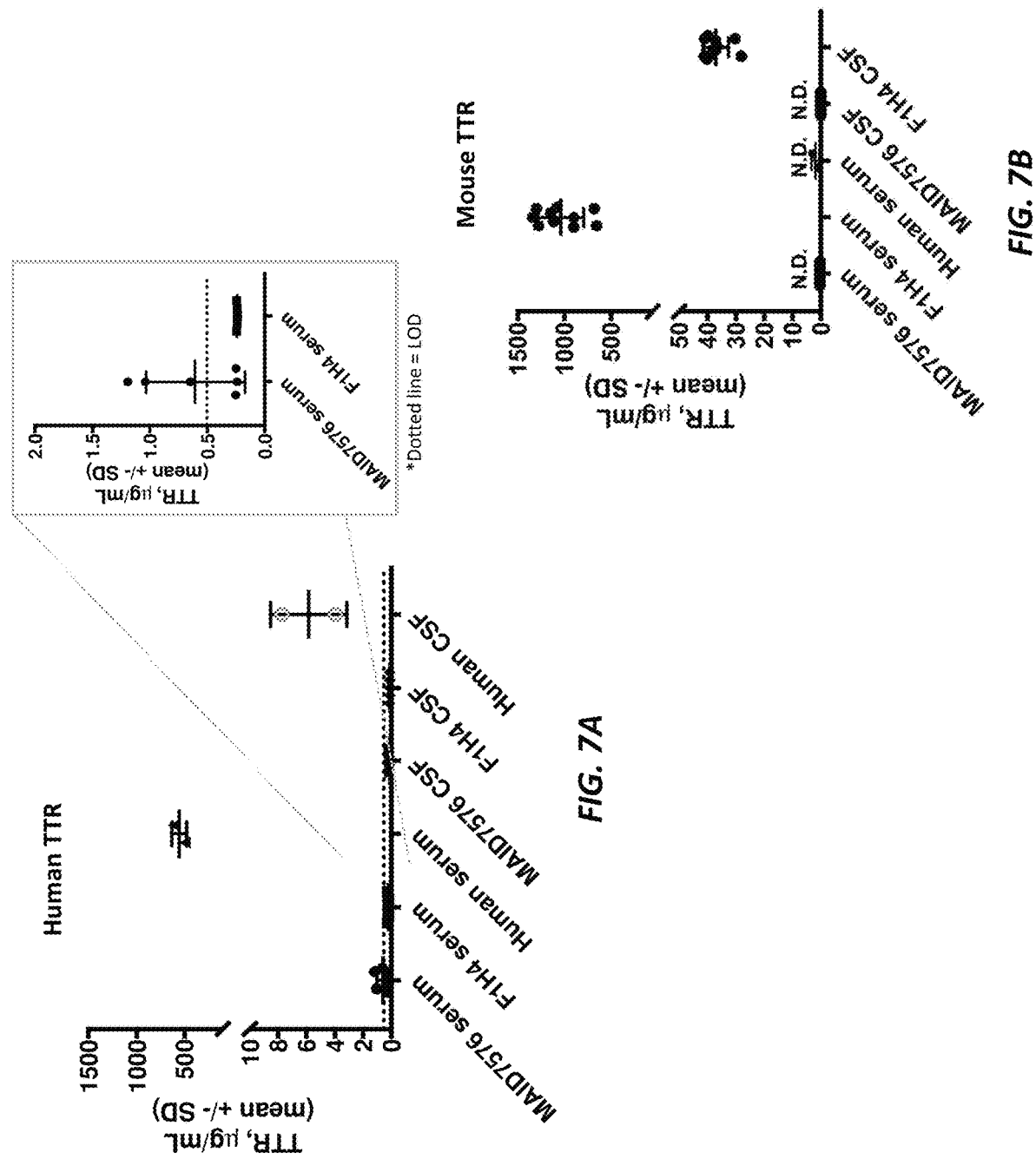
FIGS. 7A and 7B show results of ELISA assays for human TTR protein levels (FIG. 7A) and mouse TTR protein levels (FIG. 7B) in serum and cerebrospinal fluid (CSF). The samples tested include serum and CSF from F0 generation mice homozygous for the first version of the humanized mouse Ttr locus (MAID 7576; F0 allele from FIG. 3), human serum and CSF controls, and mouse (F1H4) serum and CSF controls.
Figure 7C:
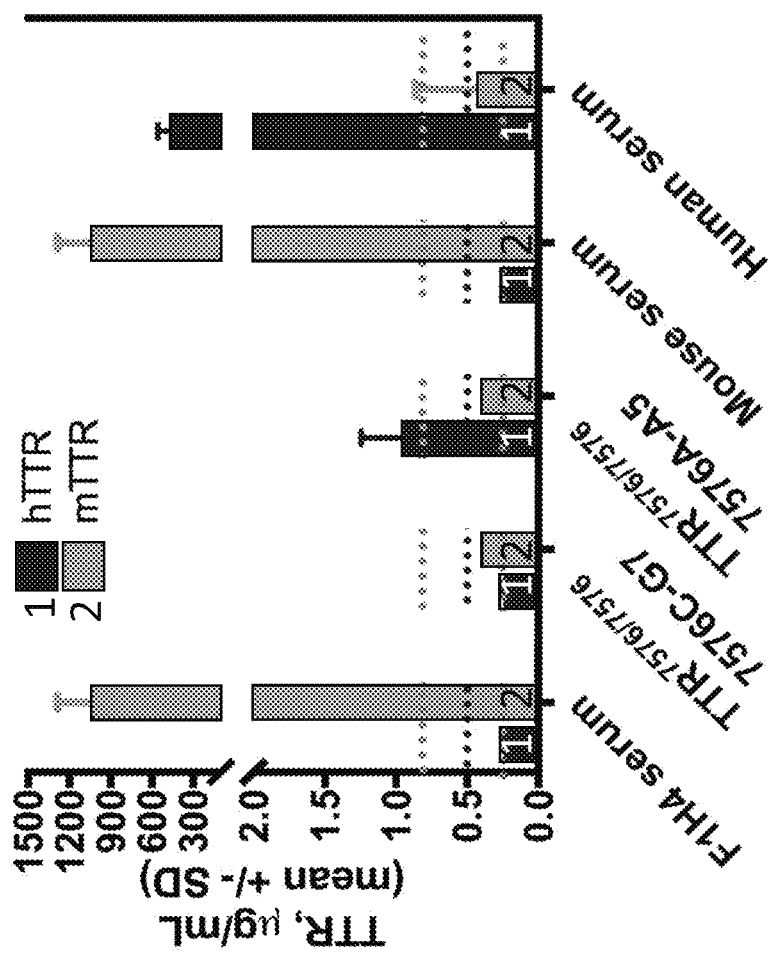
FIG. 7C shows results of ELISA assays for (1) human TTR and (2) mouse TTR protein levels in serum. The samples tested include serum samples from F0 generation mice homozygous for the first version of the humanized mouse Ttr locus (MAID 7576; F0 allele from FIG. 3) generated from a first clone (clone 7576C-G7), F0 generation mice homozygous for the first version of the humanized mouse Ttr locus (MAID 7576; F0 allele from FIG. 3) generated from a second clone (clone 7576A-A5), and wild type mice (F1H4). Mouse serum and human serum were used as controls.

An ELISA assay was done to assess human TTR and mouse TTR protein levels in serum and cerebrospinal fluid from 8-week-old, homozygous F0 generation humanized TTR mice. A human TTR ELISA kit (Aviva Systems Biology; Cat No.: OKIA00081; 1:250 dilution for serum; 1:1000 dilution for CSF) was used to assess human TTR levels. A mouse TTR ELISA kit (Aviva Systems Biology; Cat No: OKIA00111; 1:4000 dilution for serum; 1:10000 dilution for CSF) was used to assess mouse TTR levels. Human serum and human CSF were used as positive controls for human TTR and negative controls for mouse TTR, and F1H4 serum and F1H4 CSF were used as negative controls for human TTR and positive controls for mouse TTR. As shown in FIG. 7A, human TTR was detected in the serum from the humanized TTR mice but not in serum from wild type (F1H4) mice. As shown in FIG. 7B, mouse TTR was not detected in the serum from the humanized TTR mice but was detected in wild type mouse serum. Human and mouse TTR levels in serum were further assessed in humanized TTR mice derived from two separate humanized mouse Ttr ES cell clones: 7576C-G7 and 7576A-A5. As shown in FIG. 7C, human TTR was detected in the serum of humanized TTR mice derived from clone 7576A-A5.

Figure 8:
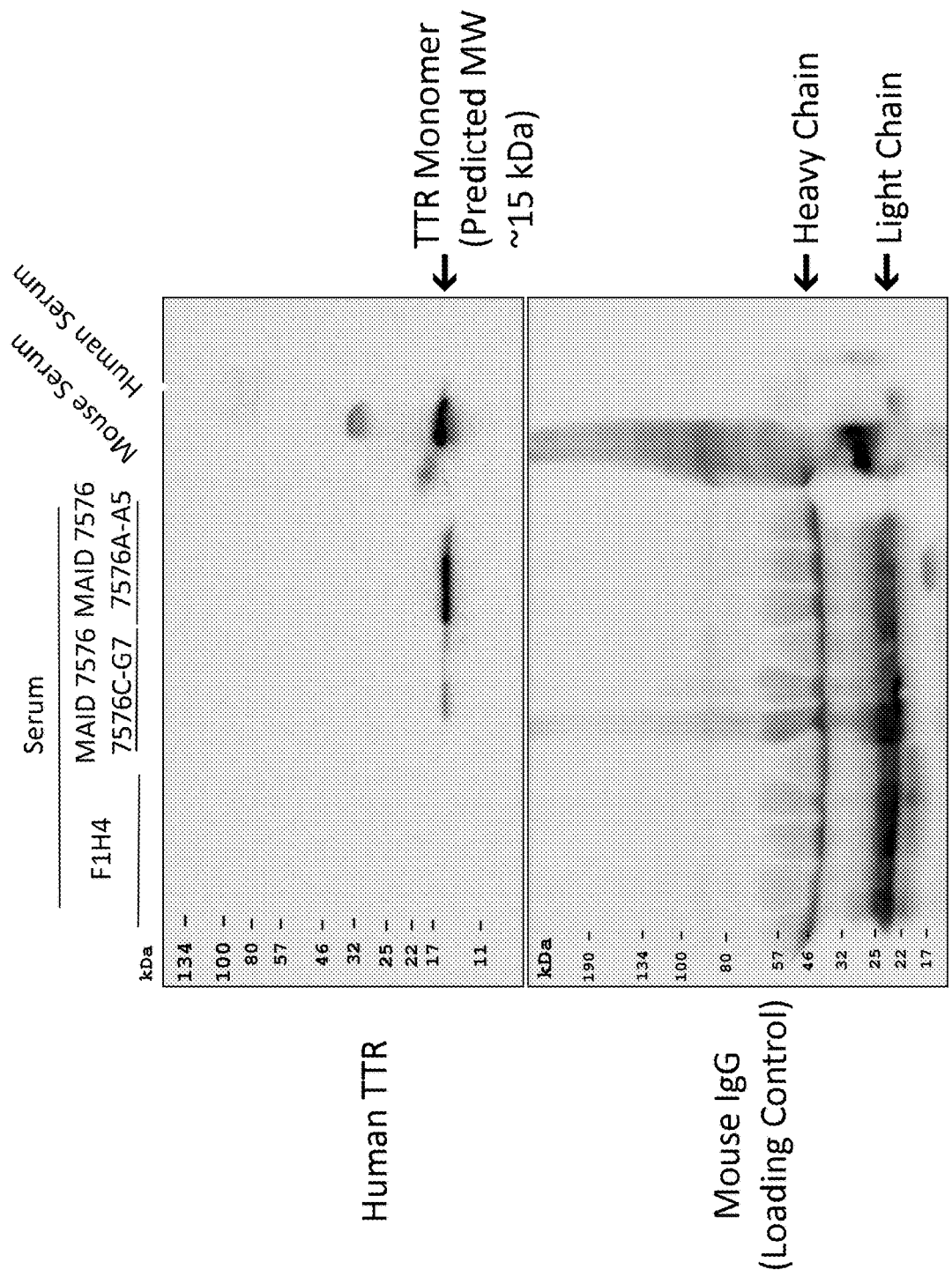
FIG. 8 shows human TTR protein expression as determined by western blot in serum samples from wild type mice (F1H4), F0 generation mice homozygous for the first version of the humanized mouse Ttr locus (MAID 7576; F0 allele from FIG. 3) generated from a first clone (clone 7576C-G7), and F0 generation mice homozygous for the first version of the humanized mouse Ttr locus generated from a second clone (7576A-A5). Mouse serum was used as a negative control, and human serum was used as a positive control. Mouse IgG was used as a loading control.
Figure 9:
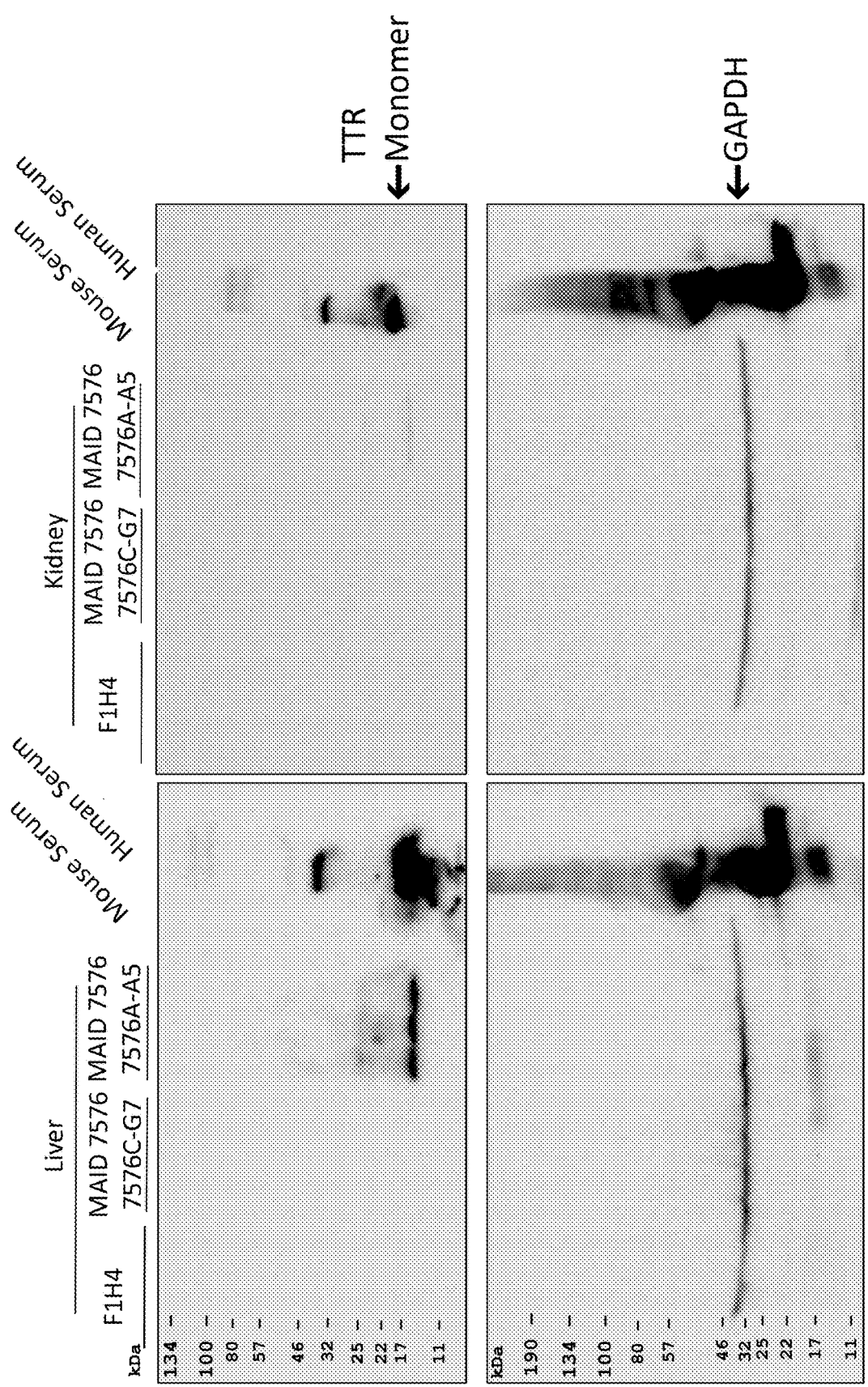
FIG. 9 shows human TTR protein expression as determined by western blot in liver and kidney samples from wild type mice (F1H4), F0 generation mice homozygous for the first version of the humanized mouse Ttr locus (MAID 7576; F0 allele from FIG. 3) generated from a first clone (clone 7576C-G7), and F0 generation mice homozygous for the first version of the humanized mouse Ttr locus generated from a second clone (7576A-A5). Mouse serum was used as a negative control, and human serum was used as a positive control. GAPDH was used as a loading control.

Human TTR protein expression was also assessed in 8-week-old, homozygous humanized TTR mice by western blot on serum samples, liver samples, and kidney samples. The results are shown in FIGS. 8-9. Serum samples (5 µL total volume per well) were boiled in Laemlli buffer (containing SDS and beta-mercaptoethanol) and resolved on a 4-20% denaturing gradient gel (anti-TTR antibody: 1:1000; Abcam; ab75815). Mouse IgG (anti mouse IgG-HRP: 1:7500, Jackson ImmunoResearch) was used as a loading control. Three mice per group were tested for humanized mouse Ttr clones 7576C-G7 and 7576A-A5. Five mice per group were tested for wild type mouse control (F1H4). Mouse serum and human serum were used as negative and positive controls, respectively. As shown in FIG. 8, human TTR was detected by western blot in serum from both humanized mouse Ttr clones.

Liver and kidney samples (100 µg total protein per well) were boiled in Laemlli buffer (containing SDS and beta-mercaptoethanol) and resolved on a 4-20% denaturing gradient gel (anti-TTR antibody: 1:1000; Abcam; ab75815). GAPDH (anti-GAPDH: 1:2000, Santa Cruz) was used as a loading control. Three mice per group were tested for humanized mouse Ttr clones 7576C-G7 and 7576A-A5. Five mice per group were tested for wild type mouse control (F1H4). Mouse serum and human serum were used as negative and positive controls, respectively. As shown in FIG. 9, human TTR was detected by western blot in serum from both homozygous humanized TTR mice generated from clone 7576A-A5.

In summary, TTR HumIn (TTR$^{7576/7576}$) F0 mice were found to have a detectable amount of circulating hTTR. In addition, mice from clone 7576C-A5 had detectable amounts of hTTR in liver and plasma.

We hypothesized that removal of the neomycin drug selection cassette may increase secretion of the human TTR. Human TTR levels were measured in plasma samples from non-terminal, submandibular bleeds on 5-week-old mice homozygous for the fully humanized mouse Ttr locus with the neomycin selection cassette (TTR$^{7576/7576}$), mice heterozygous for the fully humanized mouse Ttr locus with the neomycin selection cassette (TTR$^{7576/WT}$), mice heterozygous for the fully humanized mouse Ttr locus without the neomycin selection cassette (TTR$^{7577/WT}$), and wild type mice (F1H4). Human TTR levels were assayed with the AssayPro human TTR (hTTR) ELISA kit (cat no.: EP3010-1; 1:40000 dilution). Mouse TTR serum levels were assayed with the Aviva Systems Biology mouse TTR (mTTR) ELISA kit (cat no. OKIA00111; 1:4000 dilution). The AssayPro human TTR ELISA kit was previously determined to be specific for detecting human TTR but not mouse TTR, and the Aviva Systems Biology mouse TTR ELISA kit was previously determined to be specific for detecting mouse TTR but not human TTR (data not shown). As shown in Table 4, removal of the neomycin selection cassette resulted in a statistically significant increase in human TTR levels in the serum. MAID7576 refers to the humanized TTR locus with the neomycin selection cassette. MAID7577 refers to the humanized TTR locus with the neomycin selection cassette removed. Enhanced human TTR mRNA expression was also observed in the liver (data not shown). Mice heterozygous for hTTR and mTTR (TTR-WT$^{7576/WT}$ and TTR-WT$^{7577/WT}$) had increased circulating hTTR, possibly due to increased stability from heteromeric (e.g., cross-TTR species) interaction.

TABLE 4

Circulating Human and Mouse TTR Levels.

| | TTR$^{7576/7576}$ | TTR$^{7576/WT}$ | TTR$^{7577/WT}$ | F1H4 |
|---|---|---|---|---|
| mTTR, µg/mL (SD) | N.D. | 207.62 (15.39) | 359.9 (38.07)** | 919.96 (79.73) |
| hTTR, µg/mL (SD) | 0.61 (0.43) | 28.507 (5.61) | 39.93 (3.70)** | N.D. |

Serum and liver TTR levels were also measured in F2 generation homozygous humanized TTR mice (three per group) that were generated from a different clone: 7576B-F10. As shown in FIG. 14 (Tris-saline sucrose (TSS) control sample), human TTR was detected in liver samples at a level of more than 1000 ng/mL. As shown in FIGS. 15A and 15B (TSS sample), human TTR was detected in serum samples at a level of 80,000 ng/mL or higher.

Figure 17C:
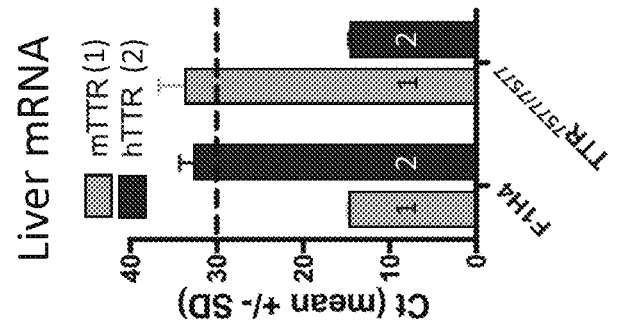
FIG. 17C shows mTTR (1) and hTTR (2) mRNA expression in liver samples from 3-month old $hTTR^{WT/WT}$ and $hTTR^{7577/7577}$ mice. Lower Ct values indicate higher expression.
Figure 17B:
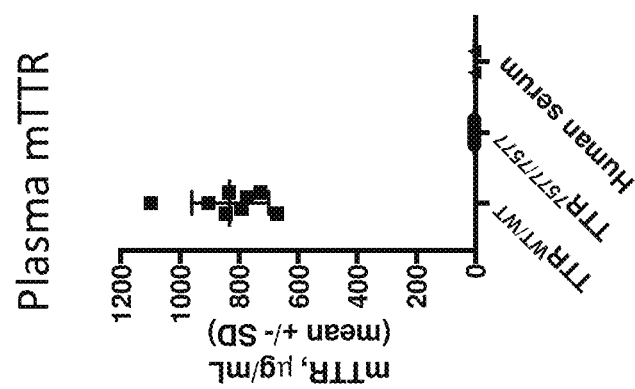
FIGS. 17A and 17B show results of an ELISA assaying human TTR and mouse TTR levels in blood plasma samples of $hTTR^{WT/WT}$ and $hTTR^{7577/7577}$ mice (3 months of age). Human serum was used as a control.
Figure 17A:
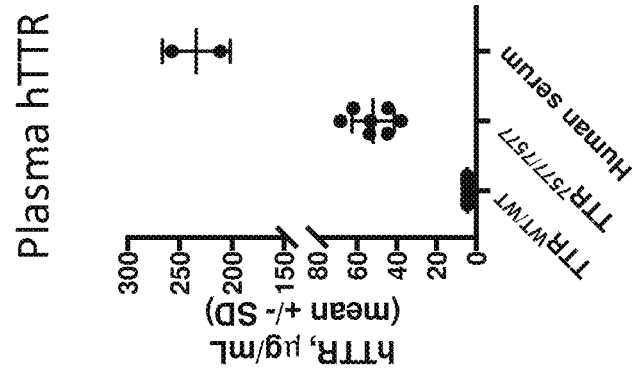

In another experiment, blood was collected via submandibular bleeds from TTR WT HumIn (v1.0, hTTR$^{7577/7577}$, clone B-F10) F2 homozygous mice at 3 months of age. hTTR levels were determined in plasma using species-specific ELISA kits (hTTR, Aviva, cat #OKIA00081; mTTR, Aviva, cat #OKIA00111). As shown in FIGS. 17A and 17B and Table 5, hTTR was secreted into circulation in TTR WT HumIn (v1.0, clone B-F10) F2 homozygous mice at 52.1+/−10.7 µg/mL, with no detectable levels of mTTR. mRNA levels of mTTR and hTTR in liver samples from the wild type control mice (F1H4) and WT HumIn (v1.0, hTTR$^{7577/7577}$, clone B-F10) mice are shown in FIG. 17C.

TABLE 5

Plasma hTTR and mTTR Levels.

| | hTTR, µg/mL (SD) | mTTR, µg/mL (SD) |
|---|---|---|
| TTR$^{WT/WT}$ | N.D. | 831.5 (129.9) |
| TTR$^{7577/7577}$ | 52.1 (10.7) | Not detectable |
| Human serum | 234.5 (n.a.) | Not detectable |

Example 3. Use of Mice Comprising a Humanized TTR Locus to Test Guide RNAs Targeting Human TTR Ex Vivo and In Vivo F0 generation humanized TTR mice cohorts were then used to test guide RNAs targeting human TTR ex vivo and in vivo. As a proof of concept, human TTR guide RNAs were first tested in primary hepatocytes isolated from F0 generation humanized TTR mice produced from clone 7576C-G7. Livers from huTTR$^{hI/hI}$ mice were perfused with 50 mL liver perfusion medium containing 1× PenStrep, followed by 50 mL liver digestion medium (HBSS, 100 mM CaCl2, 500 mM HEPES, collagenase). Once livers appeared digested, they were placed into wash medium containing 1× PenStrep and L-glutamine. The livers were torn to release the hepatocytes from the liver through gentle shaking. Once cells were released, they were put through a 70 μm mesh filter and spun at 50 g for 4 minutes at 4° C. The pellets were washed 2× with wash buffer. The pellets were then re-suspended in 20 mL of 38-40% Percoll and spun at 200 g×10 min at 4° C. The pellet was washed 2× and re-suspended in plating medium (Williams E Media, 1× Penstrep, 1× L-glutamine, 5% FBS). Cells were plated at 300,000 cells per well in 24-well collagen-coated tissue culture plates. After the cells were allowed to attach for 6-18 hours, the plating medium was replaced with medium without FBS. Reagents used are shown in Table 6.

TABLE 6

Reagents for isolation of primary hepatocytes.

| Material | Catalog Number |
|---|---|
| Liver Perfusion Media | Gibco [17701-038] |
| HBSS (1x) | Gibco [14175-079] |
| Hepatocyte Wash Media | Gibco [17704-024] |
| Williams E media | Gibco [A12176-01] |
| Penstrep (100x) | Gibco [15140163] |
| L-glutamine (200 mM) | Gibco [25030081] |
| FBS supplement | Gibco [A13450] |
| HEPES | Gibco [15630080] |
| Collagen | Gibco [A1048301] |
| Acetic acid | Sigma [A6283] |
| Liberase TM | Roche [TM05401119001] |
| Primary Hepatocyte Thawing and Plating Supplements | Gibco [CM3000] |
| Primary Hepatocyte Maintenance Supplements | Gibco [CM4000] |
| Percoll | GE [17-0891-01] |

Lipid nanoparticles (LNPs) (containing Cas9 mRNA plus a human TTR gRNA (versions 1 and 2, each targeting human TTR exon 2)) were added to the hepatocytes 24 hours post-isolation. Briefly, for each well, LNPs were added at a concentration of 500 ng in 500 μL of hepatocyte maintenance medium containing 3% mouse serum and were incubated for 5 minutes at 37° C. Plated cells were washed and 500 μL of incubated LNPs in medium was added to each well. After 48 hours, DNA lysates were prepared from the cells, and next-generation sequencing was performed for each guide RNA tested.

Figure 10:
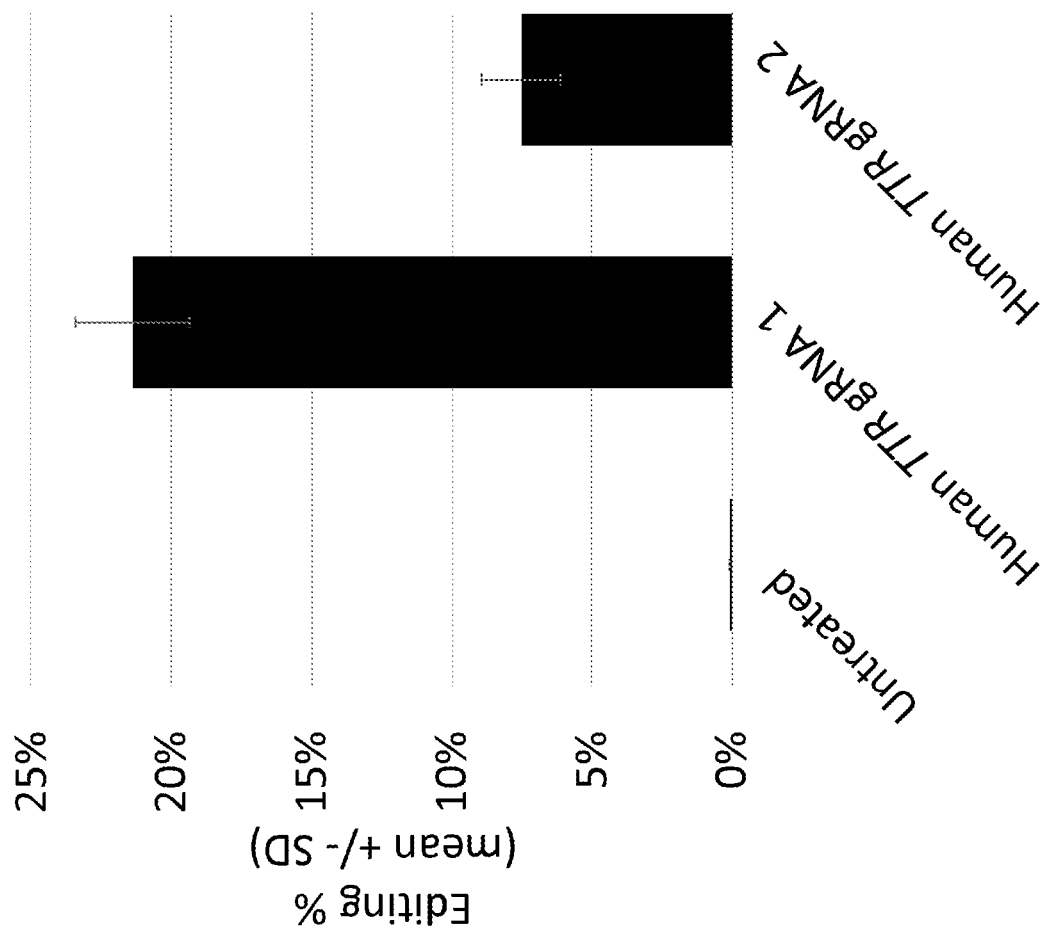
FIG. 10 shows percent genome editing (total number of insertions or deletions observed over the total number of sequences read in the PCR reaction from a pool of lysed cells) at the humanized mouse Ttr locus as determined by next-generation sequencing (NGS) in primary hepatocytes isolated from F0 generation mice homozygous for the first version of the humanized mouse Ttr locus (MAID 7576; F0 allele from FIG. 3). The samples tested included untreated hepatocytes and hepatocytes treated with lipid nanoparticles containing Cas9 mRNA and guide RNAs designed to target human TTR.
Figure 11B:
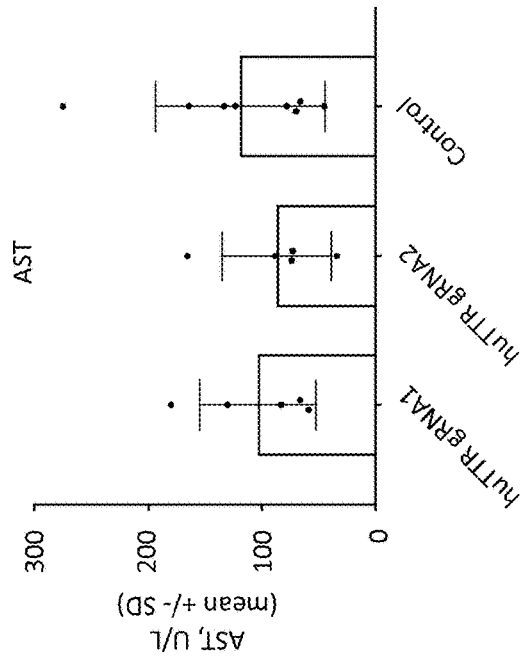
FIGS. 11A-11H show serum chemistry analysis of alanine aminotransferase (ALT) (FIG. 11A), aspartate aminotransferase (AST) (FIG. 11B), triglycerides (FIG. 11C), cholesterol (FIG. 11D), high-density lipoprotein (HDL) (FIG. 11E), low-density lipoprotein (LDL) (FIG. 11F), non-esterified fatty acids (NEFA) (FIG. 11G), and albumin (FIG. 11H) 14 days post-injection of lipid nanoparticles containing Cas9 mRNA and guide RNAs designed to target human TTR into F0 generation mice homozygous for the first version of the humanized mouse Ttr locus (MAID 7576; F0 allele from FIG. 3). U/L refers to units per liter, mg/dL refers to milligrams per deciliter, mEq/L refers to milliequivalents per liter, and g/dL refers to grams per deciliter.
Figure 11A:
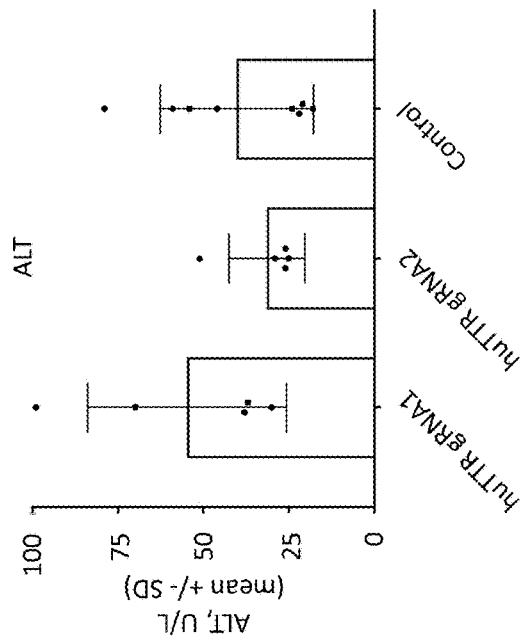
Figure 11D:
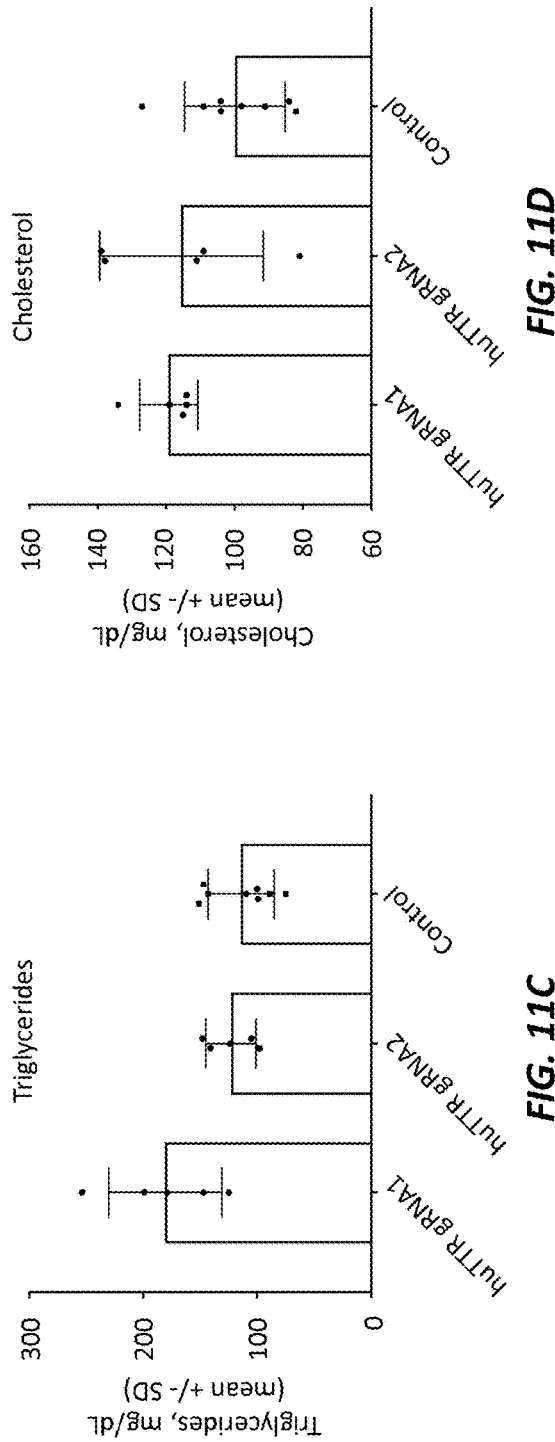
Figure 11C:
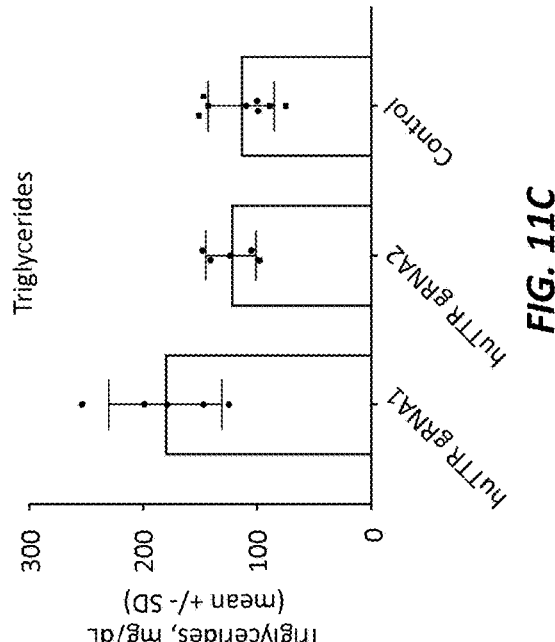
Figure 11E:
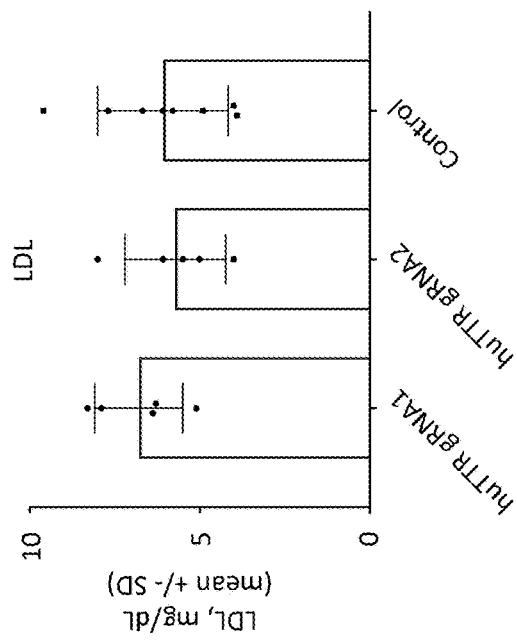
Figure 11F:
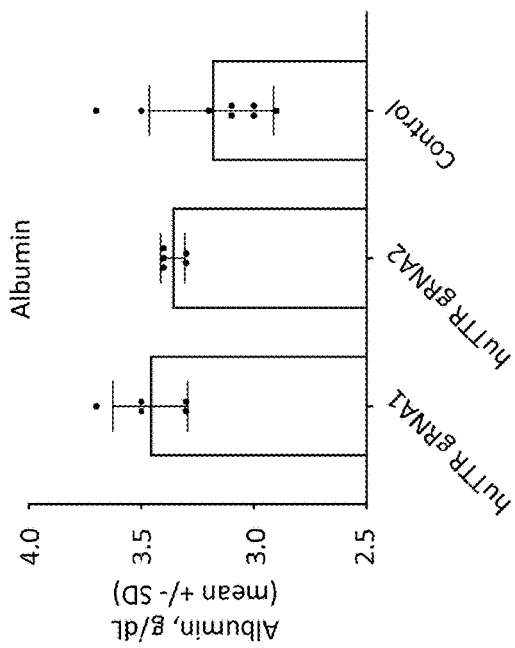
Figure 11G:
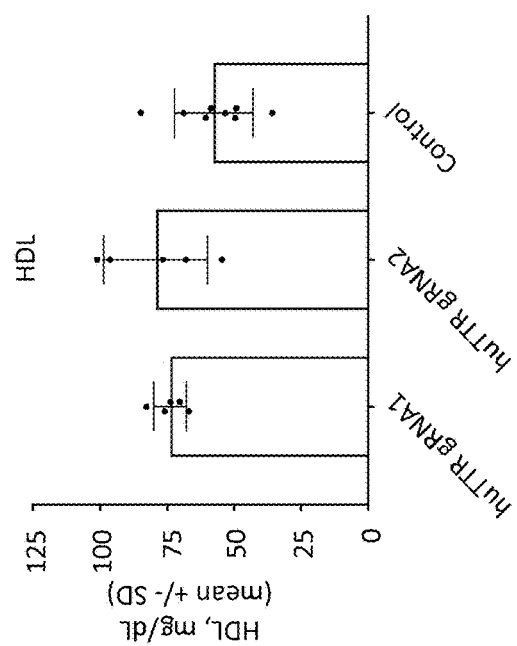
Figure 11H:
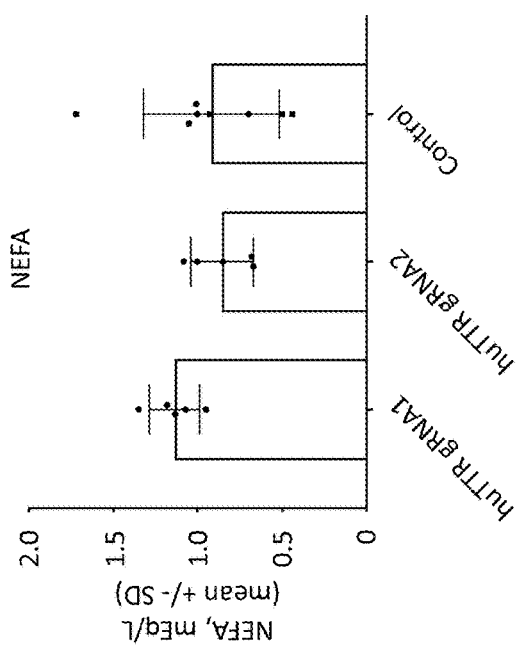

As shown in FIG. 10, editing in the humanized TTR gene was seen with both guide RNAs in primary hepatocytes isolated from humanized TTR mice. Human TTR guide RNA 1 had an editing efficiency of 20.4%, and human TTR guide RNA 2 had an editing efficiency of 7.53%. Similar results were observed for a human TTR guide RNA targeting exon 3 (editing efficiency of 17.37%; data not shown). Editing efficiency refers to the total number of insertions or deletions observed over the total number of sequences read in the PCR reaction from a pool of lysed cells as determined by next generation sequencing.

Next, human TTR guide RNAs 1 and 2 were tested in vivo in humanized TTR mice. F0 generation humanized TTR mice (Ttr$^{hI/hI}$) from clone numbers 7576A-A5 and 7576C-G7 were used. Three animal groups were targeted with fresh LNPs as shown in Table 7.

TABLE 7

Animal Groups for LNP Study.

| Group | Description |
|---|---|
| 1 | Ttr$^{hI/hI}$ 1M 1F A-A5 and 2M 1F C-G7: LNP (gRNA1)@ 2 mg/kg |
| 2 | Ttr$^{hI/hI}$ 1M 1F A-A5 and 2M 1F C-G7: LNP (gRNA2)@ 2 mg/kg |
| 3 | Ttr$^{hI/hI}$ 1M A-A5 and 2M C-G7: Tris-saline sucrose |

LNPs were formulated with human TTR guide RNAs and mRNA encoding Cas9 with one NLS and no HA tag. The LNPs had a nitrogen-to-phosphate (N/P) ratio of 4.5 and contained cationic lipid, cholesterol, DSPC, and PEG2k-DMG in a 45:44:9:2 molar ratio. The cationic lipid used in the in vitro and in vivo LNP experiments described herein was (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate. The (guide RNA):(Cas9 mRNA) ratio in each was 1:1 by weight. Additional LNP formulation details are provided in Table 8.

TABLE 8

Human TTR LNP Formulations.

| Human TTR Guide RNA | RNA (mg/mL) | Encapsulation | Z-avg (nm) | PDI | Number Ave (nm) |
|---|---|---|---|---|---|
| 1 | 0.46 | 96% | 95.22 | 0.053 | 77.51 |
| 2 | 0.61 | 97% | 94.91 | 0.016 | 76.77 |

Mice were weighed prior to injection, and LNPs (containing Cas9 mRNA plus a human TTR gRNA) were prepared to dose at 2 mg/kg by diluting in Tris-saline sucrose so that delivery volume was 200 μl per mouse. Delivery was intravenous through tail vein injection. After 8-14 days, mice were euthanized, and blood serum was harvested along with liver tissues. The tissues were processed into DNA lysates that were then analyzed by next-generation sequencing (NGS).

Serum chemistry analysis for the liver enzymes ALT, AST, triglycerides, total cholesterol, HDL, LDL, non-esterified fatty acids (NEFA), and albumin showed no statistical difference between various treatment groups. See FIGS. 11A-11H. Similar results were observed for a human TTR guide RNA targeting exon 3 (data not shown).

Figure 12:
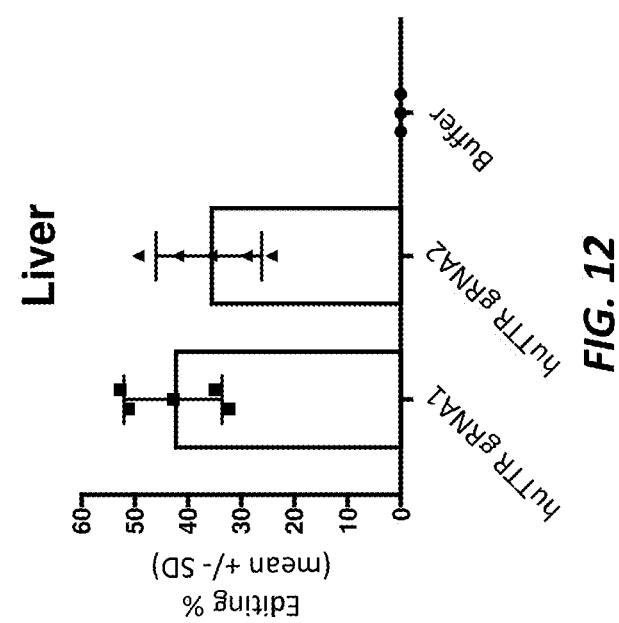
FIG. 12 shows percent genome editing (total number of insertions or deletions observed over the total number of sequences read in the PCR reaction from a pool of lysed cells) at the humanized mouse Ttr locus as determined by next-generation sequencing (NGS) in samples from liver 14 days post-injection of buffer control or lipid nanoparticles containing Cas9 mRNA and guide RNAs designed to target human TTR into F0 generation mice homozygous for the first version of the humanized mouse Ttr locus (MAID 7576; F0 allele from FIG. 3).

NGS showed significant editing in liver for human TTR gRNA 1 (average 42.8%) and human TTR gRNA 2 (average 36.0%). See FIG. 12. Editing efficiency refers to the total number of insertions or deletions observed over the total number of sequences read in the PCR reaction from a pool of lysed cells. Minimal or no statistically significant levels of gene editing were observed in other tissues (data not shown).

Next, human TTR guide RNA 1 was tested in vivo in F2 generation, homozygous humanized TTR mice from clone number 7576B-F10. Animals were weighed pre-dose for dosing calculations and then monitored 24 hours post-dose for welfare. The animals were dosed intravenously at 1 mg/kg, 0.3 mg/kg, and 0.1 mg/kg with LNPs formulated with human TTR guide RNA 1 and mRNA encoding Cas9 as described above. Tris-saline sucrose was used as a control. Three mice were tested per group. At necropsy (8 days post-dose), liver and blood (for serum) was collected for analysis. The percent editing of the humanized TTR locus observed in the liver was 50.7% at a dose of 1 mg/kg of the LNP formulated with human TTR guide RNA 1 and mRNA encoding Cas9, 13.0% at a dose of 0.3 mg/kg, and 2.3% at a dose of 0.1 mg/kg, with less than 0.1% editing observed in the control mice. Human TTR levels were then measured in liver lysate and serum from the dosed mice. Livers were lysed in RIPA and protease inhibitors at 100 mg/mL. A human TTR ELISA kit (Aviva Systems Biology; Cat No.: OKIA00081; 1:100 dilution for liver lysates; 1:5000 or 1:10000 dilution for serum) was used to assess human TTR levels. As shown in FIG. 14, a level of more than 1000 ng/mL human TTR was measured in liver lysates from control animals, and these levels were decreased by more than 50% in animals dosed at 1 mg/kg of the LNP formulated with human TTR guide RNA 1 and mRNA encoding Cas9. As shown in FIGS. 15A and 15B, human TTR was measured at levels of 80,000 ng/mL or more in serum from control animals, and human TTR levels were reduced by 66% in animals dosed at 1 mg/kg of the LNP formulated with human TTR guide RNA 1 and mRNA encoding Cas9.

Next, three different human TTR guide RNAs (human TTR guide RNAs 3, 4, and 5) were tested in vivo in homozygous humanized TTR mice. The LNP formulations contained Cas9 mRNA in a 1:2 ratio by weight to the guide RNA. The LNPs contained a cationic lipid (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate), cholesterol, DSPC, and PEG2k-DMG in a 50:38:9:3 molar ratio, respectively, and had an N:P ratio of 6.

Figure 19:
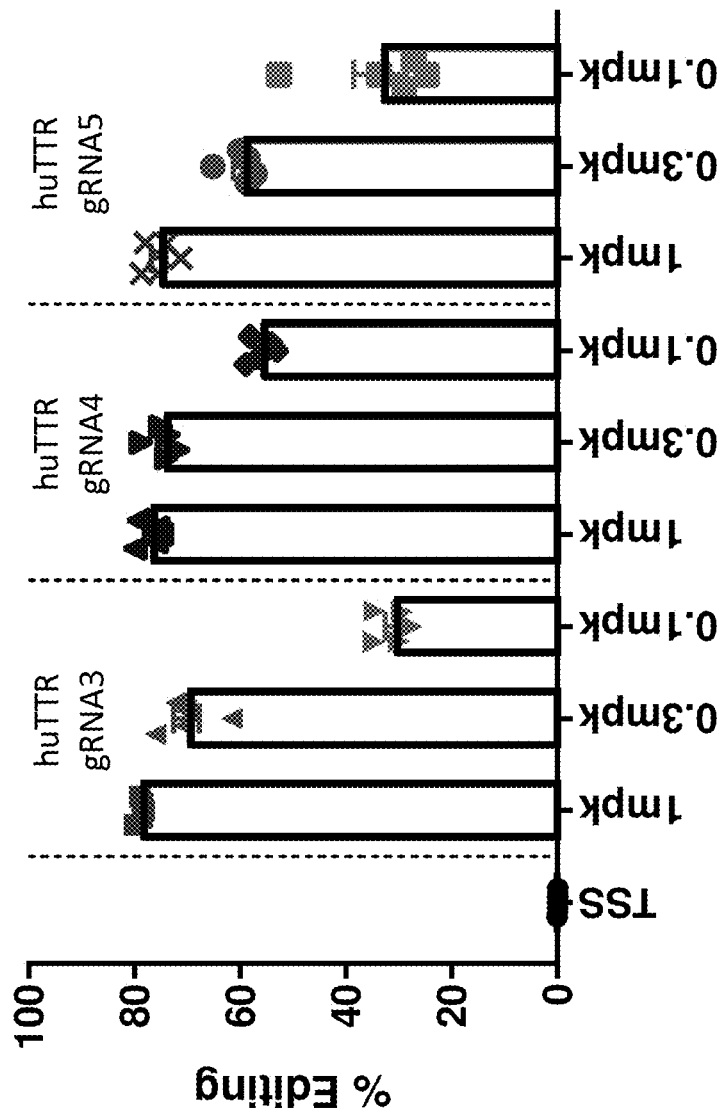
FIG. 19 shows percent genome editing at the humanized mouse Ttr locus as determined by next-generation sequencing (NGS) in samples from liver post-injection of buffer control or lipid nanoparticles containing Cas9 mRNA and guide RNAs designed to target human TTR into mice homozygous for the first version of the humanized mouse Ttr locus.

First, editing at the humanized TTR locus was assessed. Mice were weighed prior to injection, and LNPs (containing Cas9 mRNA plus a human TTR gRNA) were prepared at doses of 1 mg/kg, 0.3 mg/kg, and 0.1 mg/kg (n=5 mice per group). Delivery was intravenous through tail vein injection. As described above, mice were later euthanized, and blood serum was harvested along with liver tissues. The tissues were processed into DNA lysates that were then analyzed by next-generation sequencing (NGS). NGS showed significant editing in liver for each human TTR gRNA at all tested doses in a dose-dependent manner. See FIG. 19. Liver editing results were determined using primers designed to amplify the region of interest for NGS analysis.

Figure 20:
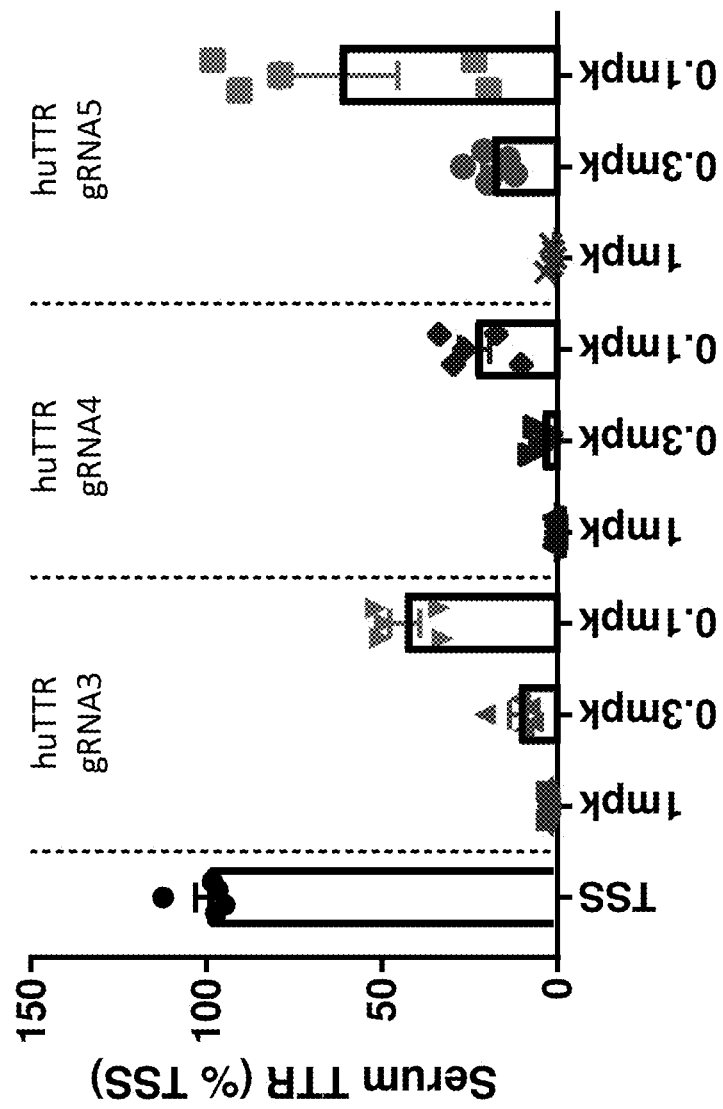
FIG. 20 shows results of an ELISA assaying human TTR levels in serum samples post-injection of buffer control or lipid nanoparticles containing Cas9 mRNA and guide RNAs designed to target human TTR into mice homozygous for the first version of the humanized mouse Ttr locus.

Second, serum TTR levels were assessed. Mice were weighed pre-dose for dosing calculations. The mice were dosed intravenously at 1 mg/kg, 0.3 mg/kg, and 0.1 mg/kg (n=5 mice per group) with LNPs formulated with human TTR guide RNA 3, 4, or 5 and mRNA encoding Cas9 as described above. The LNP formulations contained Cas9 mRNA in a 1:2 ratio by weight to the guide RNA. The LNPs contained a cationic lipid (9Z,12Z)-3-((4,4-bis(octyloxy)butanoyl)oxy)-2-((((3-(diethylamino)propoxy)carbonyl)oxy)methyl)propyl octadeca-9,12-dienoate, also called 3-((4,4-bis(octyloxy)butanoyl)oxy)-2-((((3-(diethylamino)propoxy)carbonyl)oxy)methyl)propyl (9Z,12Z)-octadeca-9,12-dienoate), cholesterol, DSPC, and PEG2k-DMG in a 50:38:9:3 molar ratio, respectively, and had an N:P ratio of 6. Tris-saline sucrose was used as a control. As described above, blood (for serum) was later collected for analysis. Human TTR levels were then measured in serum from the dosed mice. Human serum TTR levels were assessed as described above. As shown in FIG. 20, human TTR levels were significantly reduced in mice dosed with each guide RNA at all doses in a dose-dependent manner.

Example 4. Generation of Mice Comprising a Humanized TTR Locus Encoding a Chimeric Mouse/Human TTR Protein with a Mouse Signal Sequence We hypothesized that the mouse signal sequence of TTR may enhance hTTR secretion to more robust levels. Hydrodynamic delivery (HDD) plasmids were constructed containing a cDNA insert for mouse Ttr (mTtr) signal sequence+hTTR ("m/hTTR"). HDD constructs using the pRG977 vector with the cDNA inserts listed in Table 9 were injected via HDD into male C57/BL6 mice, each 59 days old. ELISAs were performed on submandibular blood on day 4 post-HDD. F1H4 plasma and human serum were included in the ELISAs as negative and positive controls, respectively.

TABLE 9

Summary of HDD Experiment.

| HDD Construct | Number Mice | Weight; g (SD) | cDNA insert |
| --- | --- | --- | --- |
| Nanoluc | 8 | 21.5 (2.23) | Nanoluc |
| Control Protein | 7 | 22.8 (1.40) | Control protein |
| hTTR | 8 | 23.4 (0.74) | hTTR signal sequence + hTTR |
| m/hTTR | 8 | 22.9 (0.66) | mTTR signal sequence + hTTR |

Figure 13:
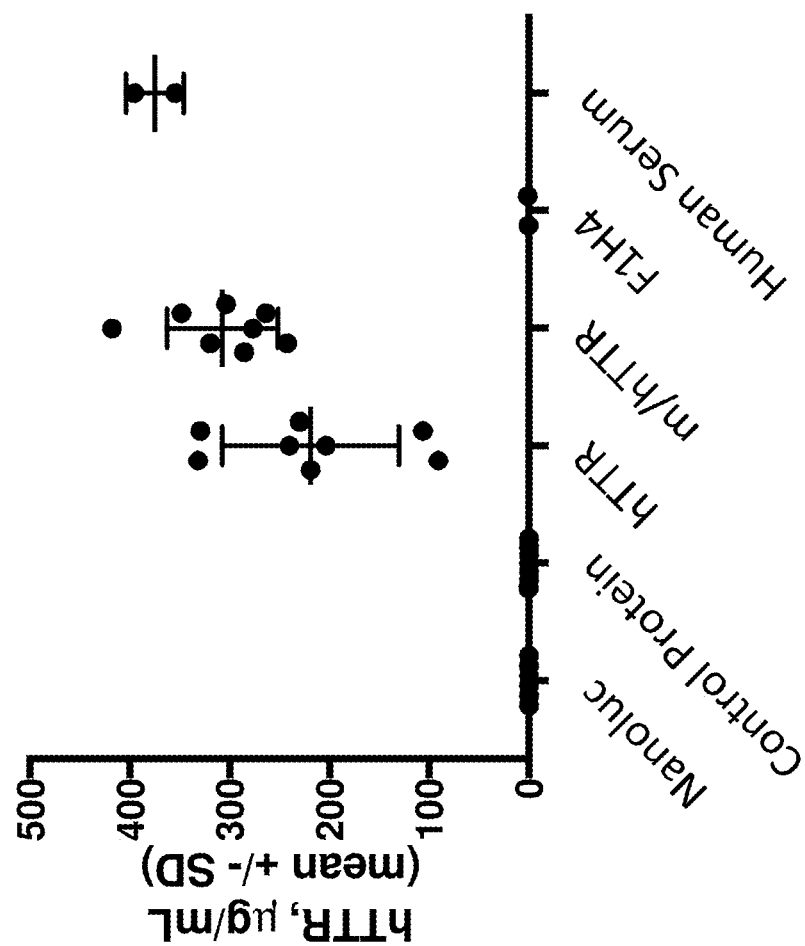
FIG. 13 shows results of an ELISA assaying serum levels of human TTR in wild type mice (F1H4), mice in which human TTR plasmids were introduced by hydrodynamic delivery (HDD), and mice in which a chimeric mouse/human TTR plasmid (region encoded by exon 1 is mouse, region encoded by exons 2-4 is human) was introduced by HDD. Two negative controls are shown, and human serum was used as a positive control.

The results are shown in FIG. 13. HDD into wild type C57/BL6 mice revealed that utilizing the mouse signal sequence of TTR did in fact increase hTTR secretion into plasma when compared to human signal sequence TTR+hTTR ("hTTR"). This demonstrated that C57/BL6 mice can be used to predict TTR constructs that will result in robust hTTR secretion.

Figure 4:
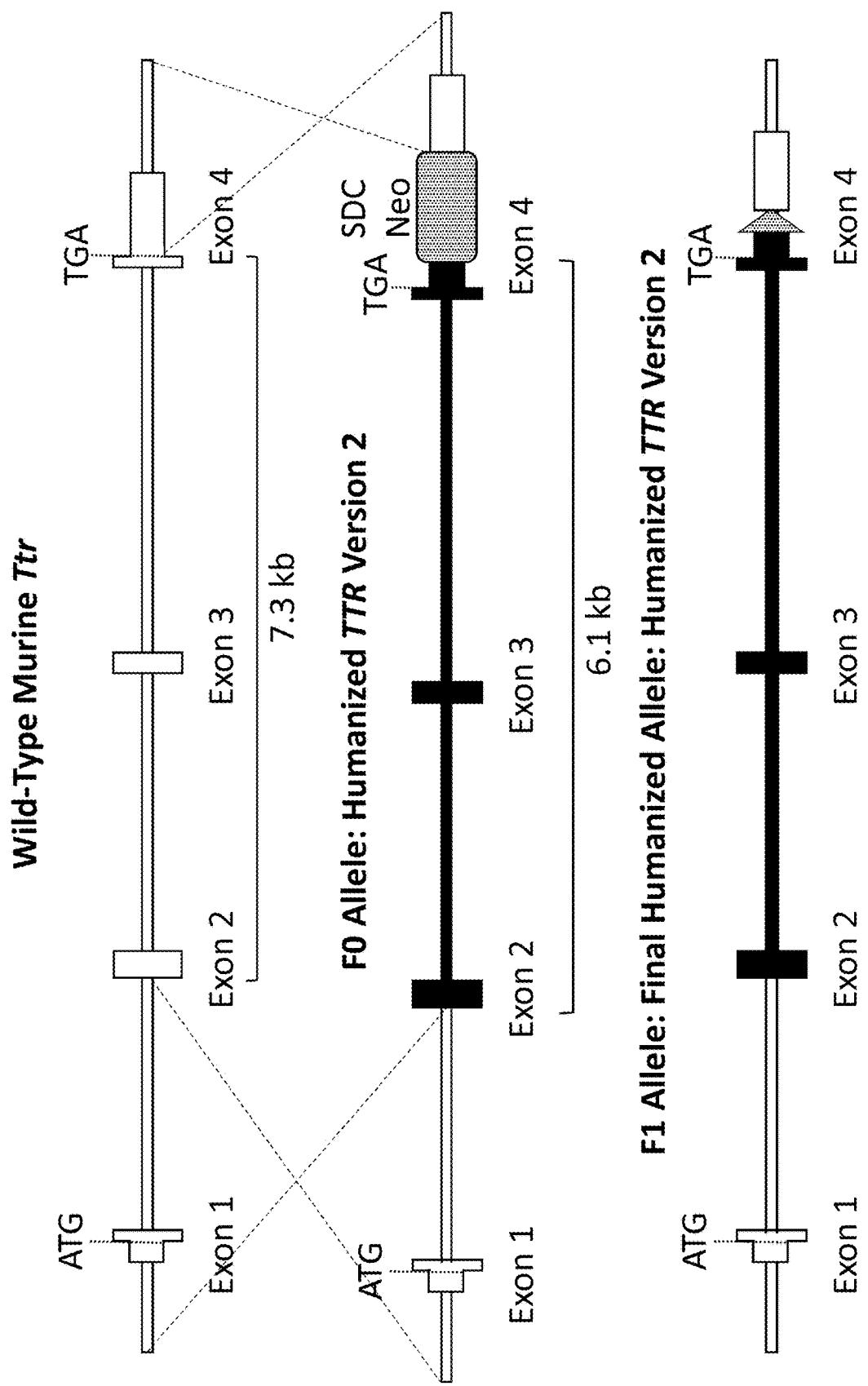
FIG. 4 shows a schematic (not drawn to scale) of the targeting to create the second version of the humanized mouse Ttr locus. The wild type mouse Ttr locus, the F0 allele of the humanized mouse Ttr locus with the SDC-Neo selection cassette, and the F1 allele of the humanized mouse Ttr locus with the loxP scar from removal of the SDC-Neo selection cassette are shown. White boxes indicate murine sequence; black boxes indicate human sequence.
Figure 5B:
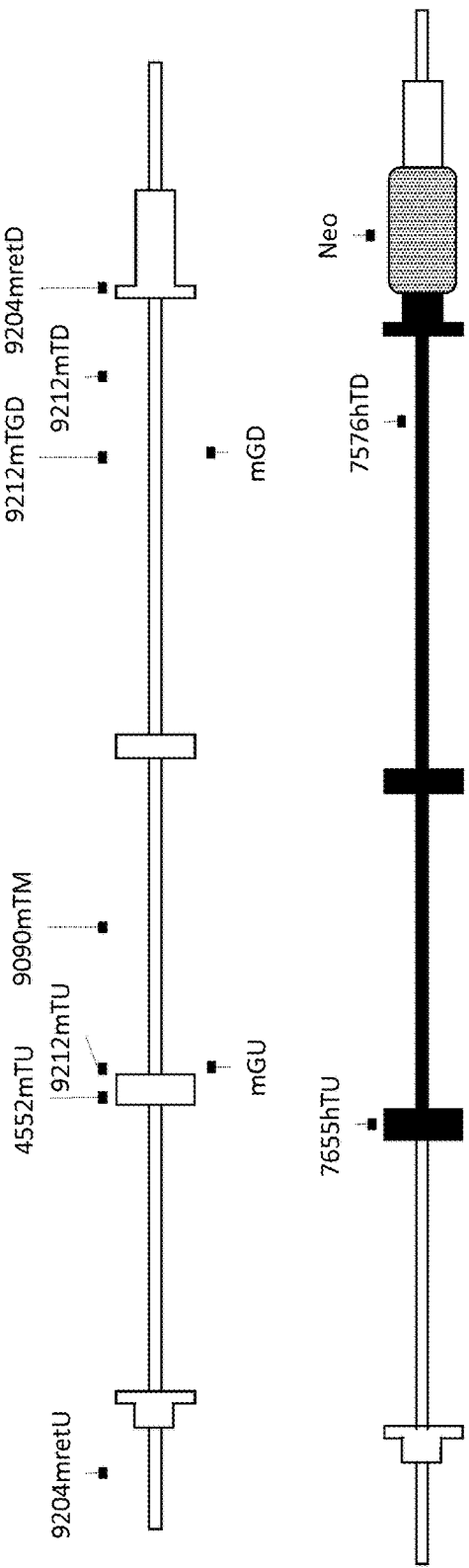
FIG. 5B shows a schematic (not drawn to scale) of the strategy for screening of the second targeted mouse Ttr locus, including loss-of-allele assays (4552mTU, 9212mTU, 9090mTM, 9212mTD), gain of allele assays (7655hTU, 7576hTD, Neo), retention assays (9204mretU, 9204mretD), and CRISPR assays designed to cover the region that is disrupted by the CRISPR guides (mGU, mGD, and 9212mTGD). White boxes indicate murine sequence; black boxes indicate human sequence.
Figure 16:
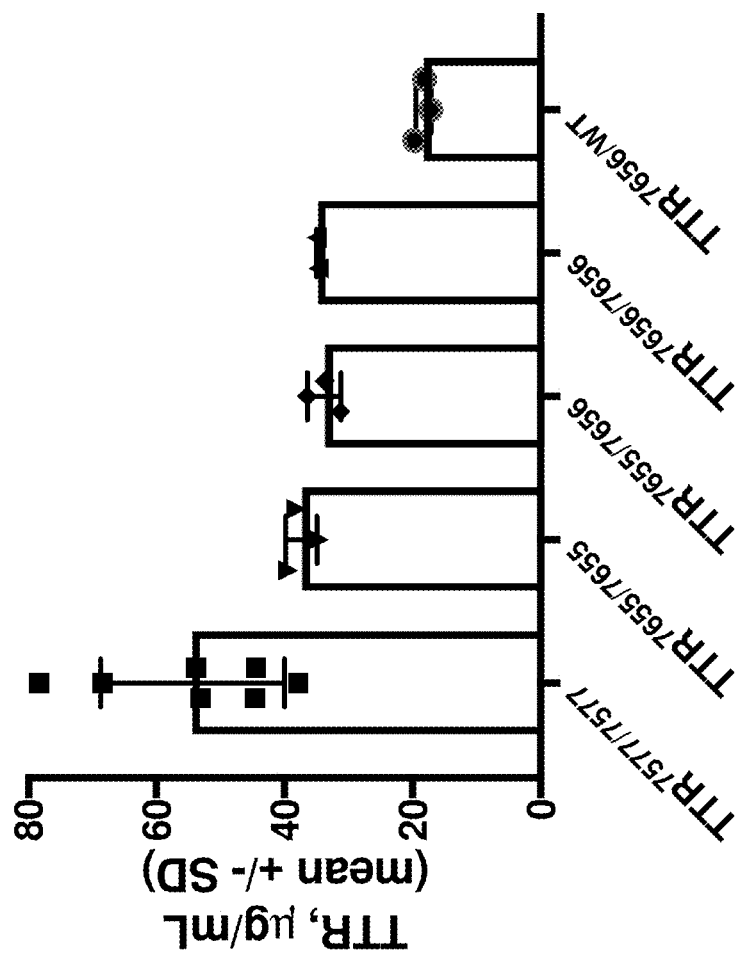
FIG. 16 shows results of an ELISA assaying human TTR levels in blood plasma samples of $hTTR^{7577/7577}$, $hTTR^{7655/7655}$, $hTTR^{7655/7656}$, and $hTTR^{7656/7656}$, and $hTTR^{7656/WT}$ mice.

Based on these results, a second humanized TTR allele was generated comprising a deletion of the region of the mouse Ttr locus from the start of the second exon to the stop codon and its replacement with the orthologous part of the human TTR gene but also including the 3' UTR of the human TTR gene. A large targeting vector comprising a 5' homology arm including 36 kb of sequence upstream from the second exon of the mouse Ttr gene and 34.5 kb of the sequence downstream of the mouse Ttr stop codon was generated to replace the approximately 7.3 kb region from the start of the second exon in the mouse Ttr gene to the mouse Ttr stop codon with the approximately 6.1 kb orthologous human TTR sequence from the start of the second exon in the human TTR gene to the end of the last human TTR exon (exon 4, including the human 3' UTR) and a self-deleting neomycin selection cassette (SDC Neo) flanked by loxP sites. See FIG. 4. To generate the humanized allele, CRISPR/Cas9 components targeting the mouse Ttr locus were introduced into F1H4 mouse embryonic stem cells together with the large targeting vector. Loss-of-allele assays, gain-of-allele assays, and retention assays using primers and probes set forth in FIG. 5B and Table 3 were performed to confirm the humanization of the mouse Ttr allele. Versions with the SDC Neo cassette and after excision of the SDC Neo cassette are shown in FIG. 4. F0 mice were then generated using the VELOCIMOUSE® method.

ing mouse signal sequence) with the neomycin selection cassette removed. The data are summarized in FIG. 16 and Table 10. As shown in FIG. 16, the hTTR$^{7577/7577}$ mice (clone B-F10) had ~55 μg/mL circulating hTTR, which is significant but lower than physiological levels in wild type mice or human serum. Humanized TTR mice with the mouse TTR signal sequence (hTTR$^{7655/7655}$, hTTR$^{7655/7656}$, and hTTR$^{7656/7656}$) did not have increased secreted TTR levels when compared to humanized TTR mice with the human TTR signal sequence (hTTR$^{7577/7577}$).

TABLE 10

Plasma TTR Levels.

| Strain | Description | hTTR, μg/mL (SD) | mTTR, μg/mL (SD) |
|---|---|---|---|
| F1H4 | Wild type control mouse | N.D. | 920 (79.7) |
| V1.0 hTTR$^{7577/7577}$ | Humanized TTR locus, cassette deleted | 54.41 (14.36) | N.D. |
| V2.0 hTTR$^{7655/7655}$ | Humanized TTR locus with mouse TTR signal sequence, cassette deleted | 37.42 (2.461) | N.D. |
| V2.0 hTTR$^{7656/7656}$ | Humanized TTR locus with mouse TTR signal sequence, cassette deleted | 34.88 (n.a.) | N.D. |
| V2.0 hTTR$^{7655/7656}$ | Humanized TTR locus with mouse TTR signal sequence, cassette deleted in one allele but present in other | 33.86 (2.827) | N.D. |
| V2.0 hTTR$^{7656/WT}$ | Heterozygous humanized TTR locus with mouse TTR signal sequence, cassette deleted | 18.36 (1.233) | 57.50 (4.264) |
| Human serum | Human serum control | 234.5 (n.a.) | N.D. |

A comparison of the human and mouse transthyretin precursor protein sequences is shown in FIG. 1A, a comparison of the human and mouse transthyretin coding sequences is shown in FIG. 1B, and a schematic showing the wild type mouse Ttr locus and the final humanized mouse Ttr locus (humanized TTR version 2 with the SDC Neo cassette deleted) is shown in FIG. 2. Sequences for the expected humanized mouse Ttr locus with the SDC Neo cassette and without the SDC Neo cassette are set forth in SEQ ID NOS: 16 and 17, respectively. MAID7655 refers to the humanized TTR locus (keeping mouse signal sequence) with the neomycin selection cassette. MAID7656 refers to the humanized TTR locus (keeping mouse signal sequence) with the neomycin selection cassette removed. The expected transthyretin precursor protein encoded by the humanized mouse Ttr locus (a chimeric mouse/human TTR protein) is set forth in SEQ ID NO: 2.

Figure 18:
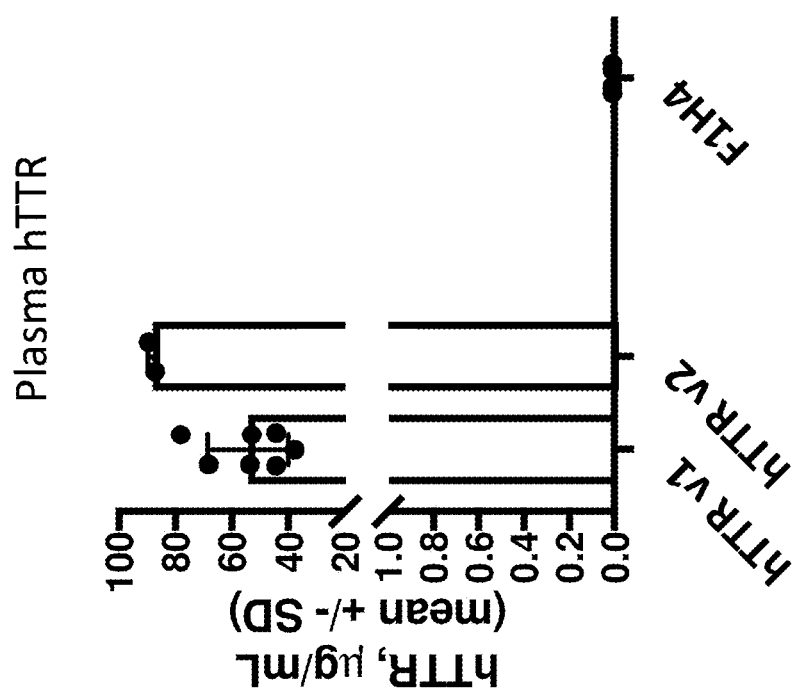
FIG. 18 shows show results of an ELISA assaying human TTR levels in blood plasma samples of wild type (F1H4), $hTTR^{7577/7577}$ (hTTR v1), and $hTTR^{7656/7656}$ (hTTRv2) mice (ages 2-3 months).

A human TTR ELISA kit (Aviva Systems Biology; Cat No.: OKIA00081; 1:2000 dilution) was then used to assess blood plasma human TTR levels in different versions of humanized TTR mice with ages between 1-3 months. The mice included a wild type control mouse and mice with various combinations of wild type, MAID7577, MAID7655, and MAID7656 alleles. MAID7577 refers to the humanized TTR locus with the neomycin selection cassette removed. MAID7655 refers to the humanized TTR locus (keeping mouse signal sequence) with the neomycin selection cassette. MAID7656 refers to the humanized TTR locus (keep- A human TTR ELISA kit (Aviva Systems Biology; Cat No.: OKIA00081; 1:2000 dilution) was then used to assess blood plasma human TTR levels in different versions of humanized TTR mice with ages between 2-3 months in another experiment. The mice included a wild type control mouse (labeled F1H4) and mice homozygous for the MAID7577 or MAID7656 alleles. MAID7577 refers to the humanized TTR locus with the neomycin selection cassette removed. MAID7656 refers to the humanized TTR locus (keeping mouse signal sequence) with the neomycin selection cassette removed. The data are summarized in FIG. 18 and Table 11. As shown in FIG. 18, the hTTR$^{7577/7577}$ mice (hTTR v1) had ~55 μg/mL circulating hTTR, which is significant but lower than physiological levels in wild type mice or human serum. Humanized TTR mice with the mouse TTR signal sequence (hTTR$^{7656/7656}$; hTTRv2) had increased secreted TTR levels when compared to humanized TTR mice with the human TTR signal sequence (hTTR$^{7577/7577}$).

TABLE 11

Plasma hTTR Levels.

| TTR Strain | hTTR, μg/mL (SD) |
|---|---|
| hTTR v2 | 88.45 (1.465) |
| F1H4 | Not detectable |

We claim:

1. A mouse comprising in its genome a genetically modified endogenous Ttr locus comprising a human TTR sequence comprising both TTR coding sequence and non-coding sequence,
   wherein the region of the endogenous Ttr locus from the start of the second Ttr exon to the Ttr stop codon has been deleted and replaced with the corresponding human TTR sequence,
   wherein the first exon and first intron of the endogenous Ttr locus have not been deleted and replaced with the corresponding human TTR sequence,
   wherein the genetically modified endogenous Ttr locus comprises a human TTR 3' untranslated region, and the endogenous Ttr 5' untranslated region has not been deleted and replaced with the corresponding human TTR sequence,
   wherein the genetically modified endogenous Ttr locus comprises the endogenous Ttr promoter, and the human TTR sequence is operably linked to the endogenous Ttr promoter, and
   wherein the mouse is homozygous for the genetically modified endogenous Ttr locus, and
   wherein serum human TTR levels in the mouse are higher than serum human TTR levels in a mouse that is heterozygous for the genetically modified endogenous Ttr locus.

2. A mouse cell comprising in its genome a genetically modified endogenous Ttr locus comprising a human TTR sequence comprising both TTR coding sequence and non-coding sequence,
   wherein the region of the endogenous Ttr locus from the start of the second Ttr exon to the Ttr stop codon has been deleted and replaced with the corresponding human TTR sequence,
   wherein the first exon and first intron of the endogenous Ttr locus have not been deleted and replaced with the corresponding human TTR sequence,
   wherein the genetically modified endogenous Ttr locus comprises a human TTR 3' untranslated region, and the endogenous Ttr 5' untranslated region has not been deleted and replaced with the corresponding human TTR sequence,
   wherein the genetically modified endogenous Ttr locus comprises the endogenous Ttr promoter, and the human TTR sequence is operably linked to the endogenous Ttr promoter, and
   wherein the mouse is homozygous for the genetically modified endogenous Ttr locus, and
   wherein serum human TTR levels in a mouse derived from the mouse cell are higher than serum human TTR levels in a mouse that is heterozygous for the modified endogenous Ttr locus.

3. A method for making the mouse of claim 1, comprising:
   (I) (a) modifying the genome of a pluripotent mouse embryonic stem cell to comprise the genetically modified endogenous Ttr locus;
   (b) identifying or selecting the genetically modified mouse embryonic stem cell comprising the genetically modified endogenous Ttr locus;
   (c) introducing the genetically modified mouse embryonic stem cell into a mouse host embryo; and
   (d) implanting and gestating the mouse host embryo in a surrogate mouse mother; or
   (II) (a) modifying the genome of a mouse one-cell stage embryo to comprise the genetically modified endogenous Ttr locus;
   (b) selecting the genetically modified mouse one-cell stage embryo comprising the genetically modified endogenous Ttr locus; and
   (c) implanting and gestating the genetically modified non mouse one-cell stage embryo in a surrogate mouse mother.

4. The mouse of claim 1, wherein the human TTR sequence at the genetically modified endogenous Ttr locus comprises the sequence set forth in SEQ ID NO: 19.

5. The mouse of claim 1, wherein the genetically modified endogenous Ttr locus encodes a protein comprising the sequence set forth in SEQ ID NO: 2.

6. The mouse of claim 1, wherein the genetically modified endogenous Ttr locus comprises a coding sequence comprising the sequence set forth in SEQ ID NO: 91.

7. The mouse of claim 1, wherein the genetically modified endogenous Ttr locus comprises the sequence set forth in SEQ ID NO: 16 or 17.

8. The mouse of claim 1, wherein the genetically modified endogenous Ttr locus does not comprise a selection cassette or a reporter gene.

9. The mouse cell of claim 2, wherein the human TTR sequence at the genetically modified endogenous Ttr locus comprises the sequence set forth in SEQ ID NO: 19.

10. The mouse cell of claim 2, wherein the genetically modified endogenous Ttr locus encodes a protein comprising the sequence set forth in SEQ ID NO: 2.

11. The mouse cell of claim 2, wherein the genetically modified endogenous Ttr locus comprises a coding sequence comprising the sequence set forth in SEQ ID NO: 91.

12. The mouse cell of claim 2, wherein the genetically modified endogenous Ttr locus comprises the sequence set forth in SEQ ID NO: 16 or 17.

13. The mouse cell of claim 2, wherein the genetically modified endogenous Ttr locus does not comprise a selection cassette or a reporter gene.

* * * * *

UNITED STATES PATENT AND TRADEMARK OFFICE
CERTIFICATE OF CORRECTION

PATENT NO. : 12,010,979 B2
APPLICATION NO. : 18/057960
DATED : June 18, 2024
INVENTOR(S) : Meghan Drummond Samuelson et al.

Page 1 of 1

It is certified that error appears in the above-identified patent and that said Letters Patent is hereby corrected as shown below:

In the Claims

Claim 3, Column 144, Line 2, delete "pluripotent"

Claim 3, Column 144, Line 19, delete "non"

Signed and Sealed this
Thirtieth Day of July, 2024

Katherine Kelly Vidal
*Director of the United States Patent and Trademark Office*

SEQUENCE LISTING

```
Sequence total quantity: 94
SEQ ID NO: 1               moltype = AA  length = 147
FEATURE                    Location/Qualifiers
source                     1..147
                           mol_type = protein
                           organism = Homo sapiens
SEQUENCE: 1
MASHRLLLLC LAGLVFVSEA GPTGTGESKC PLMVKVLDAV RGSPAINVAV HVFRKAADDT    60
WEPFASGKTS ESGELHGLTT EEEFVEGIYK VEIDTKSYWK ALGISPFHEH AEVVFTANDS   120
GPRRYTIAAL LSPYSYSTTA VVTNPKE                                      147

SEQ ID NO: 2               moltype = AA  length = 147
FEATURE                    Location/Qualifiers
REGION                     1..147
                           note = Synthetic
source                     1..147
                           mol_type = protein
                           organism = synthetic construct
SEQUENCE: 2
MASLRLFLLC LAGLVFVSEA GPAGTGESKC PLMVKVLDAV RGSPAINVAV HVFRKAADDT    60
WEPFASGKTS ESGELHGLTT EEEFVEGIYK VEIDTKSYWK ALGISPFHEH AEVVFTANDS   120
GPRRYTIAAL LSPYSYSTTA VVTNPKE                                      147

SEQ ID NO: 3               moltype = DNA  length = 7258
FEATURE                    Location/Qualifiers
source                     1..7258
                           mol_type = genomic DNA
                           organism = Homo sapiens
SEQUENCE: 3
gttgactaag tcaataatca gaatcagcag gtttgcagtc agattggcag ggataagcag    60
cctagctcag gagaagtgag tataaaagcc ccaggctggg agcagccatc acagaagtcc   120
actcattctt ggcaggatgg cttctcatcg tctgctcctc ctggactggt tctgccttg    180
atttgtgtct gaggctggcc ctacggtgag tgtttctgtg acatcccatt cctacattta   240
agattcacgc taaatgaagt agaagtgact ccttccagct tgccaaccca gcttttatta   300
ctagggcaag ggtacccagc atctattttt aatataatta attcaaactt caaaaagaat   360
gaagttccac tgagcttact gagctgggac ttgaactctg agcattctac ctcattgctt   420
tggtgcatta ggtttgtaat atctggtacc tctgtttcct cagatagatg atagaaataa   480
agatatgata ttaaggaagc tgttaatact gaattttcag aaaagtatcc ctccataaaa   540
tgtatttggg ggacaaactg caggagatta tattctggcc ctatagttat tcaaaacgta   600
tttattgatt aatctttaaa aggcttagtg aacaatattc tagtcagata tctaattctt   660
aaatcctcta gaagaattaa ctaatactat aaaatgggtc tggatgtagt tctgacatta   720
ttttataaca actggtaaga gggagtgact atagcaacaa ctaaaatgat ctcaggaaaa   780
cctgtttggc cctatgtatg gtacattaca tcttttcagt aattccactc aaatggagac   840
ttttaacaaa gcaactgttc tcaggggacc tattttctcc cttaaaattc attatacaca   900
tccctggttg atagcagtgt gtctggaggc agaaaccatt cttgctttgg aaacaattac   960
gtctgtgtta tactgagtag ggaagctcat taattgtcga cacttacgtt cctgataatg  1020
ggatcagtgt gtaattcttg tttcgctcca gatttctaat accacaaaga ataaatcctt  1080
tcactctgat caattttctt aacttctcac gtgtcttctc tacacccagg gcaccggtga  1140
atccaagtgt cctctgatgg tcaaagttct agatgctgtc cgaggcagtc ctgccatcaa  1200
tgtggccgtg catgtgttca gaaaggctgc tgatgacacc tgggagccat tgcctctgg   1260
gtaagttgcc aaagaaccct cccacaggac ttggttttat cttcccgttt gcccctcact  1320
tggtagagag aggctcacat catctgctaa agaatttaca agtagattga aaacgtagg   1380
cagaggtcaa gtatgccctc tgaaggatgc cctcttttg ttttgcttag ctaggaagtg  1440
accaggaacc tgagcatcat ttaggggcag acagtagaga aaagaaggaa tcagaactcc  1500
tctcctctag ctgtggtttg caacccttt gggtcacaga acactttatg taggtgatga  1560
aaagtaaaca ttctatgccc agaaaaaatg cacagataca cacacataca aatcatata   1620
tgtgattta ggagtttcac agattccctg tgtccctgg gtaacaccaa agctaagtgt   1680
ccttgtctta gaattttagg aaaaggtata atgtgtatta acccattaac aaaaggaaag  1740
gaattcagaa atattattaa ccaggcatct gtctgtagtt aatatggatc acccaaaacc  1800
caaggctttt gcctaatgaa cactttgggg cacctactgt gtgcaaggct ggggctgtc   1860
aagctcagtt aaaaaaaaaa agatagaaga gatggatcca tgaggcaaag tacagcccca  1920
ggctaatccc acgatcaccc gacttcatgt ccaagagtgg cttctcacct tcattagcca  1980
gttcacaatt tcatggagt tttctacctt gcactagcaa aaacttcaag gaaaatacat  2040
attaataaat ctaagcaaag tgaccagaag acagagcaat caggagaccc tttgcatcca  2100
gcagaagagg aactgctaag tatttacatc tcccacagaa agaatttctg ttgggttta   2160
attgaacccc aagaaccaca tgattcttca accattattg ggaagatcat tttcttaggt  2220
ctggttttaa ctggcttttt atttgggaat tcatttatgt ttatataaaa tgccaagcat  2280
aacatgaaaa gtggttacag gactattcta agggagagac agaatggaca ccaaaatat   2340
tccaatgttc ttgtgaatct tttccttgca ccaggacaaa aaaaaaaaga agtgaaaaga  2400
agaaaggagg aggggcataa tcagagtcag taaagacaac tgctattttt atctatcgta  2460
gctgttgcag tcaaatggga agcaatttcc aacattcaac tatggagctg gtacttacat  2520
ggaaatagaa gttgcctagt gttttgttgct ggcaaagagt tatcagagag gttaaatata  2580
taaaaggaa aagagtcaga tacaggttct tcttcctact ttaggttttc cactgtgtgt  2640
gcaaatgata ctccctggtg gtgtgcagat gcctcaaagc tatcctcaca ccacaaggga  2700
gaggagcgag atcctgctgt cctgagaag tgcagagtta aacagctgt ggccacttgc   2760
atccaatcat caatcttgaa tcacagggac tctttcttaa gtaaacatta tacctggccg  2820
ggcacggtgg ctcacgcctg taatcccagc actttggat gccaaagtgg gcatatcatc   2880
tgaggtcagg agttcaagac cagcctggcc aacatggcaa aactccgtct ttatgaaaaa  2940
```

```
tacaaaaatt agccaggcat ggtggcaggc gcctgtaatc ccagctaatt gggaggctga      3000
ggctggagaa tccctttgaat ctaggaggca gaggttgcag tgagctgaga tcgtgccatt     3060
gcactccagc ctgggtgaca agagtaaaac tctgtctcaa aaaaaaaaaa ttataccctac     3120
attctcttct tatcagagaa aaaaatctac agtgagcttt tcaaaaagtt tttacaaact      3180
ttttgccatt taatttcagt taggagtttt ccctacttct gacttagttg aggggaaatg     3240
ttcataacat gtttataaca tgtttatgtg tgttagttgg tggggtgta ttactttgcc      3300
atgccatttg tttcctccat gcgtaactta atccagactt tcacaccta taggaaaacc      3360
agtgagtctg gagagctgca tgggctcaca actgaggagg aatttgtaga agggatatac    3420
aaagtggaaa tagacaccaa atcttactgg aaggcacttg gcatctcccc attccatgag     3480
catgcagagg tgagtataca gaccttcgag ggttgttttg gttttggttt ttgctttttgg   3540
cattccagga aatgcacagt tttactcagt gtaccacaga aatgtcctaa ggaaggtgat    3600
gaatgaccaa aggttccctt tcctattata caagaaaaaa ttcacaacac tctgagaagc   3660
aaatttctttt ttgactttga tgaaaatcca cttagtaaca tgacttgaac ttacatgaaa    3720
ctactcatag tctattcatt ccactttata tgaatattga tgtatctgct gttgaaataa    3780
tagtttatga ggcagccctc cagacccac gtagagtgta tgtaacaaga gatgcaccat     3840
tttatttctc gaaaacccgt aacattcttc attccaaaac acatctggct tctcggaggt    3900
ctggacaagt gattcttggc aacacatacc tatagagaca ataaaatcaa agtaataatg    3960
gcaacacaat agataacatt taccaagcat acaccatgtg gcagacacaa ttataagtgt    4020
tttccatatt taacctactt aatcctcagg aataagccac tgaggtcagt cctattatta    4080
tccccatctt atagatgaag aaaatgaggc accaggaagt caaataactt gtcaaaggtc    4140
acaagactag gaaatacaca agtagaaatg tttacaatta aggcccaggc tgggtttgcc    4200
ctcagttctg ctatgcctcg cattatgccc caggaaactt tttcccttgt gaaagccaag    4260
cttaaaaaaa gaaaagccac atttgtaacg tgctctgttc ccctgcctat ggtgaggatc   4320
ttcaaacagt tatacatgga cccagtcccc ctgccttctc cttaatttct taagtcatttt    4380
gaaacagatg gctgtcatgg aaatagaatc cagacatgtt ggtcagagtt aaagatcaac    4440
taattccatc aaaaatagct cggcatgaaa gggaactatt ctctggctta gtcatggatg   4500
agactttcaa ttgctataaa gtggttcctt tattagacaa tgttaccagg gaaacaacag    4560
gggtttgttt gacttctggg gcccacaagt caacaagaga gccccatcta ccaaggagca    4620
tgtccctgac taccctcag ccagcagcaa gacatggacc ccagtcaggg caggagcagg   4680
gtttcggcgg cgcccagcac aagacattgc ccctagagtc tcagccccta ccctcgagta    4740
atagatctgc ctacctgaga ctgttgtttg cccaagagct gggtctcagc ctgatgggaa   4800
ccatataaaa aggttcactg acatactgcc cacatgttgt tctctttcat tagatcttag    4860
cttccttgtc tgctcttcat tcttgcagta ttcattcaac aaacattaaa aaaaaaaaaa   4920
agcattctat gtgtggaaca ctctgctaga tgctgtggat ttagaaatga aaatacatcc   4980
cgacccttgg aatggaaggg aaaggactga agtaagacag attaagcagg accgtcagcc   5040
cagcttgaag cccagataaa tacggagaac aagagagagc gagtagtgag agatgagtcc    5100
caatgcctca ctttggtgac gggtgcgtgg tgggcttcat gcagcttctt ctgataaatg    5160
cctccttcag aactggtcaa ctctacccttg gccagtgacc caggtggtca tagtagattt     5220
accaagggaa aatgaaaact tttattagga gctcttaggc ctcttcactt catggatttt    5280
ttttttcctttt tttttttgaga tggagttttg ccctgtcacc caggctggaa tgcagtggtg   5340
caatctcagc tcactgcaac ctccgcctcc caggttcaag caattctcct gcctcagcct   5400
cccgagtagc tgggactaca ggtgtgcgcc accacaccag gctaattttt gtatttttg    5460
taaagacagg tttcaccac gttggccagg ctggtctgaa ctccagacct caggtgattc    5520
acctgtctca gcctcccaaa gtgctgggat tacaggtgtg agccaccgtg cccggctact   5580
tcatggatttt tgattacag attatgcctc ttacaatttt taagaagaat caagtgggct   5640
gaaggtcaat gtcaccataa gacaaaagac atttttatta gttgattcta gggaattggc   5700
cttaagggga gcccttttctt cctaaagagat tcttaggtga ttctcacttc ctcttgcccc    5760
agtattattt ttgttttttgg tatgctcac tcagatcctt ttttcctcct atccctaagt    5820
aatccggggtt tctttttccc atatttgaaa caaaatgtat ttatgcagag tgtgtccaaa    5880
cctcaaccca aggcctgtat acaaaataaa tcaaattaaa cacatctta ctgtcttcta   5940
cctctttcct gacctcaata tatcccaact tgcctcactc tgagaaccaa ggctgtccta    6000
gcacctgagt cgcagatatt ctactgattt gacagaactg tgtgactatc tggaacagca    6060
ttttgatcca caatttgccc agtttacaaag cttaaatgag ctcagtgca tgcatatata    6120
tttcaaaatt ccaccatgat cttccacact ctgtattgta aatagagccc tgtaatgctt   6180
ttacttcgta tttcattgct tgtttatacat aaaaatatc ttttcttctt catgttagaa    6240
aatgcaaaga ataggagggt ggggggaatct ctgggcttgg agacaggaga cttgccttcc   6300
tactatggtt ccatcagaat gtagactggg acaatacaat aattcaagtc tggtttgctc    6360
atctgtaaat tgggaagaat gttttccagct ccagaatgct aaatctctaa gtctgtggtt   6420
ggcagccact attgcagcag ctcttcaatg actcaatgca gttttgcatt ctccctacct    6480
ttttttttcta aaaccaataa aatagataca gcctttaggc tttctgggat ttcccttagt     6540
caagctaggg tcatcctgac tttcggcgtg aattgcaaa acaagacctg actctgtact     6600
cctgctctaa ggactgtgca tggttccaaa ggcttagctt gccagcatat ttgagctttt    6660
tccttctgtt caaactgttc caaaatataa aagaataaaa ttaattaagt tggcactgga    6720
cttccggtgg tcagtcatgt gtgtcatctg tcacgttttt gactcgtctgg tggaaatgga    6780
tctgtctgtc ttctctcata ggtggtattc acagcaacg actccggccc cgccgctac      6840
accattgccg ccctgctgag cccctactcc tattccacca cggctgtcgt caccaatccc    6900
aaggaatgag ggacttctcc tccagtggac ctgaaggacg agggatggga tttcatgtaa    6960
ccaagagtat tccattttta ctaaagcagt gttttcaccct catatgctat gttagaagtc   7020
caggcagaga caataaaaca ttcctgtgaa aggcacttt cattccactt taacttgatt    7080
ttttaaattc ccttattgtc ccttccaaaa aaaagagaat caaattttta caagaatca     7140
aaggaattct agaagtatc tgggcagaac gctaggagag atccaaattt ccattgtctt     7200
gcaagcaaag cacgtattaa atatgatctg cagccattaa aaagacacat tctgtaaa       7258
```

SEQ ID NO: 4   moltype = DNA length = 938
FEATURE     Location/Qualifiers
source      1..938
         mol_type = other DNA
         organism = Homo sapiens
SEQUENCE: 4

```
gttgactaag tcaataatca gaatcagcag gtttgcagtc agattggcag ggataagcag    60
cctagctcag gagaagtgag tataaaagcc ccaggctggg agcagccatc acagaagtcc   120
actcattctt ggcaggatgg cttctcatcg tctgctcctc ctctgccttg ctggactggt   180
atttgtgtct gaggctggcc ctacgggcac cggtgaatcc aagtgtcctc tgatggtcaa   240
agttctagat gctgtccgag gcagtcctgc catcaatgtg gccgtgcatg tgttcagaaa   300
ggctgctgat gacacctggg agccatttgc ctctgggaaa accagtgagt ctggagagct   360
gcatgggctc acaactgagg aggaatttgt agaagggata tacaaagtgg aaatagacac   420
caaatcttac tggaaggcac ttggcatctc cccattccat gagcatgcag aggtggtatt   480
cacagccaac gactccggcc cccgccgcta caccattgcc gccctgctga gccctactc   540
ctattccacc acggctgtcg tcaccaatcc caaggaatga gggacttctc ctccagtgga   600
cctgaaggac gagggatggg atttcatgta accaagagta ttccattttt actaaagcag   660
tgttttcacc tcatatgcta tgttagaagt ccaggcagag acaataaaac attcctgtga   720
aaggcacttt tcattccact ttaacttgat ttttttaaatt cccttattgt cccttccaaa   780
aaaaagagaa tcaaaatttt acaaagaatc aaggaattc tagaaagtat ctgggcagaa   840
cgctaggaga gatccaaatt tccattgtct tgcaagcaaa gcacgtatta aatatgatct   900
gcagccatta aaaagacaca ttctgtaaaa aaaaaaaa                           938

SEQ ID NO: 5         moltype = DNA   length = 9077
FEATURE              Location/Qualifiers
source               1..9077
                     mol_type = genomic DNA
                     organism = Mus musculus
SEQUENCE: 5
ctaatctccc taggcaaggt tcatatttgt gtaggttact tattctcctt ttgttgacta    60
agtcaataat cagaatcagc aggtttggag tcagcttggc agggatcagc agcctgggtt   120
ggaaggaggg ggtataaaag ccccttcacc aggagaggg gtcacacaga tccacaagct   180
cctgacagga tggcttccct tcgactcttc ctccttggcc tcgctggact ggtatttgtg   240
tctgaagctg gccccgcggt gagtgatcct gtgagcgatc cagacatggc agttagacct   300
tagataaaga agaagtgcct tcttccagat gtgagaacta gagtactcag actctatatt   360
taccattaga ctccaaagag aagagctgga tgcctctgg ctcttccttc tattgcttta   420
gcgcattggg tctgtagtgc tcagtctctg gtgtccttag ataataaaga tatgagatta   480
acatagaaat aaagatataa aagggctgga tgtatagttt agtggtccag tgtatgccta   540
gtatgtgaaa agccttctgt tcaacctcta gcaatagaaa aacaagatat attctcggtg   600
gggctgttaa tattgaattc tcataaaatc tttaatatat ttagtatgcc tattatgttg   660
ttatatttta gttctttagc taatcaaaat gcattattga tctttctttg tcttttttg   720
gccaacactc tattccagtc tttgaaaaag tcctttaaaa gagttaatca gtataattaa   780
atgagtcagg aagtatgtga gggttatttt acaaccagag ggaattacta tagcaacagc   840
tgattagaat gatctcaaga aaaagcccat tctgtctttt tgccaccatg ccttttcagt   900
ggctccattc agatggagag gcaaacagg caatggctct cagggggcct attttccctt   960
tgaacattca ttatccatat ccctggtgca cagcagtgca tctgggggca gaaactgttc  1020
ttgctttgga acaatgctg tctatgtcat actggataaa gaagctcatt aattgtcaac  1080
acttatgtta tcataatggg atcagcatgt acttttggtt ttgttccaga gtctatcacc  1140
ggaaagaaca agccggttta ctctgaccca tttcactgac atttctcttg tctcctctgt  1200
gcccagggtg ctggagaatc caaatgtcct ctgatggtca aagtcctgga tgctgtccga  1260
ggcagccctg ctgtagacgt ggctgtaaaa gtgttcaaaa agacctctga gggatcctgg  1320
gagcccttg cctctgggta agcttgtaga agcccacca tgggaccggt tccaggttcc  1380
catttgctct tattcgtgtt agattcagac acacacaact taccagctga agggctcaga  1440
gagagggctc aggggcgaag ggcacgtatt gctcttgtaa gagacacagg tttaattcct  1500
agcaccagaa tggcagctca taaccatctg aaactcacag tcttaggaga tctgggtatc  1560
tgacattctc ttctacccac catgtgtgtg gtgcacaaat tcatgcag gcatcaaatc  1620
ttataaacaa caacaaaaaa ccaacaaacc tggtagcaaa agaagattag aaggttaaa  1680
atatgagccg agagcttttg tttttgtttg ttttgttttg ttttgtttac atttcaaatg  1740
ttatcccctt tctcggtccc cctcccaaa ccctctaccc cattctctcc tcccttctt  1800
ctatgagggt gttccccacc aacccactcc caccttcctg ctctcgaatt cccctatact  1860
gggacatcaa gccttcacag aatcaagggc ctctcctccc attgatgcco gacaatgtca  1920
tcctctgcta cctatgtggc tggagccatg gtcccttca tgtatcctcc ttggttggtg  1980
gtttagtctc tgggaggtct gggggatctg gttgattgat attattgttc ttcctatgag  2040
attgcaaacc ccttcagctc cttcggtcct ttaactcctc cactgggac cccgagctca  2100
gtccaatggt tggctgtgag catccaccag gagaggcctt ttttttttt tttaacaaag  2160
ctgctttatt atgttgctta gagcatgacc aggaaccaga gcacagtcca agactgaagg  2220
gaggaaaagg ggggagtca ataacccca tgtttcatag tggtttgcaa ccctttatta  2280
tcacagccca ctttaggcaa ataatgaaaa ttatagtctc cagggacaga gaagatggtg  2340
caggaagtga agtgcctgct cagaaaatgg gggcttgaat gtgagttccc agactctgtg  2400
taagatgcca agcatcgaag tgcatgctta taacaccagc ctgaggtag aagcttagaa  2460
acagggtac cctgaagttg cttgttcacc agtgtccctg aatgggtagg tgcatgtttg  2520
gtgagagacc ctgtctcaaa aatcaaggtg taggataatt gaaaatacct agctttgagc  2580
ttagatcatg caaatgtgta cacacactca cacacaccac acacacaaaa aaatgcagag  2640
acagagagat acagagagac agagagatac agagagagaa acagagagaa aaggagaaag  2700
taaaaaacaa ataatttaaa gacccatggc cacaaagagg ctcaaagaca agcacgtata  2760
aaaccataca catgtaattt taggagtttt cagattccct ggtacccgtg ggtgatgcac  2820
aagctttgaa tccagtcttt aaaatcttac gaagaacgtg ttcgtgtgtg ctaatttatt  2880
gatgagagga aaggaattga caaagtgccc ttccggagct cctgcatta cccagactca  2940
gggtttttt aaatgtacac tcagaacaga gtagctctgt gcaagggtag caaccacgaa  3000
gcttaataag aaacatatcg tgagagatct gcaaggcaaa gtctaggggct gaccaatctc  3060
acagtcaccc actagcatgt caacacaact tcccaccgt gctagccact tagcaatttt  3120
gtgttgttct gttttgtttt tgttttttaac aaagcaattt caagagatt tctaattcat  3180
ctaaacaaac aaaccaaaag gaaaacagca aagacgccct gagcacttag cagagcagct  3240
atgcagttat gactcctggg tggagacttt tatatcagct tcaactgaat acctagaacc  3300
tactagtgct cttcatcaat ccttgggaag gtcatttct tttggtgctg ttttgagttt  3360
```

```
ctatttgtta atgtcttcat aattatacac gtgttgagca cagcatgcaa agtgattagg   3420
ggaatctagt tggagtggaa tggataccca aatattcaga cttcttgtg actcttcttt    3480
cttgtaccca catcaaaaaa aaaaaaaatg gagatgagac atggtcagag tcactaaaac   3540
cagctgctac ttttaattac gtggggagca gtttctaaca ttgccattat tgaactgatg   3600
ctgcctgggt ggaaatggaa atcacttagt atttcttgtt ggcaaagaat tactgaatgg   3660
attaaatttc caagggaga agtcagttac aagtctttc tttgtttatt aggctttctg     3720
ctatgataaa ttacactact tccagaagtt acccttaggc catgggacac tggactatca   3780
ctctgctgtc acaagagatt acagagttag tcaaggcagc ttgtgacacc ttcagggact   3840
gtcataaact tccagcaagt cattaatcct gaatgcaata ctgtgtgtgt gtgtctatgt   3900
gtgtttgtat gtctgtgtgt gtcttatgtc tgtgtctctg tgtgtgtgtg tgtttgtgtg   3960
tgtgtgtgta tgtatgcctg tgtgtgtctt atgtctgtgt ttgtgtgtct gtgtgtgtct   4020
tatgtctgtg tttgtatgtc tgtgtgtgtc tgtgtgtgtc ttatgtctgt gtctctgtgt   4080
gtgtgtgtgt gtatgtatgt atgtatgtat gtatgtgtat gtgtttgcat ctctctgtgt   4140
gtctgcgctt atatatttgt gtatgtgttt atgtgttcgt cttgtgcgt tgttggggat   4200
tgaatccagg ggaatacaaa tgttaagaaa gaacgttacc actaagcttc acctgtaggc   4260
cttaaagctt ttctttcttt taaaaattgt aattaattca ttttcagtca ggatctccac   4320
acctcgtccc tgctgctcta gaactcacta tttaaacaca atcgccctca aacctgcagc   4380
aaccctcccg cctctaccct gcgagcacta gaataataac aggtgaccc acacgcctag   4440
attaagacct ttaaggtaaa cattttacta tattttagtc tcataagaca agatgctaca   4500
ataaagctgt acataaagtt ccctcgaatt tcttgctatt ttaactcaaa cataaggatt   4560
tcctcctttt tgattcaggt aacagaaaaa atacacaggt acatacatgt acacatga    4620
acacacacgc atcacaacca catatgcgca cgcttgtgtg atctatcatt taccatgcca   4680
ctgaactctt cttccccat aaattcctct ggacttgtgt gccctccagg aagaccgcgg   4740
agtctggaga gctgcacggg ctcaccacag atgagaagtt tgtagaagga gtgtacagag   4800
tagaactgga caccaaatcg tactggaaga cacttggcat tccccgttc catgaattcg   4860
cggatgtaag tggacacacc aagttgtttg gattttgttt ttagtctcag gaaattccct   4920
tcgctcttgc tgtacgatgg gcatgagtgg aaagtagatt ccacagccag aatccacagt   4980
gctgggaaag caagccttct gaattttct aaaactcatt tagcaacatg gcctgaacct    5040
gttcacactg cttatggtca gctaactata tttatgtaaa tattcatttc tctgttgagg   5100
aaatgttagt atttgctttt gaggcaacct ccagatacca tggagggcat gtcatagtca   5160
aagagagggc tccctatggt atttctctaa attctggcat ttcctttatt ccaaagcaca   5220
tctagtgtcc ccagaagttt gggtagacaa ttcttggcaa cacagagaat acaacatgt    5280
tcaaaaccca acagcttaat atctaaatca tcaagcaaac atcacatggc aaagggattt   5340
ctgaatcaaa actgtttcat ccttatgatc aacctatgga ggtctagcct cgacttacac   5400
ccattttacc aataagctaa gagaagctaa gttcctcatc aaggacacaa ggctagcatg   5460
tgtgagcaag tgacagagtt gccctctatg ttggttagtg tgccttagcc agtgtctcag   5520
taagaaatgg agctaaatca aaacccaagg ccaacagcca aaggcacatg agtaacctt    5580
gcttggcact gggctcagtt tccctggctc ctctcagtcc tcagttcaca gaggcagctg   5640
tcatgcaaat agaatccaag cttgttggtc agacctggag ataacaaatt ccatcaaaaa   5700
tagctcctca tgtgacctag tttgctgtct gttgctatga tacacaccat gaccgaaaag   5760
caaccctggg gagagaaggg tttatttcat cttacagctt acagttcacc atggaggaaa   5820
gccaggtggg aacctggaag tggaaattga agcagagacc agaaaggaat gctgtttact   5880
ggctggctta gctcctttc ttatacagct taggtctatg tgcccagggg atggtactgc   5940
cgagcataggg ctgagcccgc ctacatcaac cattagtcaa aaaaggtcc atagacttgc   6000
ctacaggcca atctcatgga ggcaatacc cagtggaggg tccctcttcg caggttactc     6060
tagtttgtgt caagttgaca aaacctaacc acaaagcaca aacagggtct gcccttgtgt   6120
cttagccatg gatgacactc tcagatgatg gtgttaccag acaaaccaga ggggctcacc   6180
aagagtctgc cacctaccaa ggtagtactc tactcctcac tgggcaccaa cacccatatt   6240
agctgggcca gtacaggacc cttgctgttt cctgcatgaa ttgtccatag accctgggtc   6300
tcagcctgcc gggagtacct gtaagtagtc gcctcaaaca cattattcct gttggaagac   6360
ttgtctgatt ctcttttaga actcaatcaa caaacgtttt tatttttgtt tggctttttg   6420
gagacaagat ctctcatagg ccagcctgac ttgaatgtag ctgaggatga cctgtgctgc   6480
taatcttctc gcctcttcct cccaagtggt aggataatag gcataagaca ccacagcagt   6540
tttactccat accagggctc tgaacccaga cttaaacac tctatcaact gattcacatt    6600
cccaccccat cattcaacaa acatttgaaa aataaaaccc ttctgccttg agcactctgc   6660
taaatacagc ctttgagtgc ggagtatttc ctcacaacca gggtccaaga tgaccccatc   6720
atacatacca cggaaaatta ggagatgttt ttaggtctct ttgcttgggg taatttttat   6780
gtgtgtgtgt acacagccct gtgcgtgtgt gtgtgtgtgt gtgtgtgtgt gtacaggcac   6840
acacgtgtat gcatgtagag gctacataaa aaccttaggt gtcattctca ggcactctgt   6900
tcaccccttc acacagcccg aacacacaaa atttgaggca ttagcctgga gctcaccagt   6960
taggctagac tgacttgcca gcagacccca ggctgtctcc atctccccag ctctgggatt   7020
acaaactcta tcataccaga cattttttata catattctga gcataaaatt catgtcttca   7080
ggctaacaag tcaagagctt aaatgactga gctctcttac gtggtggatt ttttttaaaa   7140
ctacataata tcttttttttt tttttcact tctgggaaag aaacaaatga gcctgagtga   7200
caatgcgaca gaaagaaat tttgaggagt gtgtgtgtct gtgtgtgtgg tggcacatgt    7260
ctctcatcta atgctagagg ctacagtaga atgctcctga attagtggcc agccaaggcc   7320
aagggctagg gttgtaactc agtggcagag ggcttgccta gcattcgcag gatttgatcc   7380
atagcgctat aaataataat aaataaatac aacagtctaa gatgattctc cctttcattt   7440
atctggatgt tattttttgtg ttagtttttac tctgtcatcc aatcattgtt tgcctctat   7500
ttggacattt aaaaaaaatc tttattccaa gtgtgttcaa agctgtatcc aaaacctgtc   7560
caccaaatga gtccaatgac atacatcttc tatattacca tctgttccag atttggctga   7620
ctcccggcac ctgggctgtt gctgcaccca tgtctcagat agtctagtga tttgagaagt   7680
gactagtaat tgcaaaatcc agactttgtc cagaaacttc tatgagctcc aaaactttca   7740
tttacattc tgccagccac aaacccgcttg tgttgtgagg agaacccgt gatgtctttc     7800
cacagcatct cagccttgtt tcttccctta aaatattcat cttttcacat tagaacatgc   7860
aaagggacag tgggagcgaa accccctggac tgggacgcac gaagcttcc tttctggtca   7920
ggctctcact gtgaaaactt aggccggttt cagcatgcag tctgctggag aatggctcct   7980
gccaacattc caggtctgga agtttgtagt ggagttgttg ataaccactg ttcgccacag   8040
gtcttttgtt tgtgggtgtc agtgtttcta ctctcctgac ttttatctga acccaagaaa   8100
```

-continued

```
gggaacaata gccttcaagc tctctgtgac tctgatctga ccagggccac ccacactgca    8160
gaaggaaact tgcaaagaga gacctgcaat tctctaagag ctccacacag ctccaaagac    8220
ttaggcagca tattttaatc taattattcg tcccccaacc ccaccccaga ggacagttag    8280
acaataaaag gaagattacc agcttagcat cctgtgaaca ctttgtctgc agctcctacc    8340
tctgaagctct gttagaacta gctgtctctc ctctctccta ggtggttttc acagccaacg    8400
actctggcca tcgccactac accatcgcag ccctgctcag cccatactcc tacagccacca    8460
cggctgtcgt cagcaacccc cagaattgag agactcagcc caggaggacc aggatcttgc    8520
caaagcagta gcatcccatt tgtaccaaaa cagtgttctt gctctataaa ccgtgttagc    8580
agctcaggaa gatgccgtga agcattctta ttaaaccacc tgctatttca ttcaaactgt    8640
gtttctttt tattcctca ttttctccc ctgctcctaa acccaaaat cttctaaaga    8700
attctagaag gtatgcgatc aaactttta aagaaagaaa atacttttg actcatggtt    8760
taaaggcatc ctttccatct tggggaggtc atgggtgctc ctggcaactt gcttgaggaa    8820
gataggtcag aaagcagagt ggaccaaccg ttcaatgttt tacagcaaa acatacacta    8880
agcatggtct gtagctatta aaagcacaca atctgaaggg ctgtagatgc acagtagtgt    8940
tttcccagag catgttcaaa agccctgggt tcaatcacaa tactgaaaag taggccaaaa    9000
aacattctga aaatgaaata tttgggtttt tttttataac ctttagtgac taaataaaga    9060
caaatctaag agactaa                                                   9077

SEQ ID NO: 6           moltype = AA  length = 147
FEATURE                Location/Qualifiers
source                 1..147
                       mol_type = protein
                       organism = Mus musculus
SEQUENCE: 6
MASLRLFLLC LAGLVFVSEA GPAGAGESKC PLMVKVLDAV RGSPAVDVAV KVFKKTSEGS    60
WEPFASGKTA ESGELHGLTT DEKFVEGVYR VELDTKSYWK TLGISPFHEF ADVVFTANDS   120
GHRHYTIAAL LSPYSYSTTA VVSNPQN                                      147

SEQ ID NO: 7           moltype = DNA  length = 1237
FEATURE                Location/Qualifiers
source                 1..1237
                       mol_type = other DNA
                       organism = Mus musculus
SEQUENCE: 7
ctaatctccc taggcaaggt tcatatttgt gtaggttact tattctcctt ttgttgacta    60
agtcaataat cagaatcagc aggtttggag tcagcttggc agggatcagc agcctgggtt   120
ggaaggaggg ggtataaaag cccccttcacc aggagaagcc gtcacacaga tccacaagct   180
cctgacagga tggcttccct tcgactcttc ctcctttgcc tcgctggact ggtatttgtg   240
tctgaagctg gccccgcggg tgctggagaa tccaaatgtc ctctgatggt caaagtcctg   300
gatgctgtcc gaggcagccc tgctgtagac gtggctgtaa aagtgttcaa aaagacctct   360
gagggatcct gggagccctt tgcctctggg aagaccgcgg agtctggaga gctgcacggg   420
ctcaccacag atgagaagtt tgtagaagga gtgtacagag tagaactgga caccaaatcg   480
tactggaaga cacttggcat ttccccgttc catgaattcg ctgatgtggt tttcacagcg   540
aacgactctg gccatcgcca ctacaccatc gcagccctgc tcagcccata ctcctacagc   600
accacgcgctg tcgtcagcaa ccccagaat tgagagactc agcccaggag gaccaggatc   660
ttgccaaagc agtagcatcc catttgtacc aaaacagtgt tcttgctcta taaaccgtgt   720
tagcagctca ggaagatgcc gtgaagcatt cttattaaac cacctgctat ttcattcaaa   780
ctgtgttct tttttattc ctcattttc tcccctgctc ctaaaaccca aaatcttcta   840
aagaattcta aaggtatgc gatcaaactt tttaagaaa gaaaatactt tttgactcat   900
ggtttaaagg catcctttcc atcttgggga ggtcatgggt gctcctggca acttgcttga    960
ggaagatagg tcagaaagca gagtggacca accgttcaag gttttacaag caaaacatac   1020
actaagcatg gtctgtagct attaaaagca cacaatctga agggctgtag atgcacagta   1080
gtgtttccc agagcatgtt caaagccct gggttcaatc acaatactga aaagtaggcc   1140
aaaaacatt ctgaaaatga atatttggg ttttttttta acctttag tgactaaata   1200
aagacaaatc taagagacta aaaaaaaaaa aaaaaaa                           1237

SEQ ID NO: 8           moltype = RNA  length = 82
FEATURE                Location/Qualifiers
misc_feature           1..82
                       note = Synthetic
source                 1..82
                       mol_type = other RNA
                       organism = synthetic construct
SEQUENCE: 8
gttggaacca ttcaaaacag catagcaagt taaataagg ctagtccgtt atcaacttga    60
aaaagtggca ccgagtcggt gc                                             82

SEQ ID NO: 9           moltype = RNA  length = 76
FEATURE                Location/Qualifiers
misc_feature           1..76
                       note = Synthetic
source                 1..76
                       mol_type = other RNA
                       organism = synthetic construct
SEQUENCE: 9
gttttagagc tagaaatagc aagttaaaat aaggctagtc cgttatcaac ttgaaaaagt    60
ggcaccgagt cggtgc                                                    76

SEQ ID NO: 10          moltype = RNA  length = 86
```

```
FEATURE              Location/Qualifiers
misc_feature         1..86
                     note = Synthetic
source               1..86
                     mol_type = other RNA
                     organism = synthetic construct
SEQUENCE: 10
gtttaagagc tatgctggaa acagcatagc aagtttaaat aaggctagtc cgttatcaac   60
ttgaaaaagt ggcaccgagt cggtgc                                       86

SEQ ID NO: 11        moltype =   length =
SEQUENCE: 11
000

SEQ ID NO: 12        moltype =   length =
SEQUENCE: 12
000

SEQ ID NO: 13        moltype =   length =
SEQUENCE: 13
000

SEQ ID NO: 14        moltype = DNA   length = 12208
FEATURE              Location/Qualifiers
misc_feature         1..12208
                     note = Synthetic
misc_feature         1..97
                     note = Mouse Sequence
misc_feature         98..7298
                     note = Human Sequence
misc_feature         7299..12108
                     note = SDC Neo Cassette
misc_feature         12109..12208
                     note = Mouse Sequence
source               1..12208
                     mol_type = other DNA
                     organism = synthetic construct
SEQUENCE: 14
agcttggcag ggatcagcag cctgggttgg aaggaggggg tataaaagcc ccttcaccag     60
gagaagccgt cacacagatc cacaagctcc tgacaggatg gcttctcatc gtctgctcct    120
cctctgcctt gctggactgg tatttgtgtc tgaggctggc cctacggtga gtgtttctgt    180
gacatcccat tcctacattt aagattcacg ctaaatgaag tagaagtgac tccttccagc    240
tttgccaacc agcttttatt actagggcaa gggtacccag catctatttt taatataatt    300
aattcaaact tcaaaagaa tgaagttcca ctgagcttac tgagctggga cttgaactct     360
gagcattcta cctcattgct ttggtgcatt aggtttgtaa tatctggtac ctctgtttcc    420
tcagatagat gatagaaata aagatatgat attaaggaag ctgttaatac tgaattttca    480
gaaaagtatc cctccataaa atgtatttgg gggacaaact gcaggagatt atattctggc    540
cctatagtta ttcaaaacgt atttattgat taatctttaa aaggcttagt gaacaatatt    600
ctagtcagat atctaattct taaatcctct agaagaatta actaatacta taaaatgggt    660
ctggatgtag ttctgacatt attttataac aactggtaag agggagtgac tatagcaaca    720
actaaaatga tctcaggaaa acctgtttgg ccctatgtat ggtacattac atctttttca    780
taattccact caaatggaga ctttttaacaa agcaactgtt ctcagggac ctattttctc     840
ccttaaaatt cattatacac atccctggtt gatagcagtg tgtctggagg cagaaaccat    900
tcttgctttg gaaacaatta cgtctgtgtt atactgagta gggaagctca ttaattgtcg    960
acacttacgt tcctgataat gggatcagtg tgtaattcat gtttcgctcc agatttctaa   1020
taccacaaag aataaatcct ttcactctga tcaattttgt taacttctca cgtgtcttct   1080
ctacacccag ggcaccggtg aatccaagtc tcctctgatg gtcaaagttc tagatgctgt   1140
ccgaggcagt cctgccatca atgtggccgt gcatgtgttc agaaaggctg ctgatgacac   1200
ctgggagcca tttgcctctg ggtaagttgca caaagaaccc tcccacagga cttggtttta   1260
tcttcccgtt tgcccctcac ttggtagaga gaggctcaca tcatctgcta aagaaatttac   1320
aagtagattg aaaaacgtag gcagaggtca agtatgccct ctgaaggatg ccctctttt    1380
gttttgctta gctaggaagt gaccaggaac ctgagcatca tttaggggca gacagtagag   1440
aaaagaagga atcagaactc ctctcctcta gctgtggttt gcaacccttt tgggtcacag   1500
aacactttat gtaggtgatg aaaagtaaac attctatgcc cagaaaaaat gcacagatac   1560
acacacatac aaaatcatat atgtgatttt aggagtttca cagattccct ggtgtccctg   1620
ggtaacacca agctaagtg tccttgtctt agaattttag gaaaaggtat aatgtgtatt    1680
aacccattaa caaaaggaaa ggaattcaga aatattatta accaggcatc tgtctgtagt   1740
taatatggat cacccaaaac ccaaggcttt gcctaatga acactttggg gcacctactg   1800
tgtgcaaggc tgggggctgt caagctcagt taaaaaaaaa aagatagaag agatggatcc   1860
atgaggcaaa gtacagcccc aggctaatcc cacgatcacc cgacttcatg tccaagagtg   1920
gcttctcacc ttcattagcc agttcacaat tttcatggag tttttctacc tgcactagca   1980
aaaacttcaa ggaaaataca tattaataaa tctaagcaaa gtgaccagaa acagagcaa    2040
tcaggagacc ctttgcatcc agcagaagag gaactgctaa gtatttacat ctccacagag   2100
aagaatttct gttgggtttt aattgaaccc caagaaccac atgattcttc aaccattatt   2160
gggaagatca ttttcttagg tctggtttta actggcttt tatttgggaa ttcatttatg     2220
tttatataaa atgccaagca taacatgaaa agtggttaca ggactattct aagggagaga   2280
cagaatggac accaaaaata ttccaatgtt cttgtgaatc ttttccttgc accaggacaa   2340
aaaaaaaaag aagtgaaaag aagaaggag gaggggcata atcagagtca gtaaagacaa    2400
ctgctatttt tatctatcgt agctgttgca gtcaaatggg aagcaatttc caacattcaa   2460
```

```
ctatggagct ggtacttaca tggaaataga agttgcctag tgtttgttgc tggcaaagag    2520
ttatcagaga ggttaaatat ataaaaggga aaagagtcag atacaggttc ttcttcctac    2580
tttaggtttt ccactgtgtg tgcaaatgat actcccggt ggtgtgcaga tgcctcaaag    2640
ctatcctcac accacaaggg agaggagcga gatcctgctg tcctggagaa gtgcagagtt    2700
agaacagctg tggccacttg catccaatca tcaatcttga atcacaggga ctctttctta    2760
agtaaacatt atacctggcc gggcacggtg gctcacgcct gtaatcccag cactttggga    2820
tgccaaagtg ggcatatcat ctgaggtcag gagttcaaga ccagcctggc caacatggca    2880
aaactccgtc tttatgaaaa atacaaaaat tagccaggca tggtggcagg cgcctgtaat    2940
cccagctaat tgggaggctg aggctggaga atcccttgga tctaggaggc agaggttgca    3000
gtgagctgag atcgtgccat tgcactccag cctgggtgac aagagtaaaa ctctgtctca    3060
aaaaaaaaaa attataccta cattctcttc ttatcagaga aaaaaatcta cagtgagctt    3120
ttcaaaaagt ttttacaaac tttttgccat ttaatttcag ttaggagttt tccctacttc    3180
tgacttagtt gaggggaaat gttcataaca tgtttataac atgtttatgt gtgttagttg    3240
gtgggggtgt attactttgc catgccattt gtttcctcca tgcgtaactt aatccagact    3300
ttcacacctt ataggaaaac cagtgagtct ggagagctgc atgggctcac aactggagag    3360
gaatttgtag aagggatata caaagtggaa atagacacca aatcttactg gaaggcactt    3420
ggcatctccc cattccatga gcatgcagag gtgagtatac agaccttcga gggttgtttt    3480
ggtttttggtt tttgcttttg gcattccagg aaatgcacag ttttactcag tgtaccacag    3540
aaatgtccta aggaaggtga tgaatgacca aaggttccct ttcctattat acaagaaaaa    3600
attcacaaca ctctgagaag caaatttctt tttgactttg atgaaaatcc acttagtaac    3660
atgacttgaa cttacatgaa actactcata gtctattcat tccactttat atgaatattg    3720
atgtatctgc tgttgaaata atagtttatg aggcagccct ccagacccca cgtagagtgt    3780
atgtaacaag agatgcacca ttttatttct cgaaaacccg taacattctt cattccaaaa    3840
cacatctggc ttctcggagg tctgacaag tgattcttgg caacacatac ctatagagac    3900
aataaaatca aagtaataat ggcaacacaa tagataacat ttaccaagca tacaccatgt    3960
ggcagacaca attataagtg ttttccatat ttaacctact taatcctcag gaataagcca    4020
ctgaggtcag tcctattatt atccccatct tatagatgaa gaaaatgagg caccaggaag    4080
tcaaataact tgtcaaaggt cacaagacta ggaaatacac aagtagaaat gtttacaatt    4140
aaggcccagg ctgggtttgc cctcagttct gctatgcctc gcattatgcc ccaggaaact    4200
ttttcccttg tgaaagccaa gcttaaaaaa agaaaagcca catttgtaac gtgctctgtt    4260
cccctgccta tggtgaggat cttcaaacag ttatacatgg acccagtccc cctgccttct    4320
ccttaatttc ttaagtcatt tgaaacagat ggctgtcatg gaaatagaat ccagacatgt    4380
tggtcagagt taaagatcaa ctaattccat caaaaatagc tcggcatgaa agggaactat    4440
tctctggctt agtcatggat gagactttca attgctataa agtggttcct ttattagaca    4500
atgttaccag ggaaacaaca gggtttgtt tgacttctgg ggccacaag tcaacaagag    4560
agccccatct accaaggagc atgtccctga ctacccctca gccagcagca agacatggac    4620
cccagtcagg gcaggagcag ggtttcggcg gcgcccagca caagacattg ccctagagt    4680
ctcagcccct accctcgagt aatagatctg cctacctgag actgttgttt gcccaagagc    4740
tgggtctcag cctgatggga accatataaa aaggttcact gactactgc ccacatgttg    4800
ttctcttttca ttagatctta gcttccttgt ctgctcttca ttcttgcagt attcattcaa    4860
caaacattaa aaaaaaaaaa aagcattcta tgtgtggaac actctgctag atgctgtgga    4920
tttagaaatg aaaatacatc ccgacccttg gaatggaagg gaaaggactg aagtaagaca    4980
gattaagcag gaccgtcagc ccagcttgca gcccagataa atacggagaa caagagagag    5040
cgagtagtga gagatgagtc ccaatgcctc actttggtga cgggtgcgtg gtgggcttca    5100
tgcagcttct tctgataaat gcctccttca gaactggtca actctacctt ggccagtgac    5160
ccaggtggtc atagtagatt taccaaggga aaatggaaac ttttattagg agctcttagg    5220
cctcttcact tcatggattt tttttttcctt ttttttttgag atggagtttt gcctgtcac    5280
ccaggctgga atgcagtggt gcaatctcag ctcactgcaa cctccgcctc ccaggttcaa    5340
gcaattctcc tgcctcagcc tcccgagtag ctgggactac aggtgtgcgc caccacacca    5400
ggctaatttt tgtatttttt gtaaagacag gttttcacca cgttggccag gctggtctga    5460
actccagacc tcaggtgatt cacctgtctc agcctcccaa agtgctggga ttacaggtga    5520
gagccaccgt gcccggctac ttcatggatt tttgattaca gattatgcct cttacaattc    5580
ttaagaagaa tcaagtgggc tgaaggtcaa tgtcaccata agacaaaaga catttttatt    5640
agttgattct agggaattgg ccttaagggg agccctttct tcctaagaga ttcttaggtg    5700
attctcactt cctcttgccc cagtattatt tttgttttg gtatggctca ctcagatcct    5760
ttttcctcc tatccctaag taatccgggt ttcttttttcc catatttaga acaaaatgta    5820
tttatgcaga gtgtgtccaa acctcaaccc aaggcctgta tacaaaataa atcaaattaa    5880
acacatcttt actgtcttct acctctttcc tgacctcaat atatcccaac ttgcctcact    5940
ctgagaacca aggctgtccc agcacctgag tcgcagatat tctactgatt tgacagaact    6000
gtgtgactat ctggaacagc attttgatcc acaatttgcc cagttacaaa gcttaaatga    6060
gctcagtgc atgcatatat attttcaaaat tccaccatga tcttccacac tctgtattgt    6120
aaatagagcc ctgtaatgct tttacttcgt atttcattgc ttgttataca taaaaatata    6180
cttttcttct tcatgttaga aaatgcaaag aataggaggg tgggggaatc tctgggcttg    6240
gagacaggag acttgccttc ctactatggt tccatcaga tgtagactgg gacaatgaa    6300
taattcaagt ctggtttgct catctgtaaa ttgggaagaa tgtttccagc tccagaatgc    6360
taaatctcta agtctgtggt tggcagccac tattgcagca gctcttcaat gactcaatgc    6420
agttttgcat tctccctacc ttttttttct aaaaccaata aaatagatac agcctttagg    6480
ctttctggga tttcccttag tcaagctagg gtcatcctga ctttcggcgt gaatttgcaa    6540
aacaagacct gactctgtac tcctgctcta aggactgtgc atggttccaa aggcttagct    6600
tgccagcata tttgagctttt tccttctgt tcaaactgtt ccaaaatata aagaataaa    6660
attaattaag ttggcactgg acttccggtg gtcagtcatg tgtgtcatct gtcacgtttt    6720
tcgggctctg gtgaaatgg atctgtcgt cttctctcat aggtggtatt cacagccaac    6780
gactccggcc cccgccgcta caccattgcc gccctgctga gccctactc ctattccacc    6840
acggctgtcg tcaccaatcc caaggaatga gggacttctc ctccagtgga cctgaaggac    6900
gagggatggg atttcatgta accaagagta ttccattttt actaaagcag tgttttcacc    6960
tcatatgcta tgttagaagt ccaggcagag acaataaaac attcctgtga aaggcacttt    7020
tcattccact ttaacttgat ttttttaaatt cccttattgt cccttccaaa aaaagagaaa    7080
tcaaaattttt acaagaatc aaaggaattc tagaaagtat ctgggcagaa cgctaggaga    7140
gatccaaatt tccattgtct tgcaagcaaa gcacgtatta aatatgatct gcagccatta    7200
```

```
aaaagacaca ttctgtaaat gagagagcct tattttcctg taaccttcag caaatagcaa   7260
aagacacatt ccaagggccc acttctttac tgtgggcact cgagataact tcgtataatg   7320
tatgctatac gaagttatat gcatgccagt agcagcaccc acgtccacct tctgtctagt   7380
aatgtccaac acctccctca gtccaaacac tgctctgcat ccatgtggct cccatttata   7440
cctgaagcac ttgatggggc ctcaatgttt tactagagcc caccccctg caactctgag    7500
accctctgga tttgtctgtc agtgcctcac tggggcgttg gataatttct taaaaggtca   7560
agttccctca gcagcattct ctgagcagtc tgaagatgtg tgcttttcac agttcaaatc   7620
catgtggctg tttcacccac ctgcctggcc ttgggttatc tatcaggacc tagcctagaa   7680
gcaggtgtgt ggcacttaac acctaagctg agtgactaac tgaacactca agtggatgcc   7740
atctttgtca cttcttgact gtgacacaag caactcctga tgccaaagcc ctgcccaccc   7800
ctctcatgcc catatttgga catggtacag gtcctcactg gccatggtct gtgaggtcct   7860
ggtcctcttt gacttcataa ttcctagggg ccactagtat ctataagagg aagagggtgc   7920
tggctcccag gccacagccc acaaaattcc acctgctcac aggttggctg gctcgaccca   7980
ggtggtgtcc cctgctctga gccagctccc ggccaagcca gcaccatggg aaccccaag    8040
aagaagagga aggtgcgtac cgatttaaat tccaatttac tgaccgtaca ccaaaatttg   8100
cctgcattac cggtcgatgc aacgagtgat gaggttcgca agaacctgat ggacatgttc   8160
agggatcgcc aggcgttttc tgagcatacc tggaaaatgc ttctgtccgt ttgccggtcg   8220
tgggcggcat ggtgcaagtt gaataaccgg aaatggtttc ccgcagaacc tgaagatgtt   8280
cgcgattatc ttctatatct tcaggcgcgc ggtctggcag taaaaactat ccagcaacat   8340
ttgggccagc taaacatgct tcatcgtcgg tccgggctgc cacgaccaag tgacagcaat   8400
gctgtttcac tggttatgcg gcggatccga aaagaaaacg ttgatgccgg tgaacgtgca   8460
aaacaggtaa atataaaatt tttaagtgta taatgatgtt aaactactga ttctaattgt   8520
ttgtgtattt taggctctag cgttcgaacg cactgatttc gaccaggttc gttcactcat   8580
ggaaaatagc gatcgctgcc aggatatacg taatctggca tttctgggga ttgcttataa   8640
caccctgtta cgtatagccg aaattgccag gatcagggtt aaagatatct cacgtactga   8700
cggtgggaga atgttaatcc atattggcag aacgaaaacg ctggttagca ccgcaggtgt   8760
agagaaggca cttagcctgg gggtaactaa actggtcgag cgatggattt ccgtctctgg   8820
tgtagctgat gatccgaata actacctgtt ttgccgggtc agaaaaaatg tgttgccgc    8880
gccatctgcc accagccagc tatcaactcg cgccctggaa gggattttg aagcaactca    8940
tcgattgatt tacggcgcta aggatgactc tggtcagaga tacctggcct ggtctggaca   9000
cagtgcccgt gtcggagccg cgcgagatat ggcccgcgct ggagtttcaa taccggagat   9060
catgcaagct ggtggctgga ccaatgtaaa tattgtcatg aactatatcc gtaacctgga   9120
tagtgaaaca ggggcaatgg tgcgcctgct ggaagatggc gattaggcgg ccggccgcta   9180
atcagccata ccacatttgt agaggtttta cttgctttaa aaaacctccc acacctcccc   9240
ctgaacctga aacataaaat gaatgcaatt gttgttgtta acttgtttat tgcagcttat   9300
aatggttaca aataaagcaa tagcatcaca aatttcacaa ataaagcatt tttttcactg   9360
cattctagtt gtggtttgtc caaactcatc aatgtatctt atcatgtctg gatccccgg    9420
ctagagttta aacactagaa ctagtggatc ccccgggatc atggcctccg cgccgggttt   9480
tggcgctcc cgcgggcgcc cccctcctca cggcgagcgc tgccacgtca gacgaagggc    9540
gcagcgagcg tcctgatcct tccgcccgga cgctcaggac agcggccgc tgctcataag    9600
actcggcctt agaaccccag tatcagcaga aggacatttt aggacgggac ttgggtgact   9660
ctagggcact ggttttcttt ccagagacg gaacaggcga ggaaaagtag tcccttctcg    9720
gcgattctgc ggagggatct ccgtggggcg gtgaacgccg atgattatat aaggacgcgc   9780
cgggtgtggc acagctagtt ccgtcgcagc cgggatttgg gtcgcggttc ttgtttgtgt   9840
atcgctgtga tcgtcacttg gtgagtagcg ggctgctggg ctggccgggg ctttcgtggc   9900
cgccgggccg ctcggtggga cggaagcgtg tggagagacc gccaagggct gtagtctggg   9960
tccgcgagca aggttgccct gaactggggg ttgggggag cgcagcaaaa tggcggctgt    10020
tcccgagtct tgaatggaag acgcttgtga ggcgggctgt gaggtcgttg aaacaaggtg   10080
gggggcatgg tgggcggcaa gaacccaagg tcttgaggcc ttcgctaatg cgggaaagct   10140
cttattcggg tgagatgggc tggggcacca tctgggacc ctgacgtgaa gtttgtcact    10200
gactggagaa ctcggtttgt cgtctgttgc ggggccgaca gttatggcgg tgccgttgag   10260
cagtgcaccc gtacctttgg gagcgcgcgc cctcgtcgtg tcgtgacgtc acccgttctg   10320
ttggcttata atgcagggtg gggccacctg ccggtaggtg tgcggtaggc ttttctccgt   10380
cgcaggacgc agggttcggg cctagggtag gctctcctga atcgacaggc gccggacctc   10440
tggtgagggg agggataagt gaggcgtcag tttctttggt cggttttatg tacctatctt   10500
cttaagtagc tgaagctccg gttttgaact atgcgctcgg ggttggcgag tgtgttttgt   10560
gaagttttt aggcacctt tgaaatgtaa tcatttgggt caatatgtaa ttttcagtgt    10620
tagactagta aattgtccgc taaattctgg ccgttttgg cttttttgtt agacgtgttg    10680
acaattaatc atcggcatag tatatcggca tagtataata cgacaaggtg aggaactaaa   10740
ccatgggatc ggccattgaa caagatggat tgcacgcagg ttctccggcc gcttgggtgg   10800
agaggctatt cggctatgac tgggcacaac agacaatcgg ctgctctgat gccgccgtgt   10860
tccggctgtc agcgcagggg cgcccggttc ttttgtcaa gaccgacctg tccggtgccc    10920
tgaatgaact gcaggacgag gcagcgcggc tatcgtggct ggccacgacg ggcgttcctt   10980
gcgcagctgt gctcgacgtt gtcactgaag cgggaaggga ctggctgcta ttgggcgaag   11040
tgccggggca ggatctcctg tcatctcacc ttgctcctgc cgagaaagta tccatcatgg   11100
ctgatgcaat gcggcggctg catacgcttg atccggctac ctgcccattc gaccaccaag   11160
cgaaacatcg catcgagcga gcacgtactc ggatggaagc cggtcttgtc gatcaggatg   11220
atctggacga agagcatcag gggctcgcgc cagccgaact gttcgccagg ctcaaggcgc   11280
gcatgcccga cggcgatgat ctcgtcgtga cccatggcga tgcctgcttg ccgaatatca   11340
tggtggaaaa tggccgcttt tctggattca tcgactgtgg ccggctgggt gtggcggacc   11400
gctatcagga catagcgttg gctacccgtg atattgctga agagcttggc ggcgaatggg   11460
ctgaccgctt cctcgtgctt tacggtatcg ccgctcccga ttcgcagcgc atcgccttct   11520
atcgccttct tgacgagttc ttctgagggg atccgctgta agtctgcaga attgatgat    11580
ctattaaaca ataaagatgt ccactaaaat ggaagtttt cctgtcatac tttgttaaga    11640
agggtgagaa cagagtacct acattttgaa tggaaggatt ggagctacgg ggtggggt     11700
ggggtgggat tagataaatg cctgctcttt actgaaggct ctttactatt gctttatgat   11760
aatgtttcat agttggatat cataatttaa acaagcaaaa ccaaattaag gccagctca    11820
ttcctcccac tcatgatcta tagatctata gatctctcgt gggatcattg tttttctctt   11880
gattcccact ttgtggttct aagtactgtg gtttccaaat gtgtcagttt catagcctga   11940
```

```
agaacgagat cagcagcctc tgttccacat acacttcatt ctcagtattg ttttgccaag    12000
ttctaattcc atcagacctc gacctgcagc cctagataa  cttcgtataa tgtatgctat    12060
acgaagttat gctaggtaac tataacggtc ctaaggtagc gagctagcga gactcagccc    12120
aggaggacca ggatcttgcc aaagcagtag catcccattt gtaccaaaac agtgttcttg    12180
ctctataaac cgtgttagca gctcagga                                      12208
```

| SEQ ID NO: 15 | moltype = DNA  length = 7476 |
|---|---|
| FEATURE | Location/Qualifiers |
| misc_feature | 1..7476 |
| | note = Synthetic |
| misc_feature | 1..97 |
| | note = Mouse Sequence |
| misc_feature | 98..7298 |
| | note = Human Sequence |
| misc_feature | 7299..7376 |
| | note = Cassette LoxP Scar |
| misc_feature | 7377..7476 |
| | note = Mouse Sequence |
| source | 1..7476 |
| | mol_type = other DNA |
| | organism = synthetic construct |

```
SEQUENCE: 15
agcttggcag ggatcagcag cctgggttgg aaggaggggg tataaaagcc ccttcaccag      60
gagaagccgt cacacagatc cacaagctcc tgacaggatg gcttctcatc gtctgctcct     120
cctctgcctt gctggactgg tatttgtgtc tgaggctggc cctacggtga gtgtttctgt     180
gacatcccat tcctacattt aagattcacg ctaaatgaag tagaagtgac ttccttccagc    240
tttgccaacc agcttttatt actagggcaa gggtacccag catctatttt taatatattt     300
aattcaaact tcaaaaagaa tgaagttcca ctgagcttac tgagctggga cttgaactct     360
gagcattcta cctcattgct ttggtgcatt aggtttgtaa tatctggtac ctctgtttcc     420
tcagatagat gatagaaata aagatatgat attaaggaag ctgttaatac tgaatttgta    480
gaaaagtatc cctccataaa atgtatttgg gggacaaact gcaggagatt atattctggc     540
cctatagtta ttcaaaacgt atttattgat taatctttaa aaggcttagt gaacaatatt     600
ctagtcagat atctaattct taaatcctct agaagaatta actaatacta taaatgggt     660
ctggatgtag ttctgacatt attttataac aactggtaag agggagtgac tataggaaca    720
actaaaatga tctcaggaaa acctgtttgg ccctatgtat ggtacattac atctttcag     780
taattccact caaatggaga cttttaacaa agcaactgtt ctcaggggac ctatttctc     840
ccttaaaatt cattatacac atccctggtt gatagcagtg tgtctggagg cagaaaccat     900
tcttgctttg gaaacaatta cgtctgtgtt atactgagta gggaagctca ttaattgtcg     960
acacttacgt tcctgataat gggatcagtg tgtaattcct gtttcgctcc agatttctaa    1020
taccacaaag aataaatcct ttcactctga tcaattttgt taacttctca cgtgtcttct    1080
ctacacccag ggcaccggtg aatccaagtg tcctctgatg gtcaaagttc tagatgcgt    1140
ccgaggcagt cctgccatca atgtggccgt gcatgtgttc agaaaggctg ctgatgacac    1200
ctgggagcca tttgcctctg ggtaagttgc caaagaaccc tcccacagga cttggtttta    1260
tcttcccgtt tgcccctcac ttggtagaga gaggctcaca tcatctgcta aagaatttac    1320
aagtagattg aaaaacgtag gcagaggtca agtatgccct ctgaaggatg ccctcttttt    1380
gttttgctta gctaggaagt gaccaggaac ctgagcatca tttaggggca gacagtagag    1440
aaaagaagga atcagaactc ctctcctcta gctgtgtgttt gcaaccctt tgggtcacag    1500
aacactttat gtaggtgatg aaaagtaaac attctatgcc cagaaaaaat gcacagatac    1560
acacacatac aaaatcatat atgtgatttt aggagtttca cagattccct ggtgtccctg    1620
ggtaacacca aagctaagtg tccttgtctt agaaatttag gaaaaggtat aatgtgtatt    1680
aacccattaa caaaggaaa ggaattcaga aatattatta accaggcatc tgtctgtagt    1740
taatatggat cacccaaaac ccaaggcttt tgcctaatga acactttggg gcacctactg    1800
tgtgcaaggc tggggggctgt caagctcagt taaaaaaaaa aagatagaag atggatcc    1860
atgaggcaaa gtacagcccc aggctaatcc cacgatcacc cgacttcatg tccaagagtg    1920
gcttctcacc ttcattagcc agttcacaat tttcatggag ttttttctacc tgcactagca    1980
aaaacttcaa ggaaaataca tattaataaa tctaagcaaa gtgaccagaa gacagagcaa    2040
tcaggagacc ctttgcatcc agcagaagag gaactgctaa gtatttacat ctccacagag    2100
aagaatttct gttgggtttt aattgaaccc caagaaccac atgattcttc aaccattatt    2160
gggaagatca ttttcttagg tctggtttta actggcttt tatttgggaa ttcatttatg    2220
tttatataaa atgccaagca taacatgaaa agtggttaca ggactattct aagggagaga    2280
cagaatggac accaaaaata ttccaatgtt cttgtgaatc ttttccttgc accaggacaa    2340
aaaaaaaaag aagtgaaaag aagaaggag gaggggcata atcagagtca gtaaagacaa    2400
ctgctatttt tatctatcgt agctgttgca gtcaaatggg aagcaatttc caacattcaa    2460
ctatggagct ggtacttaca tggaaataga agttgcctag tgtttgttgc tggcaaagag    2520
ttatcagaga ggtaaatat ataaaaggga aaagagtcag atacaggttc ttcttcctac    2580
tttaggtttt ccactgtgtg tgcaaatgat actcccctggt ggtgtgcaga tgcctcaaag   2640
ctatcctcac accacaaggg agaggagcga gatcctgctg tcctgagaa gtgcagagtt    2700
agaacagctg tggccacttg catccaatca tcaatcttga atcacaggga ctctttctta    2760
agtaaacatt atacctggcc gggcacggtg gctcacgcct gtaatcccag cactttggga    2820
tgccaaagtg gcatatcat ctgaggtcag gagttcaaga ccagcctggc caacatggca    2880
aaaactccgtc tttatgaaaa atacaaaaat tagccaggca tggtggcagg cgcctgtaat    2940
cccagctaat tgggaggctg aggctggaga tccccttgaa tctaggaggc agaggttgca    3000
gtgagctgag atcgtgccat tgcactccag cctgggtgac aagagtaaaa ctctgtctca    3060
aaaaaaaaaa attatacccta cattctcttc ttatcagaaa aaaaatcta cagtgagctt    3120
ttcaaaaagt ttttcaaaac tttttgccat ttaatttcag ttaggagttt tccctacttc    3180
tgacttagtt gagggaaat gttcataaca tgtttataac atgtttatgt gtgttagttg    3240
gtggggtgt attactttgc catgccattt gtttcctcca tgcgtaactt aatccagact    3300
ttcacacctt ataggaaaac cagtgagtct ggagagctgc atgggctcac aactgaggag    3360
gaatttgtag aagggatata caaagtggaa atagacacca aatcttactg gaaggcactt    3420
```

```
ggcatctccc cattccatga gcatgcagag gtgagtatac agaccttcga ggggttgtttt   3480
ggttttggtt tttgcttttg gcattccagg aaatgcacag ttttactcag tgtaccacag   3540
aaatgtccta aggaaggtga tgaatgacca aaggttccct ttcctattat acaagaaaaa   3600
attcacaaca ctctgagaag caaatttctt tttgactttg atgaaaatcc acttagtaac   3660
atgacttgaa cttacatgaa actactcata gtctattcat tccactttat atgaatattg   3720
atgtatctgc tgttgaaata atagtttatg aggcagccct ccagacccca cgtagagtgt   3780
atgtaacaag agatgcacca tttatttct cgaaaacccg taacattctt cattccaaaa    3840
cacatctggc ttctcggagg tctgacaag tgattcttgg caacacatac ctatagagac     3900
aataaaatca aagtaataat ggcaacacaa tagataacat ttaccaagca tacaccatgt    3960
ggcagacaca attataagtg ttttccatat ttaacctact taatcctcag gaataagcca   4020
ctgaggtcag tcctattatt atccccatct tatagatgaa gaaatgagg caccaggaag     4080
tcaaataact tgtcaaaggt cacaagacta ggaaatacac aagtagaaat gtttacaatt   4140
aaggcccagg ctgggtttgc cctcagttct gctatgcctc gcattatgcc ccaggaaact   4200
ttttcccttg tgaaagccaa gcttaaaaaa agaaaagcca catttgtaac gtgctctgtt   4260
ccctgccta tggtgaggat cttcaaacag ttatacatgg acccagtccc cctgccttct     4320
ccttaatttc ttaagtcatt tgaaacagat ggctgtcatg gaaatagaat ccagacatgt   4380
tggtcagagt taaagatcaa ctaattccat caaaaatagc tcggcatgaa agggaactat   4440
tctctggctt agtcatggat gagactttca attgctataa agtggttcct ttattagaca   4500
atgttaccag ggaaacaaca gggtttgtt tgacttctgg ggcccacaag tcaacaagag     4560
agccccatct accaaggagc atgtccctga ctaccctca gccagcagca agacatggac     4620
cccagtcagg gcaggagcag ggtttcggcg gcgcccagca caagacattg cccctagagt   4680
ctcagcccct accctcgagt aatagatctg cctacctgag actgttgttt gcccaagagc   4740
tgggtctcag cctgatggga accatataaa aaggttcact gacatactgc ccacatgttg    4800
ttctctttca ttagatctta gcttccttgt ctgctcttca ttcttgcagt attcattcaa    4860
caaacattaa aaaaaaaaa aagcattcta tgtgtggaac actctgctag atgctgtgga    4920
tttagaaatg aaaatacatc ccgacccttg gaatggaagg aaagtaagaca  4980
gattaagcag gaccgtcagc ccagcttgaa gccagataa atacggagaa caagagagag     5040
cgagtagtga gagatgagtc ccaatgcctc actttggtga cgggtgcgtg gtgggcttca   5100
tgcagcttct tctgataaat gcctcctca gaactggtca actctacctt ggccagtgac    5160
ccaggtggtc atagtagatt taccaaggga aatggaaaat ttttattagg agctcttagg   5220
cctcttcact tcatggattt tttttcctt tttttttgag atggagtttt gccctgtcac     5280
ccaggctgga atgcagtggt gcaatctcag ctcactgcaa cctccgcctc ccaggttcaa   5340
gcaattctcc tgcctcagcc tcccgagtag ctgggactac aggtgtgcgc caccacacca   5400
ggctaatttt tgtattttt gtaaagacag ttttcacca cgttggccag gctggtctga     5460
actccagacc tcaggtgatt cacctgtctc agcctcccaa agtgctggga ttacaggat    5520
gagccaccgt gcccggctac ttcatggatt tttgattaca gattatgcct cttacaattt   5580
ttaagaagaa tcaagtgggc tgaaggtcaa tgtcaccata agacaaaaga cattttattt   5640
agttgattct agggaattgg ccttaagggg agcccttttct tcctaagaga ttcttaggtg   5700
attctcactt cctcttgccc cagtattatt tttgttttg gtatgctca ctcagatcct     5760
tttttcctcc tatccctaag taatcccggt ttcttttcc catatttaga acaaaatgta    5820
tttatgcaga gtgtgtccaa acctcaaccc aaggcctgta tacaaaataa atcaaattaa   5880
acacatcttt actgtcttct acctctttcc tgacctcaat atatcccaac ttgcctcact   5940
ctgagaacca aggctgtccc agcacctgag tcgcagatat tctactgatt tgacagaact    6000
gtgtgactat ctggaacagc attttgatcc acaatttgcc cagttacaaa gcttaaatga   6060
gctctagtgc atgcatatat attttcaaaat tccaccatga tcttccacac tctgtattgt   6120
aaatagagcc ctgtaatgct tttacttcgt atttcattgc ttgttataca taaaaatata   6180
cttttcttct tcatgttaga aaatgcaaag aataggaggg tggggggaatc tctgggcttg   6240
gagacaggag acttgccttc ctactatggt tccatcagaa tgtagactgg gacaataca    6300
taattcaagt ctggtttgct catctgtaaa ttgggaagaa tgtttccagc tccagaatgc   6360
taaatctcta agtctgtggt tggcagccac tattgcagca gctcttcaat gactcaatgc   6420
agttttgcat tctccctacc ttttttttct aaaaccaata aaatagatac agccttagg    6480
ctttctggga tttcccttag tcaagctagg gtcatcctga cttttcggcgt gaatttgcaa   6540
aacaagacct gactctgtac tcctgctcta aggactgtgc atggttccaa aggcttagct    6600
tgccagcata tttgagcttt ttccttctgt tcaaactgtt ccaaaatata aaagaataaa   6660
attaattaag ttggcactgg acttccggtg gtcagtcatg tgtgtcatct gtcacgtttt   6720
tcgggctctg gtggaaatgg atctgtctgt cttctctcat aggtggtatt cacagccaac   6780
gactccggcc ccgccgcta caccattgcc gccctgctga gccctactc ctattccacc    6840
acggctgtcg tcaccaatcc caaggaatga gggacttctc ctccagtgga cctgaaggac   6900
gagggatggg atttcatgta accaagagta ttccatttt actaaagcag tgttttcacc   6960
tcatatgcta tgttagaagt ccaggcagag acaataaaac attcctgtga aaggcacttt   7020
tcattccact ttaacttgat tttttaaatt ccttattgt cccttccaaa aaaagagaa     7080
tcaaatttt acaagaatc aaaggaattc tagaaagtat ctgggcagaa cgctaggaga     7140
gatccaaatt tccattgtct tgcaagcaaa gcacgtatta aatatgatct gcagccatta   7200
aaaagacaca ttctgtaaat gagagagcct tatttttcctg taaccttcag caaatagcaa   7260
aagcacatt ccaagggccc acttcttac tgtgggcact cgagataact tcgtataatg      7320
tatgctatac gaagttatgc taggtaacta taacggtcct aaggtagcga gctagcgaga   7380
ctcagcccag gaggaccagg atcttgccaa agcagtagca tcccatttgt accaaaacag   7440
tgttcttgct ctataaaccg tgttagcagc tcagga                              7476
```

| SEQ ID NO: 16 | moltype = DNA length = 11218 |
|---|---|
| FEATURE | Location/Qualifiers |
| misc_feature | 1..11218 |
| | note = Synthetic |
| misc_feature | 1..100 |
| | note = Mouse Sequence |
| misc_feature | 101..6308 |
| | note = Human Sequence |
| misc_feature | 6309..11118 |
| | note = SDC Neo Cassette |

| misc_feature | 11119..11218 |
| | note = Mouse Sequence |
| source | 1..11218 |
| | mol_type = other DNA |
| | organism = synthetic construct |

SEQUENCE: 16

```
atgtactttt ggttttgttc cagagtctat caccggaaag aacaagccgg tttactctga   60
cccatttcac tgacatttct cttgtctcct ctgtgcccag ggcaccggtg aatccaagtg  120
tcctctgatg gtcaaagttc tagatgctgt ccgaggcagt cctgccatca atgtggccgt  180
gcatgtgttc agaaaggctg ctgatgacac ctgggagcca tttgcctctg ggtaagttgc  240
caaagaaccc tcccacagga cttggtttta tcttcccgtt tgcccctcac ttggtagaga  300
gaggctcaca tcatctgcta aagaatttac aagtagattg aaaaacgtag gcagaggtca  360
agtatgccct ctgaaggatg ccctctttt gttttgctta gctaggaagt gaccaggaac  420
ctgagcatca tttaggggca gacagtagag aaaagaagga atcagaactc ctctcctcta  480
gctgtggttt gcaaccettt tgggtcacag aacactttat gtaggtgatg aaaagtaaac  540
attctatgcc cagaaaaaat gcacagatac acacacatac aaaatcatat atgtgatttt  600
aggagtttca cagattccct ggtgtcctg ggtaacacca aagctaagtg tccttgtctt   660
agaatttag gaaaaggtat aatgtgtatt aacccattaa caaaaggaaa ggaattcaga  720
aatattatta accaggcatc tgtctgtagt taatatggat cacccaaaac ccaaggcttt  780
tgcctaatga acactttggg gcacctactg tgtgcaaggc tgggggctgt caagctcagt  840
taaaaaaaa aagatagaag agatggatcc atgaggcaaa gtacagcccc aggctaatcc  900
cacgatcacc cgacttcatg tccaagagtg gcttctcacc ttcattagcc agttcacaat  960
tttcatggag ttttttctacc tgcactagca aaaacttcaa ggaaaataca tattaataaa 1020
tctaagcaaa gtgaccagaa gacagagcaa tcaggagacc ctttgcatcc agcagaagag 1080
gaactgctaa gtatttacat ctccacagag aagaatttct gttgggtttt aattgaaccc 1140
caagaaccac atgattcttc aaccattatt gggaagatca ttttcttagg tctggttta 1200
actggctttt tatttgggaa ttcatttatg tttatataa atgccaagca taacatgaaa 1260
agtggttaca ggactattct aagggagaga cagaatggac accaaaaata ttccaatgtt 1320
cttgtgaatc ttttccttgc accaggacaa aaaaaaaag aagtgaaaag aagaaggag  1380
gaggggcata atcagagtca gtaaagacaa ctgcattttt tatctatcgt agctgttgca 1440
gtcaaatggg aagcaatttc caacattcaa ctatggagct ggtacttaca tggaaataga 1500
agttgctag tgtttgttgc tggcaaagag ttatcagaga ggttaaatat ataaagggaa 1560
aaagagtcag atacaggttc ttcttcctac tttaggtttt ccactgtgtg tgcaaatgat 1620
actccctggt ggtgtgcaga tgcctcaaag ctatcctcac accacaaggg agaggagcga 1680
gatcctgctg tcctggagaa gtgcagagtt agaacagctg tggccacttg catccaatca 1740
tcaatcttga atcacaggga ctctttctta agtaaacatt atacctggcc gggcacggtg 1800
gctcacgcct gtaatcccag cactttggga tgccaaagtg ggcatatcat ctgaggtcag 1860
gagttcaaga ccagccggc caacatggca aaactccgtc tttatgaaaa atacaaaaat 1920
tagccaggca tggtggcagg cgcctgtaat cccagctaat tgggaggctg aggctggaga 1980
atcccttgaa tctaggaggc agaggttgca gtgagctgag atcgtgccat tgcactccag 2040
cctgggtgac aagagtaaaa ctgtctctca aaaaaaaaaa attataccta cattctcttc 2100
ttatcagaga aaaaaatcta cagtgagctt tcaaaaagt ttttacaaac ttttttgccat 2160
ttaatttcag ttaggagttt tccctacttc tgacttagtt gaggggaaat gttcataaca 2220
tgtttataac atgtttatgt gtgttagttg gtggggtgt attactttgc catgccattt 2280
gtttcctcca tgcgtaactt aatccagact ttcacacctt ataggaaaac cagtgagtct 2340
ggagagctgc atgggctcac aactgaggag gaattttgtag aagggatata caagtggaa 2400
atagacacca aatcttactg gaaggcactt ggcatctccc cattcatga gcatgcagag 2460
gtgagtatac agaccttcga gggttgtttt ggttttggtt tttgcttttg gcattccagg 2520
aaaatgcacag ttttactcag tgtaccacag aaatgtccta aggaaggtga tgaatgacca 2580
aaggttcct ttcctattat acaagaaaaa attcacaaca ctctgagaag caaatttctt 2640
tttgactttg atgaaatcc acttagtaac atgacttgaa cttacatgaa actactcata 2700
gtctattcat tccactttat atgaatattg atgtatctgc tgttgaaata atagtttatg 2760
aggcagccct ccagacccca cgtagagtgt atgtaacaag agatgcacca ttttatttct 2820
cgaaaacccg taacattctt cattccaaaa cacatctggc ttctcggagg tctgacaag  2880
tgattcttgg caacacatac ctatagagac aataaaatca aagtaataat ggcaacacaa 2940
tagataacat ttaccaagca taccatgt ggcagacaca attataagtg ttttccatat 3000
ttaacctact taatcctcag gaataagcca ctgaggtcag tcctattatt atccccatct 3060
tatagatgaa gaaaatgagg caccaggaag tcaaataact tgtcaaaggt cacaagacta 3120
ggaaatacac aagtagaaat gtttacaatt aaggcccagg ctgggttttgc cctcagttct 3180
gctatgcctc gcattatgcc ccaggaaact ttttccccttg tgaaagccaa gcttaaaaaa 3240
agaaaagcca catttgtaac gtgctctgtt cccctgccta tggtgaggat cttcaaacag 3300
ttatacatgg acccagtccc cctgccttct ccttaatttc ttaagtcatt tgaaacagat 3360
ggctgtcatg gaaatagaat ccagacatgt tggtcagagt taaagatcaa ctaattccat 3420
caaaaatagc tcggcatgaa agggaactat tctctgacgtt agtcatggat gagactttca 3480
attgctataa agtggttcct ttattagaca atgttaccag ggaacaaaca ggggtttgtt 3540
tgacttctgg ggcccacaag tcaacaagag agccccatct accaaggagc atgtccctga 3600
ctaccctca gccagcagca agacatggac cccagtcagg caggagcag ggtttcggcg  3660
gcgcccagca caagacattg cccctagagt ctcagcccct accctcgagt aatagatcg  3720
cctacctgag actgttgttt gcccaagagc tgggtctcag cctgatggga accatataaa 3780
aaggttcact gacatactgc ccacatgttg ttctctttca ttagatctta gcttccttgt 3840
ctgctcttca ttcttgcagt attcattcaa caaacattaa aaaaaaaaaa aagcattcta 3900
tgtgtggaac actctgctag atgctgtgga tttagaaatg aaaatacatc ccgaccettg 3960
gaatggaagg gaaaggactg aagtaagaca gattaagcag gaccgtcagc ccagcttgaa 4020
gccagataa atacggagaa caagaggaga cgagtagtga ggtgagtc ccaatgcctc  4080
actttggtga cgggtgcgtg gtgggcttca tgcagcttct tctgataaat gcctccttca 4140
gaactggtca actctacctt ggccagtgac ccaggtggtc atagtagatt taccaaggga 4200
aaatggaaac tttattagg agctcttagg cctcttcact tcatggatttt ttttttcctt 4260
tttttttgag atggagtttt gccctgtcac ccaggctgga atgcagtggt gcaatctcag 4320
ctcactgcaa cctccgcctc ccaggttcaa gcaattctcc tgcctcagcc tcccgagtag 4380
```

```
ctgggactac aggtgtgcgc caccacacca ggctaatttt tgtatttttt gtaaagacag   4440
gttttcacca cgttggccag gctggtctga actccagacc tcaggtgatt cacctgtctc   4500
agcctcccaa agtgctggga ttacaggtgt gagccaccgt gcccggctac ttcatggatt   4560
tttgattaca gattatgcct cttacaattt ttaagaagaa tcaagtgggc tgaaggtcaa   4620
tgtcaccata agacaaaaga catttttatt agttgattct agggaattgg ccttaagggg   4680
agcccttttct tcctaagaga ttcttaggtg attctcactt cctcttgccc cagtattatt   4740
tttgtttttg gtatggctca ctcagatcct ttttcctcc tatccctaag taatccgggt   4800
ttcttttttcc catatttaga acaaaatgta tttatgcaga gtgtgtccaa acctcaaccc   4860
aaggcctgta tacaaaataa atcaaattaa acacatcttt actgtcttct acctctttct   4920
tgacctcaat atatcccaac ttgcctcact ctgagaacca aggctgtccc agcacctgag   4980
tcgcagatat tctactgatt tgacagaact gtgtgactat ctggaacagc attttgatcc   5040
acaatttgcc cagttacaaa gcttaaatga gctctagtgc atgcatatat atttcaaaat   5100
tccaccatga tcttccacac tctgtattgt aaatagagcc ctgtaatgct tttacttcgt   5160
atttcattgc ttgttataca taaaaatata cttttctct tcatgttaga aaatgcaaaa   5220
aataggaggg tgggggaatc tctgggcttg gagacaggag acttgccttc ctactatggt   5280
tccatcagaa tgtagactgg gacaatacaa taattcaagt ctggtttgct catctgtaaa   5340
ttgggaagaa tgtttccagc tccagaatgc taaatctcta agtctgtggt tggcagccac   5400
tattgcagca gctcttcaat gactcaatgc agttttgcat tctccctacc ttttttttct   5460
aaaaccaata aaatagatac agcctttagg cttctgggga ttttcccttag tcaagctagg   5520
gtcatcctga ctttcggcgt gaatttgcaa aacaagacct gactctgtac tcctgctcta   5580
aggactgtgc atggttccaa aggcttagct tgccagcata tttgagcttt ttccttctgt   5640
tcaaactgtt ccaaaatata aaagaataaa attaattaag ttggcactgg acttccggtg   5700
gtcagtcatg tgtgtcatct gtcacgtttt tcgggctctg gtggaaatgg atctgtctgt   5760
cttctctcat aggtggtatt cacagccaac gactccggcc ccgccgcta caccattgcc   5820
gccctgctga gcccctactc ctattccacc acggctgtcg tcaccaatcc caaggaatga   5880
gggacttctc ctccagtgga cctgaaggac gagggatgg atttcatga accaagagta   5940
ttccattttt actaaagcag tgttttcacc tcatatgcta tgttagaagt ccaggcagag   6000
acaataaaac attcctgtga aaggcacttt tcattccact ttaacttgat ttttaaatt    6060
cccttattgt cccttccaaa aaaaagagaa tcaaattttt acaagaatc aaaggaattc    6120
tagaaagtat ctgggcagaa cgctaggaga gatccaaatt tccattgtct tgcaagcaaa   6180
gcacgtatta aatatgatct gcagcattga aaagacaca ttctgtaaat gagagagcct    6240
tattttcctg taaccttcag caaatagcaa aagacacatt ccaagggccc acttctttac   6300
tgtgggcact cgagataact tcgtataatg tatgctatac gaagttatat gcatgccagt   6360
agcagcaccc acgtccacct tctgtctagt aatgtccaac acctccctca gtccaaacac   6420
tgctctgcat ccatgtggct cccatttata cctgaagcac ttgatggggc ctcaatgttt   6480
tactagagcc caccccctg caactctgag accctctgga tttgtctgtc agtgcctcac    6540
tggggcgttg gataatttct taaaggtca agttccctca gcagcattct ctgagcagtc    6600
tgaagatgtg tgcttttcac agttcaaatc catgtggctg tttcacccac ctgcctggcc   6660
ttgggttatc tatcaggacc tagcctagaa gcaggtgtg ggcacttaac acctaagctg    6720
agtgactaac tgaacactca agtggatgcc atctttgtca cttcttgact gtgacacaag   6780
caactcctga tgccaaagcc ctgcccaccc ctctcatgcc catatttgga catggtacag   6840
gtcctcactg gccatggtct gtgaggtcct ggtcctcttt gacttcataa ttcctagggg   6900
ccactagtat ctataagagg aagagggtgc tggctcccag gccacagccc acaaaattcc   6960
acctgctcac aggttggctg gctcgaccca ggtggtgtcc cctgtctga gccagctccc    7020
ggccaagcca gcaccatggg aacccccaag aagaagagga aggtgcgtac cgatttaaat   7080
tccaatttac tgaccgtaca ccaaaatttg cctgcattac cggtcgatgc aacgagtgat   7140
gaggttcgca agaacctgat ggacatgttc agggatcgcc aggcgttttc tgagcatacc   7200
tggaaaatgc ttctgtccgt ttgccggtcg tgggcggcat ggtgcaagtt gaataaccga   7260
aaatggtttc ccgcagaacc tgaagatgcg cgcgattatc ttctatatct tcaggcgcgc   7320
ggtctggcag taaaaactat ccagcaacat ttgggccagc taaacatgct tcatcgtcgg   7380
tccgggctgc cacgaccaag tgacagcaat gctgtttcac tggttatgcg gcggatccga   7440
aaagaaaacg ttgatgccgg tgaacgtgca aaacaggtaa atataaaatt tttaagtgta   7500
taatgatgtt aaactactga ttctaattgt ttgtgtattt taggctctag cgttcgaacg   7560
cactgatttc gaccaggttc gttcactcat ggaaaatagc gatcgctgcc aggatatacg   7620
taatctggca ttttctgggga ttgcttataa caccctgtta cgtatagccg aaattgccag   7680
gatcagggtt aaagatatct cacgtactga cggtgggaaa atgttaatcc atattggcag   7740
aacgaaaacg ctggttagca ccgcaggtgt agagaaggca cttagcctgg gggtaactaa   7800
actggtcgag cgatggattt ccgtctctgg tgtagctgat gatccgaata actacctgtt   7860
ttgccgggtc agaaaaaatg tgttgccgc gccatctgcc accagccgac tatcaactcg   7920
cgcccctggaa gggattttttg aagcaactca tcgattgatt tacgcgcta aggatgactc   7980
tggtcagaga tacctggcct ggtctggaca cagtgcccgt gtcggagccg cgcgagatat   8040
ggcccgcgct ggagtttcaa taccggagat catgcaagct ggtggctgga ccaatgtaaa   8100
tattgtcatg aactatatcc gtaacctgga tagtgaaaca ggggcaatgg tgcgcctgct   8160
ggaagatggc gattaggcgg ccggccgcta atcagccata ccacatttgt agaggtttta   8220
cttgctttaa aaaacctccc acacctcccc ctgaacctga aacataaaat gaatgcaatt   8280
gttgttgtta acttgtttat tgcagcttat aatggttaca aataaagcaa tagcatcaca   8340
aatttcacaa ataaagcatt ttttcactg cattctagtt gtggtttgtc caaactcatc    8400
aatgtatctt atcatgtctg gatccccgg ctagagttta aactagaa ctagtggatc      8460
ccccgggatc atggcctccg cgccggggtt tggcgcctcc gcggcgcgcc cccctcctca   8520
cggcgagcgc tgccacgtca gacgaagggc gcagcgagcg tcctgatcct tccgcccgga   8580
cgctcaggac agcgccgc tgctcataag actcggcctt agaacccag tatcagcaga     8640
aggacatttt aggacgggac ttgggtgact ctagggcact ggttttcttt ccagagagcg   8700
gaacaggcga ggaaaagtag tcccttcctg gcgattctgc ggaggatct ccgtgggcg      8760
gtgaacgcga atgattatat aaggacgcgc acagcagttct cgtcgcagc                8820
cgggatttgg gtcgcggttc ttgtttgtgg atcgctgtga tcgtcacttg gtgagtagcg   8880
ggctgctggg ctgccgggg ctttcgtggc cgcggccg ctcggtggga cggaagcgtg      8940
tggagagacc gccaagggct gtagtctggg tccgcgagca aggttgccct gaactggggg   9000
ttgggggggag cgcagcaaaa tggcggctgt tcccgagtct tgaatggaag acgcttgtga   9060
ggcgggctgt gaggtcgttg aaacaaggtg gggggcatgg tgggcggcaa gaacccaagg   9120
```

```
tcttgaggcc ttcgctaatg cgggaaagct cttattcggg tgagatgggc tggggcacca    9180
tctggggacc ctgacgtgaa gtttgtcact gactggagaa ctcggtttgt cgtctgttgc    9240
gggggcggca gttatggcgg tgccgttggg cagtgcaccc gtacctttgg gagcgcgcgc    9300
cctcgtcgtg tcgtgacgtc acccgttctg ttggcttata atgcagggtg gggccacctg    9360
ccggtaggtg tgcggtaggc ttttctccgt cgcaggacgg agggttcggg cctagggtag    9420
gctctcctga atcgacaggc gccggacctc tggtgagggg agggataagt gaggcgtcag    9480
tttctttggt cggttttatg tacctatctt cttaagtagc tgaagctccg gttttgaact    9540
atgcgctcgg ggttggcgag tgtgttttgt gaagttttt aggcaccttt tgaaatgtaa     9600
tcatttgggt caatatgtaa tttcagtgt tagactagta aattgtccgc taaattctga     9660
ccgttttgg cttttttgtt agacgtgttg acaattaatc atcggcatag tatatcggca     9720
tagtataata cgacaaggtg aggaactaaa ccatgggatc ggccattgaa caagatggat    9780
tgcacgcagg ttctccggcc gcttgggtgg agaggctatt cggctatgac tgggcacaac    9840
agacaatcgg ctgctctgat gccgccgtgt tccggctgtc agcgcagggg cgcccggttc    9900
tttttgtcaa gaccgacctg tccggtgccc tgaatgaact gcaggacgag gcagcgcggc    9960
tatcgtggct ggccacgacg ggcgttcctt gcgcagctgt gctcgacgtt gtcactgaag   10020
cgggaaggga ctggctgcta ttgggcgaag tgccggggca ggatctcctg tcatctcacc   10080
ttgctcctgc cgagaaagta tccatcatgg ctgatgcaat gcggcggctg catacgcttg   10140
atccggctac ctgcccattc gaccaccaag cgaaacatcg catcgagcga gcacgtactc   10200
ggatggaagc cggtcttgtc gatcaggatg atctggacga agagcatcag ggctcgcgc    10260
cagccgaact gttcgccagg ctcaaggcgc gcatgcccga cggcgatgat ctcgtcgtga   10320
cccatggcga tgcctgcttg ccgaatatca tggtggaaaa tggccgcttt tctggattca   10380
tcgactgtgg ccggctgggt gtggcggacc gctatcagga catagcgttg gctacccgtg   10440
atattgctga gagcttggc ggcgaatggg ctgaccgctt cctcgtgctt tacggtatcg    10500
ccgctcccga ttcgcagcgc atcgccttct atcgccttct tgacgagttc ttctgagggg   10560
atccgctgta agtctgcaga aattgatgat ctattaaaca ataaagatgt ccactaaaat   10620
ggaagttttt cctgtcatac tttgttaaga agggtgagaa cagagtacct acattttgaa   10680
tggaaggatt ggagctacgg gggtgggggt ggggtgggat tagataaatg cctgctcttt   10740
actgaaggct ctttactatt gctttatgat aatgtttcat agttggatat cataatttaa   10800
acaagcaaaa ccaaattaag ggccagctca ttcctcccac tcatgatcta tagatctata   10860
gatctctcgt gggatcattg ttttctctt gattcccact ttgtggttct aagtactgtg    10920
gtttccaaat gtgtcagttt catagcctga agaacgagat cagcagcctc tgttccacat   10980
acacttcatt ctcagtattg ttttgccaag ttctaattcc atcagacctc gacctgcagc   11040
ccctagataa cttcgtataa tgtatgctat acgaagttat gctaggtaac tataacggtc   11100
ctaaggtagc gagctagcga gactcagccc aggaggacca ggatcttgcc aaagcagtag   11160
catcccattt gtaccaaaac agtgttcttg ctctataaac cgtgttagca gctcagga     11218

SEQ ID NO: 17            moltype = DNA   length = 6486
FEATURE                  Location/Qualifiers
misc_feature             1..6486
                         note = Synthetic
misc_feature             1..100
                         note = Mouse Sequence
misc_feature             101..6308
                         note = Human Sequence
misc_feature             6309..6386
                         note = Cassette LoxP Scar
misc_feature             6387..6486
                         note = Mouse Sequence
source                   1..6486
                         mol_type = other DNA
                         organism = synthetic construct
SEQUENCE: 17
atgtactttt ggttttgttc cagagtctat caccggaaag aacaagccgg tttactctga      60
cccatttcac tgacatttct cttgtctcct ctgtgcccag ggcaccggtg aatccaagtg     120
tcctctgatg gtcaaagttc tagatgctgt ccgaggcagt cctgccatca atgtggccgt     180
gcatgtgttc agaaaggctc ctgatgacac ctgggagcca tttgcctctg ggtaagttgt     240
caaagaaccc tcccacagga cttggtttta tcttcccgtt tgcccctcac ttggtagaga     300
gaggctcaca tcatctgcta aagaatttac aagtagattg aaaaacgtag gcagaggtca     360
agtatgccct ctgaaggatg ccctcttttt gttttgctta gctaggaagt gaccaggaac     420
ctgagcatca tttaggggga gacagtagag aaaagaagga atcagaactc ctctcctcta     480
gctgtggttt gcaacccttt tgggtcacag aacactttat gtaggtgatg aaaagtaaac     540
attctatgcc cagaaaaaat gcacagatac acacacatac aaaatcatat atgtgatttt     600
aggagtttca cagattccct ggtgtccctg ggtaacacca aagctaagtg tccttgtctt     660
agaatttttag gaaaagtat aatgtgtatt aacccattaa caaaaggaaa ggaattcaga    720
aatattatta accaggcatc tgtctgtagt taatatggat cacccaaaac ccaaggcttt     780
tgcctaatga acactttggg gcacctactg tgtgcaaggc tgggggctgt caagctcagt     840
taaaaaaaaa aagatagaag agatggatcc atgaggcaaa gtacagcccc aggctaatcc     900
cacgatcacc cgacttcatg tccaagagtg gcttctcacc ttcattagcc agttcacaat     960
tttcatggag tttttctacc tgcactagca aaaacttcaa ggaaaataca tattaataaa    1020
tctaagcaaa gtgaccagaa gacagagcaa tcaggagacc ctttgcatcc agcagaaagag   1080
gaactgctaa gtatttacat ctccacagag aagaatttct gttgggtttt aattgaaccc    1140
caagaaccac atgattcttc aaccattatt gggaagatca ttttcttagg tctggtttta    1200
actggctttt tatttgggaa ttcatttatg tttatataaa atgccaagca taacatgaaa    1260
agtggttaca ggactattct aaggagaga cagaatggaaccaaaaaata ttccaatgtt     1320
cttgtgaatc ttttccttgc accaggacaa aaaaaaaaag aagtgaaaag aagaaaggag    1380
gagggcata atcagagtca gtaaagacaa ctgctatttt tatctatcgt agctgttgca    1440
gtcaaatggg aagcaatttc caacattcaa ctatggagct ggtacttaca tggaaataga    1500
agttgcctag tgtttgttgc tggcaaagag ttatcagaga ggttaaatat ataaaggga     1560
aaagagtcag atacaggttc ttcttcctac tttaggtttt ccactgtgtg tgcaaatgat    1620
```

```
actccctggt ggtgtgcaga tgcctcaaag ctatcctcac accacaaggg agaggagcga 1680
gatcctgctg tcctggagaa gtgcagagtt agaacagctg tggccacttg catccaatca 1740
tcaatcttga atcacaggga ctctttctta agtaaacatt atacctggcc gggcacggtg 1800
gctcacgcct gtaatcccag cactttggga tgccaaagtg ggcatatcat ctgaggtcag 1860
gagttcaaga ccagcctggc caacatggca aaactccgtc tttatgaaaa atacaaaaat 1920
tagccaggca tggtggcagg cgcctgtaat cccagctaat tgggaggctg aggctgagga 1980
atcccttgaa tctaggaggc agaggttgca gtgagctgag atcgtgccat tgcactccag 2040
cctgggtgac aagagtaaaa ctctgtctca aaaaaaaaaa attataccta cattctcttc 2100
ttatcagaga aaaaaatcta cagtgagctt ttcaaaaagt ttttacaaac tttttgccat 2160
ttaatttcag ttaggagttt tccctacttc tgacttagtt gaggggaaat gttcataaca 2220
tgtttataac atgtttatgt gtgttagttg gtggggtgt attactttgc catgccattt 2280
gtttcctcca tgcgtaactt aatccagact ttcacacctt ataggaaaac cagtgagtct 2340
ggagagctgc atgggctcac aactgaggag gaatttgtag aagggatata caaagtggaa 2400
atagacacca aatcttactg gaaggcactt ggcatctccc cattccatga gcatgcagag 2460
gtgagtatac agaccttcga gggttgtttt ggttttggtt tttgcttttg gcattccagg 2520
aaatgcacag ttttactcag tgtaccacag aaatgtccta aggaaggtga tgaatgacca 2580
aaggttccct ttcctattat acaagaaaaa attcacaaca ctctgagaag caaattctct 2640
tttgactttg atgaaaatcc acttagtaac atgacttgaa cttacatgaa actactcata 2700
gtctattcat tccactttat atgaatattg atgtatctgc tgttgaaata atagtttatg 2760
aggcagccct ccagacccca cgtagagtgt atgtaacaag agatgcacca ttttatttct 2820
cgaaaacccg taacattctt cattccaaaa cacatctggc ttctcggagg tctgacaag 2880
tgattcttgg caacacatac ctatagagac aataaaatca aagtaataat ggcaacacaa 2940
tagataacat ttaccaagca tacaccatgt ggcagacaca attataagtg ttttccatat 3000
ttaacctact taatcctcag gaataagcca ctgaggtcag tcctattatt atccccatct 3060
tatagatgaa gaaaatgagg caccaggaag tcaaataact tgtcaaaggt cacaagacta 3120
ggaaatacac aagtagaaat gtttacaatt aaggcccagg ctgggtttgc cctcagttct 3180
gctatgcctc gcattatgcc ccaggaaact ttttcccttg tgaaagccaa gcttaaaaaa 3240
agaaaagcca catttgtaac gtgctctgtt ccctgccta tggtgaggat cttcaaacag 3300
ttatacatgg acccagtccc cctgccttct ccttaatttc ttaagtcatt tgaaacagat 3360
ggctgtcatg gaaatagaat ccagacatgt tggtcagagt taaagatcaa ctaattccat 3420
caaaaatagc tcggcatgaa agggaactat tctctggctt agtcatggat gagactttca 3480
attgctataa agtggttcct ttattagaca atgttaccag ggaaacaaca ggggtttgtt 3540
tgacttctgg ggcccacaag tcaacaagag agccccatct accaaggagc atgtccctga 3600
ctacccctca gccagcagca agacatggac cccagtcagg gcaggagcag ggtttcggcg 3660
gcgcccagca caagacattg ccccctagagt ctcagccct accctcgagt aatagatctg 3720
cctacctgag actgttgttt gcccaagagc tgggtctcag cctgatggga accatataaa 3780
aaggttcact gacatactgc ccacatgttg ttctctttca ttagatctta gcttccttgt 3840
ctgctcttca ttcttgcagt attcattcaa caaacattaa aaaaaaaaaa aagcattcta 3900
tgtgtggaac actctgctag atgctgtgga tttagaaatg aaaatacatc ccgacccttg 3960
gaatggaagg gaaaggactg aagtaagaca gattaagcag gaccgtcagc ccagcttgaa 4020
gcccagataa atacgagaa caagagagag cgagtagtga gagatgagtc ccaatgcctc 4080
actttggtga cgggtgcgtg gtgggcttca tgcagcttct tctgataaat gcctccttca 4140
gaactggtca actctacctt ggccagtgac ccaggtggtc atagtagatt taccaaggga 4200
aaatggaaac ttttattagg agctcttagg cctcttcact tcatggattt ttttttcctt 4260
tttttttgag atggagtttt gccctgtcac ccaggctgga atgcagtggt gcaatctcag 4320
ctcactgcaa cctccgcctc ccaggttcaa gcaattctcc tgcctcagcc tcccgagtag 4380
ctgggactac aggtgtgcgc caccacacca ggctaatttt tgtattttt gtaaagacag 4440
gttttcacca cgttgccag gctggtctga actccagacc tcaggtgatt cacctgtctc 4500
agcctcccaa agtgctggga ttacaggtgt gagccaccgt gcccggctac ttcatggatt 4560
tttgattaca gattatgcct cttacaattt ttaagaagaa tcaagtgggc tgaaggtcaa 4620
tgtcacataa agacaaaaga catttttatt agttgattct agggaattgg ccttaagggg 4680
agcccttttct tcctaagaga ttcttaggtg attctcactt cctcttgccc cagtattatt 4740
tttgtttttg gtatgctca ctcagatcct ttttcctcc tatccctaag taatccgggt 4800
ttcttttttcc catatttaga acaaaatgta tttatgcaga gtgtgtccaa acctcaaccc 4860
aaggcctgta tacaaaataa atcaaattaa acacatcttt actgtcttct acctcttcc 4920
tgacctcaat atatcccaac ttgcctcact ctgagaacca aggctgtccc agcacctgag 4980
tcgcagatat tctactgatt tgacagaact gtgtgactat ctggaacagc attttgatcc 5040
acaatttgcc cagttacaaa gcttaaatga gctctagtgc atgcatatat atttcaaaat 5100
tccaccatga tcttccacac tctgtattgt aaatagagcc ctgtaatgct tttacttcgt 5160
atttcattgc ttgttataca taaaaatata cttttcttct tcatgttaga aaatgcaaag 5220
aataggaggg tgggggaatc tctgggcttg agacaggag acttgccttc ctactatggt 5280
tccatcagaa tgtagactgg gacaaatacaa taattcaagt ctggtttgct catctgtaaa 5340
ttgggaagaa tgtttccagc tccagaatgc taaatctcta agtctgtggt tggcagccac 5400
tattgcagca gctcttcaat gactcaatgc agttttgcat tctccctacc tttttcttct 5460
aaaaccaata aaatagatac agcctttagg ctttctggga tttcccttag tcaagctagg 5520
gtcatcctga ctttcggcgt gaatttgcaa aacaagacct gactctgtac tcctgctcta 5580
aggactgtgc atggttccaa aggcttagct tgccagcata tttgagcttt ttccttctgt 5640
tcaaactgtt ccaaaatata aagaataaa ttaattaag ttggcactgg acttccggtg 5700
gtcagtcatg tgtgtcatct gtcacgtttt tcgggctctg gtggaaatgg atctgtctgt 5760
cttctctcat aggtggtatt cacagccaac gactccggcc cccgccgcta caccattgcc 5820
gccctgctga gccccactc ctattccacc acggctgtcg tcaccaatcc caaggaatga 5880
gggacttctc ctccagtgga cctgaaggac gagggatggg atttcatgta accaagagta 5940
ttccatttttt actaaagcag tgttttcacc tcatatgcta tgttagaagt ccaggcagag 6000
acaataaaac attcctgtga aaggcacttt tcattccgat tttaacttgat tttttaaatt 6060
cccttattgt cccttccaaa aaaaagagaa tcaaaatttt acaaagaatc aaaggaattc 6120
tagaaagtat ctgggcagaa cgctaggaga gatccaaatt tccattgtct tgcaagcaaa 6180
gcacgtatta aatatgatct gcagccatta aaaagacaca ttctgtaaat gagagagcct 6240
tatttttcctg taaccttcag caaatagcaa aagacacatt ccagggcccc acttcttac 6300
tgtgggcact cgagataact tcgtataatg tatgctatac gaagttatgc taggtaacta 6360
```

| | | | | | |
|---|---|---|---|---|---|
| taacggtcct | aaggtagcga | gctagcgaga | ctcagcccag | gaggaccagg | atcttgccaa | 6420
| agcagtagca | tcccatttgt | accaaaacag | tgttcttgct | ctataaaccg | tgttagcagc | 6480
| tcagga | | | | | 6486

SEQ ID NO: 18        moltype = DNA  length = 7201
FEATURE              Location/Qualifiers
source               1..7201
                      mol_type = other DNA
                      organism = Homo sapiens
SEQUENCE: 18

| | | | | | |
|---|---|---|---|---|---|
| atggcttctc | atcgtctgct | cctcctctgc | cttgctggac | tggtatttgt | gtctgaggct | 60
| ggccctacgg | tgagtgtttc | tgtgacatcc | cattcctaca | tttaagattc | acgctaaatg | 120
| aagtagaagt | gactccttcc | agctttgcca | accagctttt | attactaggg | caagggtacc | 180
| cagcatctat | ttttaatata | attaattcaa | acttcaaaga | aatgaagtt | ccactgagct | 240
| tactgagctg | ggacttgaac | tctgagcatt | ctacctcatt | gctttggtgc | attaggtttg | 300
| taatatctgg | tacctctgtt | tcctcagata | gatgatagaa | ataaagatat | gatattaagg | 360
| aagctgttaa | tactgaattt | tcagaaaagt | atccctccat | aaaatgtatt | tgggggacaa | 420
| actgcaggag | attatattct | ggccctatag | ttattcaaaa | cgtatttatt | gattaatctt | 480
| taaaaggctt | agtgaacaat | attctagtca | gatatctaat | tcttaaatcc | tctagaagaa | 540
| ttaactaata | ctataaaatg | ggtctggatg | tagttctgac | attatttat | aacaactggt | 600
| aagagggagt | gactatagca | acaactaaaa | tgatctcagg | aaaacctgtt | tggccctatg | 660
| tatggtacat | tacatctttt | cagtaattcc | actcaaatgg | agactttaa | caaagcaact | 720
| gttctcaggg | gacctatttt | ctcccttaaa | attcattata | cacatccctg | gttgatagca | 780
| gtgtgtctgg | aggcagaaac | cattcttgct | ttggaaacaa | ttacgtctgt | gttatactga | 840
| gtagggaagc | tcattaattg | tcgacactta | cgttcctgat | aatgggatca | gtgtgtaatt | 900
| cttgtttcgc | tccagatttc | taataccaca | aagaataact | cctttcactc | tgatcaattt | 960
| tgttaacttc | tcacgtgtct | tctctacacc | cagggcaccg | gtgaatccaa | gtgtcctctg | 1020
| atggtcaaag | ttctagatgc | tgtccgaggc | agtcctgcca | tcaatgtggc | cgtgcatgtg | 1080
| ttcagaaaag | ctgctgatga | cacctgggag | ccatttgcct | ctgggtaagt | tgccaaagaa | 1140
| ccctcccaca | ggacttggtt | ttatcttccc | gtttgcactc | cacttggtag | agagaggctc | 1200
| acatcatctg | ctaaagaatt | tacaagtaga | ttgaaaaacg | taggcagagg | tcaagtatgc | 1260
| cctctgaagg | atgccctctt | tttgttttgc | ttagctagga | agtgaccagg | aacctgagca | 1320
| tcatttaggg | gcagacagta | gagaaaagaa | ggaatcagaa | ctcctctcct | ctagctgtgg | 1380
| tttgcaaccc | ttttgggtca | cagaaacactt | tatgtaggtg | atgaaaagta | aacattctat | 1440
| gcccagaaaa | aatgcacaga | tacacacaca | tacaaaatca | tatatgtgat | tttaggagtt | 1500
| tcacagattc | cctggtgtcc | ctgggtaaca | ccaaagctaa | gtgtccttgt | cttagaattt | 1560
| taggaaaagg | tataatgtgt | attaacccat | taacaaaagg | aaaggaattc | agaaatatta | 1620
| ttaaccaggc | atctgtctgt | agttaatatg | gatcacccaa | aacccaaggc | ttttgcctaa | 1680
| tgaacacttt | ggggcaccta | ctgtgtgcaa | ggctgggggc | tgtcaagctc | agttaaaaaa | 1740
| aaaaagatag | aagagatgga | tccatgaggc | aaagtacagc | cccaggctaa | tcccacgatc | 1800
| acccgacttc | atgtccaaga | gtggcttctc | accttcatta | gccagttcac | aatttttcatg | 1860
| gagttttct | acctgcacta | gcaaaaactt | caaggaaaat | acatattaat | aaatctaagc | 1920
| aaagtgacca | gaagacagag | caatcaggag | acccttgca | tccagcagaa | gggaaagagt | 1980
| taagtattta | catctccaca | gagaagaatt | tctgttgggt | tttaattgaa | ccccaagaac | 2040
| cacatgattc | ttcaaccatt | attgggaaga | tcatttttctt | aggtctggtt | ttaactggct | 2100
| ttttatttgg | gaattcattt | atgtttatat | aaaatgccaa | gcataacatg | aaaagtggtt | 2160
| acaggactat | tctaagggag | agacagaatg | gacaccaaaa | atattccaat | gttcttgtga | 2220
| atcttttcct | tgcaccagga | caaaaaaaaa | aagaagtgaa | aagaagaaag | gaggagggc | 2280
| ataatcagag | tcagtaaaga | caactgctat | ttttatctat | cgtagctgtt | gcagtcaaat | 2340
| gggaagcaat | ttccaacatt | caactatgga | gctggtactt | acatggaaat | agaagttgcc | 2400
| tagtgtttgt | tgctggcaaa | gagttatcag | agaggttaaa | tatataaaag | ggaaaagagt | 2460
| cagatacagg | ttcttcttcc | tactttaggt | ttccactgt | gtgtgcaaat | gatactccc | 2520
| ggtggtgtgc | agatgcctca | aagctatcct | cacaccacaa | gggagaggag | cgagatcctg | 2580
| ctgtcctgga | gaagtgcaga | gttagaacag | ctgtggccac | ttgcatccaa | tcatcaatct | 2640
| tgaatcacag | ggactctttc | ttaagtaaac | attataccctg | gccgggcacg | gtggctcacg | 2700
| cctgtaatcc | cagcactttg | ggatgccaaa | gtgggcatat | catctgaggt | caggagttca | 2760
| agaccagcct | ggccaacatg | gcaaaactcc | gtctttatga | aaaatacaaa | aattagccag | 2820
| gcatggtggc | aggcgcctgt | aatcccagct | aattgggagg | ctgaggctgg | agaatccctt | 2880
| gaatctagga | ggcagaggtt | gcagtgagct | gagatcgtgc | cattgcactc | cagcctgggt | 2940
| gacaagagta | aaactcgtc | tcaaaaaaaa | aaaattatac | ctacattctc | ttcttatcgg | 3000
| agaaaaaaat | ctacagtgag | cttttcaaaa | agttttttaca | aacttttttgc | catttaatttt | 3060
| cagttaggag | ttttccctac | ttctgactta | gttgagggga | aatgttcata | acatgtttat | 3120
| aacatgttta | tgtgtgttag | ttggtggggg | tgtattactt | tgccatgcca | tttgtttcct | 3180
| ccatgcgtaa | cttaatccag | actttcacac | cttataggaa | aaccagtgag | tctggagagc | 3240
| tgcatgggct | cacaactgag | gaggaattg | tagaagggat | atacaaagtg | gaaatagaca | 3300
| ccaaatctta | ctgaaggca | cttggcatct | ccccattcca | tgagcatgca | gaggtgagta | 3360
| tacagacctt | cgagggttgt | tttggttttg | gttttgctt | ttggcattcc | aggaaaatgca | 3420
| cagttttact | cagtgtacca | cagaaatgtc | ctaaggaagg | tgatgaatga | ccaaaggttc | 3480
| cctttcctat | tatacaagaa | aaaattcaca | acactctgga | aagcaaattt | cttttttgact | 3540
| ttgatgaaaa | tccacttagt | aacatgactt | gaacttacat | gaaactactc | atagtctatt | 3600
| cattccacttt | tatatgaata | ttgatgtatc | tgctgttgaa | ataatagttt | atgaggcagc | 3660
| cctcagacc | ccacgtagag | tgtatgtaac | aagagatgca | ccattttatt | tctcgaaaac | 3720
| ccgtaacatt | cttcattcca | aaacacatct | ggcttctcgg | aggtctggac | aagtgattct | 3780
| tggcaacaca | tacctataga | gacaataaaa | tcaaagtaat | aatggcaaca | caatagataa | 3840
| catttaccaa | gcatacacca | tgtggcagac | acaattataa | gtgttttcca | tatttaacct | 3900
| acttaatcct | caggaataag | ccactgaggt | cagtccatt | attatcccca | tcttatagat | 3960
| gaagaaaatg | aggcaccagg | aagtcaaata | acttgtcaaa | ggtcacaaga | ctaggaaata | 4020
| cacaagtaga | aatgttaca | attaaggccc | aggctgggtt | tgccctcagt | tctgctatgc | 4080
| ctcgcattat | gccccaggaa | acttttttccc | ttgtgaaagc | caagcttaaa | aaaagaaaag | 4140

```
ccacatttgt aacgtgctct gttccctgc ctatggtgag gatcttcaaa cagttataca   4200
tggacccagt cccctgcct tctccttaat ttcttaagtc atttgaaaca gatggctgtc   4260
atggaaatag aatccagaca tgttggtcag agttaaagat caactaattc catcaaaaat   4320
agctcggcat gaaagggaac tattctctgg cttagtcatg gatgagactt tcaattgcta   4380
taaagtggtt cctttattag acaatgttac cagggaaaca acagggggttt gtttgacttc   4440
tggggcccac aagtcaacaa gagagcccca tctaccaagg agcatgtccc tgactacccg   4500
tcagccagca gcaagacatg gacccccagtc agggcaggag cagggtttcg gcggcgccca   4560
gcacaagaca ttgcccctag agtctcagcc cctaccctcg agtaatagat ctgcctacct   4620
gagactgttg tttgcccaag agctgggtct cagcctggtg ggaaccatat aaaaaggttc   4680
actgacatac tgcccacatg ttgttctctt tcattagatc ttagcttcct tgtctgctct   4740
tcattcttgc agtattcatt caacaaacat taaaaaaaaa aaaaagcatt ctatgtgtgg   4800
aacactctgc tagatgctgt ggatttagaa atgaaaatac atcccgaccc ttggaatgga   4860
agggaaagga ctgaagtaag acagattaag caggaccgtc agcccagctt gaagcccaga   4920
taaatacgga gaacaagaga gagcgagtag tgagagatga gtcccaatgc ctcactttgg   4980
tgacgggtgc gtggtgggct tcatgcagct tcttctgata aatgcctcct tcagaactgg   5040
tcaactctac cttggccagt gacccaggtg gtcatagtag atttaccaag ggaaaatgga   5100
aactttattt aggagctctt aggcctcttc acttcatgga tttttttttc cttttttttt   5160
gagatggagt tttgccctgt cacccaggct ggaatgcagt ggtgcaatct cagctcactg   5220
caacctccgc ctcccaggtt caagcaattc tcctgcctca gcctcccgag tagctgggac   5280
tacaggtgtg cgccaccaca ccaggctaat ttttgtattt tttgtaaaga caggttttca   5340
ccacgttggc caggctggtc tgaactccag acctcaggtg attcacctgt ctcagcctcc   5400
caaagtgctg ggattacagg tgtgagccac cgtgcccggc tacttcatgg attttttgatt  5460
acagattatg cctcttacaa ttttttaagaa gaatcaagtg ggctgaaggt caatgtcacc   5520
ataagacaaa agacattttt attagttgat tctagggaat tggccttaag gggagccctt   5580
tcttcctaag agattcttag gtgattctca cttcctcttg ccccagtatt attttgtgttt  5640
ttggtatggc tcactcagat cctttttttcc tcctatccct aagtaatccg ggtttcttt   5700
tcccatattt agaacaaaat gtatttatgc agagtgtgtc caaacctcaa cccaaggcct   5760
gtatacaaaa taaatcaaat taaacacatc tttactgtct tctacctctt tcctgacctc   5820
aatatatccc aacttgcctc actctgagaa ccaaggctgt cccagcacct gagtcgcaga   5880
tattctactg atttgacaga actgtgtgac tatctgagac agcattttga tccacaattt   5940
gcccagttac aaagcttaaa tgagctctag tgcatgcata tatatttcaa aattccacca   6000
tgatcttcca cactctgtat tgtaaataga gccctgtaat gcttttacttt cgtatttcat   6060
tgcttgttat acataaaaat atacttttct tcttcatgtt agaaaatgca aagaatagga   6120
gggtggggga atctctgggc ttggagacag gagacttgcc ttcctactat ggttccatca   6180
gaatgtagac tgggacaata caataattca agtctggtt gctcatctgt aaattgggaa   6240
gaatgttttcc agctccagaa tgctaaatct ctaagtctgt ggttggcagc cactattgca   6300
gcagctcttc aatgactcaa tgcagttttg cattctccct acctttttttt tctaaaacca   6360
ataaaataga tacagccttt aggctttctg ggatttccct tagtcaagct agggtcatcc   6420
tgactttcgg cgtgaatttg caaaacaaga cctgactctg tactcctgct ctaaggactg   6480
tgcatggttc caaaggctta gcttgccagc atatttgagc tttttccttc tgttcaaact   6540
gttccaaaat ataaaagaat aaaattaatt aagttggcac tggacttccg gtggtcagtc   6600
atgtgtgtca tctgtcacgt ttttcgggct ctggtgaaa tggatctgtc tgtcttctct   6660
cataggtggt attcacagcc aacgactccg gcccccgccg ctacaccatt gccgccctgc   6720
tgagccccta ctcctattcc accacggctg tcgtcaccaa tcccaaggaa tgagggactt   6780
ctcctccagt ggacctgaag gacgagggat gggatttcat gtaaccaaga gtattccatt   6840
tttactaaag cagtgttttc acctcatatg ctatgttaga agtccaggca gagacaataa   6900
aacattcctg tgaaaggcac ttttcattcc actttaactt gatttttttaa attccctat   6960
tgtccccttcc aaaaaaaaga gaatcaaaat tttacaaaga atcaaaggaa ttctagaaag   7020
tatctgggca gaacgctagg agagatccaa atttccattg tcttgcaagc aaagcacgta   7080
ttaaatatga tctgcagcca ttaaaaagac acattctgta aatgagagag ccttattttc   7140
ctgtaaccttt cagcaaatag caaaagacac attccaaggg cccacttctt tactgtgggc   7200
a                                                                  7201
SEQ ID NO: 19           moltype = DNA  length = 6208
FEATURE                 Location/Qualifiers
source                  1..6208
                        mol_type = other DNA
                        organism = Homo sapiens
SEQUENCE: 19
ggcaccggtg aatccaagtg tcctctgatg gtcaaagttc tagatgctgt ccgaggcagt     60
cctgccatca atgtggccgt gcatgtgttc agaaaggctg ctgatgacac ctgggagcca    120
tttgcctctg ggtaagttgc caaagaaccc tccacagga cttggttttta tcttcccgtt    180
tgcccctcac ttggtagaga gaggctcaca tcatctgcta aagaatttac aagtagattg    240
aaaaacgtag gcagaggtca agtatgccct ctgaaggatg cccctctttt gttttgcttta   300
gctaggaagt gaccaggaac ctgagcatca tttagggca gacagtagag aaaagaagga    360
atcagaactc ctctcctcta gctgtggttt gcaaccctt tgggtcacag aacactttat    420
gtaggtgatg aaaagtaaac attctatgcc cagaaaaaat gcacagatac acacacatac    480
aaaatcatat atgtgatttt aggagttca cagattccct ggtgtccctg ggtaacacca    540
aagctaagtg tccttgtctt agaattttag gaaaaggtat aatgtgtatt aacccattaa    600
caaaaggaaa ggaattcaga aatattatta accaggcatc tgtctgtagt taatatggat    660
cacccaaaac ccaaggcttt tgcctaatga acacttgggg gcacctactg tgtgcaaggc    720
tgggggctgt caagctcagt taaaaaaaaaa agatagaag agatggatcc atgaggcaaa    780
gtacagcccc aggctaatcc cacgatcacc cgacttcatg tccaagagtg gcttctcacc    840
tccattcaga agttcacaat tttcatggag tttttcattg gactgcagc aaaacttcaa    900
ggaaaatcaca tattaataaaa tctaagcaaa gtgaccagaa gacagagcaa tcaggagacc    960
ctttgcatcc agcagaagag gaactgctaa gtatttcat ctccacagag aagaatttct   1020
gttgggtttt aattgaaccc caagaccac atgattcttc aaccattatt gggaagatca   1080
ttttcttagg tctggttttat actggctttt tatttggaaa ttcattatg ttatatataaa   1140
atgccaagca taacatgaaa agtggttaca ggactattct aagggagaga cagaatggac   1200
```

```
accaaaaata ttccaatgtt cttgtgaatc ttttccttgc accaggacaa aaaaaaaaag     1260
aagtgaaaag aagaaaggag gaggggcata atcagagtca gtaaagacaa ctgctatttt     1320
tatctatcgt agctgttgca gtcaaatggg aagcaatttc caacattcaa ctatggagct     1380
ggtacttaca tggaaataga agttgcctag tgtttgttgc tggcaaagag ttatcagaga     1440
ggttaaatat ataaaaggga aaagagtcag atacaggttc ttcttcctac tttaggtttt     1500
ccactgtgtg tgcaaatgat actccctggt ggtgtgcaga tgcctcaaag ctatcctcac     1560
accacaaggg agaggagcga gatcctgctg tcctggagaa gtgcagagtt agaacagctg     1620
tggccacttg catccaatca tcaatcttga atcacaggga ctctttctta agtaaacatt     1680
atacctggcc gggcacggtg gctcacgcct gtaatcccag cactttggga tgccaaagtg     1740
ggcatatcat ctgaggtcag gagttcaaga ccagcctggc caacatggca aaactccgtc     1800
tttatgaaaa atacaaaaat tagccaggca tggtggcagg cgcctgtaat cccagctaat     1860
tgggaggctg aggctggaga atcccttgaa tctaggaggc agaggttgca gtgagctgag     1920
atcgtgccat tgcactccag cctgggtgac aagagtaaaa ctctgtctca aaaaaaaaaa     1980
attataccta cattctcttc ttatcagaga aaaaaatcta cagtgagctt ttcaaaaagt     2040
ttttacaaac ttttttgcca ttaatttcag ttaggagttt tccctacttc tgacttagtt     2100
gaggggaaat gttcataaca tgtttataac atgtttatgt gtgttagttg gtggggtgt      2160
attactttgc catgccattt gtttcctcca tgcgtaactt aatccagact ttcacacctt     2220
ataggaaaac cagtgagtct ggagagctgc atgggctcac aactgaggag gaatttgtag     2280
aagggatata caaagtggaa atagacacca aatcttactg gaaggcactt ggcatctccc     2340
cattccatga gcatgcagag gtgagtatac agaccttcga gggttgtttt ggttttggtt     2400
tttgcttttg gcattccagg aaatgcacag ttttactcag tgtaccacag aaatgtccta     2460
aggaaggtga tgaatgacca aaggttccct ttcctattat acaagaaaaa attcacaaca     2520
ctctgagaag caaatttctt tttgactttg atgaaaatcc acttagtaac atgacttgaa     2580
cttacatgaa actactcata gtctattcat tccactttat atgaatattg atgtatctgc     2640
tgttgaaata atagttatg aggcagccct ccagacccca cgtagagtgt atgtaacaag      2700
agatgcacca ttttatttct cgaaaacccg taacattctt cattccaaaa catctgctg     2760
ttctcggagg tctggacaag tgattcttgg caacacatac ctatagagac aataaaatca     2820
aagtaataat ggcaacacaa tagataacat ttaccaagca tacaccatgt ggcagacaca     2880
attataagtg ttttccatat ttaacctact taatcctcag gaataagcca ctgaggtcag     2940
tcctattatt atccccatct tatagatgaa gaaaatgagg caccaggaag tcaaataact     3000
tgtcaaaggt cacaagacta ggaaatacac aagtagaaat gtttacaatt aaggcccagg     3060
ctgggtttgc cctcagttct gctatgcctc gcattatgcc ccaggaaact ttttcccttg     3120
tgaaagccaa gcttaaaaaa agaaaagcca catttgtaac gtgctctgtt ccctgccta      3180
tggtgaggat cttcaaacag ttatacatgg acccagtccc cctgccttct ccttaatttc     3240
ttaagtcatt tgaaacagat ggctgtcatg gaaatagaat ccagacatgt tggtcagagt     3300
taaagatcaa ctaattccat caaaaatagc tcggcatgaa agggaactat tctctggctt     3360
agtcatggat gagactttca attgctataa agtggttcct ttattagaca atgttaccag     3420
ggaaacaaca ggggtttgtt tgacttctgg ggcccacaag tcaacaagag agccccatct     3480
accaaggagc atgtccctga ctaccccctca gccagcagca agacatggc cccagtcagg     3540
gcaggagcag ggtttcggcg gcgcccagca caagacattg cccctagagt ctcagcccct     3600
accctcgagt aatagatctg cctacctgag actgttgttt gcccaagagc tgggtctcag     3660
cctgatggga accatataaa aaggttcact gacatactgc ccacatgttg ttctctttca     3720
ttagatctta gcttccttgt ctgctcttca ttcttgcagt attcattcaa caaacattaa     3780
aaaaaaaaaa aagcattcta tgtgtggaac actctgctag atgctgtgga tttagaaatgt    3840
aaaatacatc ccgaccccttg gaatggaagg gaaaggactg aagtaagaca gattaagcag    3900
gaccgtcagc ccagcttgaa gcccagataa atacggagaa caagagagag cgagtagtga     3960
gagtgagtc ccaatgcctc acttttggtga cgggtgggtg gtgggcttca tgcagcttct     4020
tctgataaat gcctccttca gaactggtca actctacctt ggccagtgac ccaggtggtc     4080
atagtagatt taccaaggga aaatggaaac ttttattagg agctcttagg cctcttcact     4140
tcatggattt tttttttcctt tttttttgag atggagtttt gccctgtcac ccaggctgga     4200
atgcagtggt gcaatctcag ctcactgcaa cctccgcctc ccaggttcaa gcaattctcc     4260
tgcctcagcc tcccgagtag ctgggactac aggtgtgcgc caccacacca ggctaatttt     4320
tgtatttttt gtaaagacag gttttcacca cgttggccag gctggtctga actccagacc     4380
tcaggtgatt cacctgtctc agcctcccaa agtgctggga ttacaggtgt gagccaccgt     4440
gcccgctac ttcatggatt tttgattaca gattatgcct cttacaattt ttaagaagaa       4500
tcaagtgggc tgaaggtcaa tgtcaccata agacaaaaga catttttatt agttgattcc     4560
agggaattgg ccttaagggg agccctttct tcctaagaga ttcttaggtg attctcactt     4620
cctcttgccc cagtattatt tttgttttg gtatggctca ctcagatcct ttttttcctcc     4680
tatcctaag taatccgggt ttcttttttcc catatttaga acaaaatgta tttatgcaga     4740
gtgtgtccaa acctcaaccc aaggcctgta tacaaaataa atcaaattaa acacatcttt     4800
actgtcttct acctctttcc tgacctcaat atatcccaac ttgcctcact ctgagaacca     4860
aggctgtccc agcacctgag tcgcagatat tctactgatt tgacagaact gtgtgactat     4920
ctggaacagc attttgatcc acaatttgcc cagttacaaa gcttaaatga gctctagtgc     4980
atgcatatat ctttcaaaat tccaccatga tcttcccaac tctgtattgt aaatagacc      5040
ctgtaatgct tttacttcgt atttcattgc ttgttataca taaaaatata cttttcttct     5100
tcatgttaga aaatgcaaag aataggaggg tgggggaatc tctgggcttg gagacaggag     5160
acttgccttc ctactatggt tccatcagaa tgtagactgg gacaatacaa taattcaagt     5220
ctggtttgct catctgtaaa ttgggaagaa tgtttccagc tccagaatgc taaatctcta     5280
agtctgtggt tggcagccac tattgcagca gctcttcaat gactcaatgc agttttgcat     5340
tctccctacc ttttttttct aaaaccaata aaatagatac agcctttagg cttctgggaa     5400
tttcccttag tcaagctagg gtcatcctga ctttcggcgt gaatttgcaa aacaagacct     5460
gactctgtac tcctgctcta aggactgtgc atggttccaa aggcttagct tgccagcata     5520
tttgagcttt ttccttctgt tcaaactgtt ccaaaatata aagaataaaa attaattaag     5580
ttggcactgg acttccggtg gtcagtcatg tgtgtcatct atcacgttt tcgggctctg       5640
gtggaaatgg atctgtctgt cttctctcat aggtgggtatt cacgccaac gactccggcc      5700
cccgccgcta caccattgcc gccctgctga gcccctactc ctattccacc acggctgtcg     5760
tcaccaatcc caaggaatga gggacttctc ctccagtgga cctgaaggac gagggatggg     5820
atttcatgta accaagagta ttccattttt actaaagcag tgttttcacc tcatatgcta     5880
tgttagaagt ccaggcagag acaataaaac attcctgtga aaggcacttt tcattccact     5940
```

```
ttaacttgat ttttaaatt cccttattgt cccttccaaa aaaaagagaa tcaaaatttt  6000
acaaagaatc aaaggaattc tagaaagtat ctgggcagaa cgctaggaga gatccaaatt  6060
tccattgtct tgcaagcaaa gcacgtatta aatatgatct gcagccatta aaaagacaca  6120
ttctgtaaat gagagagcct tattttcctg taaccttcag caaatagcaa aagacacatt  6180
ccaagggccc acttctttac tgtgggca                                      6208
```

| | | |
|---|---|---|
| SEQ ID NO: 20 | moltype = DNA length = 8300 | |
| FEATURE | Location/Qualifiers | |
| source | 1..8300 | |
| | mol_type = other DNA | |
| | organism = Mus musculus | |

```
SEQUENCE: 20
atggcttccc ttcgactctt cctcctttgc ctcgctggac tggtatttgt gtctgaagct    60
ggccccgcgg tgagtgatcc tgtgagcgat ccagacatgg cagttagacc ttagataaag   120
aagaagtgcc ttcttccaga tgtgagaact agagtactca gactctatat ttaccattag   180
actccaaaga gaagagctgg agtgcctctg gctcttcctt ctattgcttt agcgcattgg   240
gtctgtagtg ctcagtctct ggtgtccttA gataataaag atatgagatt aacatagaaa   300
taaagatata aaagggctgg atgtatagtt tagtggtcca tgtatgcct agtatgtgaa    360
aagccttctg ttcaacctct agcaataaga aaacaagata tattctcggt ggggctgtta   420
atattgaatt ctcataaaat ctttaatata tttagtatgc ctattatgtt gttatatttt   480
agttcttag ctaatcaaaa tgcattattg atctttcttt gtcttttttt ggccaacact    540
ctattccagt ctttgaaaaa gtcctttaaa agagttaatt agtataatta aatgagtcag   600
gaagtatgtg agggttattt tacaaccaga gggaattact atagcaacag ctgattagaa   660
tgatctcaag aaaaagccca ttctgtcttt ttgcaccatg caccttttcag tggctccatt  720
cagatggaga ggcaaacaga gcaatggctc tcagagggcc tattttccct ttgaacattc   780
attatccata tccctggtgc acagcagtgc atctgggggc agaaactgtt cttgctttgg   840
aaacaatgct gtctatgtca tactggataa agaagctcat taattgtcaa cacttatgtt   900
atcataatgg gatcagcatg tacttttggt ttgttccag agtctatcac cggaaagaac    960
aagccggttt actctgaccc atttcactga catttctctt gtctcctctg tgcccagggt  1020
gctggagaat ccaaatgtcc tctgatggtc aaagtcctgg atgctgtccg aggcagccct  1080
gctgtagacg tggctgtaaa agtgttcaaa aagaccctg agggatcctg ggagccctt    1140
gcctctgggt aagcttgtag aaagcccacc atgggaccgg ttccaggttc ccatttgctc  1200
ttattcgtgt tagattcaga cacacacaac ttaccagcta gagggctcag agagagggct  1260
cagggcgaa gggcacgtat tgctcttgta agagacacag gtttaattcc tagcaccaga  1320
atggcagctc ataaccatct gaaactcaca gtcttaggag atctgggtat ctgacattct  1380
cttctaccca ccatgtgtgt ggtgcacaaa ttcacatgca ggcatcaaat cttataaaca  1440
acaacaaaaa accaacaaac ctggtagcaa aagaagatta gaaggttaaa catatgagcc  1500
gagagctttt gttttgtttt gttttgtttt gttttgttta cattttcaaat gttatcccct  1560
ttctcggtcc ccctcccccaa accctctacc ccattctctc ctccccttct tctatgaggg  1620
tgttcccac caacccactc ccaccttcct gctctcgaat tccctatac tgggacatca  1680
agccttcaca gaatcaaggg cctctcctcc cattgatgcc cgacaatgtc atcctctgct  1740
acctatgtgt ctggagccat gggtcccttc atgtatcctc cttggttggt ggtttagtct  1800
ctgggaggtc tgggggatct ggttgattga tattattgtt cttcctatga gattgcaaac  1860
cccttcagct ccttcggtcc tttaactcct ccactgggga ccccgagctc agtccaatgg  1920
ttggctgtga gcatccacca gcagaggcct tttttttttt tttaacaaa gctgctttat    1980
tatgttgctt agagcatgac caggaaccag agcacagtcc aagactgaag ggaggaaaag  2040
gggggagtc aataacccca ctgtttcata gtggttttga accctttat atcacagccc   2100
actttaggca aataatgaaa attatagtct ccaggacag agaagatggt gcaggaagtg   2160
aagtgcctgc tcagaaaatg ggggcttgaa tgtgagttcc cagactctgt gtaagatgcc  2220
cagcatcgaa gtgcatgctt ataacaccag cctggaggta gaagcttaga aacagggta   2280
ccctgaagtt gcttgttcac cagtgtccct gaatgggtag gtgcatgttt ggtgagagac  2340
cctgtctcaa aaatcaaggt gtaggataat tgaaaatacc tagctttgag cttagatcat  2400
gcaaatgtgt acacacactc acacacacca cacacacaaa aaaatgcaga gacagagaga  2460
tacagagaga cagagagata cagagacaga cagagagaga aaaggagaaa gtaaaaaaca  2520
aataattaa agacccatgg ccacaaagag gctcaaagac aagcacgtat aaaaccatac  2580
acatgtaatt ttaggagttt tcagattccc tggtacccgt gggtgatgca caagctttga  2640
atccagtct taaatcttta cgaagaacgt gttcgtgtgt gctaatttat tgatgagagg   2700
aaaggaattg acaaagtgcc cttccggagc ttcctgcatt acccagactc agggtttttt  2760
taaatgtaca ctcagaacag agtagctctg tgcaagggta gcaaccacga agcttaataa  2820
gaaacatatc gtgagagatc tgcaaggcaa atctaggggc tgaccaatct cacagtcacc  2880
cactagcatg tcaacacaac ttcccacctg tgctagccac ttagcaattt tgtgttgttc  2940
tgtttgtt ttgtttttaa caaagcaatt tcaaagagat ttctaattca tctaaacaaa    3000
caaccaaaa ggaaaacagc aaagacgccc tgagcactta gcagagcagc tatgcagtta   3060
tgactcctgg gtgagactt tatatcaggc ttcaactgaa tacctagaac ctactagtgc   3120
tcttcatcaa tccttgggaa ggtcattttc ttttggtgct gttttgagtt tctatttgtt  3180
aatgtcttca taattataca cgtgttgagc acagcatgca aagtgattag gggaatctag  3240
ttggagtgga atggataccc aaatattcag acttcttgt gactcttctt tcttgtaccc   3300
acatcaaaaa aaaaaaaaat ggagatgaga catggtcaga gtcactaaaa ccagctgcta  3360
cttttaatta cgtggggagc agtttctaac attgccatta ttgaactgat gctgcctgga  3420
tggaaatgga aatcacttag tatttcttgt tggcaaagaa ttactgaatg gattaaattt  3480
ccaagggag aagtcagtta caagtctttt ctttgtttat taggcttct gctatgataa    3540
attacactac ttcagaagt tacccttagg ccatgggaca ctggactatc actctgctgt   3600
cacaagagat tacagagtta gtcaaggcag cttgtgacac cttcagggac tgtcataaac  3660
ttccagcaag tcattaatcc tgaatgcaat actgtgtctatg tgtgtctatg tgtgtttgta 3720
tgtctgtgtg tgtcttatgt ctgtgtctct gtgtgtgtgt gtgtttgtgt gtgtgtgt   3780
atgtatgcct gtgtgtgtct gtgtctgtg tttgtgtgtc tgtgtgtgtc ttatgtctgt  3840
gtttgtatgt ctgtgtgtgt ctgtgtgtgt ttatgtctg tgtctgtgtg tgtgtgtgt  3900
tgtatgtatg tatgtatgta tgtatgtgta tgtgtttgca tctctctgtg tgtctgcgct  3960
tatatatttg tgtatgtgtt tatgtgttcg cctttgtgcg ttgttgggga ttgaatccag  4020
```

```
gggaatacaa atgttaagaa agaacgttac cactaagctt cacctgtagg ccttaaagct   4080
tttctttctt ttaaaaattg taattaattc attttcagtc aggatctcca cacctcgtcc   4140
ctgctgctct agaactcact atttaaacac aatcgccctc aaacctgcag caaccctccc   4200
gcctctaccc tgcgagcact agaataataa caggtgaccc cacacgccta gattaagacc   4260
tttaaggtaa acattttact atattttagt ctcataagac aagatgctac aataaagctg   4320
tacataaagt tccctcgaat ttcttgctat tttaactcaa acataaggat ttcctccttt   4380
ttgattcagg taacagaaaa aatacacagg tacatacatg tacacacatg aacacacacg   4440
catcacaacc acatatgcgc acgcttgtgt gatctatcat ttaccatgcc actgaactct   4500
tctttcccca taaattcctc tggacttgtg tgccctccag gaagaccgcg gagtctggag   4560
agctgcacgg gctcaccaca gatgagaagt ttgtagaagt agtgtacaga gtagaactgg   4620
acaccaaatc gtactggaag acacttggca tttcccgtt ccatgaattc gcggatgtaa   4680
gtggacacac caagttgttt ggattttgtt tttagtctca ggaaattccc ttcgctcttg   4740
ctgtacgatg ggcatgagtg gaaagtagat tccacagcca gaatccacag tgctgggaaa   4800
gcaagccttc tgaattttc taaaactcat ttagcaacat ggcctgaacc tgttcacact   4860
gcttatggtc agctaactat atttatgtaa atattcattt ctctgttgag gaaatgttag   4920
tattttgcttt tgaggcaacc tccagatacc atggagggca tgtcatagtc aaagagaggg   4980
ctccctatgg tatttctcta aattctggca tttccttat tccaaagcac atctagtgtc   5040
cccagaagtt tgggtagaca attcttggca acacagagaa ttacaacatg ttcaaaaccc   5100
aacagcttaa tatctaaatc atcaagcaaa catcacatgg caaagggatt tctgaatcaa   5160
aactgtttca tccttatgat caacctatgg aggtctagcc tcgacttaca cccatttac   5220
caataagcta agagaagcta agttcctcat caaggacaca aggctagcat gtgtgagcaa   5280
gtgacagagt tgccctctat gttggttagt gtgccttagc cagtgtctca gtaagaaatg   5340
gagctaaatc aaaacccaag gccaacagcc aaaggcacat gagtaacctt tgcttggcac   5400
tgggctcagt ttccctggct cctctcagtc tcagttcac agaggcagct gtcatgcaaa   5460
tagaatccaa gcttgttggt cagacctgga gataacaaat tccatcaaaa atagctcctc   5520
atgtgaccta gtttgctgtc tgttgctatg atacacacca tgaccgaaaa gcaacctgg   5580
ggagagaagg gttttatttca tcttacagct tacagttgca catggaggaa agccaggtgg   5640
gaacctggaa gtggaaattg aagcagagac cagaaaggaa tgctgtttac tggctggctt   5700
agctcctttt cttatacagc ttaggtctat gtgcccaggg gatggtactg ccgagcatag   5760
gctgacccg cctacatcaa ccattagtca aaaaaggtc catagacttg cctacaggcc   5820
aatctcatgg aggcaatacc ccagtggagg gtccctcttc gcaggttact ctagttttgt   5880
tcaagttgac aaaacctaac cacaaagcac aaacagggtc tgcccttgtg cttagccat   5940
ggatgacact ctcagatgat ggtgttacca gacaaaccag aggggctcac caagagtctg   6000
ccacctacca aggtagtact ctactcctca ctgggcacca acacccatat tagctggggcc   6060
agtacaggac ccttgctgtt tcctgcatga attgtccata gacccctgggt ctcagcctgc   6120
cgggagtacc tgtaagtagt cgcctcaaac acattattcc tgttggaaga cttgtctgat   6180
tctcttttag aactcaatca acaaacgttt ttatttgtt ttggctttt ggagacaaga   6240
tctctcatag gccagcctga cttgaatgta gctgaggatg acctgctg ctaatcttct   6300
cgcctcttcc tcccaagtgg taggataata ggcataagac accacagcag ttttactcca   6360
taccagggct ctgaacccag acttttaaaca ctctatcaac tgattcacat tcccaccca   6420
tcattcaaca aacatttgaa aaataaaacc cttctgcctt gagcactctg ctaaatacag   6480
cctttgagtg cggagtattt cctcacaacc agggtccaag atgaccccat catacatacc   6540
acggaaaatt aggagatgtt tttaggtctc tttgcttggg tgaattttta tgtgtgtgtg   6600
tacacagccc tgtgcgtgtg tgtgtgtgtg tgtgtgtgtg tgtacaggca cacacgtgta   6660
tgcatgtaga ggctacataa aaaccttagg tgtcattctc aggcactctg ttcaccctt   6720
cacacagccc gaacacacaa aatttgaggc attagcctgg agctcaccag ttaggctaga   6780
ctgacttgcc agcagacccc aggctgctct catctcccca gctctgggat tacaaactct   6840
atcataccag acatttttat acatattctg agcataaaat tcatgtcttc aggctaacaa   6900
gtcaagagct taaatgactg agctctctta cgtggtggat ttttttaaa actacataat   6960
atcttttttt tttttttcac ttctggggaa gaaacaaatg agcctgagtg acaatgcgac   7020
agaaaagaaa ttttgaggag tgtgtgtgtc tgtgtgtgtg gtggcacatg cctctcatct   7080
aatgctagag gctacagtag aatgctcctg aattagtggc cagccaaggc caagggctag   7140
ggttgtaact cagtggcaga gggcttgcct agcattcgca ggatttgatc catagcgcta   7200
taaataataa taaataaata caacagtcta agatgattct ccctttcatt tatctggatg   7260
ttattttgt gttagttta ctctgtcatc caatcattgt ttgccctata tttgacatt   7320
taaaaaaaat ctttattcca agtgtgttca aagctgtatc caaaacctgt ccaccaaatg   7380
agtccaatga catacatctt ctatattacc atctgttcca gatttggctg actcccggca   7440
cctgggctgt tgctgcaccc atgtctcaga tagtctagtg attgagaag tgactagtaa   7500
ttgcaaaatc cagactttgt ccagaaactt ctatgagctc caaaactttc atttacattt   7560
ctgccagcca caaacgcctt gtgttgtgga gagaaccctg tgatgtcttc ccacagcatc   7620
tcagccttgt ttcttccctt aaaatattca tcttttcaca ttagaacatg caaagggaca   7680
gtgggagcga aaccctgga ctgggacgca cgaagcctcc cttctgtc aggctctcac   7740
tgtagaaact taggccggtt tcagcatgca gtctgctgga gaatggctcc tgccaacatt   7800
ccaggtctgg aagtttgtag tggagttgtt gataaccact gttcgccaca ggtctttgtc   7860
ttgtgggtgt cagtgtttct actctcctga cttttatctg aacccaagaa agggaacaat   7920
agccttcaag ctctctgtga ctctgatctg accagggcca cccacactgc agaaggaaac   7980
ttgcaaagag agacctgcaa ttctctaaga gctccacaca gctccaaaga cttaggcagc   8040
atattttaat ctaattattc gtcccccaac cccaccccag aggacagtta gacaataaaa   8100
ggaagattac cagcttagca tcctgtgaac actttgtctg cagctcctac ctctgggctc   8160
tgttagaact agctgtctct cctctctcct aggtggtttt cacagccaac gactctggcc   8220
atcgccacta caccatcgca gccctgctca gcccatactc ctacagcacc acggctgtcg   8280
tcagcaaccc ccagaattga                                              8300

SEQ ID NO: 21      moltype = DNA  length = 24
FEATURE            Location/Qualifiers
misc_feature       1..24
                   note = Synthetic
source             1..24
                   mol_type = other DNA
```

```
                        organism = synthetic construct
SEQUENCE: 21
cacagacaat cagacgtacc agta                                              24

SEQ ID NO: 22           moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 22
ccagctttgc cagtttacga                                                   20

SEQ ID NO: 23           moltype = DNA   length = 18
FEATURE                 Location/Qualifiers
misc_feature            1..18
                        note = Synthetic
source                  1..18
                        mol_type = other DNA
                        organism = synthetic construct
SEQUENCE: 23
ttggacggtt gccctctt                                                     18

SEQ ID NO: 24           moltype = DNA   length = 22
FEATURE                 Location/Qualifiers
misc_feature            1..22
                        note = Synthetic
source                  1..22
                        mol_type = other DNA
                        organism = synthetic construct
SEQUENCE: 24
gatggcttcc cttcgactct tc                                                22

SEQ ID NO: 25           moltype = DNA   length = 25
FEATURE                 Location/Qualifiers
misc_feature            1..25
                        note = Synthetic
source                  1..25
                        mol_type = other DNA
                        organism = synthetic construct
SEQUENCE: 25
cactgacatt tctcttgtct cctct                                             25

SEQ ID NO: 26           moltype = DNA   length = 21
FEATURE                 Location/Qualifiers
misc_feature            1..21
                        note = Synthetic
source                  1..21
                        mol_type = other DNA
                        organism = synthetic construct
SEQUENCE: 26
gggctcacca cagatgagaa g                                                 21

SEQ ID NO: 27           moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 27
cactgttcgc cacaggtctt                                                   20

SEQ ID NO: 28           moltype = DNA   length = 20
FEATURE                 Location/Qualifiers
misc_feature            1..20
                        note = Synthetic
source                  1..20
                        mol_type = other DNA
                        organism = synthetic construct
SEQUENCE: 28
gctcagccca tactcctaca                                                   20

SEQ ID NO: 29           moltype = DNA   length = 18
FEATURE                 Location/Qualifiers
misc_feature            1..18
                        note = Synthetic
source                  1..18
```

```
                    mol_type = other DNA
                    organism = synthetic construct
SEQUENCE: 29
gcccaggagg accaggat                                                 18

SEQ ID NO: 30       moltype = DNA   length = 20
FEATURE             Location/Qualifiers
misc_feature        1..20
                    note = Synthetic
source              1..20
                    mol_type = other DNA
                    organism = synthetic construct
SEQUENCE: 30
ggcaacttgc ttgaggaaga                                               20

SEQ ID NO: 31       moltype = DNA   length = 20
FEATURE             Location/Qualifiers
misc_feature        1..20
                    note = Synthetic
source              1..20
                    mol_type = other DNA
                    organism = synthetic construct
SEQUENCE: 31
gcagcaaccc agcttcactt                                               20

SEQ ID NO: 32       moltype = DNA   length = 19
FEATURE             Location/Qualifiers
misc_feature        1..19
                    note = Synthetic
source              1..19
                    mol_type = other DNA
                    organism = synthetic construct
SEQUENCE: 32
actgagctgg gacttgaac                                                19

SEQ ID NO: 33       moltype = DNA   length = 19
FEATURE             Location/Qualifiers
misc_feature        1..19
                    note = Synthetic
source              1..19
                    mol_type = other DNA
                    organism = synthetic construct
SEQUENCE: 33
tgcctcactc tgagaacca                                                19

SEQ ID NO: 34       moltype = DNA   length = 19
FEATURE             Location/Qualifiers
misc_feature        1..19
                    note = Synthetic
source              1..19
                    mol_type = other DNA
                    organism = synthetic construct
SEQUENCE: 34
ggtggagagg ctattcggc                                                19

SEQ ID NO: 35       moltype = DNA   length = 18
FEATURE             Location/Qualifiers
misc_feature        1..18
                    note = Synthetic
source              1..18
                    mol_type = other DNA
                    organism = synthetic construct
SEQUENCE: 35
ggccgtgcat gtgttcag                                                 18

SEQ ID NO: 36       moltype = DNA   length = 23
FEATURE             Location/Qualifiers
misc_feature        1..23
                    note = Synthetic
source              1..23
                    mol_type = other DNA
                    organism = synthetic construct
SEQUENCE: 36
ggttcccatt tgctcttatt cgt                                           23

SEQ ID NO: 37       moltype = DNA   length = 23
FEATURE             Location/Qualifiers
misc_feature        1..23
                    note = Synthetic
```

```
                            source          1..23
                                            mol_type = other DNA
                                            organism = synthetic construct
                    SEQUENCE: 37
                    cccacactgc agaaggaaac ttg                                           23

SEQ ID NO: 38           moltype = DNA   length = 23
                    FEATURE                 Location/Qualifiers
                    misc_feature            1..23
                                            note = Synthetic
                    source                  1..23
                                            mol_type = other DNA
                                            organism = synthetic construct
                    SEQUENCE: 38
                    ggttcccatt tgctcttatt cgt                                           23

SEQ ID NO: 39           moltype = DNA   length = 22
                    FEATURE                 Location/Qualifiers
                    misc_feature            1..22
                                            note = Synthetic
                    source                  1..22
                                            mol_type = other DNA
                                            organism = synthetic construct
                    SEQUENCE: 39
                    ccagcttagc atcctgtgaa ca                                            22

SEQ ID NO: 40           moltype = DNA   length = 20
                    FEATURE                 Location/Qualifiers
                    misc_feature            1..20
                                            note = Synthetic
                    source                  1..20
                                            mol_type = other DNA
                                            organism = synthetic construct
                    SEQUENCE: 40
                    ggcaacttgc ttgaggaaga                                               20

SEQ ID NO: 41           moltype = DNA   length = 22
                    FEATURE                 Location/Qualifiers
                    misc_feature            1..22
                                            note = Synthetic
                    source                  1..22
                                            mol_type = other DNA
                                            organism = synthetic construct
                    SEQUENCE: 41
                    tgtggagttc agtagtgtgg ag                                            22

SEQ ID NO: 42           moltype = DNA   length = 25
                    FEATURE                 Location/Qualifiers
                    misc_feature            1..25
                                            note = Synthetic
                    source                  1..25
                                            mol_type = other DNA
                                            organism = synthetic construct
                    SEQUENCE: 42
                    cactgacatt tctcttgtct cctct                                         25

SEQ ID NO: 43           moltype = DNA   length = 23
                    FEATURE                 Location/Qualifiers
                    misc_feature            1..23
                                            note = Synthetic
                    source                  1..23
                                            mol_type = other DNA
                                            organism = synthetic construct
                    SEQUENCE: 43
                    gggacatctc ggtttcctga ctt                                           23

SEQ ID NO: 44           moltype = DNA   length = 22
                    FEATURE                 Location/Qualifiers
                    misc_feature            1..22
                                            note = Synthetic
                    source                  1..22
                                            mol_type = other DNA
                                            organism = synthetic construct
                    SEQUENCE: 44
                    tccacactac tgaactccac aa                                            22

SEQ ID NO: 45           moltype = DNA   length = 21
                    FEATURE                 Location/Qualifiers
                    misc_feature            1..21
```

```
                     note = Synthetic
source               1..21
                     mol_type = other DNA
                     organism = synthetic construct
SEQUENCE: 45
cggaacactc gctctacgaa a                                              21

SEQ ID NO: 46        moltype = DNA  length = 18
FEATURE              Location/Qualifiers
misc_feature         1..18
                     note = Synthetic
source               1..18
                     mol_type = other DNA
                     organism = synthetic construct
SEQUENCE: 46
gggccagctt cagacaca                                                  18

SEQ ID NO: 47        moltype = DNA  length = 22
FEATURE              Location/Qualifiers
misc_feature         1..22
                     note = Synthetic
source               1..22
                     mol_type = other DNA
                     organism = synthetic construct
SEQUENCE: 47
cccagggtgc tggagaatcc aa                                             22

SEQ ID NO: 48        moltype = DNA  length = 22
FEATURE              Location/Qualifiers
misc_feature         1..22
                     note = Synthetic
source               1..22
                     mol_type = other DNA
                     organism = synthetic construct
SEQUENCE: 48
gccaagtgtc ttccagtacg at                                             22

SEQ ID NO: 49        moltype = DNA  length = 21
FEATURE              Location/Qualifiers
misc_feature         1..21
                     note = Synthetic
source               1..21
                     mol_type = other DNA
                     organism = synthetic construct
SEQUENCE: 49
gttccctttc ttgggttcag a                                              21

SEQ ID NO: 50        moltype = DNA  length = 23
FEATURE              Location/Qualifiers
misc_feature         1..23
                     note = Synthetic
source               1..23
                     mol_type = other DNA
                     organism = synthetic construct
SEQUENCE: 50
gatgctactg ctttggcaag atc                                            23

SEQ ID NO: 51        moltype = DNA  length = 20
FEATURE              Location/Qualifiers
misc_feature         1..20
                     note = Synthetic
source               1..20
                     mol_type = other DNA
                     organism = synthetic construct
SEQUENCE: 51
cctgagctgc taacacggtt                                                20

SEQ ID NO: 52        moltype = DNA  length = 23
FEATURE              Location/Qualifiers
misc_feature         1..23
                     note = Synthetic
source               1..23
                     mol_type = other DNA
                     organism = synthetic construct
SEQUENCE: 52
agctacagac catgcttagt gta                                            23

SEQ ID NO: 53        moltype = DNA  length = 24
FEATURE              Location/Qualifiers
```

```
misc_feature          1..24
                      note = Synthetic
source                1..24
                      mol_type = other DNA
                      organism = synthetic construct
SEQUENCE: 53
tgccagttta ggaggaatat gttc                                                24

SEQ ID NO: 54         moltype = DNA   length = 25
FEATURE               Location/Qualifiers
misc_feature          1..25
                      note = Synthetic
source                1..25
                      mol_type = other DNA
                      organism = synthetic construct
SEQUENCE: 54
ctgaggaaac agaggtacca gatat                                               25

SEQ ID NO: 55         moltype = DNA   length = 24
FEATURE               Location/Qualifiers
misc_feature          1..24
                      note = Synthetic
source                1..24
                      mol_type = other DNA
                      organism = synthetic construct
SEQUENCE: 55
agtcacacag ttctgtcaaa tcag                                                24

SEQ ID NO: 56         moltype = DNA   length = 17
FEATURE               Location/Qualifiers
misc_feature          1..17
                      note = Synthetic
source                1..17
                      mol_type = other DNA
                      organism = synthetic construct
SEQUENCE: 56
gaacacggcg gcatcag                                                        17

SEQ ID NO: 57         moltype = DNA   length = 20
FEATURE               Location/Qualifiers
misc_feature          1..20
                      note = Synthetic
source                1..20
                      mol_type = other DNA
                      organism = synthetic construct
SEQUENCE: 57
tcctgtggga gggttctttg                                                     20

SEQ ID NO: 58         moltype = DNA   length = 20
FEATURE               Location/Qualifiers
misc_feature          1..20
                      note = Synthetic
source                1..20
                      mol_type = other DNA
                      organism = synthetic construct
SEQUENCE: 58
ccctctctct gagccctcta                                                     20

SEQ ID NO: 59         moltype = DNA   length = 21
FEATURE               Location/Qualifiers
misc_feature          1..21
                      note = Synthetic
source                1..21
                      mol_type = other DNA
                      organism = synthetic construct
SEQUENCE: 59
gctgcctaag tctttggagc t                                                   21

SEQ ID NO: 60         moltype = DNA   length = 20
FEATURE               Location/Qualifiers
misc_feature          1..20
                      note = Synthetic
source                1..20
                      mol_type = other DNA
                      organism = synthetic construct
SEQUENCE: 60
ccctctctct gagccctcta                                                     20

SEQ ID NO: 61         moltype = DNA   length = 25
```

```
                            -continued
FEATURE              Location/Qualifiers
misc_feature         1..25
                     note = Synthetic
source               1..25
                     mol_type = other DNA
                     organism = synthetic construct
SEQUENCE: 61
gagaggagag acagctagtt ctaac                                         25

SEQ ID NO: 62        moltype = DNA  length = 23
FEATURE              Location/Qualifiers
misc_feature         1..23
                     note = Synthetic
source               1..23
                     mol_type = other DNA
                     organism = synthetic construct
SEQUENCE: 62
agctacagac catgcttagt gta                                           23

SEQ ID NO: 63        moltype = DNA  length = 22
FEATURE              Location/Qualifiers
misc_feature         1..22
                     note = Synthetic
source               1..22
                     mol_type = other DNA
                     organism = synthetic construct
SEQUENCE: 63
gccctcttca tacaggaatc ac                                            22

SEQ ID NO: 64        moltype = DNA  length = 19
FEATURE              Location/Qualifiers
misc_feature         1..19
                     note = Synthetic
source               1..19
                     mol_type = other DNA
                     organism = synthetic construct
SEQUENCE: 64
cggacagcat ccaggactt                                                19

SEQ ID NO: 65        moltype = DNA  length = 26
FEATURE              Location/Qualifiers
misc_feature         1..26
                     note = Synthetic
source               1..26
                     mol_type = other DNA
                     organism = synthetic construct
SEQUENCE: 65
tcatgtaatc tggcttcaga gtggga                                        26

SEQ ID NO: 66        moltype = DNA  length = 27
FEATURE              Location/Qualifiers
misc_feature         1..27
                     note = Synthetic
source               1..27
                     mol_type = other DNA
                     organism = synthetic construct
SEQUENCE: 66
tgggaggcaa ttcttagttt caatgga                                       27

SEQ ID NO: 67        moltype = DNA  length = 23
FEATURE              Location/Qualifiers
misc_feature         1..23
                     note = Synthetic
source               1..23
                     mol_type = other DNA
                     organism = synthetic construct
SEQUENCE: 67
tcccaaaggt gtctgtctgc aca                                           23

SEQ ID NO: 68        moltype = DNA  length = 22
FEATURE              Location/Qualifiers
misc_feature         1..22
                     note = Synthetic
source               1..22
                     mol_type = other DNA
                     organism = synthetic construct
SEQUENCE: 68
ctcctttgcc tcgctggact gg                                            22
```

| | | |
|---|---|---|
| SEQ ID NO: 69 | moltype = DNA length = 19 | |
| FEATURE | Location/Qualifiers | |
| misc_feature | 1..19 | |
| | note = Synthetic | |
| source | 1..19 | |
| | mol_type = other DNA | |
| | organism = synthetic construct | |
| SEQUENCE: 69 | | |
| cggacagcat ccaggactt | | 19 |
| | | |
| SEQ ID NO: 70 | moltype = DNA length = 29 | |
| FEATURE | Location/Qualifiers | |
| misc_feature | 1..29 | |
| | note = Synthetic | |
| source | 1..29 | |
| | mol_type = other DNA | |
| | organism = synthetic construct | |
| SEQUENCE: 70 | | |
| agaaggagtg tacagagtag aactggaca | | 29 |
| | | |
| SEQ ID NO: 71 | moltype = DNA length = 27 | |
| FEATURE | Location/Qualifiers | |
| misc_feature | 1..27 | |
| | note = Synthetic | |
| source | 1..27 | |
| | mol_type = other DNA | |
| | organism = synthetic construct | |
| SEQUENCE: 71 | | |
| tgtttgtggg tgtcagtgtt tctactc | | 27 |
| | | |
| SEQ ID NO: 72 | moltype = DNA length = 21 | |
| FEATURE | Location/Qualifiers | |
| misc_feature | 1..21 | |
| | note = Synthetic | |
| source | 1..21 | |
| | mol_type = other DNA | |
| | organism = synthetic construct | |
| SEQUENCE: 72 | | |
| caccacggct gtcgtcagca a | | 21 |
| | | |
| SEQ ID NO: 73 | moltype = DNA length = 23 | |
| FEATURE | Location/Qualifiers | |
| misc_feature | 1..23 | |
| | note = Synthetic | |
| source | 1..23 | |
| | mol_type = other DNA | |
| | organism = synthetic construct | |
| SEQUENCE: 73 | | |
| cttgccaaag cagtagcatc cca | | 23 |
| | | |
| SEQ ID NO: 74 | moltype = DNA length = 23 | |
| FEATURE | Location/Qualifiers | |
| misc_feature | 1..23 | |
| | note = Synthetic | |
| source | 1..23 | |
| | mol_type = other DNA | |
| | organism = synthetic construct | |
| SEQUENCE: 74 | | |
| aggtcagaaa gcagagtgga cca | | 23 |
| | | |
| SEQ ID NO: 75 | moltype = DNA length = 23 | |
| FEATURE | Location/Qualifiers | |
| misc_feature | 1..23 | |
| | note = Synthetic | |
| source | 1..23 | |
| | mol_type = other DNA | |
| | organism = synthetic construct | |
| SEQUENCE: 75 | | |
| cccaggcaat tcctaccttc cca | | 23 |
| | | |
| SEQ ID NO: 76 | moltype = DNA length = 28 | |
| FEATURE | Location/Qualifiers | |
| misc_feature | 1..28 | |
| | note = Synthetic | |
| source | 1..28 | |
| | mol_type = other DNA | |
| | organism = synthetic construct | |
| SEQUENCE: 76 | | |
| tctgagcatt ctacctcatt gctttggt | | 28 |

```
SEQ ID NO: 77          moltype = DNA   length = 23
FEATURE                Location/Qualifiers
misc_feature           1..23
                       note = Synthetic
source                 1..23
                       mol_type = other DNA
                       organism = synthetic construct
SEQUENCE: 77
aggctgtccc agcacctgag tcg                                            23

SEQ ID NO: 78          moltype = DNA   length = 23
FEATURE                Location/Qualifiers
misc_feature           1..23
                       note = Synthetic
source                 1..23
                       mol_type = other DNA
                       organism = synthetic construct
SEQUENCE: 78
tgggcacaac agacaatcgg ctg                                            23

SEQ ID NO: 79          moltype = DNA   length = 23
FEATURE                Location/Qualifiers
misc_feature           1..23
                       note = Synthetic
source                 1..23
                       mol_type = other DNA
                       organism = synthetic construct
SEQUENCE: 79
aaggctgctg atgacacctg gga                                            23

SEQ ID NO: 80          moltype = DNA   length = 27
FEATURE                Location/Qualifiers
misc_feature           1..27
                       note = Synthetic
source                 1..27
                       mol_type = other DNA
                       organism = synthetic construct
SEQUENCE: 80
agattcagac acacacaact taccagc                                        27

SEQ ID NO: 81          moltype = DNA   length = 28
FEATURE                Location/Qualifiers
misc_feature           1..28
                       note = Synthetic
source                 1..28
                       mol_type = other DNA
                       organism = synthetic construct
SEQUENCE: 81
agacctgcaa ttctctaaga gctccaca                                       28

SEQ ID NO: 82          moltype = DNA   length = 27
FEATURE                Location/Qualifiers
misc_feature           1..27
                       note = Synthetic
source                 1..27
                       mol_type = other DNA
                       organism = synthetic construct
SEQUENCE: 82
agattcagac acacacaact taccagc                                        27

SEQ ID NO: 83          moltype = DNA   length = 24
FEATURE                Location/Qualifiers
misc_feature           1..24
                       note = Synthetic
source                 1..24
                       mol_type = other DNA
                       organism = synthetic construct
SEQUENCE: 83
ttgtctgcag ctcctacctc tggg                                           24

SEQ ID NO: 84          moltype = DNA   length = 23
FEATURE                Location/Qualifiers
misc_feature           1..23
                       note = Synthetic
source                 1..23
                       mol_type = other DNA
                       organism = synthetic construct
SEQUENCE: 84
```

```
aggtcagaaa gcagagtgga cca                                            23

SEQ ID NO: 85           moltype = DNA   length = 29
FEATURE                 Location/Qualifiers
misc_feature            1..29
                        note = Synthetic
source                  1..29
                        mol_type = other DNA
                        organism = synthetic construct
SEQUENCE: 85
ttgacatgtg tgggtgagag attttactg                                      29

SEQ ID NO: 86           moltype = DNA   length = 22
FEATURE                 Location/Qualifiers
misc_feature            1..22
                        note = Synthetic
source                  1..22
                        mol_type = other DNA
                        organism = synthetic construct
SEQUENCE: 86
cccagggtgc tggagaatcc aa                                             22

SEQ ID NO: 87           moltype = RNA   length = 16
FEATURE                 Location/Qualifiers
misc_feature            1..16
                        note = Synthetic
source                  1..16
                        mol_type = other RNA
                        organism = synthetic construct
SEQUENCE: 87
gttttagagc tatgct                                                    16

SEQ ID NO: 88           moltype = RNA   length = 67
FEATURE                 Location/Qualifiers
misc_feature            1..67
                        note = Synthetic
source                  1..67
                        mol_type = other RNA
                        organism = synthetic construct
SEQUENCE: 88
agcatagcaa gttaaaataa ggctagtccg ttatcaactt gaaaaagtgg caccgagtcg    60
gtgcttt                                                              67

SEQ ID NO: 89           moltype = RNA   length = 77
FEATURE                 Location/Qualifiers
misc_feature            1..77
                        note = Synthetic
source                  1..77
                        mol_type = other RNA
                        organism = synthetic construct
SEQUENCE: 89
gttttagagc tagaaatagc aagttaaaat aaggctagtc cgttatcaac ttgaaaaagt    60
ggcaccgagt cggtgct                                                   77

SEQ ID NO: 90           moltype = DNA   length = 444
FEATURE                 Location/Qualifiers
misc_feature            1..444
                        note = Synthetic
source                  1..444
                        mol_type = other DNA
                        organism = synthetic construct
SEQUENCE: 90
atggcttctc atcgtctgct cctcctctgc cttgctggac tggtatttgt gtctgaggct    60
ggccctacgg gcaccggtga atccaagtgt cctctgatgg tcaaagttct agatgctgtc   120
cgaggcagtc ctgccatcaa tgtggccgtg catgtgttca gaaaggctgc tgatgacacc   180
tgggagccat tgcctctgg gaaaaccagt gagtctggag agctgcatgg gctcacaact   240
gaggaggaat ttgtagaagg gatatacaaa gtggaaatga caccaaatc ttactggaag   300
gcacttggca tctcccccatt ccatgagcat gcagaggtgg tattcacagc caacgactcc   360
ggcccccgcc gctacaccat tgccgccctg ctgagcccca ctcctattc caccacggct   420
gtcgtcacca atcccaagga atga                                          444

SEQ ID NO: 91           moltype = DNA   length = 444
FEATURE                 Location/Qualifiers
misc_feature            1..444
                        note = Synthetic
source                  1..444
                        mol_type = other DNA
                        organism = synthetic construct
SEQUENCE: 91
```

```
atggcttccc ttcgactctt cctcctttgc ctcgctggac tggtatttgt gtctgaagct    60
ggccccgcgg gcaccggtga atccaagtgt cctctgatgg tcaaagttct agatgctgtc   120
cgaggcagtc ctgccatcaa tgtggccgtg catgtgttca gaaaggctgc tgatgacacc   180
tgggagccat ttgcctctgg gaaaaccagt gagtctggag agctgcatgg gctcacaact   240
gaggaggaat ttgtagaagg gatatacaaa gtggaaatag acaccaaatc ttactggaag   300
gcacttggca tctccccatt ccatgagcat gcagaggtgg tattcacagc caacgactcc   360
ggcccccgcc gctacaccat tgccgccctg ctgagcccct actcctattc caccacggct   420
gtcgtcacca atcccaagga atga                                          444

SEQ ID NO: 92          moltype = DNA    length = 444
FEATURE                Location/Qualifiers
misc_feature           1..444
                       note = Synthetic
source                 1..444
                       mol_type = other DNA
                       organism = synthetic construct
SEQUENCE: 92
atggcttccc ttcgactctt cctcctttgc ctcgctggac tggtatttgt gtctgaagct    60
ggccccgcgg gtgctggaga atccaaatgt cctctgatgg tcaaagtcct ggatgctgtc   120
cgaggcagcc ctgctgtaga cgtggctgta aaagtgttca aaaagacctc tgagggatcc   180
tgggagccct ttgcctctgg gaagaccgcg gagtctggag agctgcacgg gctcaccaca   240
gatgagaagt ttgtagaagg agtgtacaga gtagaactgg gtactggaag   300
acacttggca tttccccgtt ccatgaattc gcggatgtgg ttttcacagc caacgactct   360
ggccatcgcc actacaccat cgcagccctg ctcagcccat actcctacag caccacggct   420
gtcgtcagca accccccagaa ttga                                         444

SEQ ID NO: 93          moltype = DNA    length = 4176
FEATURE                Location/Qualifiers
misc_feature           1..4176
                       note = Synthetic
misc_feature           1..3
                       note = Start Codon
misc_feature           10..30
                       note = 5' NLS
misc_feature           4126..4173
                       note = 3' NLS
misc_feature           4174..4176
                       note = Stop Codon
source                 1..4176
                       mol_type = other DNA
                       organism = synthetic construct
SEQUENCE: 93
atggacaagc ccaagaaaaa gcggaaagtg aagtacagca tcggcctgga catcggcacc    60
aactctgtgg gctgggccgt gatcaccgac gagtacaagg tgcccagcaa gaaattcaag   120
gtgctgggca acaccgacag gcacagcatc aagaagaacc tgatcggcgc cctgctgttc   180
gacagcggcg aaacagccga ggccaccaga ctgaagagaa ccgccagaag aagatacacc   240
aggcggaaga acaggatctg ctatctgcaa gagatcttca gcaacgagat ggccaaggtg   300
gacgacagct tcttccacag actgaagag tccttcctgg tggaagagga caagaagcac   360
gagagacacc ccatcttcgg caacatcgtg gacgaggtgg cctaccacga aagtaccccc   420
accatctacc acctgagaaa gaaactggtg gacagcaccg acaaggccga cctgagactg   480
atctacctgg ccctggccca catgatcaag ttcagaggcc acttcctgat cgagggcgac   540
ctgaaccccg acaacagcga cgtggacaag ctgttcatcc agctggtgca gacctacaac   600
cagctgtttc g aggaaaaccc catcaacgcc agcggcgtgg acgccaaggc tatcctgtct   660
gccagactga gcaagagcag aaggctgaa atctgatcg cccagctgcc cggcgagaag   720
aagaacggcc tgttcggcaa cctgattgcc ctgagcctgg gcctgacccc caacttcaag   780
agcaacttcg acctggccga ggatgccaaa ctgcagctga gcaaggacac ctacgacgac   840
gacctggaca acctgctggc ccagatcggc gaccagtacg ccgacctgtt cctggccgcc   900
aagaacctgt ctgacgccat cctgctgagc gacatcctga gtgaacacg cgagatcacc   960
aaggccccc tgagcgcctc tatgatcaag agatacgacg agcaccacca ggacctgacc  1020
ctgctgaaag ctctcgtgcg gcagcagctg cctgagaagt acaaagaaat cttcttcgac  1080
cagagcaaga acggctacgc cggctacatc gatggcggcg ctagccagga agagttctac  1140
aagttcatca gcccatcct ggaaaagatg gacggcaccg aggaactgct cgtgaagctg  1200
aacagagagg acctgctgag aaagcagaga accttcgaca acggcagcat cccccaccag  1260
atccacctgg gagagctgca cgctatcctg agaaggcagg aagatttttta cccattcctg  1320
aaggacaacc gggaaaagat cgagaagatc ctgaccttca ggatccccta ctacgtgggc  1380
cccctggcca gaggcaacag cagattcgcc tggatgacca aaagagcga ggaaaccatc  1440
acccccctgga acttcgagga agtggtggac aagggcgcca cgcccagag cttcatcgag  1500
agaatgacaa acttcgataa gaacctgccc aacgagaagg tgctgcccaa gcacagcctg  1560
ctgtacgagt acttcaccgt gtacaacgag ctgaccaagg tgaaatacgt gaccgagggg  1620
atgagaaagc cgccttcct gagcggcgag cagaaaaagg ccatcgtgga cctgctgttc  1680
aagaccaaca gaaagtgac cgtgaagcag ctgaaagagg actacttcaa gaaaatcgag  1740
tgcttcgact ccgtggaaat ctccggccgt gaagatagat caacgcctc cctgggcaca  1800
taccacgatc tgctgaaaat tatcaaggac aaggacttcc tggataacga gagaacgag  1860
gacattctgg aagatatcgt gctgaccctg acactgtttg aggacgcga gatgatcgaa  1920
gaaaggctga aaacctacgc tcacctgttc gacgacaaag tgatgaagca gctgaagaga  1980
aggcggtaca ccgctgggg caggctgagc agaaagctga tcaacggcat cagagacaag  2040
cagagcggca agacaatcct ggattccctg aagtccgacg gcttcgccaa ccggaacttc  2100
atgcagctga tccacgacga cagcctgaca ttcaaagaga catccagaa agcccaggtg  2160
tccggccagg gcgactctct gcacgagcat atcgctaacc tggccggcag ccccgctatc  2220
```

```
aagaagggca tcctgcagac agtgaaggtg gtggacgagc tcgtgaaagt gatgggcaga    2280
cacaagcccg agaacatcgt gatcgagatg gctagagaga accagaccac ccagaaggga    2340
cagaagaact cccgcgagag gatgaagaga atcgaagagg gcatcaaaga gctgggcagc    2400
cagatcctga agaacaccc cgtggaaaac acccagctgc agaacgagaa gctgtacctg    2460
tactacctgc agaatggccg ggatatgtac gtggaccagg aactggacat caacagactg    2520
tccgactacg atgtggacca tatcgtgcct cagagctttc tgaaggacga ctccatcgat    2580
aacaaagtgc tgactcggag cgacaagaac agaggcaaga gcgacaacgt gccctccgaa    2640
gaggtcgtga agaagatgaa gaactactgg cgacagctgc tgaacgccaa gctgattacc    2700
cagaggaagt tcgataacct gaccaaggcc gagagaggcg gcctgagcga gctggataag    2760
gccggcttca tcaagaggca gctggtggaa accagacaga tcacaaagca cgtggcacag    2820
atcctggact cccggatgaa cactaagtac gacgaaaacg ataagctgat ccgggaagtg    2880
aaagtgatca ccctgaagtc caagctggtg tccgatttcc ggaaggattt ccagttttac    2940
aaagtgcgcg agatcaacaa ctaccaccac gcccacgacg cctacctgaa cgccgtcgtg    3000
ggaaccgccc tgatcaaaaa gtaccctaag ctggaaagcg agttcgtgta cggcgactac    3060
aaggtgtacg acgtgcggaa gatgatcgcc aagagcgagc aggaaatcgg caaggctacc    3120
gccaagtact tcttctacag caacatcatg aacttttta aggccgaaat caccctgacc    3180
aacggcgaga tcagaaagcg ccctctgatc gagacaaacg gcgaaaccgg ggagatcgtg    3240
tgggataagg gcagagactt cgccacagtc gaaaggtgc tgagcatgcc ccaagtgaat    3300
atcgtgaaaa agaccgaggt gcagacaggc ggcttcagca agagtctat cctgcccaag    3360
aggaacagcg acaagctgat cgccagaaag aaggactggg accccaagaa gtacggcggc    3420
ttcgacagcc ctaccgtggc ctactctgtg ctggtggtgg ctaaggtgga aaagggcaag    3480
tccaagaaac tgaagagtgt gaaagagctg ctggggatca ccatcatgga aagaagcagc    3540
tttgaagaga accctatcga ctttctggaa gccaaggct acaaagaagt gaaaaaggac    3600
ctgatcatca gctgcctaa gtactccctg ttcgagctgg aaaacggcag aaagagaatg    3660
ctggcctctg ccggcgaact gcagaaggga aacgagctgg ccctgcctag caaatatgtg    3720
aacttcctgt acctggcctc ccactatgag aagctgaagg gcagccctga ggacaacgaa    3780
cagaaacagc tgtttgtgga acagcataag cactacctgg acgagatcat cgagcagatc    3840
agcgagttcc caagagagt gatcctggcc gacgccaatc tggacaaggt gctgtctgcc    3900
tacaacaagc acaagggaca gccctatcag agcgaggccg agaatatcat ccacctgttc    3960
accctgacaa acctgggcgc tcctgccgcc ttcaagtact tgacaccac catcgaccgg    4020
aagaggtaca ccagcaccaa agaggtgctg gacgccaccc tgatccacca gagcatcacc    4080
ggcctgtacg agacaagaat cgacctgtct cagctgggag gcgacaagag acctgccgcc    4140
actaagaagg ccggacaggc caaaagaag aagtga                               4176
```

```
SEQ ID NO: 94           moltype = AA   length = 1391
FEATURE                 Location/Qualifiers
REGION                  1..1391
                        note = Synthetic
REGION                  4..10
                        note = MISC_FEATURE - 5' NLS
REGION                  1376..1391
                        note = MISC_FEATURE - 3' NLS
source                  1..1391
                        mol_type = protein
                        organism = synthetic construct
SEQUENCE: 94
MDKPKKKRKV KYSIGLDIGT NSVGWAVITD EYKVPSKKFK VLGNTDRHSI KKNLIGALLF    60
DSGETAEATR LKRTARRRYT RRKNRICYLQ EIFSNEMAKV DDSFFHRLEE SFLVEEDKKH    120
ERHPIFGNIV DEVAYHEKYP TIYHLRKKLV DSTDKADLRL IYLALAHMIK FRGHFLIEGD    180
LNPDNSDVDK LFIQLVQTYN QLFEENPINA SGVDAKAILS ARLSKSRRLE NLIAQLPGEK    240
KNGLFGNLIA LSLGLTPNFK SNFDLAEDAK LQLSKDTYDD DLDNLLAQIG DQYADLFLAA    300
KNLSDAILLS DILRVNTEIT KAPLSASMIK RYDEHHQDLT LLKALVRQQL PEKYKEIFFD    360
QSKNGYAGYI DGGASQEEFY KFIKPILEKM DGTEELLVKL NREDLLRKQR TFDNGSIPHQ    420
IHLGELHAIL RRQEDFYPFL KDNREKIEKI LTFRIPYYVG PLARGNSRFA WMTRKSEETI    480
TPWNFEEVVD KGASAQSFIE RMTNFDKNLP NEKVLPKHSL LYEYFTVYNE LTKVKYVTEG    540
MRKPAFLSGE QKKAIVDLLF KTNRKVTVKQ LKEDYFKKIE CFDSVEISGV EDRFNASLGT    600
YHDLLKIIKD KDFLDNEENE DILEDIVLTL TLFEDREMIE ERLKTYAHLF DDKVMKQLKR    660
RRYTGWGRLS RKLINGIRDK QSGKTILDFL KSDGFANRNF MQLIHDDSLT FKEDIQKAQV    720
SGQGDSLHEH IANLAGSPAI KKGILQTVKV VDELVKVMGR HKPENIVIEM ARENQTTQKG    780
QKNSRERMKR IEEGIKELGS QILKEHPVEN TQLQNEKLYL YYLQNGRDMY VDQELDINRL    840
SDYDVDHIVP QSFLKDDSID NKVLTRSDKN RGKSDNVPSE EVVKKMKNYW RQLLNAKLIT    900
QRKFDNLTKA ERGGLSELDK AGFIKRQLVE TRQITKHVAQ ILDSRMNTKY DENDKLIREV    960
KVITLKSKLV SDFRKDFQFY KVREINNYHH AHDAYLNAVV GTALIKKYPK LESEFVYGDY   1020
KVYDVRKMIA KSEQEIGKAT AKYFFYSNIM NFFKTEITLA NGEIRKRPLI ETNGETGEIV   1080
WDKGRDFATV RKVLSMPQVN IVKKTEVQTG GFSKESILPK RNSDKLIARK KDWDPKKYGG   1140
FDSPTVAYSV LVVAKVEKGK SKKLKSVKEL LGITIMERSS FEKNPIDFLE AKGYKEVKKD   1200
LIIKLPKYSL FELENGRKRM LASAGELQKG NELALPSKYV NFLYLASHYE KLKGSPEDNE   1260
QKQLFVEQHK HYLDEIIEQI SEFSKRVILA DANLDKVLSA YNKHRDKPIR EQAENIIHLF   1320
TLTNLGAPAA FKYFDTTIDR KRYTSTKEVL DATLIHQSIT GLYETRIDLS QLGGDKRPAA   1380
TKKAGQAKKK K                                                        1391
```